(12) United States Patent
Bramlage et al.

(10) Patent No.: US 9,050,375 B2
(45) Date of Patent: *Jun. 9, 2015

(54) BI-SPECIFIC DIGOXIGENIN BINDING ANTIBODIES

(75) Inventors: Birgit Bramlage, Kulmbach (DE); Ulrich Brinkmann, Weilheim (DE); Rebecca Croasdale, Antdorf (DE); Simone Dill, Kulmbach (DE); Wilma Dormeyer, Munich (DE); Guy Georges, Habach (DE); Michael Grote, Mainleus (DE); Alexander Haas, Munich (DE); Eike Hoffmann, Seefeld (DE); Ludger Markus Ickenstein, Kulmbach (DE); Kerstin Jahn-Hofmann, Neu-Isenburg (DE); Matthias John, Hallstadt (DE); Silke Metz, Bad Toelz (DE); Olaf Mundigl, Weilheim (DE); Werner Scheuer, Penzberg (DE); Jan Olaf Stracke, Munich (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/382,505

(22) PCT Filed: Jun. 30, 2010

(86) PCT No.: PCT/EP2010/059243
§ 371 (c)(1),
(2), (4) Date: Jan. 5, 2012

(87) PCT Pub. No.: WO2011/003780
PCT Pub. Date: Jan. 13, 2011

(65) Prior Publication Data
US 2012/0282280 A1    Nov. 8, 2012

(30) Foreign Application Priority Data

Jul. 6, 2009   (EP) ................................. 09164612

(51) Int. Cl.
| | |
|---|---|
| *C07K 16/46* | (2006.01) |
| *A61K 49/00* | (2006.01) |
| *A61K 49/16* | (2006.01) |
| *A61K 47/48* | (2006.01) |
| *A61K 31/704* | (2006.01) |
| *A61K 39/395* | (2006.01) |
| *B82Y 5/00* | (2011.01) |
| *C07K 16/16* | (2006.01) |
| *C07K 16/28* | (2006.01) |
| *C07K 16/32* | (2006.01) |
| *C07K 16/44* | (2006.01) |
| *C12N 15/11* | (2006.01) |
| *C12N 15/113* | (2010.01) |
| *A61K 39/00* | (2006.01) |

(52) U.S. Cl.
CPC ......... *A61K 47/48676* (2013.01); *A61K 31/704* (2013.01); *A61K 39/39533* (2013.01); *A61K 47/48746* (2013.01); *A61K 2039/505* (2013.01); *B82Y 5/00* (2013.01); *C07K 16/16* (2013.01); *C07K 16/2803* (2013.01); *C07K 16/2863* (2013.01); *C07K 16/2896* (2013.01); *C07K 16/32* (2013.01); *C07K 16/44* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/622* (2013.01); *C07K 2317/77* (2013.01); *C07K 2317/92* (2013.01); *C07K 2319/30* (2013.01); *C12N 15/111* (2013.01); *C12N 15/1138* (2013.01); *C12N 2310/14* (2013.01); *C12N 2310/3513* (2013.01); *C12N 2320/32* (2013.01)

(58) Field of Classification Search
CPC .................. A61K 47/48676; A61K 47/48746; A61K 47/48728; A61K 39/39553; A61K 2039/505; A61K 2300/00; C07K 2317/31; C07K 2317/77; C07K 2317/622; C07K 16/44; C07K 16/30; C07K 16/468; C12N 15/111; C12N 15/113; C12N 15/1135; C12N 15/1138; C12N 2310/14; C12N 2320/32
See application file for complete search history.

(56) References Cited

U.S. PATENT DOCUMENTS

| | | | |
|---|---|---|---|
| 5,344,757 | A | 9/1994 | Holtke et al. |
| 6,492,123 | B1 | 12/2002 | Holliger et al. |
| 7,074,405 | B1 | 7/2006 | Hansen et al. |
| 7,429,381 | B2 | 9/2008 | Hansen et al. |

(Continued)

FOREIGN PATENT DOCUMENTS

| | | |
|---|---|---|
| JP | 08-029419 | 2/1996 |
| WO | 98/08875 A1 | 3/1998 |

(Continued)

OTHER PUBLICATIONS (PCT Written Opinion of the ISA for PCT/EP2010/004051, counterpart of U.S. Appl. No. 13/382,502, filed Mar. 26, 2011)

(Continued)

*Primary Examiner* — Sheela J Huff
*Assistant Examiner* — Jessica H Roark
(74) *Attorney, Agent, or Firm* — Janet M. Martineau

(57) ABSTRACT

This invention relates to bispecific antibodies and antibody fragments against a target protein and a hapten, wherein the hapten is PEG or biotin, most preferably digoxigenin, methods for their production, their use as a delivery platform for therapeutic or diagnostic agents, pharmaceutical compositions containing said antibodies, and uses thereof.

17 Claims, 103 Drawing Sheets

(56) References Cited

U.S. PATENT DOCUMENTS

Figure 1:
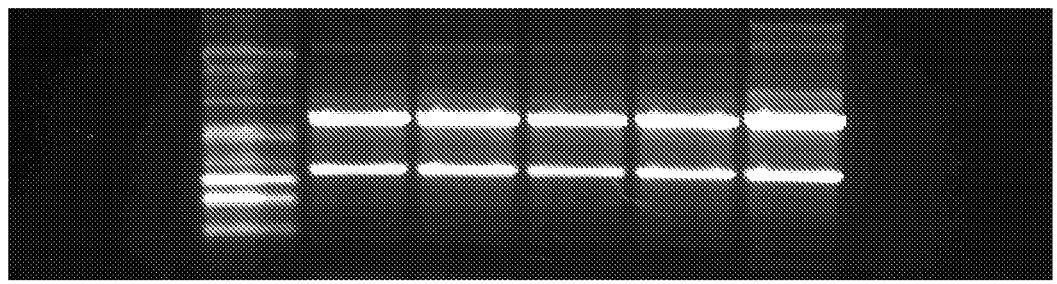

| | | | |
|---|---|---|---|
| 2002/0031781 | A1 | 3/2002 | Khaw et al. |
| 2006/0104899 | A1* | 5/2006 | Hansen et al. ............... 424/1.49 |
| 2008/0152661 | A1* | 6/2008 | Rozema et al. ............ 424/178.1 |
| 2009/0252731 | A1 | 10/2009 | Hansen et al. |
| 2012/0269723 | A1 | 10/2012 | Brinkmann et al. |

FOREIGN PATENT DOCUMENTS

| | | |
|---|---|---|
| WO | 98/40502 | 9/1998 |
| WO | 2004/091571 | 10/2004 |
| WO | 2005004809 A2 | 1/2005 |
| WO | 2006/023491 | 3/2006 |

OTHER PUBLICATIONS

Bohien et al., "CD3X Anti-Hapten Bispecific Antibodies And diabodies: A New Universal Tool For T-cell Retargetting" Experimntal Hematology 23(8):776, Abstract 127, (Aug. 27, 1995).

Goldenberg et al., "Antibody pretargeting advances cancer radioimmunodetection and radioimmunotherapy" J Clin Oncol. 24(5):823-34 (Feb. 10, 2006).

Haisma et al., "Targeting of adenoviral vectors through a bispecific single-chain antibody" Cancer Gene Therapy 7(6):901-904 ( 2000).

Mirochnik et al., "Targeting of biotinylated oligonuceotides to prostate tumors with antibody-based delivery vehicles" Journal of Drug Targeting 15(5):342-350 (Jun. 2007).

Orcutt et al., "A modular IgG-scFv bispecific antibody topology." Protein Engineering, Design & Selection (e-pub. Dec. 17, 2009), 23(4):221-228 (Apr. 2010).

PCT International Search Report for counterpart application PCT/EP2010/059243 Oct. 4, 2010.

PCT Written Opinion of the ISA for counterpart application PCT/EP2010/059243 Oct. 4, 2010.

Peer et al., "Systemic Leukocyte-Directed siRNA Delivery Revealing Cyclin D1 as an Anti-Inflammatory Target" Science 319:627-630 (Feb. 2008).

Satoshi et al., CAS Registry Database, (Chemi [Online] 'Bispecific antibody for antigen determination' XP002047466 retrieved from Chemical), Jan. 1, 1996.

Song et al., "Antibody mediated in vivo delivery of small interfering RNAs via cell-surface receptors" Nature Biotechnology 23(6):709-717 (Jun. 2005).

Wang et al., "Antigen targeting to dendritic cells with bispecific antibodies" Journal of Immunological Methods 306:80-92 ( 2005).

\* cited by examiner

Fig. 8 a)
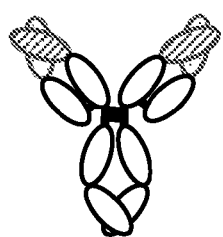
Fig. 8 b)
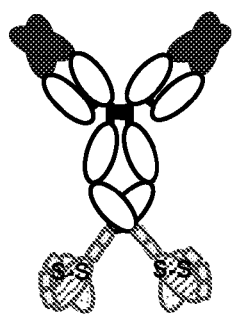
Fig. 8 c)
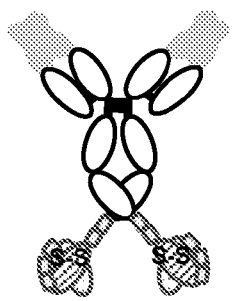
Fig. 8 d)
| Construct Name | Expression mg/L |
|---|---|
| A – hu<Dig> IgG | 18.8 |
| B – <IGF1R-DIG>2321 (disulfide stabilized) | 6.4 |
| C – <Her2-DIG>2321 (disulfide-stabilized) | 34.3 |

Fig. 9 a)
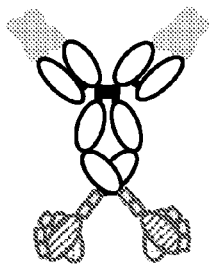
Fig. 9 b)
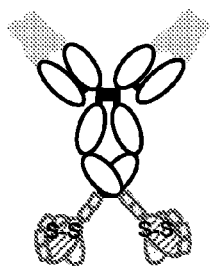
Fig. 9 c)
| Sample | Σ (mg) | Aggregates |
|---|---|---|
| Her2DIGHu2-2320 | 1 | 22 % |
| Her2DIGHu2-2321 | 31 | 0 % |

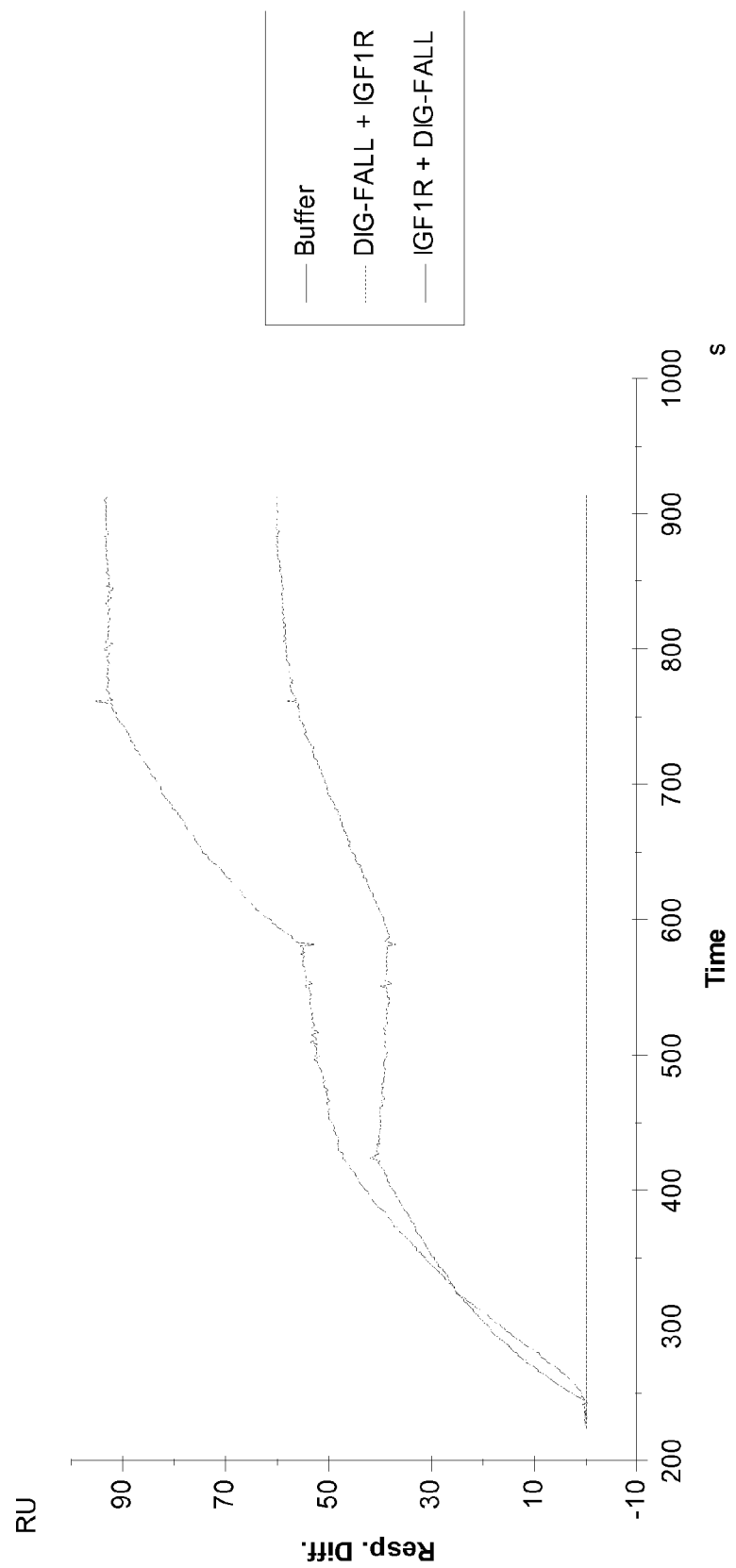
16 b)

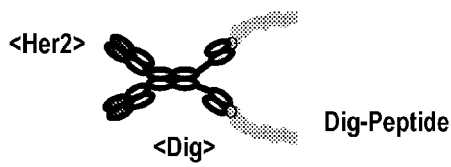
Fig. 17 a)
Fig. 17 b)
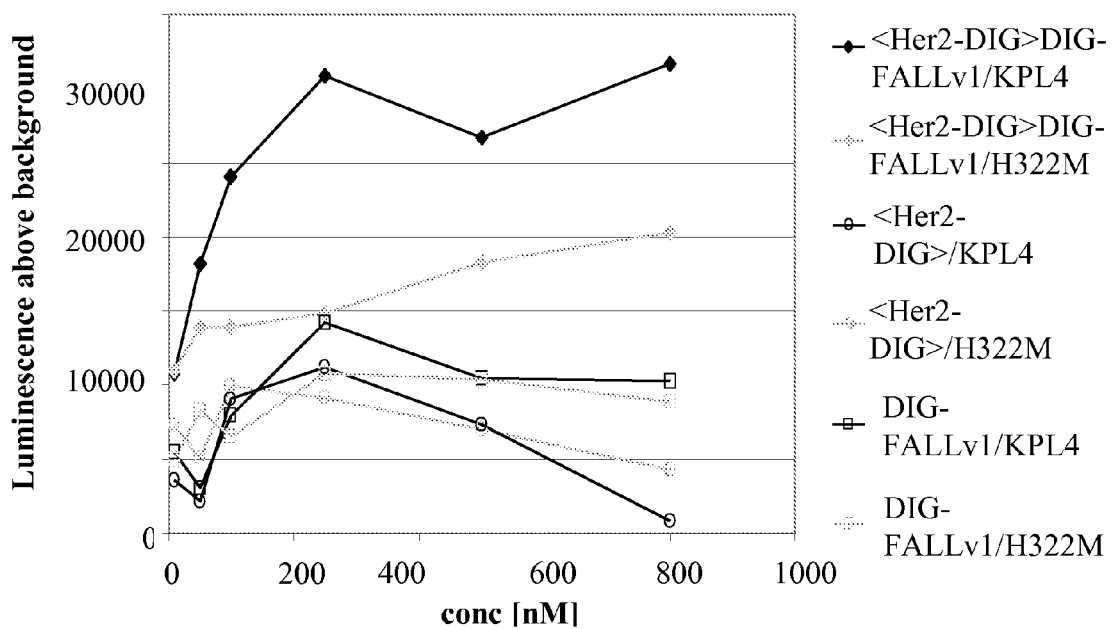
Fig. 17 c)
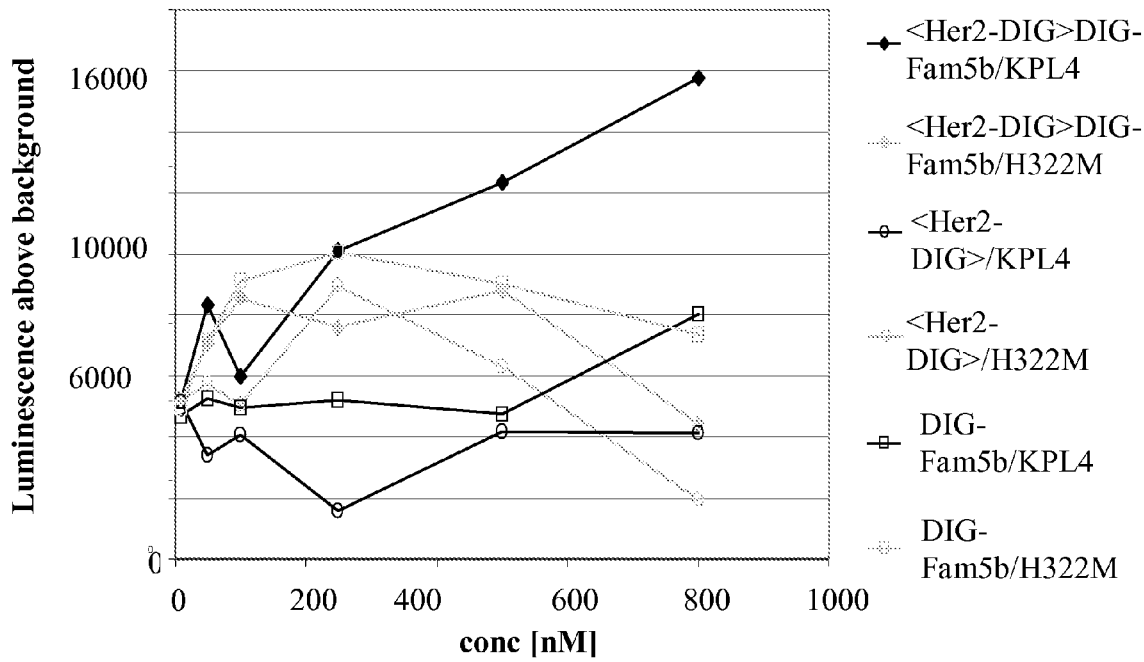

| ratio <Her2-Dig>:Doxo | Area (Ex: 488 nm / Em: 540 nm) [mAU*min] |
|---|---|
| 1:0 | 0 |
| 1:0,5 | 1,1 |
| 1:1 | 2,4 |
| 1:2 | 3,4 |
| 1:3 | 3,3 |
| 1:5 | 4,9 |
| 0:1 | 0 |

| ratio <Her2-Dig>:Dig-Cy5 | Area (Ex: 650 nm / Em: 667 nm) [mAU*min] |
|---|---|
| 1:0 | 2 |
| 1:0,5 | 30 |
| 1:1 | 68 |
| 1:2 | 135 |
| 1:3 | 209 |
| 1:5 | 381 |
| 0:1 | 0 |

Citrine
Cy3

Fig 45 a)

|  | complex murine Fab DIG-Cy5 |
|---|---|
| Data collection |  |
| Beamline | X06SA (SLS) |
| Space group | P 42 21 2 |
| Cell dimensions |  |
| a, b, c (Å) | 138.103 138.103 123.696 |
| α, β, γ (°) | 90.00 90.00 90.00 |
| Wavelength | 0.9795 |
| Resolution (Å) | 50.0-2.80 |
| Rsym | 10.1 (32.1) |
| I / s | 26.38 (9.11) |
| Completeness (%) | 98.1 (95.0) |
| Redundancy | 14.7 |
| Refinement |  |
| Resolution (Å) | 46.040 – 2.798 |
| No. reflections (test) | 29999 (1534) |
| $R$work / $R$free | 20.340 / 23.12 |
| No. atoms |  |
| Protein | 6660 |
| Ligand | 2x28 |
| Water | 348 |
| $B$-factor (Å $^2$) |  |
| Protein | 23.65 |
| Ligand | 16.00 |
| Water | 32.29 |
| R.m.s deviations |  |
| Bonds (Å) | 0.006 |
| Angles (°) | 1.292 |
| Ramachandran |  |
| Core (%) | 87.4 |
| Disallowed (%) | 0.4 |

Fig. 47 f)

| Affinity to siRNA-DIG | kd (1/s) | KD (nM) |
|---|---|---|
| <IGF1R-DIG> Dig on CH3 | 9,81E-03 | 20 |
| <IGF1R-DIG> Dig on Ckappa | 9,71E-03 | 23 |
| <IGF1R-DIG-DIG> hexavalent | 9,17E-03 | 24 |
| Affinity to IGF-1R | kd (1/s) | KD (nM) |
| <IGF1R-DIG> Dig on CH3 | 1,09E-03 | 5 |
| <IGF1R-DIG> Dig on Ckappa | 7,99E-04 | 3 |
| <IGF1R-DIG-DIG> hexavalent | 7,64E-04 | 3 |

| Affinity for DIG-siRNA | | kd (1/s) | KD (nM) |
|---|---|---|---|
| <IGF1R-DIG> 2321 | 5,03E+0 | 1,17E-02 | 23 |
| <IGF1R-scFab-DIG> 2321 | 8,32E+0 | 1,12E-02 | 14 |
| <IGF1R-dsFab-DIG> 2321 | 5,79E+0 | 7,82E-02 | 14 |

Affinity for DIG-siRNA

| Capture | Antibody | ka (1/Ms) | kd (1/s) | KD (M) |
|---|---|---|---|---|
| human VEGFR2-Fc | <VEGFR2(D1F7)-DIG>_001 | 3.44E+06 | 6.54E-03 | 1.90E-09 |
| | <VEGFR2(D1F7)-scFab-DIG> | 4.98E+06 | 6.70E-03 | 1.35E-09 |
| | <VEGFR2(D1F7)-dsFab-DIG> | 2.49E+06 | 9.68E-03 | 3.89E-09 |
| mouse VEGFR2-Fc | <VEGFR2(D1F7)-DIG>_001 | 3.89E+06 | 6.56E-03 | 1.69E-09 |
| | <VEGFR2(D1F7)-scFab-DIG> | 3.21E+06 | 8.92E-03 | 2.78E-09 |
| | <VEGFR2(D1F7)-dsFab-DIG> | 2.01E+06 | 1.14E-02 | 5.65E-09 |

| Molar ratio AK:DIG-Cy5 | Area (Ex: 650 nm / Em: 667 nm) [mAU*min] | | |
|---|---|---|---|
| | MAb Her2-DIG | MAb Her2 | MAb IGF-1R |
| 1:0 | 2 | 2 | 1 |
| 1:0,5 | 46 | 2 | 1 |
| 1:1 | 94 | 2 | 1 |
| 1:2 | 159 | 2 | 1 |
| 1:3 | 175 | 2 | 1 |
| 1:5 | 177 | 2 | 1 |
| 0:1 | 1 | 0 | 0 |

Figure 50:
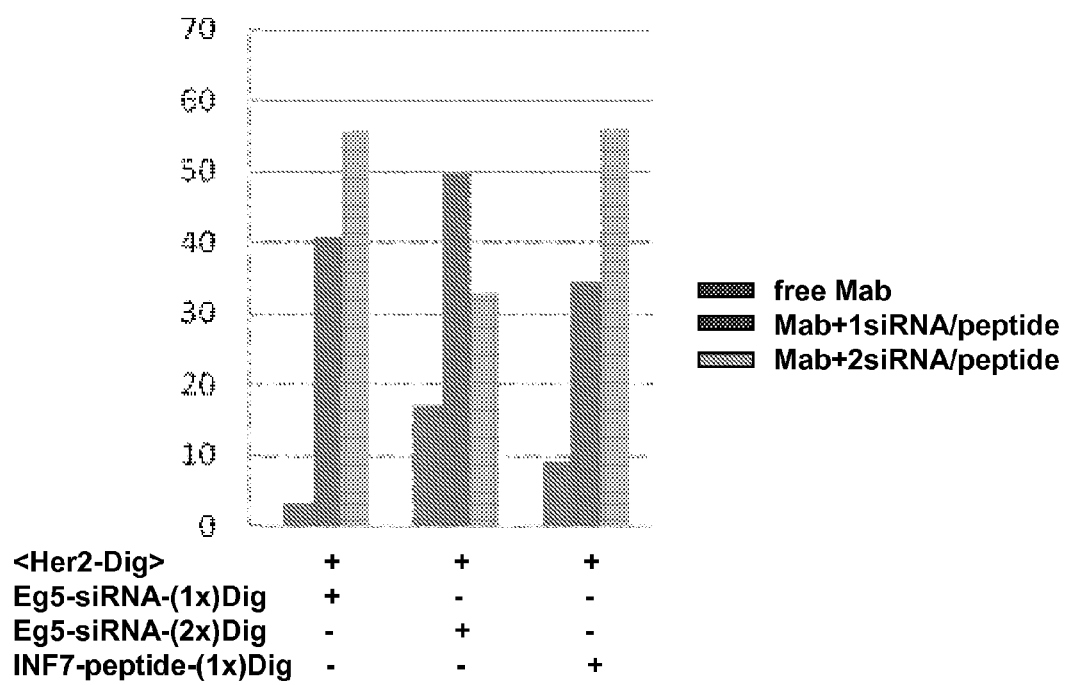

Fig. 50 a) (replacement sheet)
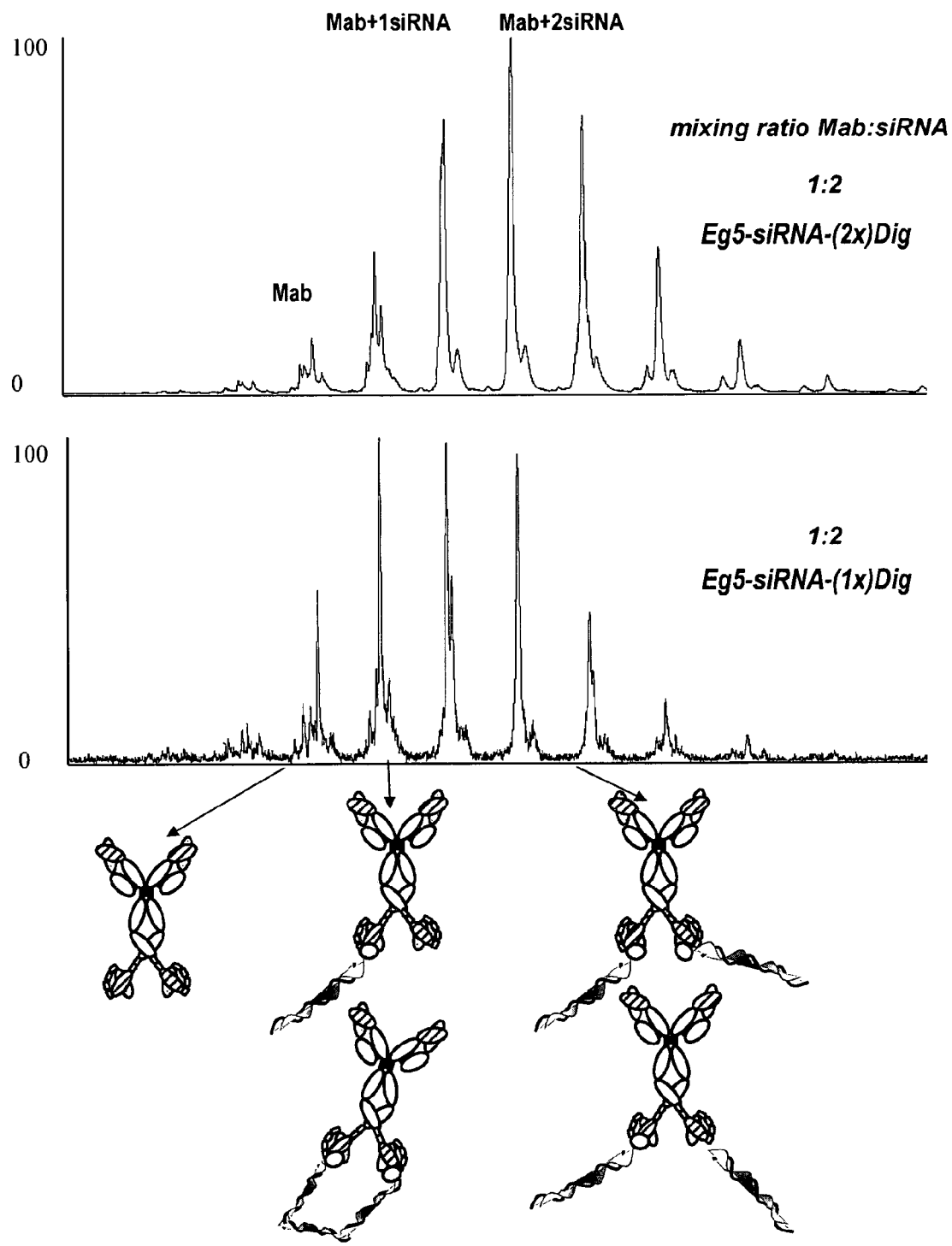

Fig. 51 a)

| cell surface antigen | molecule | format |
|---|---|---|
| IGF1-Receptor | <IGF1R-DIG> Fv | scFv/dsscFv; Dig - CH3 |
| IGF1-Receptor | <IGF1R-DIG> Fv | scFv/dsscFv; Dig - Ckappa |
| IGF1-Receptor | <IGF1R-DIG> Fv | dsscFv; Dig- CH3+Ckappa |
| IGF1-Receptor | <IGF1R-DIG> Fab | scFab; Dig- CH3 |
| IGF1-Receptor | <IGF1R-DIG> Fab | dsscFab; Dig- CH3 |
| VEGF-Receptor 2 | <VEGFR2-DIG> Fv | scFv/dsscFv; Dig - CH3 |
| VEGF-Receptor 2 | <VEGFR2-DIG> Fab | scFab; Dig- CH3 |
| VEGF-Receptor 2 | <VEGFR2-DIG> Fab | dsscFab; Dig- CH3 |
| CD33 | <CD33-DIG> Fab | dsscFab; Dig- CH3 |
| CD33 | <CD33-DIG> Fv | scFv/dsscFv; Dig - CH3 |
| LeY carbohydrate | <LeY-DIG> Fab | dsscFab; Dig- CH3 |
| LeY carbohydrate | <LeY-DIG> Fv | scFv/dsscFv; Dig - CH3 |
| CD22 | <CD22-DIG> Fv | dsscFv; Dig - CH3 |
| Her2 | <Her2-DIG> Fv | dsscFv; Dig - CH3 |
| CDCP1 | <CDCP1-DIG> Fv | dsscFv; Dig - CH3 |

Dig-
Ckappa
(or lambda)

Dig-CH3

Dig-CH3 +
Ckappa/lambda

Dig-CH3

Dig-CH3 scdsFab
(VH44-VL100)

Fig. 51 c)

| Capture | Antibody | ka (1/Ms) | kd (1/s) | KD (M) |
|---|---|---|---|---|
| human VEGFR2-Fc | <VEGFR2(D1F7)-DIG>_001 | 3.44E+06 | 6.54E-03 | 1.90E-09 |
| | <VEGFR2(D1F7)-scFab-DIG> | 4.98E+06 | 6.70E-03 | 1.35E-09 |
| | <VEGFR2(D1F7)-dsFab-DIG> | 2.49E+06 | 9.68E-03 | 3.89E-09 |
| mouse VEGFR2-Fc | <VEGFR2(D1F7)-DIG>_001 | 3.89E+06 | 6.56E-03 | 1.69E-09 |
| | <VEGFR2(D1F7)-scFab-DIG> | 3.21E+06 | 8.92E-03 | 2.78E-09 |
| | <VEGFR2(D1F7)-dsFab-DIG> | 2.01E+06 | 1.14E-02 | 5.65E-09 |

|            | ka (1/Ms) | kd (1/s)  | KD (nM) |
|------------|-----------|-----------|---------|
| CDCP1-ECD  | 2.02E+05  | 1.32E-03  | 7       |
|            | 2.02E+05  | 1.60E-03  | 8       |
| DIG-siRNA  | 4.37E+05  | 0.0097    | 22      |
|            | 5.54E+05  | 0.011     | 20      |

BI-SPECIFIC DIGOXIGENIN BINDING ANTIBODIES

RELATED APPLICATIONS

This application is a national stage entry of International Application No. PCT/EP2010/059243, filed Jun. 30, 2010, which claims the benefit of European Patent Application No. EP 09164612.5, filed Jul. 6, 2009. The contents of these Applications are hereby incorporated by reference in their entirety.

SEQUENCE LISTING

The instant application contains a Sequence Listing which has been filed electronically in ASCII format and is hereby incorporated by reference in its entirety. Said ASCII copy, created on Sep. 15, 2014, is named 2014.SEP.15 P4794 US Sequence Listing.txt and is 200,509 bytes in size.

The present invention relates to bi-specific antibodies and antibody fragments against a target protein and a hapten, methods for their production, their use as a delivery platform for therapeutic or diagnostic agents comprising a nucleic acid, pharmaceutical compositions containing said antibodies, and uses thereof.

Molecular medicine requires agents specifically and efficiently interacting with target cells. The efficient in vivo delivery of functional therapeutic or diagnostic agents to a target tissue or cell still remains one of the biggest obstacles in drug development. One approach is to couple the payloads to a delivery vehicle that specifically targets cells, for example to an antibody. Payloads must be coupled with good stability to assure specific targeting and avoid systemic nonspecific release of the payload. However, to enable entry into the cell, the payload is ideally released at or within target cells. To combine good stability within the circulation with effective release at the target is a major bottleneck in conjugate development. Most state of the art conjugates consist not of one defined molecule type but are a cocktail of molecules with different amounts of payloads coupled at varying positions. A major drawback of these conjugates is that conjugation procedures need to be adapted for each antibody and each payload; therefore payloads cannot easily be interchanged, also the covalent linkage may cause immunogenicity.

A wide variety of recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234). Also several other new formats wherein the antibody core structure (IgA, IgD, IgE, IgG or IgM) is no longer retained such as dia-, tria- or tetrabodies, minibodies, several single chain formats (scFv, BisscFv), which are capable of binding two or more antigens, have been developed (Holliger P, et al, Nature Biotech 23 (2005) 1126-1136; Fischer N., Léger O., Pathobiology 74 (2007) 3-14; Shen J, et al., Journal of Immunological Methods 318 (2007) 65-74; Wu, C. et al., Nature Biotech. 25 (2007) 1290-1297).

Bispecific antibodies are capable of simultaneous binding of two different targets and thus also capable of delivering a great variety of payloads to the target tissues or cells. To date bispecific antibodies specific for certain cell targets have been described. However this methodology has a major disadvantage as it requires that antibodies be raised against every agent desired for diagnostic and therapeutic use.

U.S. Pat. No. 7,429,381 discloses a two-step pretargeting method, wherein a bispecific antibody specific for a HSG hapten and a cell-surface protein is first administered to the cell and is then used to capture a HSG hapten to which a therapeutic or diagnostic cation or a therapeutic or diagnostic agent is chelated to. Haptens are small molecules, such as pesticides, drugs, hormones, and toxins, which are usually nonimmunogenic unless coupled with some macromolecules such as proteins. However the use of bispecific anti-HSG-hapten antibodies in a two-step pretargeting method has several limitations.

The major disadvantage is the complexity of the approach, which involves preparation and dosing of two separate reagents and consequential timing and ratio issues. In addition, it is not possible to analyse the resulting complex of the bispecific antibody and the therapeutic or diagnostic agent. It is therefore difficult to predict pharmacological properties, stoichiometry and possible degradation products of the therapeutic or diagnostic agent captured by the bispecific antibody.

In addition, currently used conjugates can not be applied for most therapeutic agents since conjugation often results in reduced or eliminated activity of the therapeutic agent or in undesired alterations of the binding capabilities of the antibody.

Therefore there is a need for a well-defined, efficient and specific delivery platform for therapeutic and diagnostic agents with effective release of the payload at the target that can be broadly applied.

The present invention relates to a bi-specific antibody specific against a hapten and a target protein, comprising a first antigen-binding site that binds to a hapten and a second antigen-binding site that binds to a target protein, wherein the hapten is conjugated to a nucleic acid. Preferred haptens are digoxigenin, biotin and polyethyleneglycol (PEG).

The invention provides methods for producing the bispecific antibodies or antibody fragments, as well as methods for using them, in particular their use as a delivery platform for therapeutic and diagnostic agents, as well as pharmaceutical compositions and diagnostic tools comprising said antibodies.

Preferred embodiments include bi-specific antibodies or antibody fragments against a target protein and digoxigenin, comprising a first antigen-binding site that binds to digoxigenin (referred to as "Dig" or "DIG") and a second antigen-binding site that binds to a target protein. Said binding sites of the bi-specific antibodies or antibody fragments are referred to as "<target protein>" (or shortly, "<target>") and "<Dig>", respectively.

In other embodiments bi-specific antibodies or antibody fragments against a target protein and a hapten different from digoxigenin are envisaged. Preferred haptens are biotin and PEG.

Below embodiments are exemplified for bi-specific antibodies or antibody fragments against a target protein and digoxigenin, as well as methods for using them, in particular their application as a delivery platform. Even though digoxigenin is the most preferred hapten envisaged in this invention, these embodiments are also applicable for biotin and PEG.

Further this invention relates to monoclonal bi-specific antibodies and antibody fragments that comprise a first antigen-binding site that binds to digoxigenin and a second antigen-binding site that binds to a target protein, DNAs that encode such antibodies and antibody fragments, and vectors for expressing the DNAs. Preferably, said bi-specific antibodies are humanized and chimeric antibodies.

One embodiment of the invention is a bispecific antibody binding to digoxigenin and a target protein comprising a first antigen-binding site that binds to digoxigenin and a second antigen-binding site that binds to a target protein, comprising a) a monospecific bivalent antibody consisting of two full length antibody heavy chains and two full length antibody light chains whereby each chain is comprising only one variable domain, b) two peptide-linkers, c) two monospecific monovalent single chain antibodies each consisting of an antibody heavy chain variable domain, an antibody light chain variable domain, and a single-chain-linker between said antibody heavy chain variable domain and said antibody light chain variable domain;

and preferably said single chain antibodies are linked to the same terminus (C- and N-terminus) of the monospecific bivalent antibody heavy chains or, alternatively to the same terminus (preferably the C-terminus) of the monospecific bivalent antibody light chains, and more preferably to the same terminus (C- and N-terminus) of the monospecific bivalent antibody heavy chains.

In one embodiment, said monospecific bivalent parent antibody under a) is a human antibody, preferably, a recombinant human antibody.

Preferably said peptide-linkers under b) are peptides with an amino acid sequence with a length of at least 10 amino acids. In one embodiment said peptide-linker is (GxS)n with G=glycine, S=serine, (x=3 and n=3, 4, 5 or 6) or (x=4 and n=2, 3, 4 or 5) (SEQ ID NO:120), preferably x=4 and n=2 or 3, more preferably with x=4, n=2.

Preferably the said single-chain-linker under c) is a peptide with an amino acid sequence with a length of at least 15 amino acids, more preferably with a length of at least 20 amino acids. In one embodiment said single-chain-linker is (GxS)n with G=glycine, S=serine, (x=3 and n=4, 5 or 6) or (x=4 and n=3, 4 or 5) (SEQ ID NO:121), preferably with x=4, n=4 or 5, more preferably with x=4, n=4.

Preferably said two monospecific monovalent single chain antibodies under c) comprise an antibody heavy chain variable domain SEQ ID NO. 3, SEQ ID NO 3 with the mutations S49A, I57A and A60P, or SEQ. ID NO. 2, an antibody light chain variable domain SEQ ID NO 5, or SEQ. ID NO. 1., and a single-chain-linker between said antibody heavy chain variable domain and said antibody light chain variable domain. Preferably, said two monospecific monovalent single chain antibodies under c) comprise as heavy chain Fd-Fragment ($V_H$ and $CH_1$) SEQ. ID NO. 4 or SEQ. ID NO. 36 and as L-chain SEQ. ID NO. 6 or SEQ. ID NO. 37.

In one embodiment of the invention the bispecific antibody according to the invention is characterized in that said antigen-binding site specifically binding to DIG comprises as heavy chain variable domain SEQ ID NO. 3, SEQ ID NO 3 with the mutations S49A, I57A and A60P, or SEQ. ID NO. 2 and as light chain variable domain SEQ ID NO 5, or SEQ. ID NO. 1. In another embodiment said antigen-binding site specifically binding to DIG comprises as heavy chain Fd-Fragment ($V_H$ and $CH_1$) SEQ. ID NO. 4. or SEQ. ID NO. 36 and as L-chain SEQ. ID NO. 6 or or SEQ. ID NO. 37.

The term "mutation" as used herein refers to one or more amino acid substitutions in a CDR and/or variable region of an antibody according to the invention. The term "with the mutations S49A, I57A and A60P" relate to 3 substitutions in the heavy chain variable domain of SEQ ID NO. 3 (numbering according to Kabat).

Furthermore said single chain antibodies are preferably disulfide stabilized. Such further disulfide stabilization of single chain antibodies is achieved by the introduction of a disulfide bond between the variable domains of the single chain antibodies and is described e.g. in WO 94/029350, Rajagopal, V., et al., Prot. Engin. Vol. 10 (12) 1453-59 (1997); Kobayashi, H., et al., Nuclear Medicine & Biology, Vol. 25, 387-393 (1998); or Schmidt, M., et al., Oncogene 18, 1711-1721 (1999).

In further embodiments the inventive antibody comprises a humanized digoxigenin binding module, comprising at least a single chain variable fragment (scFv) capable of binding digoxigenin. Said scFv preferably comprises one humanized $V_L$ and one humanized $V_H$ chain tethered together by a linker. In another embodiment, said antibody further comprises a Fc region composed of two heavy chains that contribute two or three constant domains.

In a preferred embodiment, the bi-specific antibody of the invention comprises a structure which is based on a full length antibody binding to a target protein, to which two (optionally disulfide-stabilized) single chain variable fragments (scFv) binding to digoxigenin, are linked via the a peptide-linker. In a further embodiment said antibody comprises humanized IgG with two digoxigenin binding sites.

The digoxigenin binding modules can be connected to cell targeting entities in a variety of formats. For example, not only 'classical' antibody fragments and antibody derived modules such as Fabs or Fvs can be applied for that, but also single-domain antibody-like entities which have previously been described in the literature. In addition to C-terminal fusions to the H-chain, additional formats as described in the examples are part of this invention.

In one embodiment of the invention, said target protein is a cell surface or a intracellular antigen, preferably said target protein is a cell surface or intracellular tumor-associated antigen.

In one preferred embodiment, said bispecific antibody comprise a first antigen-binding site that binds to digoxigenin and a second antigen-binding site that binds to Her2. Preferably said bispecific antibody specifically binding to Her2 and digoxigenin comprises a heavy chain of SEQ. ID NO. 7 or SEQ. ID NO. 8, and a light chain of SEQ. ID NO. 9.

In one preferred embodiment, said bispecific antibody comprise a first antigen-binding site that binds to digoxigenin and a second antigen-binding site that binds to IGF1R. Preferably said bispecific antibody specifically binding to IGF1R and digoxigenin comprises a heavy chain of SEQ. ID NO. 10 or SEQ. ID NO. 11, and a light chain of SEQ. ID NO. 12.

In one preferred embodiment, said bispecific antibody comprise a first antigen-binding site that binds to digoxigenin and a second antigen-binding site that binds to CD22. Preferably said bispecific antibody specifically binding to CD22 and digoxigenin comprises a heavy chain of SEQ. ID NO. 13 or 55, and a light chain of SEQ. ID NO.14 or 56.

In one preferred embodiment, said bispecific antibody comprise a first antigen-binding site that binds to digoxigenin and a second antigen-binding site that binds to CD33. Preferably said bispecific antibody specifically binding to CD33 and digoxigenin comprises a heavy chain of SEQ. ID NO. 59, and a light chain of SEQ. ID NO.60.

In one preferred embodiment, said bispecific antibody comprise a first antigen-binding site that binds to digoxigenin and a second antigen-binding site that binds to VEGFR1. Preferably said bispecific antibody specifically binding to VEGFR1 and digoxigenin comprises a heavy chain of SEQ. ID NO. 51, and a light chain of SEQ. ID NO.52.

In one preferred embodiment, said bispecific antibody comprise a first antigen-binding site that binds to digoxigenin and a second antigen-binding site that binds to Her2 (Lieberman). Preferably said bispecific antibody specifically binding to Her2 (Lieberman) and digoxigenin comprises a heavy chain of SEQ. ID NO. 53 and a light chain of SEQ. ID NO. 54.

In one preferred embodiment, said bispecific antibody comprise a first antigen-binding site that binds to digoxigenin and a second antigen-binding site that binds to LeY. Preferably said bispecific antibody specifically binding to LeY and digoxigenin comprises a heavy chain of SEQ. ID NO. 57 and a light chain of SEQ. ID NO. 58.

In one preferred embodiment of the invention said bi-specific antibody is used as a payload delivery vehicle for a therapeutic or diagnostic agent. The therapeutic or diagnostic agent is conjugated with digoxigenin and thus coupled by the antigen-binding site of the bi-specific antibody of the invention. This complex is defined and stable and specifically delivers the payload to a target cell or tissue. Since the digoxygenated therapeutic or diagnostic agents are coupled in a non-covalent manner to the bi-specific antibody, the payload is stably bound to its delivery vehicle during circulation but also gets efficiently released after internalization. The conjugation with digoxigenin does not affect the activity of most therapeutic or diagnostic agents. The bi-specific antibody does not contain an unusual covalent addition and therefore obviates any risk of immunogenicity. Therefore this simple conjugation procedure can be used for a great variety of payload molecules in combination with only one single antibody; for example peptides, proteins, small molecules, imaging reagents and nucleic acids, as detailed in the description of the specific embodiments and examples below. Complexes of digoxygenated diagnostic or therapeutic agents with bispecific antibody derivatives containing Dig-binding modules may confer benign biophysical behaviour and improved PK parameters to the diagnostic or therapeutic agent, e.g. to diagnostic or therapeutic proteins, peptides or small molecules. Furthermore, such complexes are capable to target the delivery load to cells which display the antigen that is recognized by the bispecific antibody variant.

The fate of the digoxygenated therapeutic or diagnostic payload molecules can be easily monitored in the patient with commonly used diagnostic agents specific for digoxigenin, for example with assays such as Tina-quant Digoxin method for detection of Digoxin and treatment of Digoxin overdosis (Roche/Hitachi, No. 12218623001 and U.S. Pat. No. 7,100, 001). Free digoxigenin or overdoses of the digoxygenated therapeutic or diagnostic payload molecules coupled to the bispecific antibodies can be cleared by clinically approved polyclonal anti-Digoxigenin antibodies (such antibodies are contained e.g. in the above mentioned assays).

In one embodiment the bi-specific antibody is recharged in vivo after cell-specific delivery of the payload.

In a preferred embodiment the bi-specific antibody comprises a first antigen-binding site specific for digoxigenin and a second antigen-binding site specifically binding to cell surface or intracellular tumor-associated antigens. Thus the bi-specific antibody loaded with the therapeutic or diagnostic agent is specifically delivered to a target cell or tissue, preferably to a tumor.

The above-described use of bi-specific antibodies as a targeted cell/tissue-specific delivery platform can be applied for a great variety of different payloads, in particular those detailed below.

In one embodiment, said bi-specific antibody is used as a payload delivery vehicle for therapeutic and/or diagnostic peptides or proteins. Coupling of peptidic or proteinous payloads can enhance the therapeutic potency of antibodies, for example toxin conjugates in cancer therapy. The therapeutic and/or diagnostic peptides or proteins are conjugated to digoxigenin and thereby coupled via an antibody-hapten interaction to the bispecific antibodies described above. This defined and stable complex specifically delivers the peptide or protein payload to a target cell or tissue and the peptide or protein payload is then released within the target cells.

In one preferred embodiment the digoxygenated peptide or protein is coupled to a bi-specific antibody which has a first antigen-binding site specific for digoxigenin and a second antigen-binding site specific for a target protein, preferably a cell surface antigen or a intracellular antigen, preferably said a cell surface or intracellular antigen is a tumor-associated antigen. In one preferred embodiment these complexes are composed of one humanized <target-protein>-<Dig> IgG which binds at its two high affinity Dig-binding sites two (one each site) digoxygenated peptides. The peptides retain good biological activity despite being digoxygenated, as well as while being complexed to the antibody. Furthermore, the specificity and activity of the bi-specific antibody of the invention is not affected by attachment of the digoxygenated peptide. The cell surface target binding site of the bispecific antibody derivative retains its binding specificity and affinity in the presence of complexed digoxygenated peptides. Preferably, said target protein is Her 2. In another preferred embodiment, said target protein is IGFR1. In another preferred embodiment, said target protein is CD22.

Upon binding of a digoxigenated peptide or protein to bi-specific antibodies of the invention, the peptide or protein retains its full biological activity. Surprisingly it was found that the recombinant humanized bispecific antibodies and antibody fragments of the invention improve the PK and stability of therapeutic peptides.

Non-limiting examples of preferred digoxygenated peptides are Dig-Mellitin, Dig-Fam5B, Dig-INF7, Dig-FallV1 and DigFallV2.

In one aspect of the invention, the bi-specific antibodies are used for delivery of cytotoxic peptides to antigen-expressing tumor cells. Thus this invention provides a specific delivery platform for targeted cancer therapy.

In one preferred embodiment the bi-specific antibody is used as a payload delivery vehicle for therapeutic or diagnostic small molecules. In one preferred embodiment these complexes are composed of one humanized <target protein>-<Dig> IgG which binds at its two high affinity Dig-binding sites two (one each site) digoxygenated compounds. The compounds retain biological activity despite being digoxygenated, as well as while being complexed to the antibody. The cell surface target binding site of the bispecific antibody derivative retains its binding specificity and affinity in the presence of complexed Dig-Compounds.

In one preferred embodiment digoxygenated small molecules are coupled to bispecific <target protein>-<Dig> antibody derivatives. Thereby defined stable molecule complexes are generated that release the payload within the target cells.

In one preferred embodiment, said small molecule is digoxygenated and coupled to a bispecific antibody which comprises a first antigen-binding site that binds to digoxigenin and a second antigen-binding site that binds to a target protein. Preferably, said target protein is a marker for tumor cells. In one preferred embodiment, said target protein is Her2. In another preferred embodiment, said target protein is IGF1R. In yet another preferred embodiment, said target protein is CD22.

In one preferred embodiment said bi-specific antibody is used as a payload delivery vehicle for digoxigenated cytotoxic molecule. Preferably said cytotoxic molecules are thus specifically delivered to antigen-expressing tumor cells. Thus this invention provides a specific delivery platform for targeted cancer therapy.

In one preferred embodiment the bi-specific antibody is used as a payload delivery for digoxigenated radioisotopes or radioisotopes attached to a digoxigenated small molecule. Thus this invention provides a specific delivery platform for radiotherapy. The digoxygenated radioisotope or radioisotopes attached to a digoxigenated small molecule display effective tissue penetration, fast clearance, and are retained only on cells covered by <Target>-<Dig> bispecific antibodies (target tissue/tumor). This enables specific targeting and avoids systemic nonspecific release of therapeutic radioisotopes. In one preferred embodiment, the bi-specific antibody bound to the target cell or tissue is 're-charged' with the digoxygenated radioisotope or radioisotope attached to a digoxigenated small molecule in vivo. In one preferred embodiment the bi-specific antibodies of the invention are used for delivery of digoxigenated radioisotopes or radioisotopes attached to a digoxigenated small molecule to diseased tissues. Preferably, said diseased tissue is a tumor.

In one preferred embodiment the bi-specific antibody is used as a payload delivery vehicle for imaging reagents. For imaging purposes, a good signal-to-background ratio is desired which requires good tissue penetration as well as good tissue targeting. Antibodies display good stability and good targeting but only moderate tissue penetration. These drawbacks are now overcome.

In a preferred embodiment, complexes of digoxygenated fluorescent substrates with bispecific antibody derivatives containing recombinant Dig-binding modules are applied for specific imaging of tissues or cells that carry the target antigen. In a preferred embodiment, these tissues or cells are imaged in vivo. These complexes are composed of one humanized <Target>-<Dig> IgG which binds at its two high affinity Dig-binding sites two (one each site) digoxygenated substrates that can be visualized by imaging technologies. In one preferred embodiment, the imaging compound is a fluorophor. In another preferred embodiment, said imaging compound is a radioactively labeled compound. The imaging compounds retain their properties despite being digoxygenated, as well as while being complexed to the antibody. In one preferred embodiment, said imaging compound is Cy5. The cell surface target binding site of the bispecific antibody derivative retains its binding specificity and affinity in the presence of complexed Dig-Compounds. In one preferred embodiment, said bispecific antibody comprises a first antigen-binding site that binds to digoxigenin and a second antigen-binding site that binds to a target protein. Preferably, said target protein is a marker for tumor cells. In one preferred embodiment, said target protein is Her2. In another preferred embodiment, said target protein is IGF1R. In yet another preferred embodiment, said target protein is CD22.

The digoxygenated imaging compounds display effective tissue penetration, fast clearance, and are retained only on cells covered by <Target>-<Dig> bispecific antibodies (target tissue/tumor). This enables effective time-resolved imaging, and assessment of tumor vascularization, or changes within tumor vascularization. In one preferred embodiment, the bi-specific antibody bound to the target cell or tissue is 're-charged' with the digoxygenated dye in vivo. In one preferred embodiment the bi-specific antibodies of the invention are used for imaging of diseased tissues. Preferably, said diseased tissue is a tumor.

Specific targeting and delivery of nucleic acids to and into target tissues and target cells is a mayor bottleneck, which has not satisfactorily been solved by current technologies. Most so far described nucleic acids delivery entities consist not of one defined molecule but rather are a cocktail of molecules or particles. However, for therapeutic applications, homogenous defined entities are desired. Antibody or antibody-fragment-mediated nucleic acid delivery has been shown in some examples (for example Lieberman et al, Antibody mediated in vivo delivery of small interfering RNAs via cell-surface receptors, Nature Biotechnology [1087-0156] Song yr:2005 vol:23 pg:709) but still faces severe technical hurdles. Of particular interest is the specific targeting and delivery of double stranded RNA molecules (dsRNA) to and into target tissues and target cells. Double-stranded ribonucleic acid (dsRNA) molecules have been shown to block gene expression in a highly conserved regulatory mechanism known as RNA interference (RNAi). DsRNAs can be conjugated to antibodies with good stability to assure specific targeting and avoid systemic nonspecific release. On the other hand, the dsRNA has to be released at or within target cells to enable entry into the cell. Targeted dsRNAs frequently accumulate in endosomes from which they need to escape to be active. However, effective non-toxic non-immunogenic endosome escape mechanisms for targeted dsRNAs still have to be found.

These drawbacks are now overcome using the bi-specific antibody of the invention as a payload delivery vehicle for nucleic acids. Thus this invention provides a specific delivery platform for targeted gene therapy and targeted RNAi delivery.

In one preferred embodiment complexes of digoxygenated nucleic acids with bispecific antibody derivatives containing recombinant Dig-binding modules are applied for specific targeting of nucleic acids to antigen expressing cells. Such complexes are capable to target the peptides to cells which display the antigen that is recognized by the bispecific antibody variant. These complexes are composed of one humanized <Target>-<Dig> IgG which binds at its two high affinity Dig-binding sites two (one each site) digoxygenated nucleic acids. The nucleic acids retain their functionality despite being digoxygenated, as well as while being complexed to the antibody. In addition, the cell surface target binding site of the bispecific antibody derivative retains its binding specificity and affinity in the presence of complexed digoxygenated nucleic acids. Preferably, the complexes of digoxygenated nucleic acids with bispecific <Target>-<DIG> antibody variants can be applied to target the nucleic acids specifically to cells that express the target antigen. Thereby, the cells that are recognized by surface antigens are selectively addressed by the nucleic acids, activities caused by the nucleic acids (e.g. RNAi or nucleic acid mediated cytotoxicity) are therefore enhanced in the antigen-expressing cells. In one embodiment, these activities are further enhanced by additionally applying targeted endosome modulating agents. Preferably, the nucleic acids are not only specifically delivered to antigen expressing cells but also become internalized into the target cells. Since the digoxygenated nucleic acids are coupled in a non-covalent manner to the bi-specific antibody of the invention, the payload (i.e. nucleic acids) get released after internalization. In a preferred embodiment, such target antigen is a marker for tumor cells. In one preferred embodiment, said target antigen is Her2. In another preferred embodiment, said target antigen is IGF1R. In yet another preferred embodiment, said target antigen is CD22.

In a preferred embodiment, the nucleic acid is DNA, in another preferred embodiment said nucleic acid is dsRNA. In one preferred embodiment said double-stranded RNA is used for inhibiting the expression of a target gene.

Methods for coupling digoxigenin to nucleic acids and analytical methods for their characterization are part of this invention.

To mediate their activity (for example the specific destruction of mRNAs by siRNAs), therapeutic or diagnostic nucleic acids have to access the cytoplasm of their target cells. One important factor for delivery of specific nucleic acid activity is that the molecules are not only delivered to cells, but also that sufficient amounts of the nucleic acids has to be transferred into the cytoplasm of these cells. For that, these molecules have to penetrate a biological membrane at least once. Since biologics do not pass easily across membranes, this process is a bottleneck that must be overcome for effective delivery of nucleic acid activity. Means to overcome this bottleneck can be membrane penetration, protein translocation across membranes, or endosome-escape or vesicular-escape mechanisms that may involve membrane disrupting processes.

In one preferred embodiment, the bispecific antibodies of the invention are used as a payload delivery module for nucleic acids to which a modulators of endosome functionality, or with endosome escape/disruption modules are linked. Preferably said endosome escape module comprises a peptide.

In one preferred embodiment, such an endosome escape module comprises Dynamic Poly Conjugates (DPCs). DPCs are chemical entities that upon cell binding and internalization cause endosome escape of siRNAs (Rozema D B et. al., Dynamic PolyConjugates for targeted in vivo delivery of siRNA to hepatocytes. Proceedings of the National Academy of Sciences of the United States of America; 2007 Aug. 7; 104(32):12982-7 PMID:17652171). Such DPCs are composed of PBAVE (polymers of butyl-aminovinyl ethers) scaffolds to which PEG molecules are attached reversibly using a bifunctional maleamate linkage. For the latter, carboxylated dimethyl maleic acid (CDM) can be applied. The PEG units are used to shield the endosomolytic positive charges of the PBAVE. Also linked to the PBAVE is the siRNA cargo (e.g. via a reversible disulfide linkage). The resulting delivery vehicles are called siRNA Dynamic PolyConjugates because siRNA, shielding groups (and additional targeting ligands) are conjugated to a polymer in a reversible manner. The endosomolytic properties of such DPCs which cause the cytoplasmic delivery of siRNA is induced by its chemical environment: The decrease in pH within maturing endolysomes induces release of the CDM-PEG, exposing positive charges of PBAVE which in turn mediates endsmolysis.

Therefore, in one preferred embodiment the endosomolytic features of DPCs with the specific targeting properties of the bispecific Digoxygenin delivery system are combined. Preferably, these complexes are composed of one humanized <Target>-<Dig> IgG which binds at its two high affinity Dig-binding sites two (one each site) digoxygenated nucleic acids conjugated to DPCs.

In one embodiment the bispecific antibodies complexed with digoxygenated nucleic acids are used for imaging analyses. In this embodiment, the nucleic acids are simultaneously labeled with digoxigenin and a detectable label. Thereby it is possible to visualize the localization of nucleic acids targeted to antigen expressing cells by microscopy or other imaging technologies. Preferably said detectable label is a fluorescence label. In one embodiment the localization of nucleic acids is visualized in cells, i.e. in vitro. In another preferred embodiment the localization of nucleic acids is visualized in vivo.

Polyclonal antibodies specific for digoxigenin are widely used in diagnostic assays. However, small stable fragments and -fusion proteins are desirable but cannot be generated from these hybridoma-derived antibodies. Therefore there is a need for recombinant humanized or chimeric <Dig> or <Dig> fusion proteins as diagnostic reagents. In one embodiment of the invention, the inventive bispecific antibodies or fragments are used as diagnostic tools and reagents. These include, but are not limited to functional recombinant human IgG, Fab fragment, scFv, and disulfide-stabilized Fv specific for Digoxigenin. Preferably, the bi-specific antibody or antibody fragment recognizes digoxygenated compounds or molecules, for example, but not limited to digoxygenated proteins, peptides or nucleic acids. In a preferred embodiment, said bispecific antibodies or fragments are conjugated to an enzyme, protein A, (Strept)Avidin, or a fusion protein for use in diagnostic assays.

Polyclonal <Dig> (Fab) is therapeutically applied to counteract Digitoxin overdoses. The existing products may be rather undefined and probably immunogenic. The bispecific antibodies or antibody fragments of the invention bind specifically to digoxigenin and are well defined with low or no immunogenicity. In one embodiment the recombinant humanized or chimeric <Dig> or <Dig> fragments are used as Digitoxin antidote.

As used herein, "antibody" refers to a binding protein that comprises antigen-binding sites. The terms "binding site" or "antigen-binding site" as used herein denotes the region(s) of an antibody molecule to which a ligand actually binds. In one embodiment of the current invention each of the binding sites comprises an antibody heavy chain variable domain (VH) and/or an antibody light chain variable domain (VL), and preferably is formed by a pair consisting of an antibody light chain variable domain (VL) and an antibody heavy chain variable domain (VH).

In one embodiment of the invention, said antibody comprises a single chain variable fragment (scFv).

Antibody specificity refers to selective recognition of the antibody for a particular epitope of an antigen. Natural antibodies, for example, are monospecific. "Bispecific antibodies" according to the invention are antibodies which have two different antigen-binding specificities. Where an antibody has more than one specificity, the recognized epitopes may be associated with a single antigen or with more than one antigen. Antibodies of the present invention are specific for two different antigens, i.e. digoxigenin as first antigen and a target protein as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies according to the invention are at least "bivalent" and may be "trivalent" or "multivalent" (e.g. ("tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized. For an antibody with more than two antigen binding sites, some binding sites may be identical, so long as the protein has binding sites for two different antigens. That is, whereas a first binding site is specific for digoxigenin, a second binding site is specific for a target protein.

Like natural antibodies, an antigen binding sites of an antibody of the invention typically contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences. Also included within the scope of the invention are functional antigen binding sites comprised of fewer CDRs (i.e., where binding specificity is determined by three, four or five CDRs). For example, less than a complete set of 6 CDRs may be sufficient for binding. In some cases, a VH or a VL domain will be sufficient.

In certain embodiments, antibodies of the invention further comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, an antibody of the invention has a constant domain structure of an IgG type antibody, but has four antigen binding sites. This is accomplished by linking two complete antigen binding sites (e.g., a single chain Fv) specifically binding to DIG to either to N- or C-terminus heavy or light chain of a full antibody specifically binding to a target protein. The four antigen-binding sites preferably comprise two binding sites for each of two different binding specificities.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner, et al. are also available for the preparation of human monoclonal antibodies (Cole, P. J., et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of an antigen in an in vitro assay, preferably in a cell-based ELISA with CHO cells expressing wild-type antigen. Binding means a binding affinity (KD) of $10^{-8}$ M or less, preferably $10^{-13}$ M to $10^{-9}$ M. Binding of the antibody to the antigen or FcγRIII can be investigated by a BIAcore assay (Pharmacia Biosensor AB, Uppsala, Sweden). The affinity of the binding is defined by the terms ka (rate constant for the association of the antibody from the antibody/antigen complex), kD (dissociation constant), and KD (kD/ka).

As used herein, the term "coupled" specifically refers to the antibody-hapten interaction by which a digoxigenated therapeutic or diagnostic payload is non-covalently bound to the bispecific antibodies of the invention.

The term "small molecule", or "small compound" as used herein, refers to organic or inorganic molecules either synthesized or found in nature, generally having a molecular weight less than 10,000 grams per mole, optionally less than 5,000 grams per mole, and optionally less than 2,000 grams per mole.

The term "peptide" as used herein refers to any polymer compound produced by amide formation between an .alpha.-carboxyl group of one amino acid and an .alpha.-amino group of another group. The term "protein" as used herein refers to polypeptides of specific sequence of more than about 50 residues.

The term "nucleic acid" as used herein means an oligomer or polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Non-naturally occurring nucleic acids are oligomers or polymers which contain nucleobase sequences which do not occur in nature, or species which contain functional equivalents of naturally occurring nucleobases, sugars, or inter-sugar linkages, like peptide nucleic acids (PNA), threose nucleic acids (TNA), locked nucleic acids (LNA), or glycerol nucleic acids (GNA). This term includes oligomers that contain the naturally occurring nucleic acid nucleobases adenine (A), guanine (G), thymine (T), cytosine (C) and uracil (U), as well as oligomers that contain base analogs or modified nucleobases. Nucleic acids can derive from a variety of natural sources such as viral, bacterial and eukaryotic DNAs and RNAs. Other nucleic acids can be derived from synthetic sources, and include any of the multiple oligonucleotides that are being manufactured for use as research reagents, diagnostic agents or potential and definite therapeutic agents. The term includes oligomers comprising of a single strand nucleic acid or a double strand nucleic acid.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

In one embodiment of the invention the bispecific antibody comprises a full length antibody as scaffold. The term "full length antibody" denotes an antibody consisting of two "full length antibody heavy chain" and two "full length antibody light chain". A "full length antibody heavy chain" is a polypeptide consisting in N-terminal to C-terminal direction of an antibody heavy chain variable domain (VH), an antibody constant domain 1 (CH1), an antibody hinge region, an antibody constant domain 2 (CH2), an antibody constant domain 3 (CH3), and optionally an antibody constant domain 4 (CH4) in case of an antibody of the subclass IgE. A "full length antibody light chain" is a polypeptide consisting in N-terminal to C-terminal direction of an antibody light chain variable domain (VL), and an antibody light chain constant domain (CL). The full length antibody chains a linked together via inter-polypeptide disulfide bonds between the CL-domain and the CH1 domain and between the hinge regions of the full length antibody heavy chains.

The binding sites in an antibody according to the invention may be each formed by a pair of two variable domains, i.e. of one heavy chain variable domain and one light chain variable domain. The minimal binding site determinant in an antibody is the heavy chain CDR3 region.

In one embodiment of the disulfide stabilized single chain antibodies, the disulfide bond between the variable domains of the single chain antibodies comprised in the antibody according to the invention is independently for each single chain antibody selected from:

i) heavy chain variable domain position 44 to light chain variable domain position 100, ii) heavy chain variable domain position 105 to light chain variable domain position 43, or iii) heavy chain variable domain position 101 to light chain variable domain position 100.

In one embodiment the disulfide bond between the variable domains of the single chain antibodies comprised in the antibody according to the invention is between heavy chain variable domain position 44 and light chain variable domain position 100.

In one embodiment the disulfide bond between the variable domains of the single chain antibodies comprised in the antibody according to the invention is between heavy chain variable domain position 105 and light chain variable domain position 43.

In a further embodiment said tetravalent bispecific antibody is characterized in that said monospecific bivalent antibody is of human IgG1 subclass, or of human IgG1 subclass with the mutations L234A and L235A.

In a further embodiment said tetravalent bispecific antibody is characterized in that said monospecific bivalent antibody is of human IgG2 subclass.

In a further embodiment said tetravalent bispecific antibody is characterized in that said monospecific bivalent antibody is of human IgG3 subclass.

In a further embodiment said tetravalent bispecific antibody is characterized in that said monospecific bivalent antibody is of human IgG4 subclass or, of IgG4 subclass with the additional mutation S228P.

In a further embodiment the bispecific antibody is characterized by
- two antigen-binding sites are each formed by the two pairs of heavy and light chain variable domains of the monospecific bivalent antibody and both bind to the same epitope,
- the additional two antigen-binding sites are each formed by the heavy and light chain variable domain of one single chain antibody,
- the single chain antibodies are each linked to one heavy chain or to one light chain via a peptide-linker, whereby each antibody chain terminus is linked only to a single chain antibody.

The term "peptide-linker" as used within the invention denotes a peptide with amino acid sequences, which is preferably of synthetic origin. These peptide-linkers according to invention are used to link the different antigen-binding sites and/or antibody fragments eventually comprising the different antigen-binding sites (e.g. single chain Fv, full length antibodies, a VH domain and/or a VL domain, Fab, (Fab)2, Fc part) together to form a bispecific antibody according to the invention The peptide-linkers can comprise one or more of the following amino acid sequences listed in Table 1 as well as further arbitrarily selected amino acids.

TABLE 1

Peptide-linker amino acid sequences

| Peptidic-linker amino acid sequence | SEQ ID NO: | Reference |
|---|---|---|
| A3GSG-XS-GASAS | 64 | M. J. Wright, and M. P. Deonarain, Mol. Immun. 44 (2007) 2860-2869 |
| G(S)15G | 65 | |
| G(S)15GAS | 66 | |
| G[SG4]3T | 67 | |
| [GS]5 | 68 | Yang, Anal. Bioanal. Chem. 390 (2008) 2133 |
| G3[SG4]2SG | 69 | |
| G3[SG4]2SG2 | 70 | |
| G3[SG4]2SGN | 71 | |
| [G3S]5 | 72 | |
| [G3S]5G3 | 73 | |
| [G4S]2 | 74 | |
| [G4S]3 | 75 | Batra, J. K., et al., J. Biol. Chem. 265 (1990) 15198-15202. |
| [G4S]3G | 76 | |
| [G4S]3G2 | 77 | |
| [G4S]3G2N | 78 | |
| [G4S]3GAS | 79 | |
| [G4S]4 | 80 | |
| [G4S]5 | 81 | |
| [G4S]5G | 82 | |
| [G4S]5G2 | 83 | |
| [G4S]6 | 84 | |
| [GQ4]3 | 85 | |
| [GQ4]3G | 86 | |
| [GQ4]3GN2 | 87 | |
| K[G4S]3G2N | 88 | |
| [LS]2G2 | 89 | |
| [LS]2PGK | 90 | |
| [LS]2PG2 | 91 | |
| LSPNRGEC | 92 | |

TABLE 1-continued

Peptide-linker amino acid sequences

| Peptidic-linker amino acid sequence | SEQ ID NO: | Reference |
|---|---|---|
| RT[G3S]3G2T | 93 | Appl. Microbiol. Biotechnol. 48 (1997) 487-492 |
| [SG4]3 | 94 | |
| [SG4]3G | 95 | |
| [SG4]3G2 | 96 | |
| [SG4]3G2N | 97 | |
| [SG4]3G2T | 98 | |
| [SG4]3GAS | 99 | |
| [SG4]5 | 100 | |
| [SG4]5G | 101 | |
| [SG4]5G2 | 102 | |
| [SG4]5GAS | 103 | |
| [G2S]2GRT[G3S]3GGT | 104 | App. Microbiol. Biotechnol. 48 (1997) 487-492 |
| [G3S]3 | 105 | |
| [G3S]4 | 106 | |

The term "single-chain-linker" as used within the invention denotes a peptide with amino acid sequences, which is preferably of synthetic origin. These peptide-linkers according to invention are used to link a VH and a VL domain to form a single chain Fv. The single-chain-linker can comprise one or more of the following amino acid sequences listed in Table 2, as well as further arbitrarily selected amino acids.

TABLE 2

Single-chain-linker amino acid sequences.

| Single-chain-linker amino acid sequence | SEQ ID NO: | Reference |
|---|---|---|
| A3GSG2[AS]2 | 107 | M. J. Wright, M. P. Deonarain, Mol. Immunol. 44 (2007) 2860-2869 |
| AGQG2V | 108 | J. Biol. Chem. 266 (1991) 16343 |
| EGKS[SG]2SESKEF | 109 | Biochem. 35 (1996) 545-553 |
| EGKS[SG]2SESKST | 110 | Bird, R. E., et al., Science 242 (1988) 423-426;Batra, J. K., et al., J. Biol. Chem. 265 (1990) 15198-15202; Batra, J. K., et al., Biochem. Biophys. Res. Commun. 139 (1990) 1-6. |
| EGKS[SG]2SESKSTQ | 111 | Bird, R. E., et al., Science 242 (1988) 423-426; Davis, G. T., et al., Biol. Technology 9 (1991) 133-137. |
| EGKS[SG]2SESKVD | 112 | Chaudhary, 088. V. K. et al., Proc. Natl. Acad. Sci. USA 87 (1990) 1066-1070. |
| ESGSVS2E2LAFRSLD | 113 | Batra, J. K., et al., J. Biol. Chem. 265 (1990) 15198-15202 |
| G(S)15G | 65 | |
| G(S)15GAS | 66 | |
| G[SG4]3T | 67 | |
| G3[SG4]2SG | 69 | |
| G3[SG4]2SG2 | 70 | |
| G3[SG4]2SGN | 71 | |
| G3SA3 | 114 | J. Immunol. Meth. 282 (2003) 33-43 |
| GSTSGSGKS2EGKG | 115 | Bedzyk, W. D., et al., J. Biol. Chem. 265 (1990) |

TABLE 2-continued

Single-chain-linker amino acid sequences.

| Single-chain-linker amino acid sequence | SEQ ID NO: | Reference |
|---|---|---|
| | | 18615-18620; Biol. Pharmaceut. Bull. 22 (1999) 1068-1072; J. Biol. Chem. 266 (1991) 14095-14103; Proc. Natl. Acad Sci. USA 89 (1992) |
| [G4S]2 | 74 | |
| [G3S]5 | 72 | |
| [G3S]5G3 | 73 | |
| [G4S]3 | 75 | Batra, J. K., et al., J. Biol. Chem. 265 (1990) 15198-15202. |
| [G4S]3G | 76 | |
| [G4S]3G2 | 77 | |
| [G4S]3G2N | 78 | |
| [G4S]3GAS | 79 | |
| [G4S]4 | 80 | |
| [G45]5 | 81 | |
| [G45]5G | 82 | |
| [G45]5G2 | 83 | |
| [G4S]6 | 84 | |
| [GQ4]3 | 85 | |
| [GQ4]3G | 86 | |
| [GQ4]3GN2 | 87 | |
| K[G4S]3G2N | 88 | |
| KESGSVS2EQLAQFRSLD | 116 | Bird, R. E., et al., Science 242 (1988) 423-426. |
| LSPNRGEC | 92 | |
| [LS]2G2 | 89 | |
| [LS]2PG2 | 91 | |
| [LS]2PGK | 90 | |
| S2AD2AK2D2AK2D2 AK2D2AK2DG | 117 | Pantoliano, M. W., et al., Biochem. (1991) J. mol. recog. 12 (1999) 258 |
| S2AD2AK2D001K2D2 AK2D2AK2DAS | 118 | |
| S2AD2AK2D001K2D2 AK2D2AK2DG | 119 | J. Biol. Chem. 266 (1991) 14095-14103 |
| [SG4]3 | 94 | |
| [SG4]3G | 95 | |
| [SG4]3G2 | 96 | |
| [SG4]3G2N | 97 | |
| [SG4]3G2T | 98 | |
| [SG4]3GAS | 99 | |
| [SG4]5 | 100 | |
| [SG4]5G | 101 | |
| [SG4]5G2 | 102 | |
| [SG4]5GAS | 103 | |

Due to their chemical and physical properties, such as molecular weight and domain architecture including secondary modifications, the downstream processing of antibodies is very complicated. For example, are not only for formulated drugs but also for intermediates in downstream processing (DSP) concentrated solutions required to achieve low volumes for economic handling and application storage. But with increasing concentration of the antibody a tendency to form aggregates can be observed. These aggregated antibodies have impaired characteristics compared to the isolated antibody. It has now been found that aggregation of the antibodies according to the invention can be reduced by the introduction of disulfide bonds between the heavy and light chain variable domains of the single chain antibodies connected to the monospecific bivalent parent antibody. This improved stability is not only useful during the production process but also for the storage of the antibodies. In one embodiment the disulfide bond between the variable domains of the single chain antibodies comprised in the antibody according to the invention is independently for each single chain antibody selected from:

i) heavy chain variable domain position 44 to light chain variable domain position 100, ii) heavy chain variable domain position 105 to light chain variable domain position 43, or iii) heavy chain variable domain position 101 to light chain variable domain position 100.

In one embodiment the disulfide bond between the variable domains of the single chain antibodies comprised in the antibody according to the invention is between heavy chain variable domain position 44 and light chain variable domain position 100.

In one embodiment the disulfide bond between the variable domains of the single chain antibodies comprised in the antibody according to the invention is between heavy chain variable domain position 105 and light chain variable domain position 43.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ and μ, respectively. The light chain constant regions which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788). While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). In one embodiment an antibody according to the invention has a reduced FcR binding compared to an IgG1 antibody. Thus the monospecific bivalent parent antibody is in regard to FcR binding of IgG4 subclass or of IgG1 or IgG2 subclass with a mutation in S228, L234, L235 and/or D265, and/or contains the PVA236 mutation. In one embodiment the mutations in the monospecific bivalent parent antibody are S228P, L234A, L235A, L235E and/or PVA236.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 183-202 (1999); Geisse, S., et al., Protein Expr. Purif. 8 271-282 (1996); Kaufman, R. J., Mol. Biotechnol. 16 151-161 (2000); Werner, R. G., Drug Res. 48 870-880 (1998).

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 109-123 (2000); Barnes, L. M., et al., Biotech. Bioeng. 73 261-270 (2001). Transient expression is described by, e.g., Durocher, Y., et al., Nucl. Acids. Res. 30 E9 (2002). Cloning of variable domains is described by Orlandi, R., et al., Proc. Natl. Acad. Sci. USA 86 3833-3837 (1989); Carter, P., et al., Proc. Natl. Acad. Sci. USA 89 4285-4289 (1992); and Norderhaug, L., et al., J. Immunol. Methods 204 77-87 (1997). A preferred transient expression system (HEK 293) is described by Schlaeger, E.-J., and Christensen, K., in Cytotechnology 30 71-83 (1999) and by Schlaeger, E.-J., in J. Immunol. Methods 194 191-199 (1996).

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenylsepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A. Appl. Biochem. Biotech. 75 93-102 (1998)).

One aspect of the invention is a pharmaceutical composition comprising an antibody according to the invention. Another aspect of the invention is a pharmaceutical composition comprising an antibody according to the invention coupled to a digoxigenated therapeutic or diagnostic agent. In another aspect, the present invention provides a composition, e.g. a pharmaceutical composition, containing an antibody coupled to a digoxigenated therapeutic or diagnostic agent according to the present invention, formulated together with a pharmaceutical carrier.

Another aspect of the invention is said pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody coupled to a digoxigenated therapeutic or diagnostic agent according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewing's sarcoma, including refractory versions of any of the above cancers, or a combination of one or more of the above cancers.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 546ff (1978). However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al, PNAS. 69 (1972) 7110ff.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

SHORT DESCRIPTION OF THE FIGURES

Figure 2:
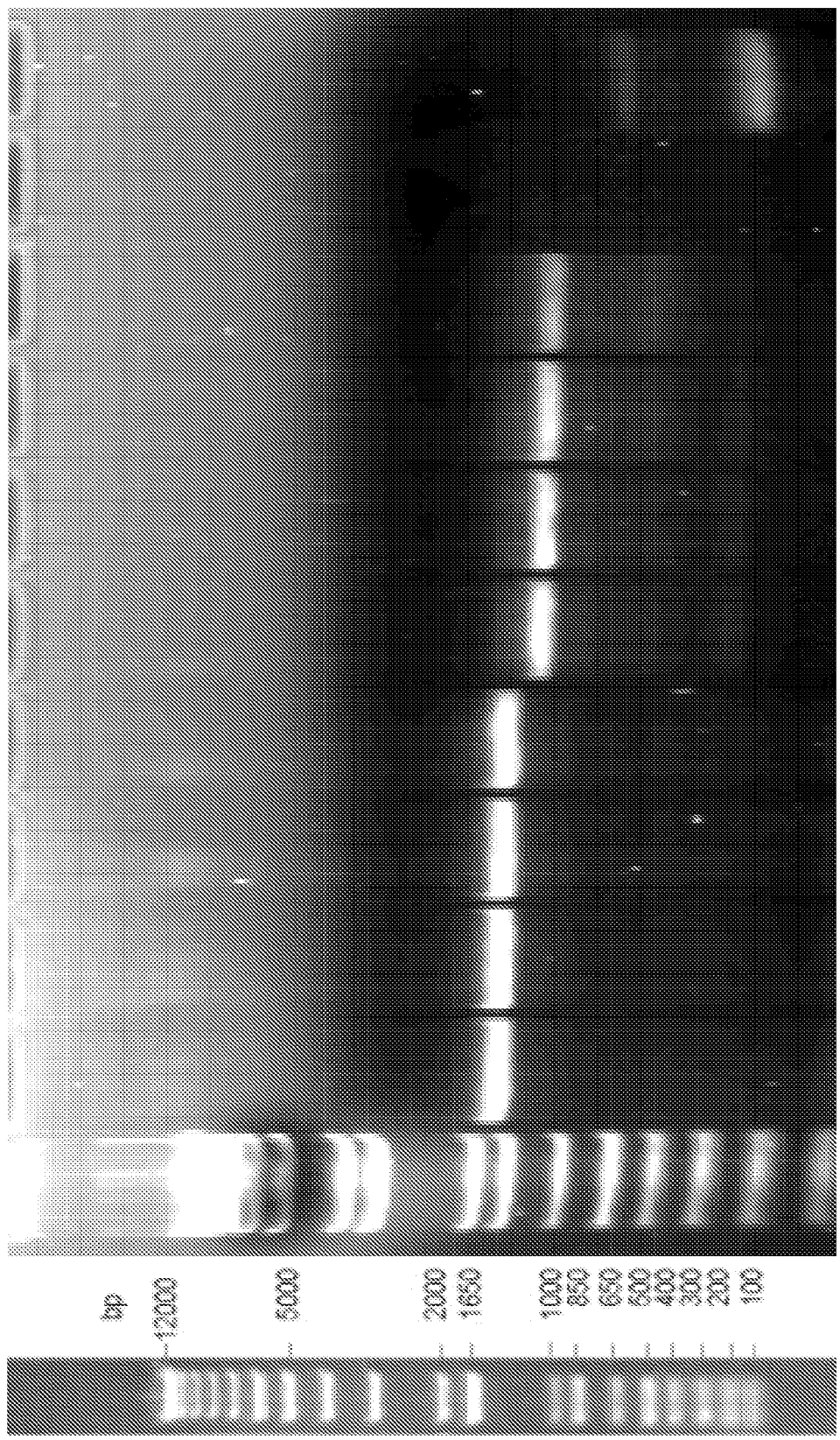
Figure 3:
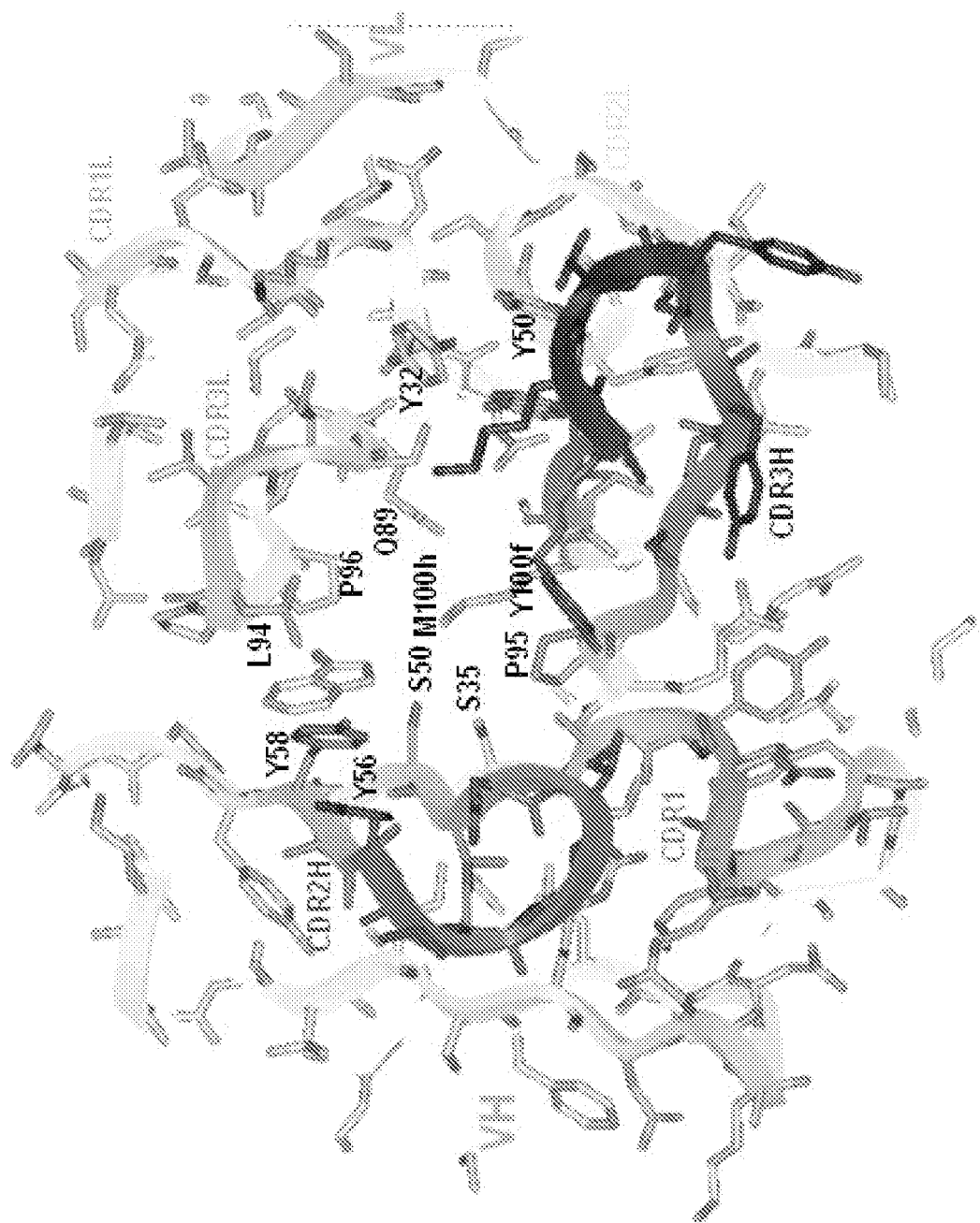
Figure 4:
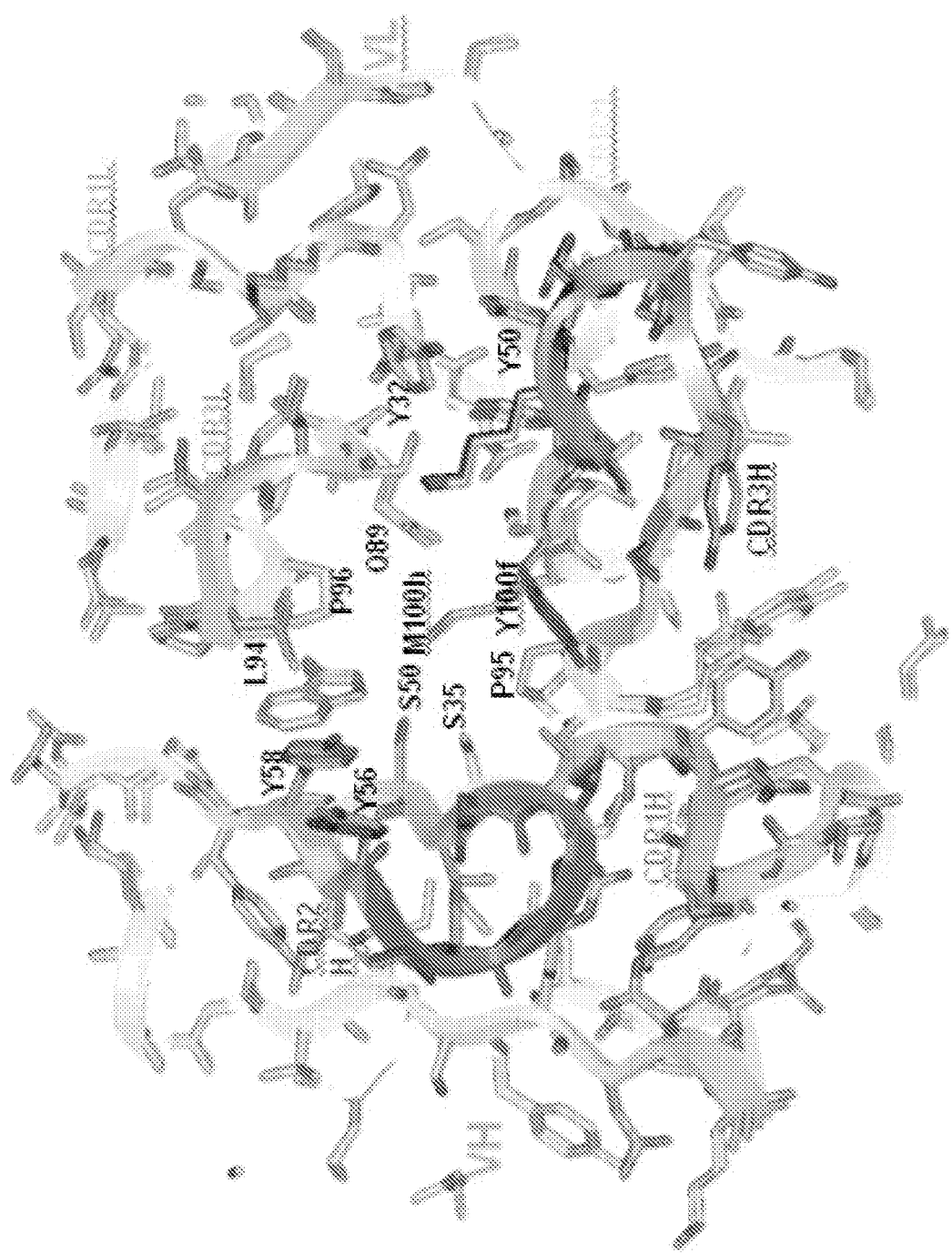
Figure 5:
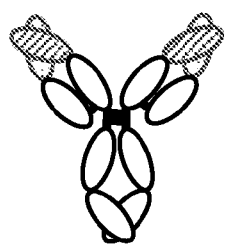
Figure 5:
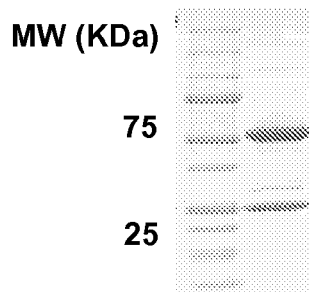
Figure 5:
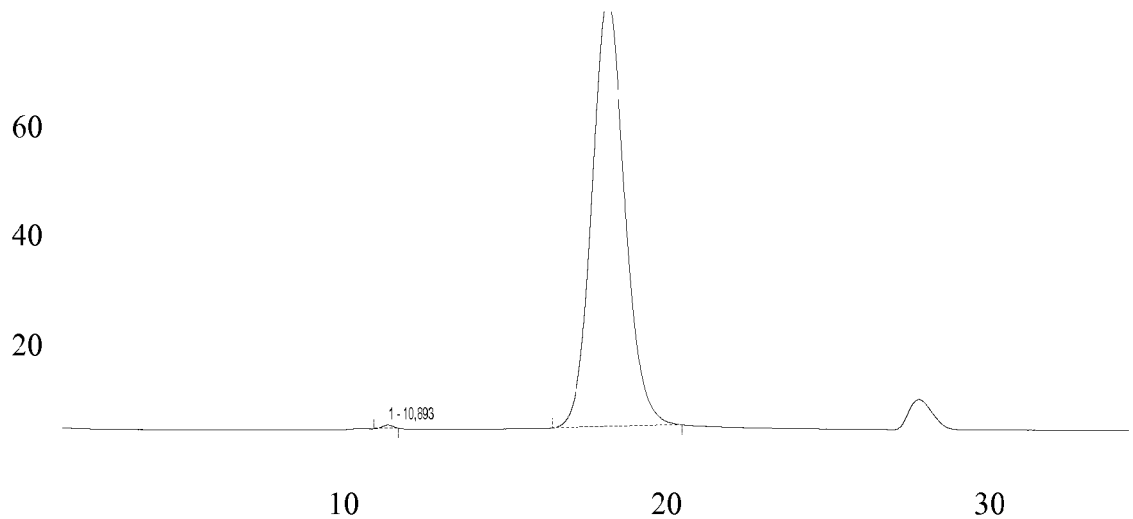
Figure 6:
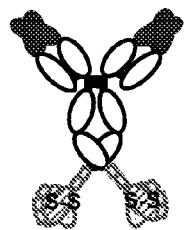
Figure 6:
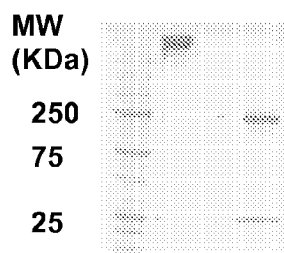
Figure 6C:
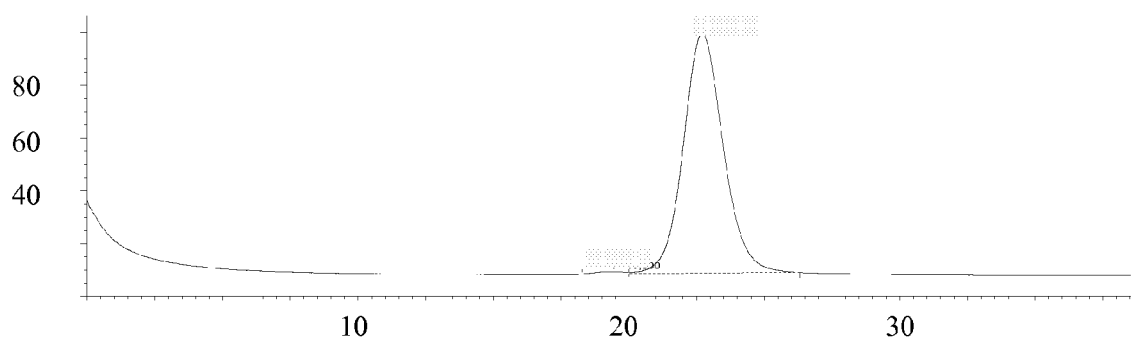
Figure 7:
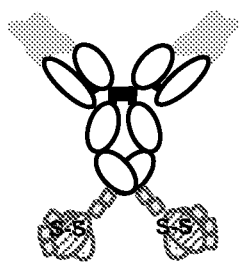
Figure 7:
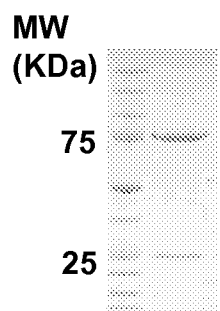
Figure 7C:
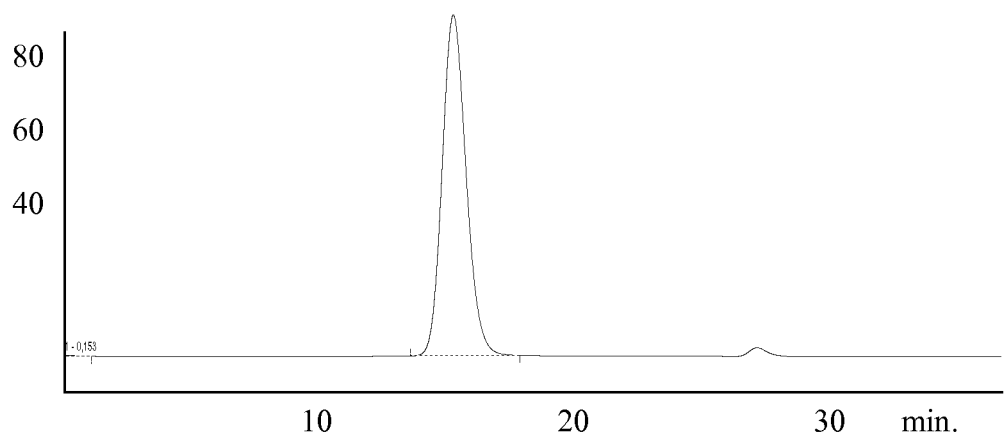
Figure 10:
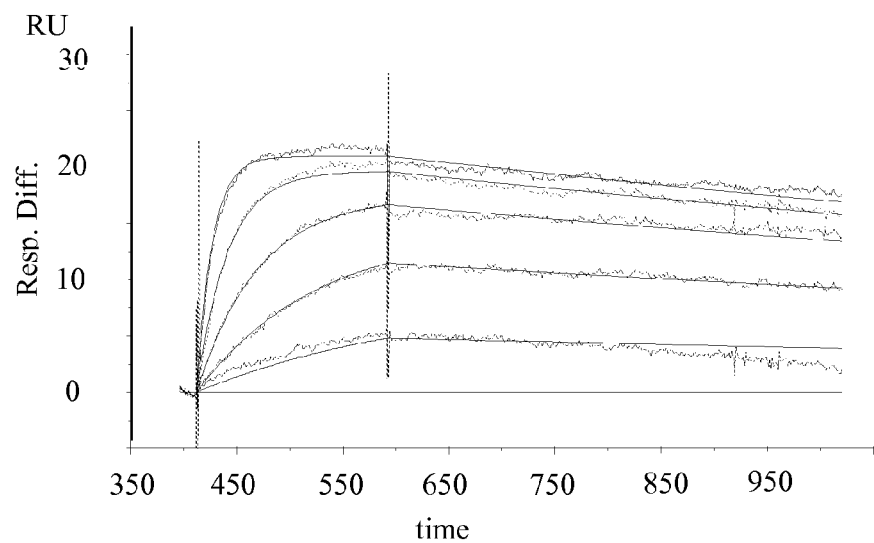
Figure 10:
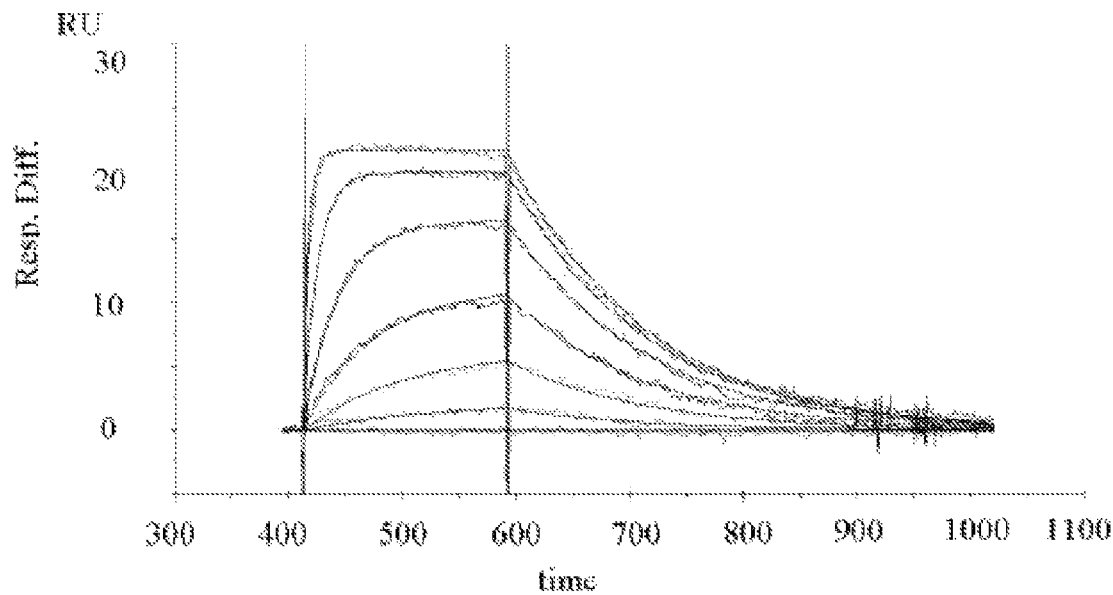
Figure 10:
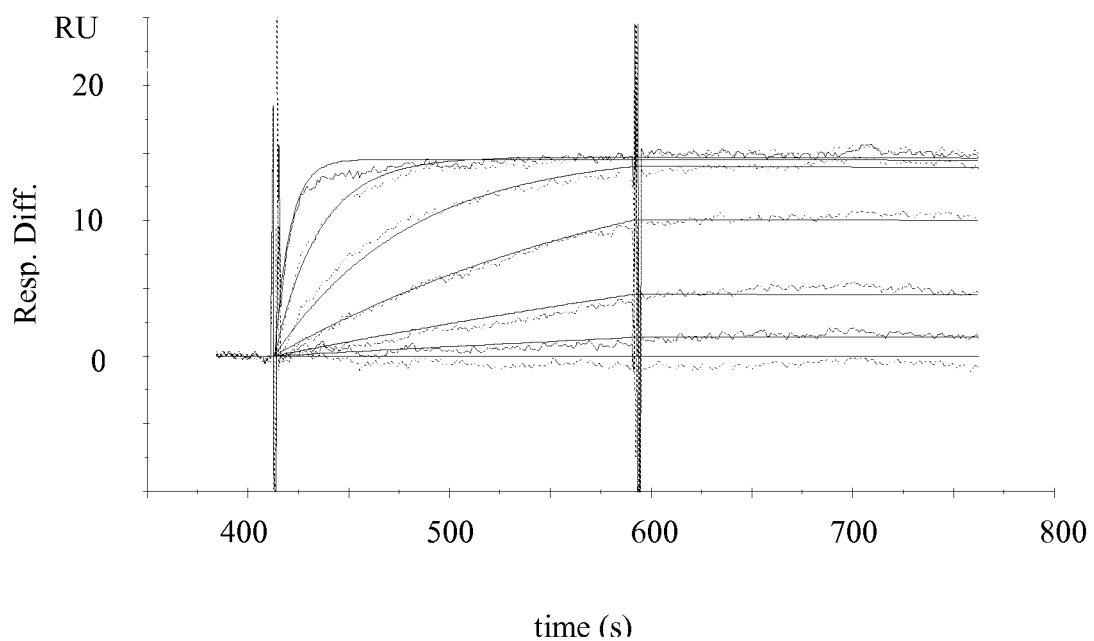
Figure 10:
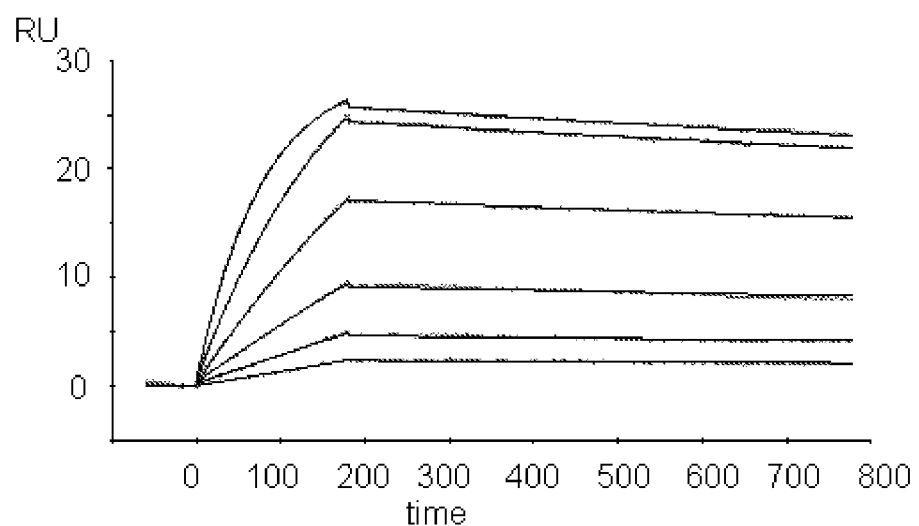
Figure 10:
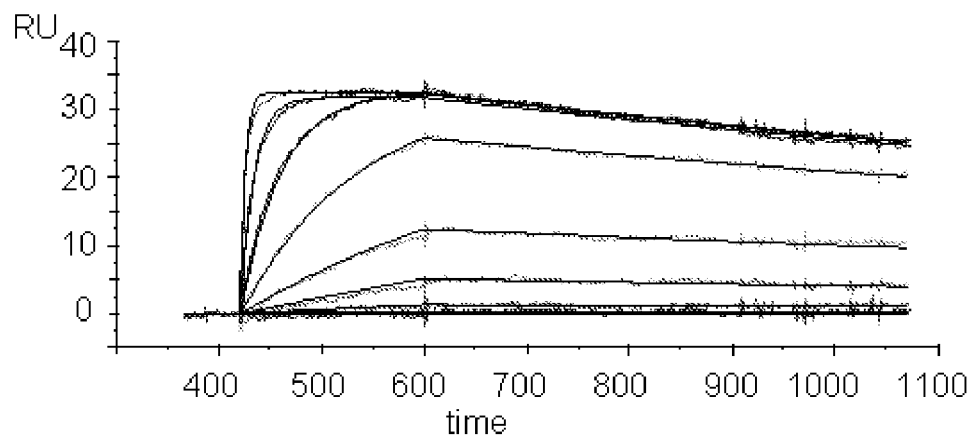
Figure 10:
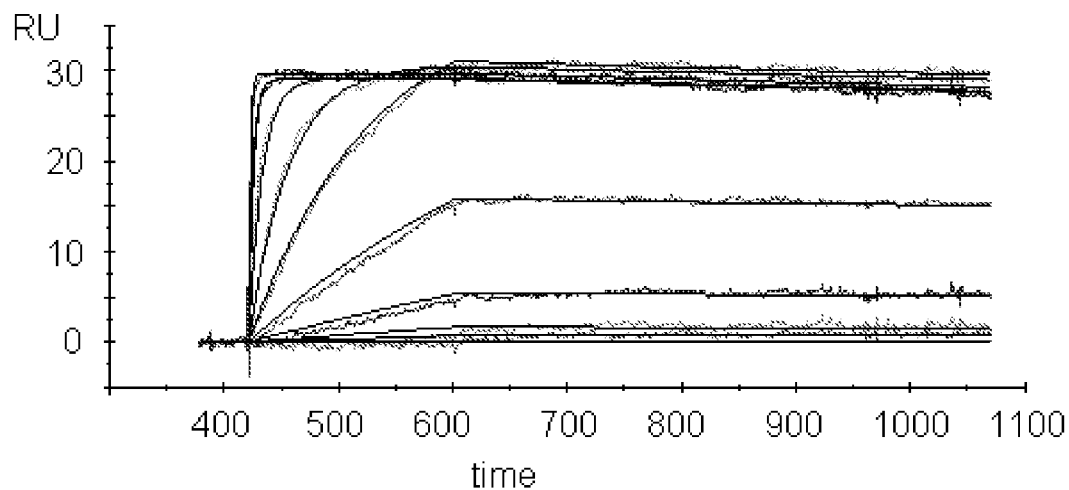
Figure 11:
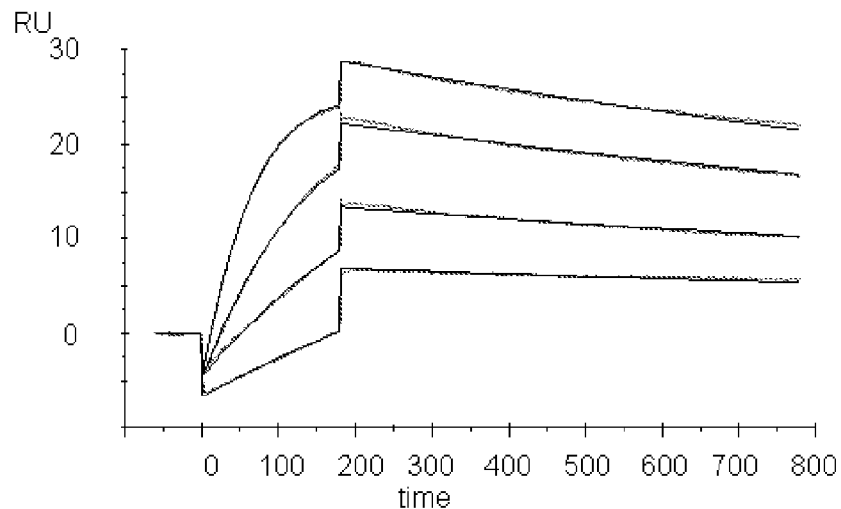
Figure 11:
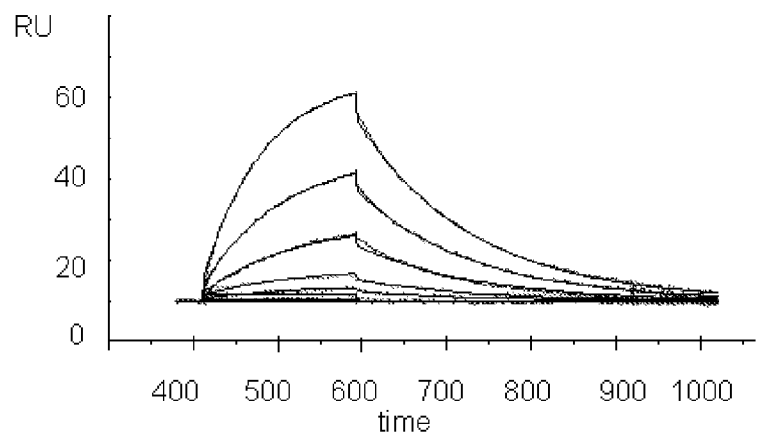
Figure 11:
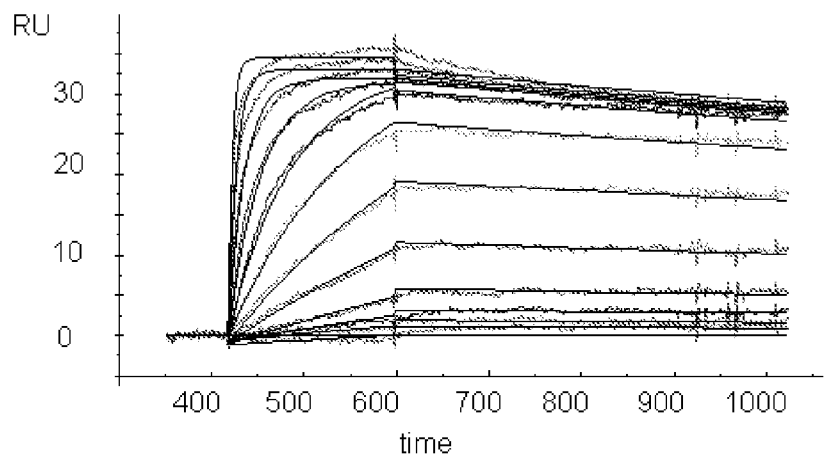
Figure 12:
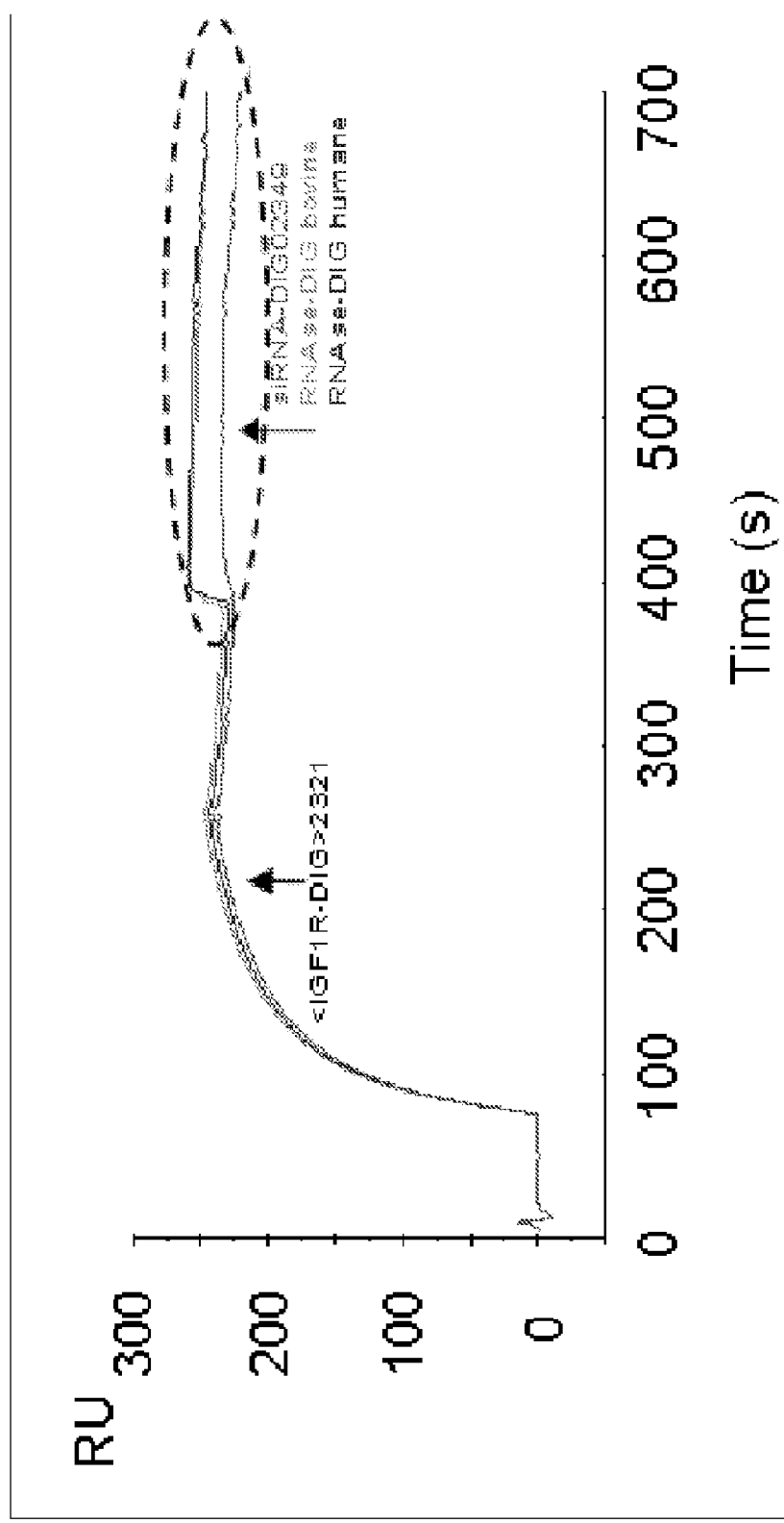
Figure 13:
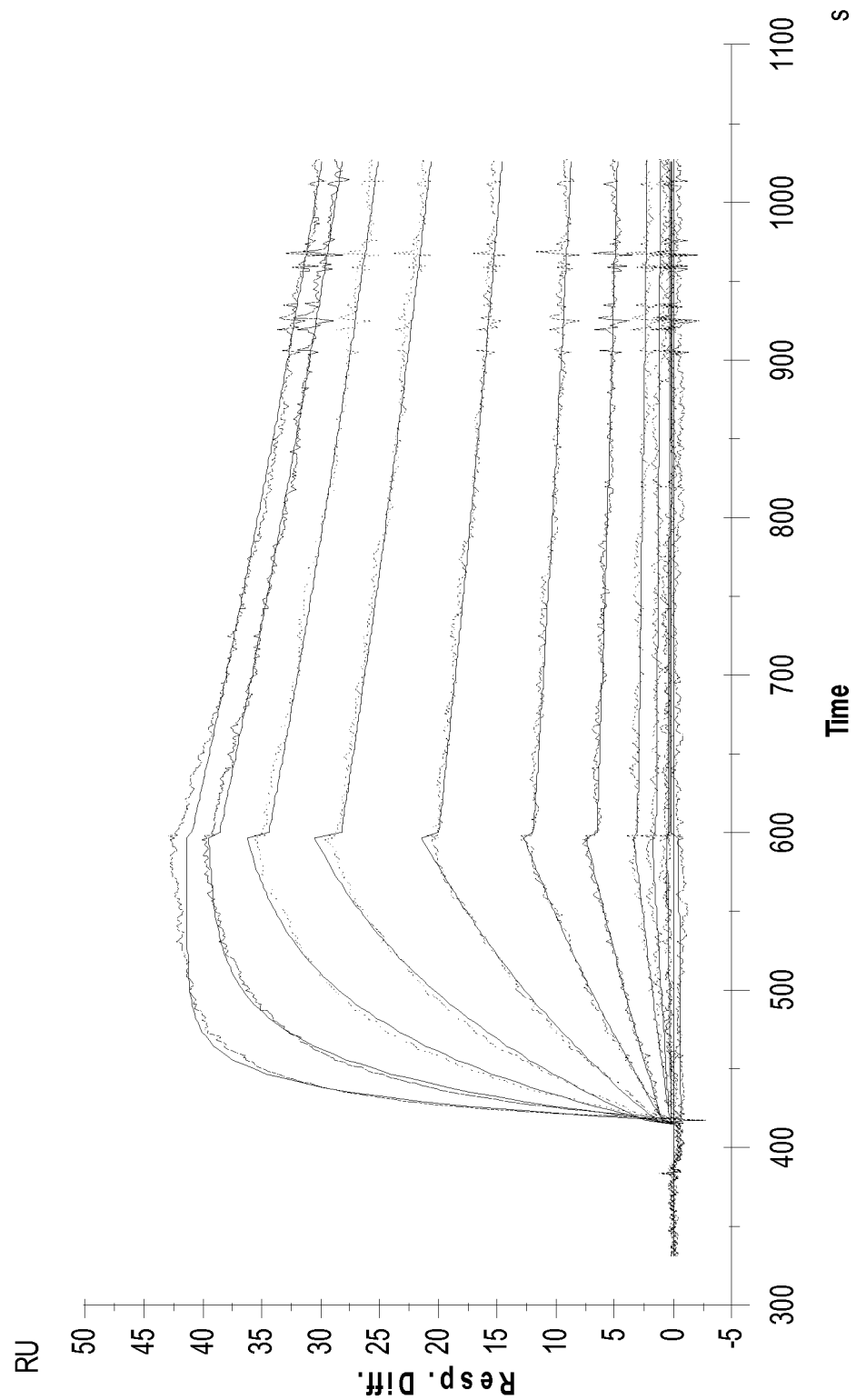
Figure 13:
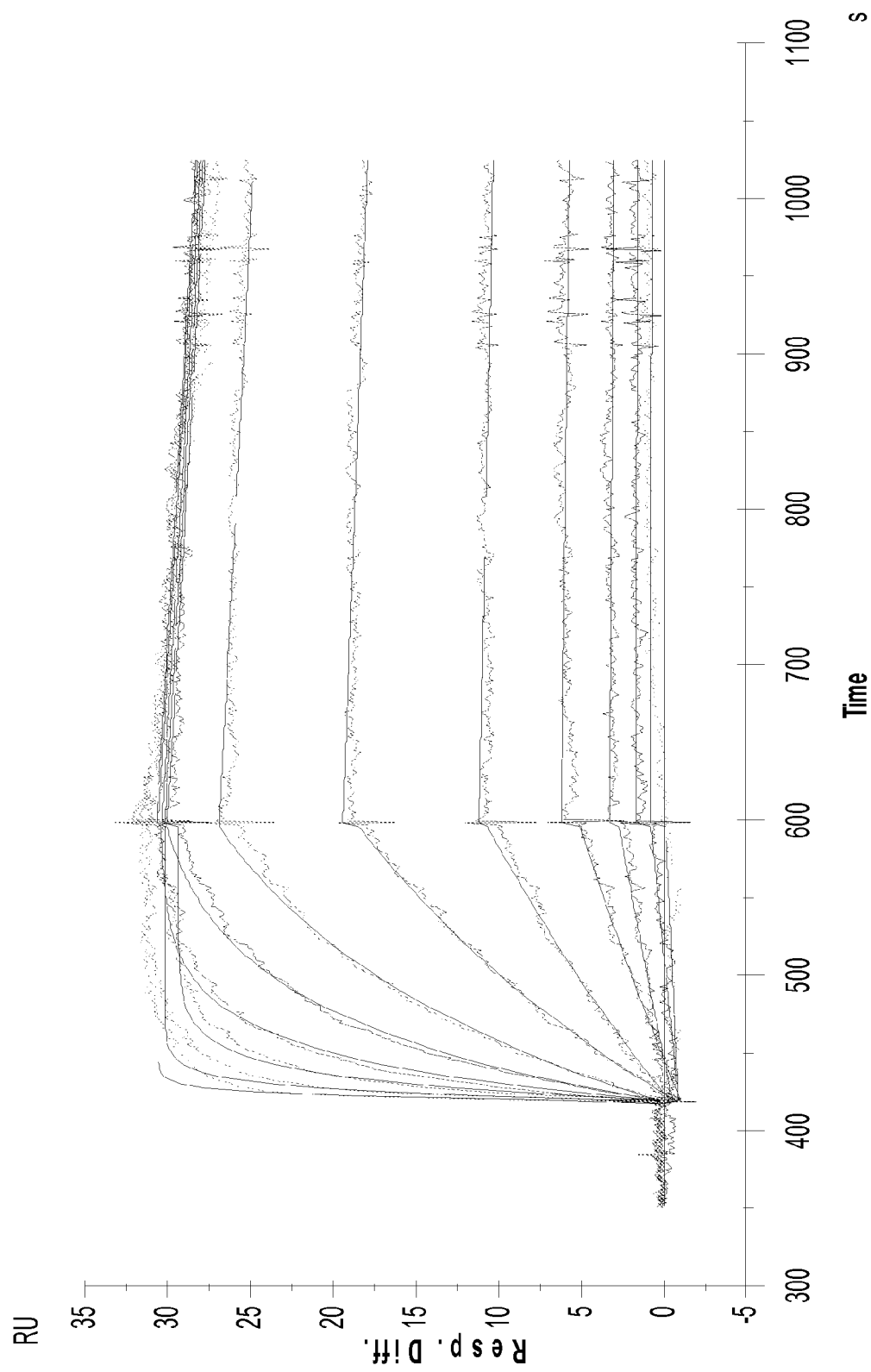
Figure 14:
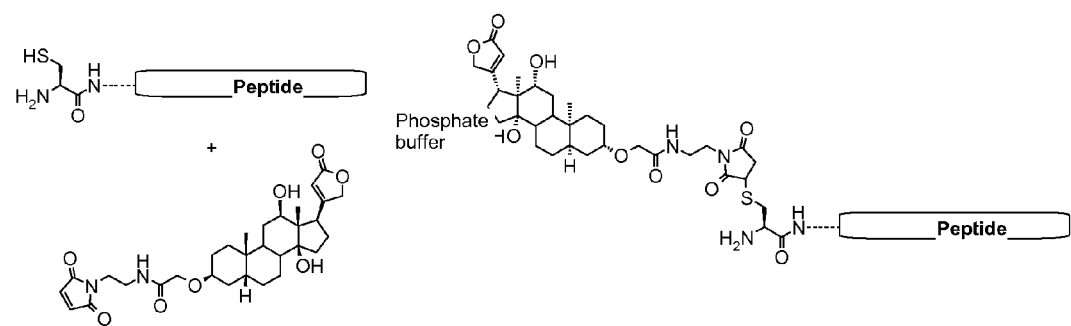
Figure 15:
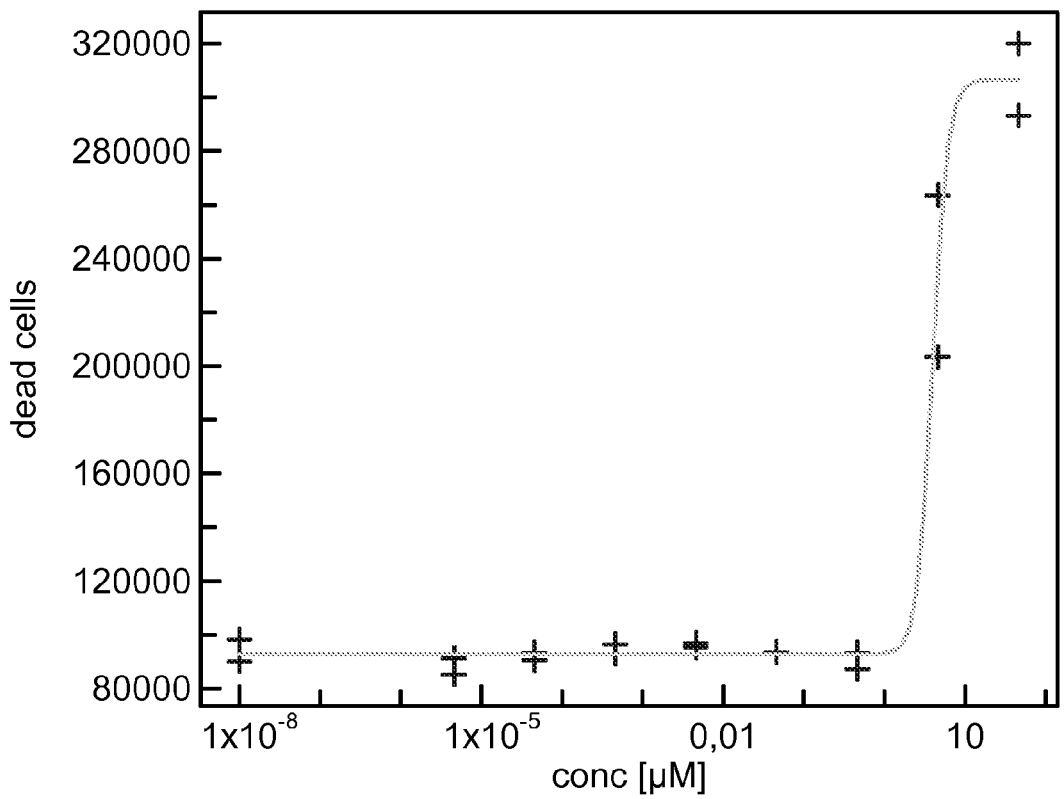
Figure 15:
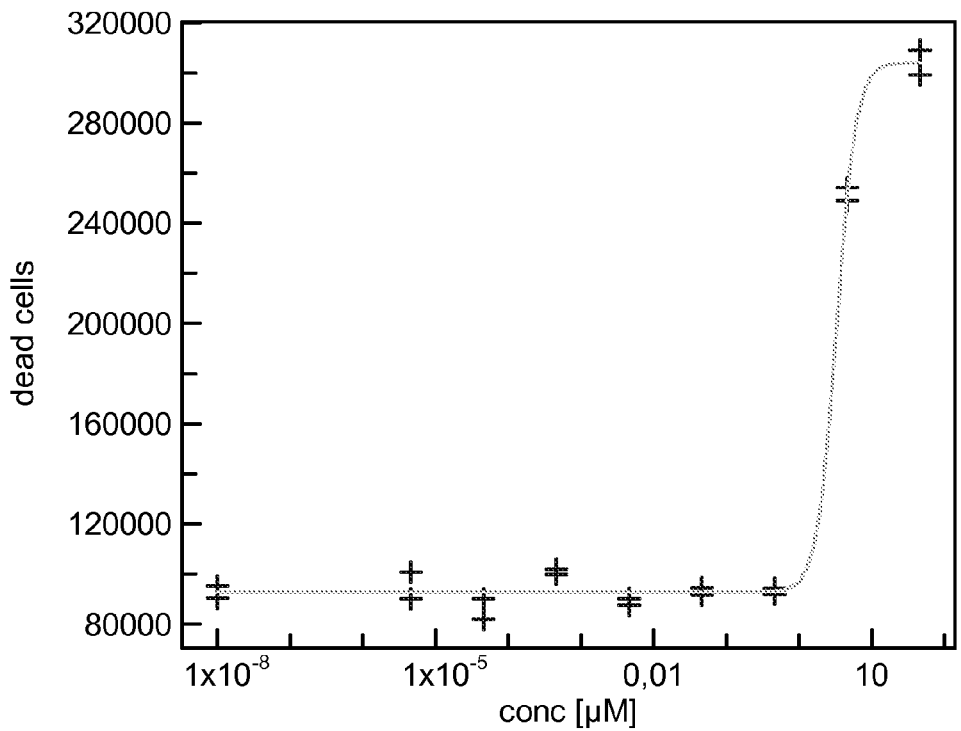
Figure 15:
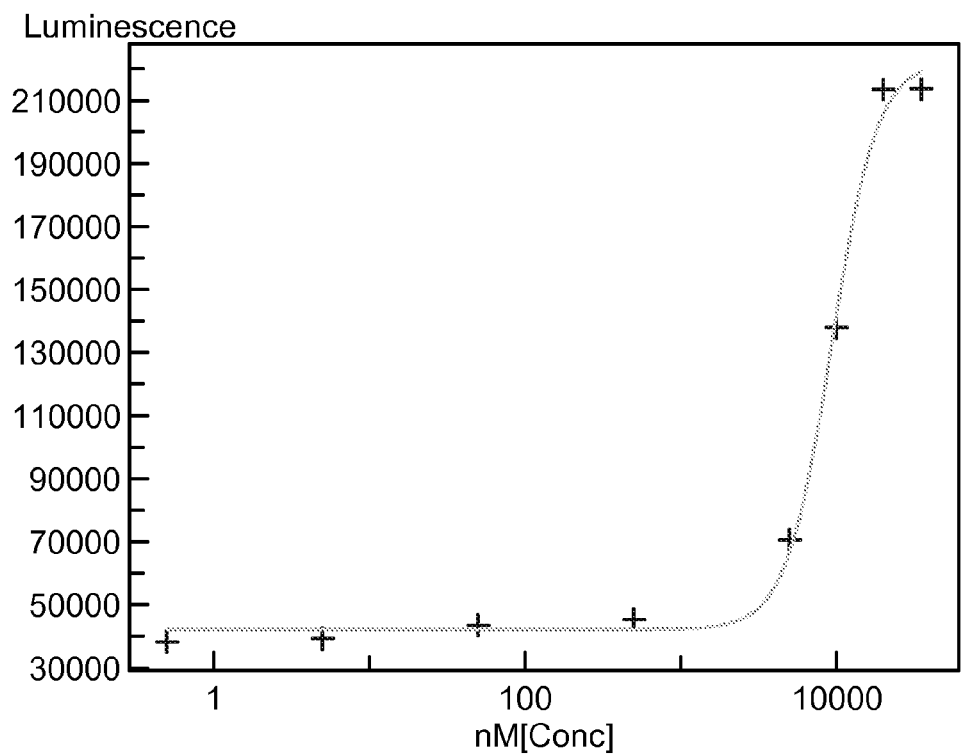
Figure 15:
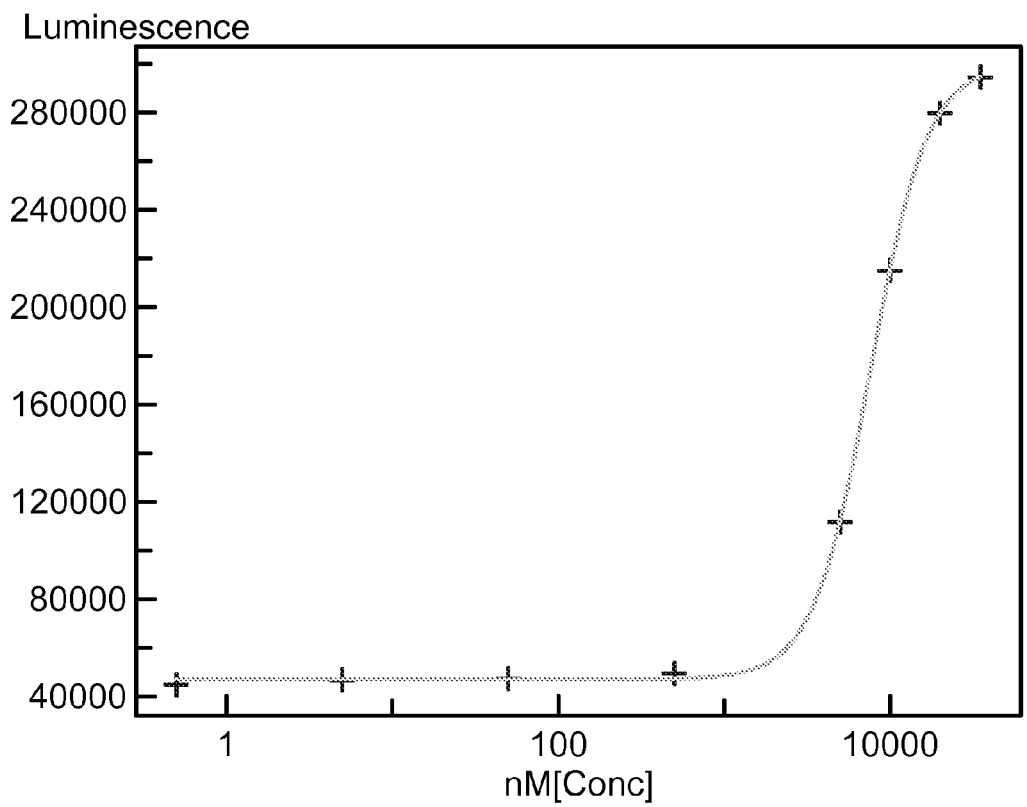
Figure 15:
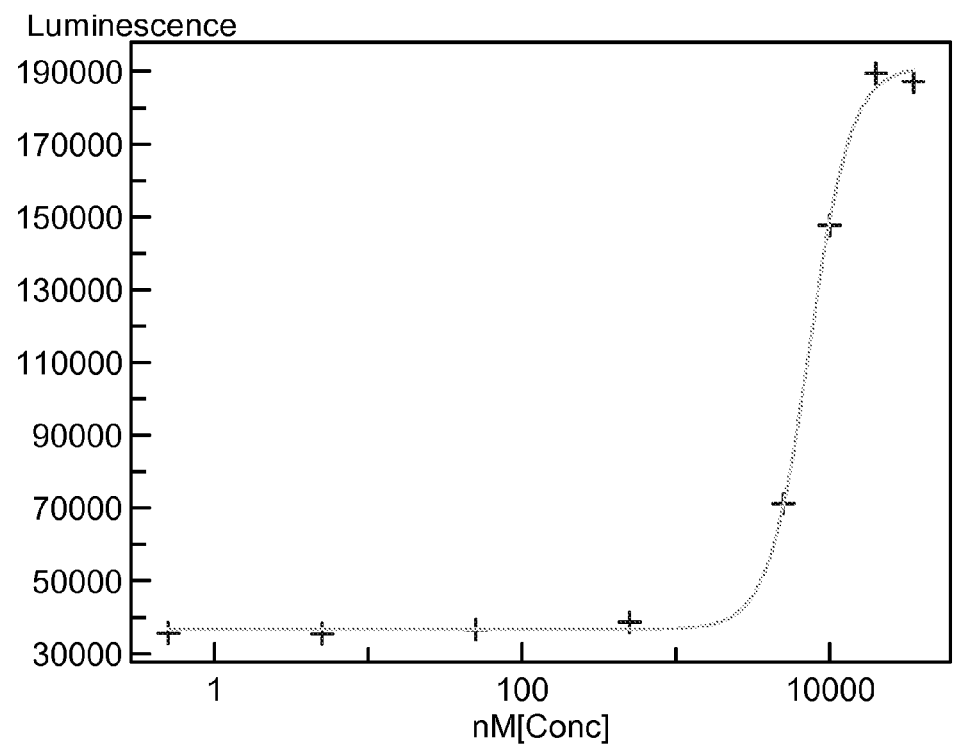
Figure 15:
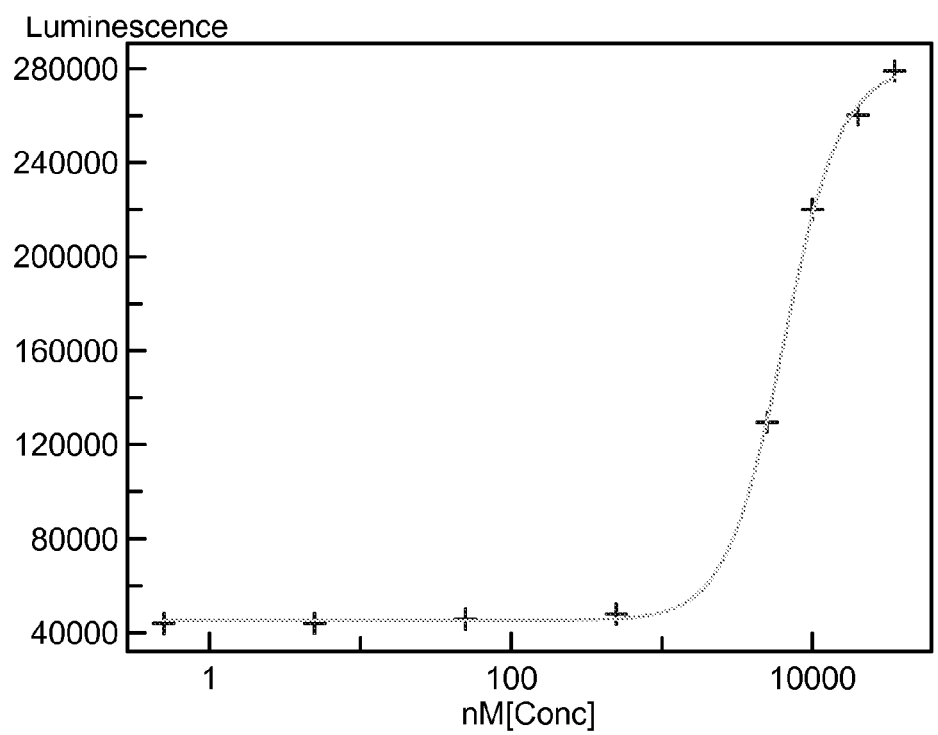
Figure 16:
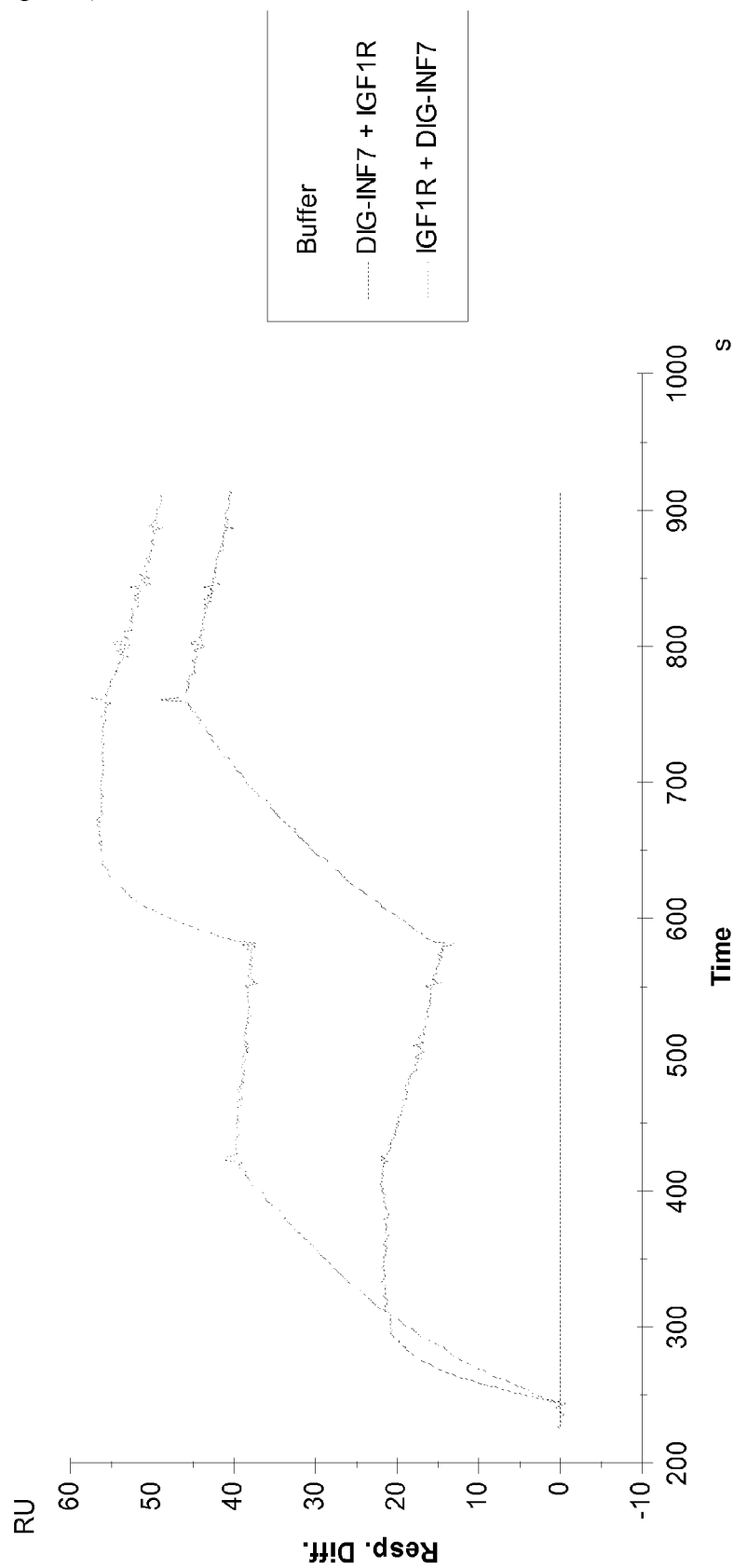
Figure 18:
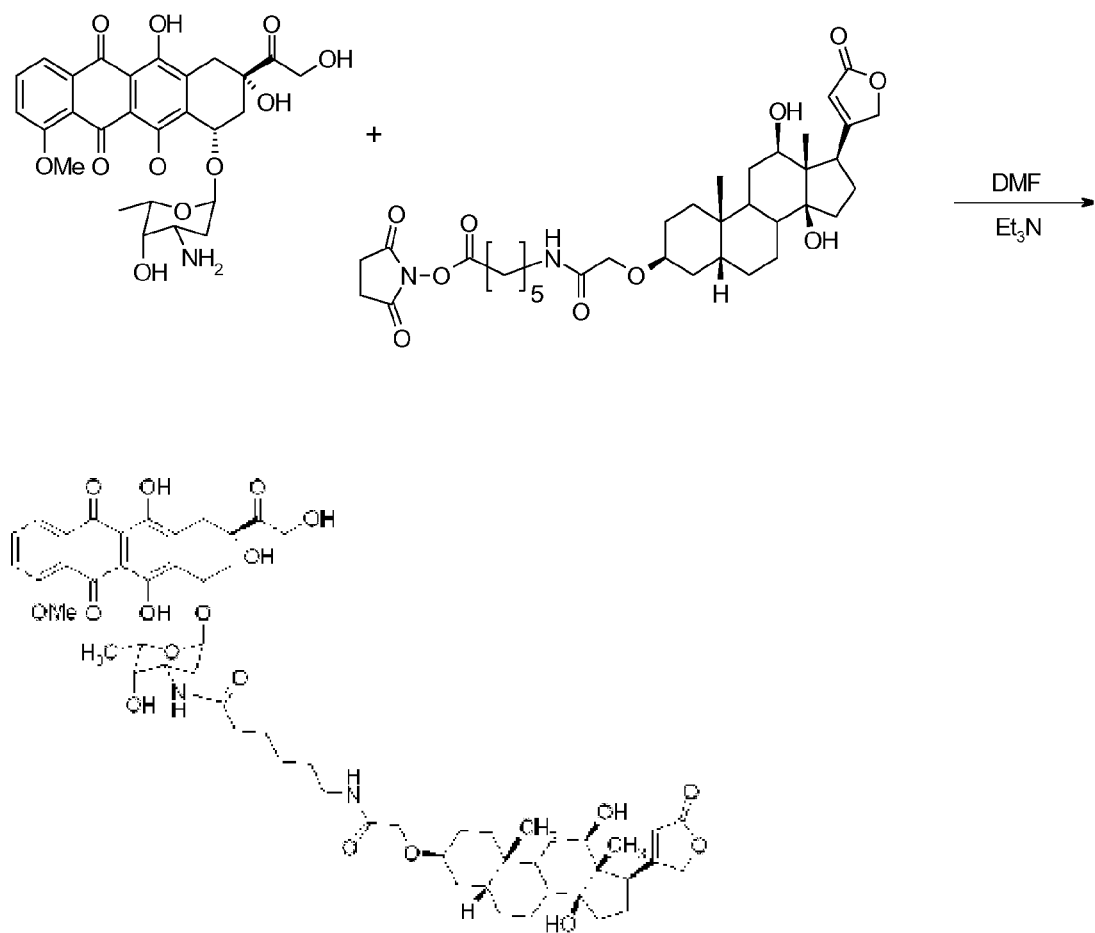
Figure 19:
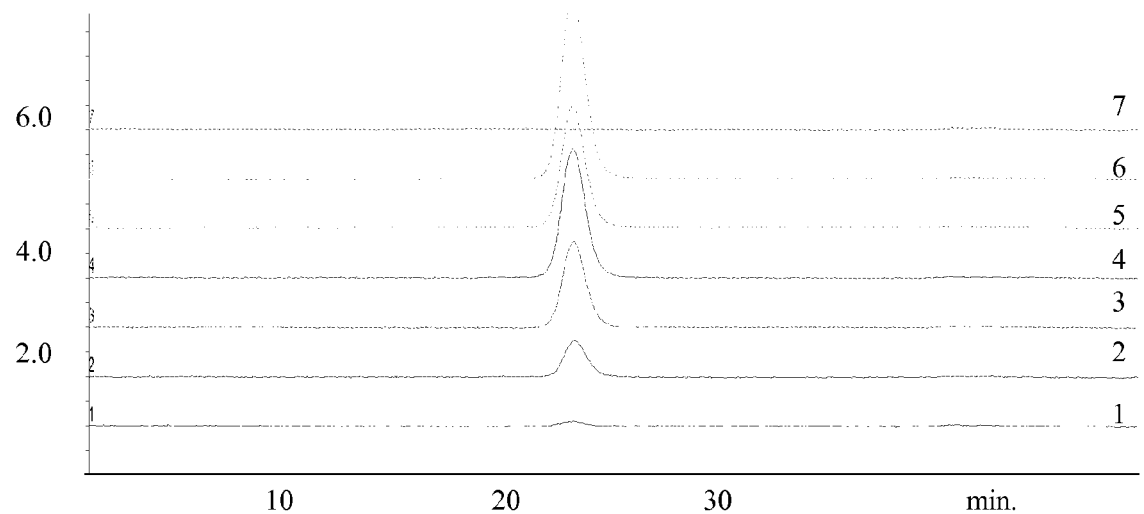
Figure 20:
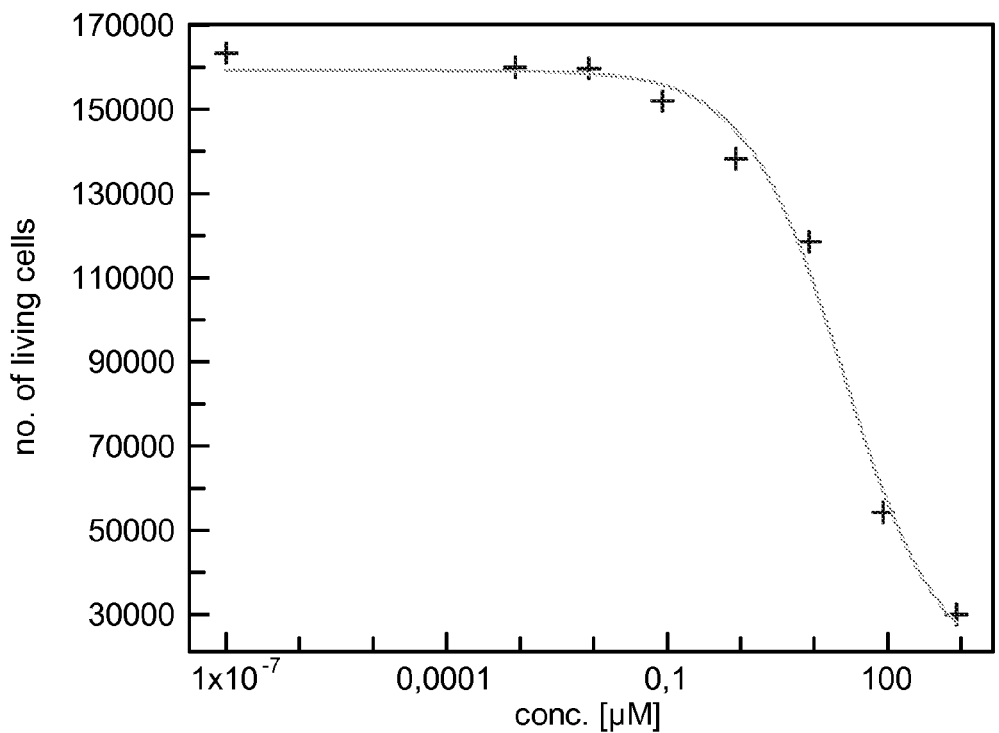
Figure 20:
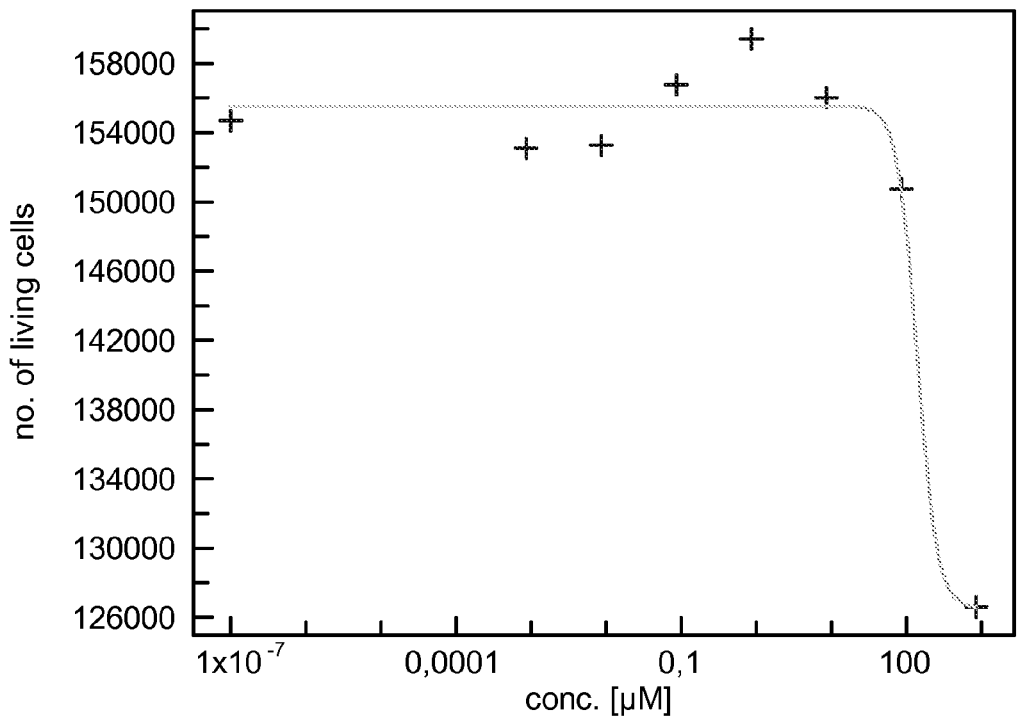
Figure 20:
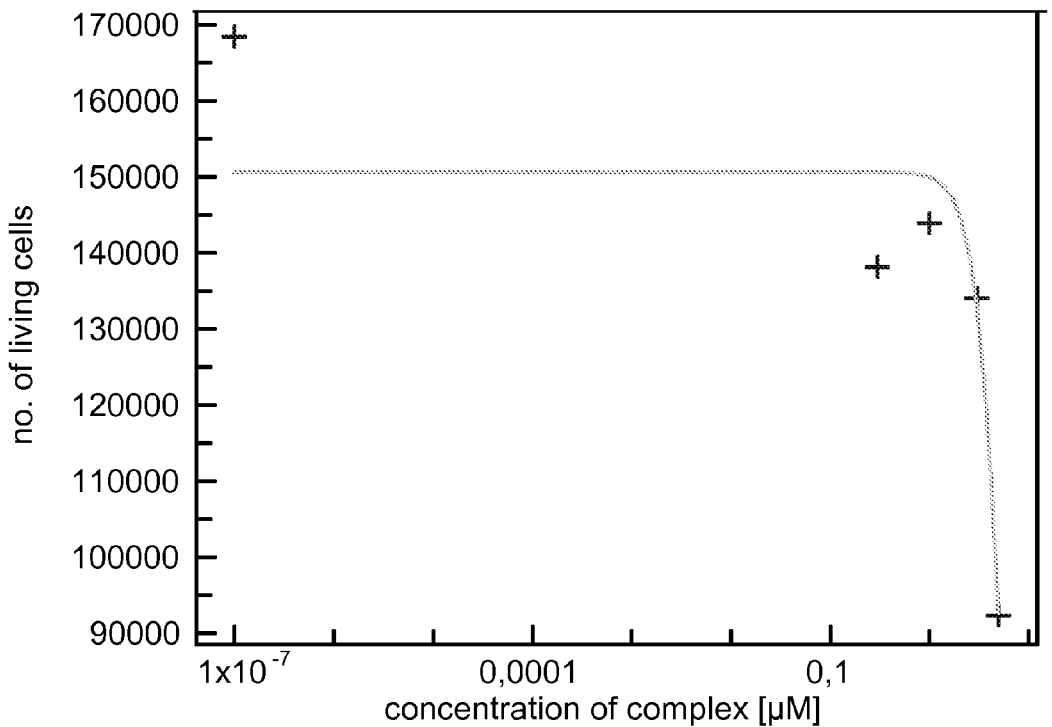
Figure 21:
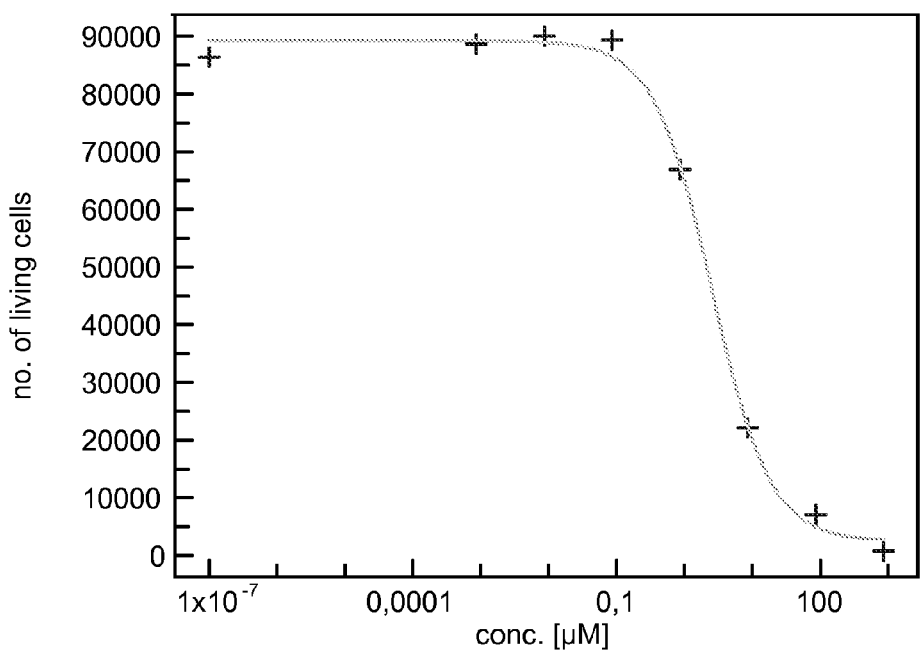
Figure 21:
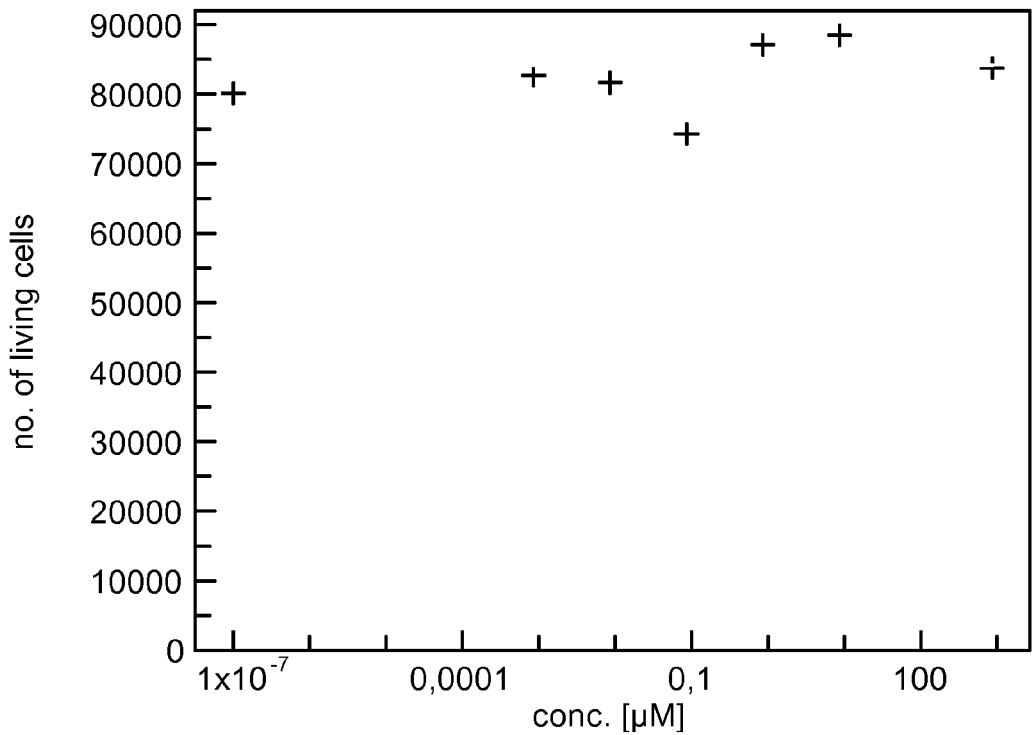
Figure 21:
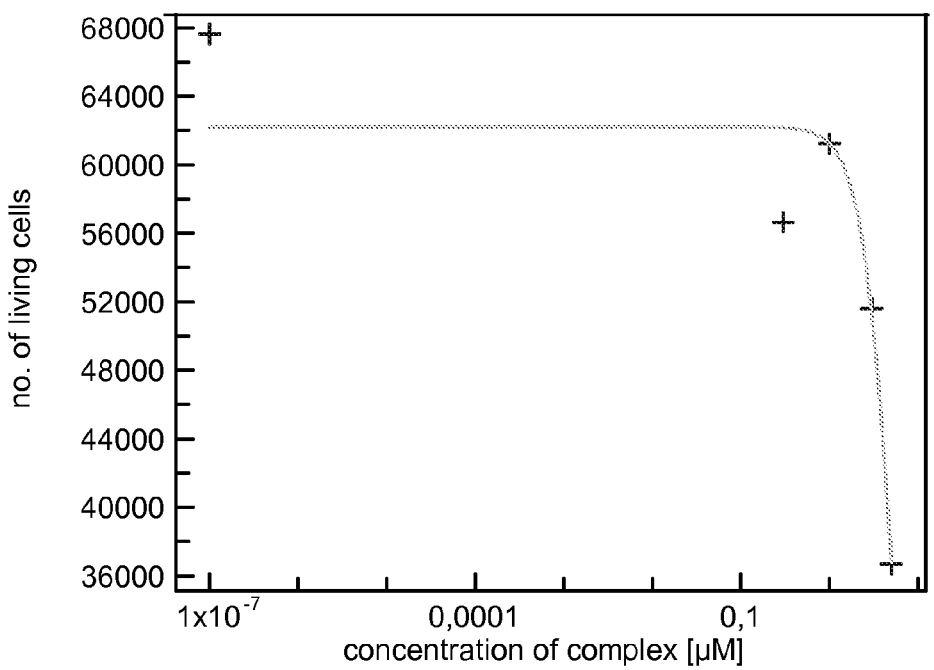
Figure 22:
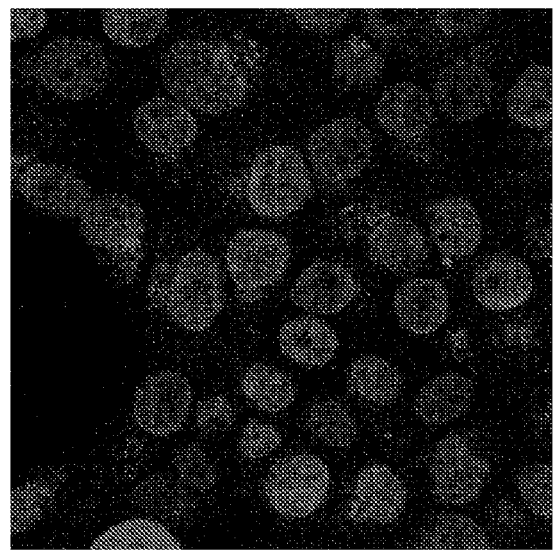
Figure 22B:
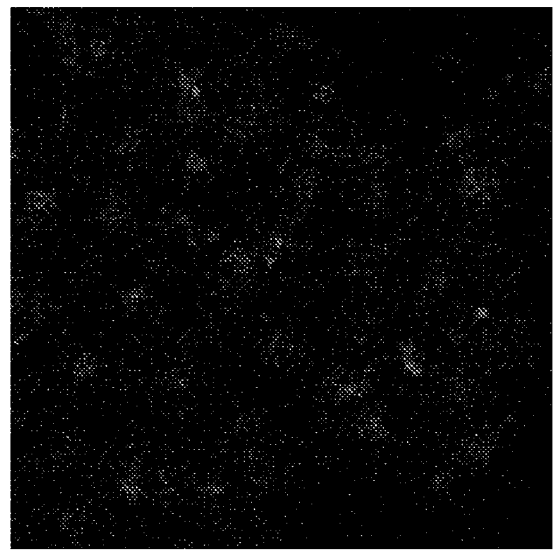
Figure 22:
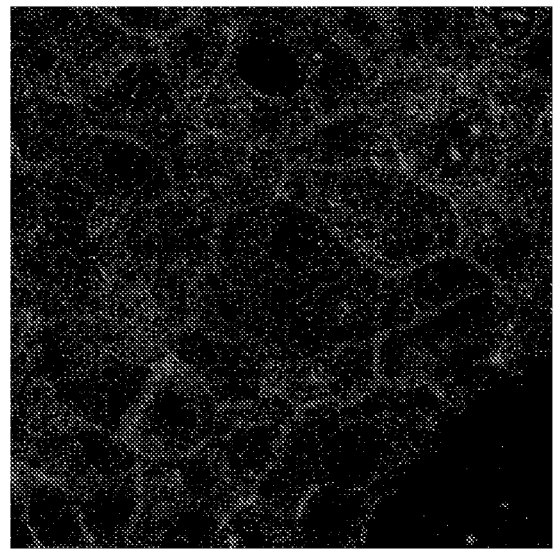
Figure 23:
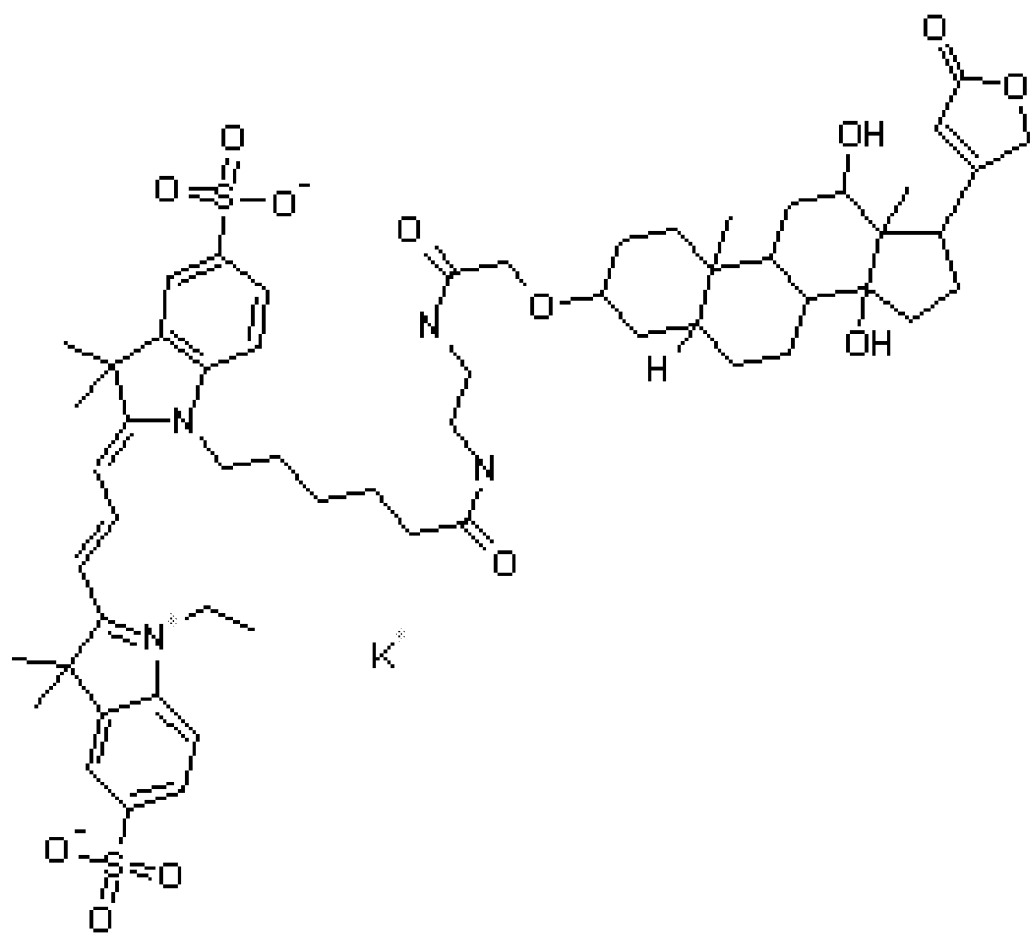
Figure 24:
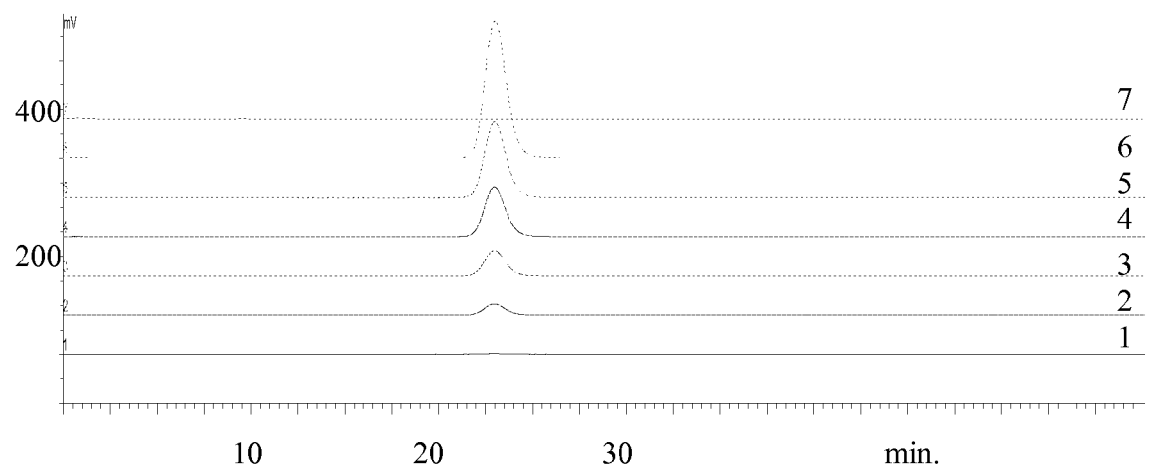
Figure 25:
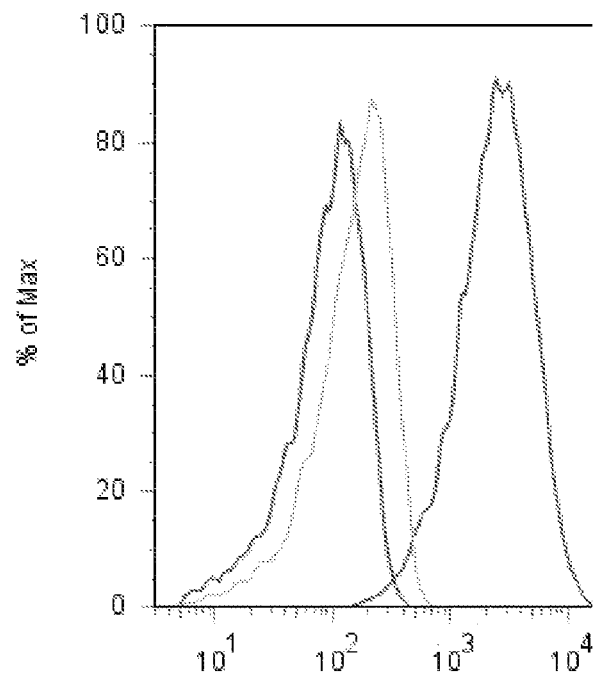
Figure 25:
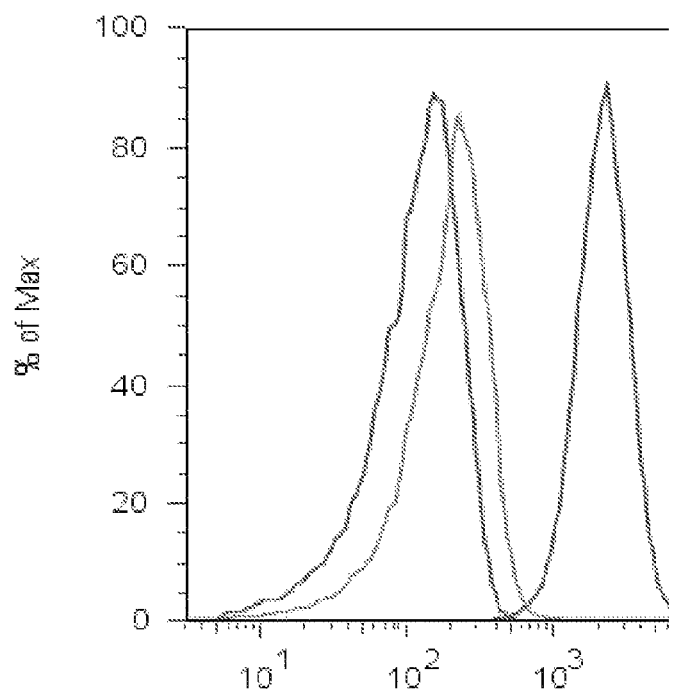
Figure 26:
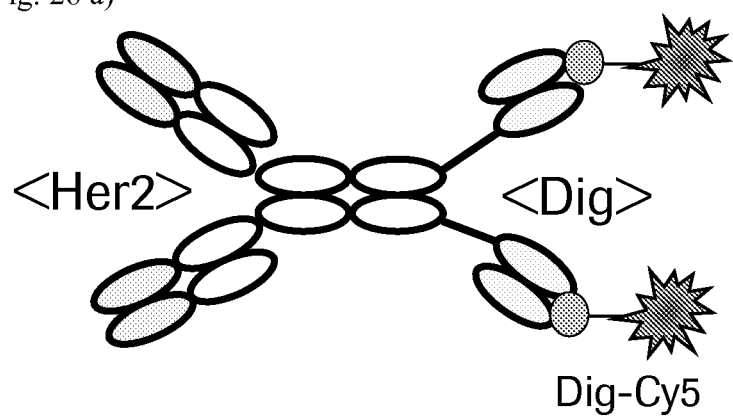
Figure 26:
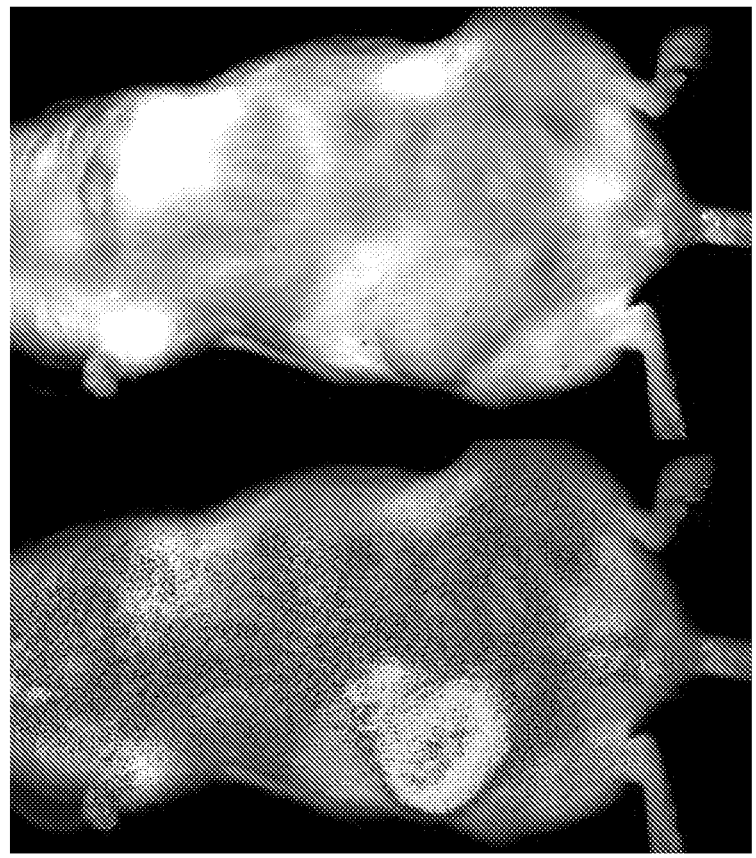
Figure 27:
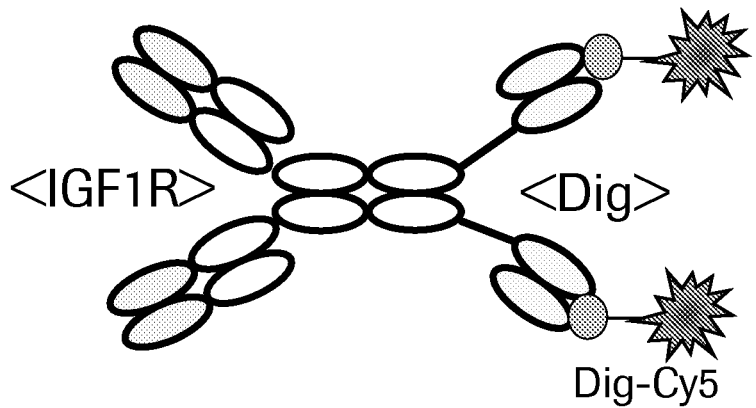
Figure 27:
Figure 27:
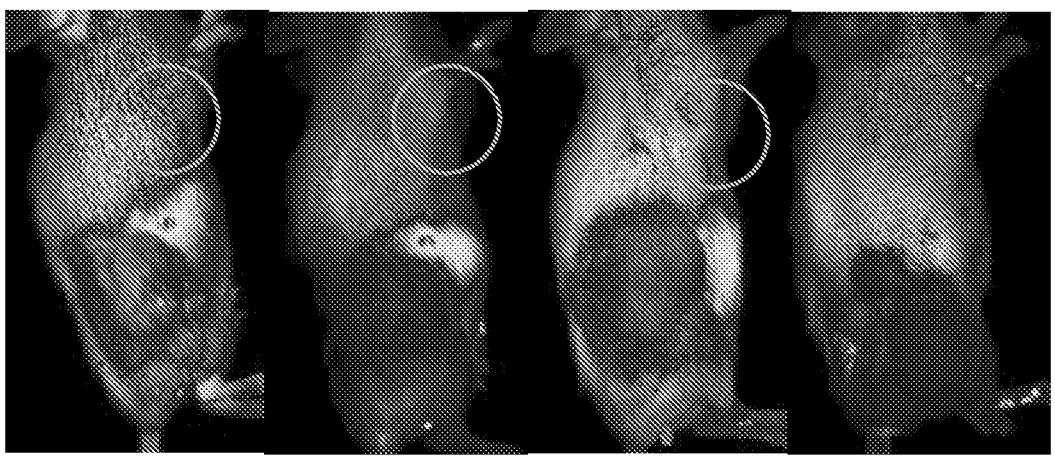

FIG. 1: mRNAs isolated from <DIG> hybridoma 19-11.
FIG. 2: PCR fragments generated from 19-11 mRNAs.
FIG. 3: Predicted structure of murine <DIG> Fv.
FIG. 4: Predicted structure of humanized <DIG> Fv.
FIG. 5: Purification of humanized <Dig> IgG. a) Schematic model of humanized <Dig> IgG, b): reducing SDS-PAGE, c): HP-size exclusion chromatography.
FIG. 6: Purification of humanized <IGF1R> <Dig> bispecific variant. a): Schematic model of humanized <IGF1R> <Dig> bispecific antibody, b): reducing SDS-PAGE, c): HP-size exclusion chromatography (1 mg/ml).
FIG. 7: Purification of humanized <Her2> <Dig> bispecific variant. a): Schematic model of humanized <Her2> <Dig> bispecific antibody, b): reducing SDS-PAGE, c): HP-size exclusion chromatography (1 mg/ml).
FIG. 8: *a*) Schematic models of humanized <Dig> IgG (b) Schematic model of humanized <IGF1R> <Dig> bispecific antibody, (c) Schematic model of humanized <Her2> <Dig> bispecific antibody d) Expression levels are given in protein yields (mg of purified protein per liter of cell-culture supernatant in such non-optimized transient expression experiments).
FIG. 9: Expression levels, aggregation and stability of humanized <Her2> <Dig> bispecific antibody before and after disulfide-stabilization. a) Schematic model of <Her2> <Dig>–2320 (not stabilized) b) schematic model of <Her2> <Dig>–2321 (disulfide stabilized) c) Expression levels, aggregation and stability of humanized <Her2> <Dig> bispecific antibody before and after disulfide-stabilization.
FIG. 10: Binding of recombinant humanized <Dig> IgG antibody and hybridoma-derived murine <Dig>19-11 antibody to digoxigenated antigens. Binding properties were analyzed by surface plasmon resonance (SPR) technology using a Biacore T100 or Biacore 3000 instrument. a) humanized <Dig> IgG antibody. Binding of DIG-BP4 to hu <DIG> IgG, KD=<76 pM b) humanized <Dig> IgG antibody. Binding of Eg5-siRNA-DIG to hu <DIG> IgG, KD=12 nM c) humanized <DIG> IgG antibody. Binding of Eg5-siRNA-(2×)DIG to hu <DIG> IgG, KD=8 pM. d) hybridoma-derived murine <Dig>19-11 antibody. Binding of DIG-BP4, KD=33 nM e) hybridoma-derived murine <Dig>19-11 antibody. Binding of Eg5-siRNA-DIG, KD=269 pM f) hybridoma-derived murine <Dig>19-11 antibody. Binding of Eg5-siRNA-(2×)DIG, KD=17 pM.
FIG. 11: Binding of recombinant humanized <Her2> <Dig> bispecific antibody to digoxigenated antigens. Binding properties were analyzed by surface plasmon resonance (SPR) technology using a Biacore T100 or Biacore 3000 instrument. a) Binding of DIG-BP4 KD=68 pM b) Binding of Eg5-siRNA-DIG, KD=35 nM c) Binding of Eg5-siRNA-(2×) DIG, KD=162 pM.
FIG. 12: Binding of recombinant humanized <Dig> disulfide-stabilized scFV fusion protein to DIG-RNAses (human and bovine). Binding properties were analyzed by surface plasmon resonance (SPR) technology using a Biacore T100 or Biacore 3000 instrument.
FIG. 13: Binding of recombinant murine 44-100 stabilized <Her2> <Dig> bispecific antibody to digoxigenated antigens. Binding properties were analyzed by surface plasmon resonance (SPR) technology using a Biacore T100 or Biacore 3000 instrument. a) Binding of Eg5-siRNA-DIG, KD=467 pM b) Binding of Eg5-siRNA-(2×)DIG, KD=40 pM.
FIG. 14: Structure of peptide-digoxygenin complexes.
FIG. 15: Biological activity of the Melittin, Fallv1 and Fallv2 peptides and their DIG-modified variants. a) H322M treated with Dig-Mellitin, b) H322M treated with Mellitin c) H322M treated with FALLv1 d) H322M treated with Dig-FALLv1 e) H322M treated with FALLv2 f) H322M treated with Dig-FALLv2.
FIG. 16: IgG complexes with digoxygenated peptides retain binding specificity and affinity towards the cell surface antigens, independent of the order of binding. a) additive binding of DIG-INF7 and IGF1R to <IGF1R> <Dig>, b) additive binding of DIG-FALL and IGF1R to <IGF1R> <Dig>.
FIG. 17: Specific delivery of peptides to antigen expressing cells by application of complexes of bispecific antibody derivatives with digoxigenated peptides. a) schematic structure b) FALLv1 c) Fam5b.
FIG. 18: Generation and composition of digoxigenated doxorubicin.
FIG. 19: Size exclusion chromatography of digoxigenated doxorubicin-<Her2>-<Dig> bispecific antibody complex indicates charging with digoxygenated doxorubicin and homogeneity of charged molecules. a) chromatogramme: 1: Her2 Dig Doxo (1:0) 2: Her2 Dig Doxo (1:0.5), 3: Her2 Dig Doxo (1:1), 4: Her2 Dig Doxo (1:2), 5: Her2 Dig Doxo (1:3), 6: Her2 Dig Doxo (1:5). 7: Her2 Dig Doxo (0:1), b) analysis.
FIG. 20: Specific targeting of digoxygenated doxorubicin—<IGF1R>-<DIG> bispecific antibody complex to IGF1R positive cells. a) H322M treated with doxorubicin, b) H322M treated with DIG-doxorubicin c) H322M treated with <IGF1R> <Dig>2321 loaded with DIG-doxorubicin.
FIG. 21: Specific targeting of digoxygenated doxorubicin—<Her2>-<DIG> bispecific antibody complex to Her2 positive cells. a) KPL4 treated with doxorubicin, b) KPL4 treated with DIG-doxorubicin c) KPL4 treated with <Her2> <Dig>2321 loaded with DIG-doxorubicin.
FIG. 22: Specific targeting and endosomal accumulation of digoxygenated doxorubicin. 120' incubation @ 5.0 µg/ml. a) Doxorubicin alone, b) Dig-Doxorubicin. c)<IGF-1R>-Dig> Dig-Doxorubicin
FIG. 23: Structure of digoxygenated Cy5.
FIG. 24: Size exclusion chromatography of digoxygenated Cy5<Her2>-<Dig> bispecific antibody complex indicates charging with digoxygenated Cy5 and homogeneity of charged molecules. a) chromatogramme: 1: Her2 Dig Cy5 (1:0) 2: Her2 Dig Cy5 (1:0.5), 3: Her2 Dig Cy5 (1:1), 4: Her2 Dig Cy5 (1:2), 5: Her2 Dig Cy5 (1:3), 6: Her2 Dig Cy5 (1:5). 7: Her2 Dig Cy5 (0:1), b) analysis.
FIG. 25: FACS analysis of Raji or Ramos cells incubated with <CD22>-<Dig> antibody coupled to digoxygenated Cy5. a) CD22 positive Raji cells. The DIG-Cy % combination binds very good to the bispecific <CD22>-WT<Dig> primary antibody (single peak). Multiple peaks: Raji Cy5DIG, Raji cells only. b) CD22 positive Ramos cells. The secondary entity alone (Cy5DIG) gives only a small background and the combination with CD22 WT-DIG has a stronger shift (single peak) indicating a specific binding to the cells.
FIG. 26: Tumor imaging with bispecific <Her2>-<Dig> antibody coupled to digoxygenated Cy5: a) Schematic structure of bispecific <Her2>-<Dig> antibody, b)<Her2Dig>$^{dig}$Cy5, NIRF 24 hrs after iv injection.
FIG. 27: Tumor imaging with bispecific <IGF1R>-<Dig> antibody coupled to digoxygenated Cy5. a) Schematic structure of bispecific <IGF1R>-<Dig> antibody b)<IGF1R-DIG-hu2>+DIG-Cy5. c) DIG-Cy5
FIG. 28: Tumor imaging with bispecific <Her2>-<Dig> antibody coupled to digoxygenated Cy5. a) Schematic structure b) digoxygenated Cy5 injection 48 h after injection of <Her2>-<Dig> antibody 2321. y-axis: average NIRF signal intensity/Exp. time (1/ms).

Figure 29:
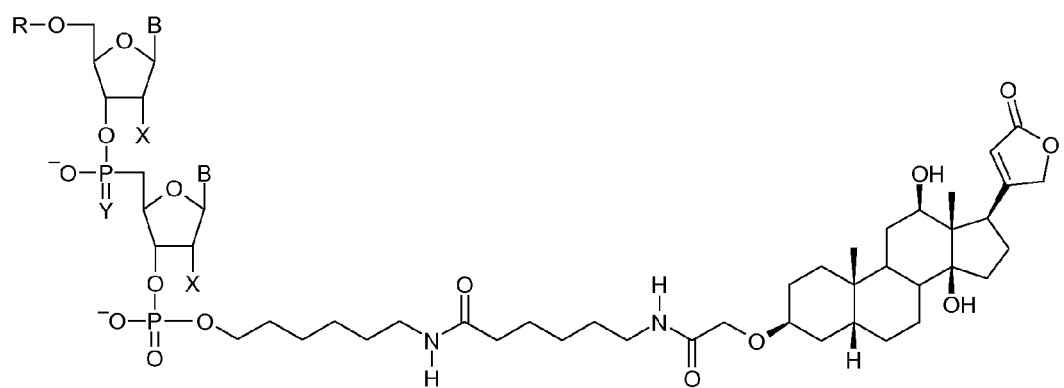

FIG. 29: Schematic structure of a digoxigenated nucleic acid. B: adenine, guanine, cytosine, Uracil, deoxythymidine; X: OH, H; Y: O, S; R: RNA sequence.

Figure 30:
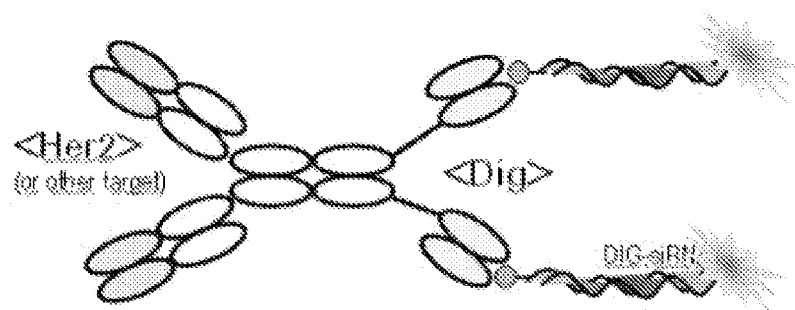
Figure 30:
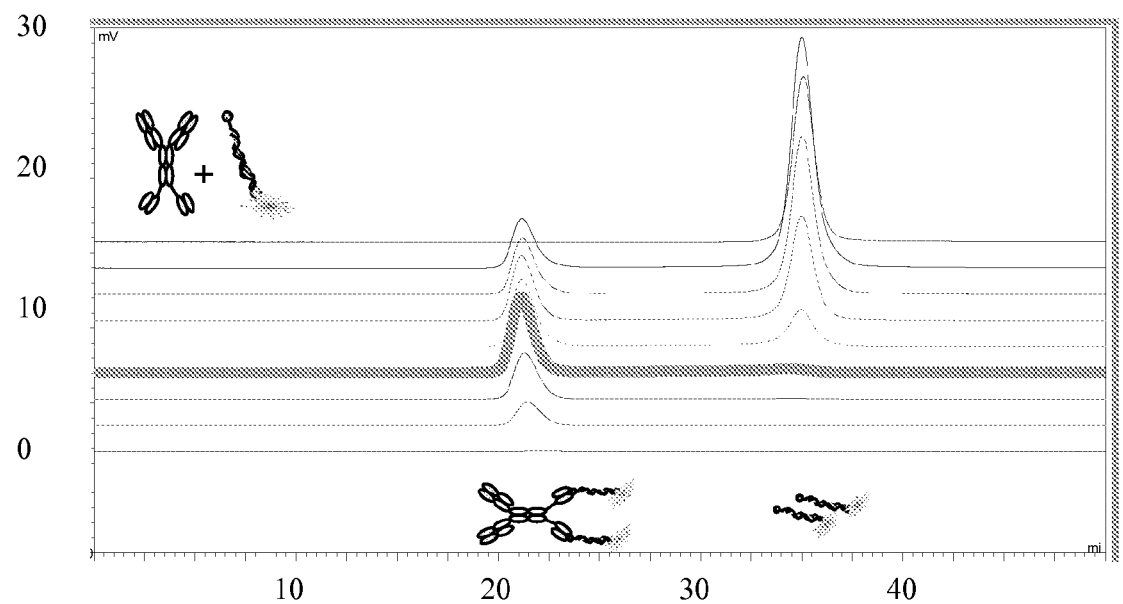

FIG. 30: Size exclusion chromatography analyses with bispecific targeting modules and fluorescently labeled nucleic acids. a) Schematic structure b) chromatogramme.

Figure 31:
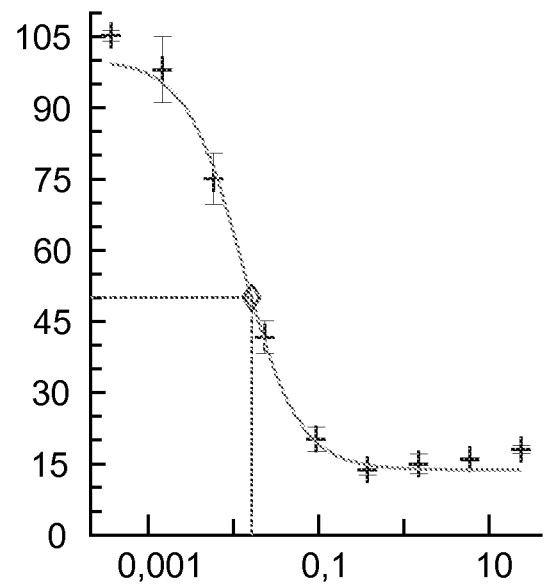
Figure 31:
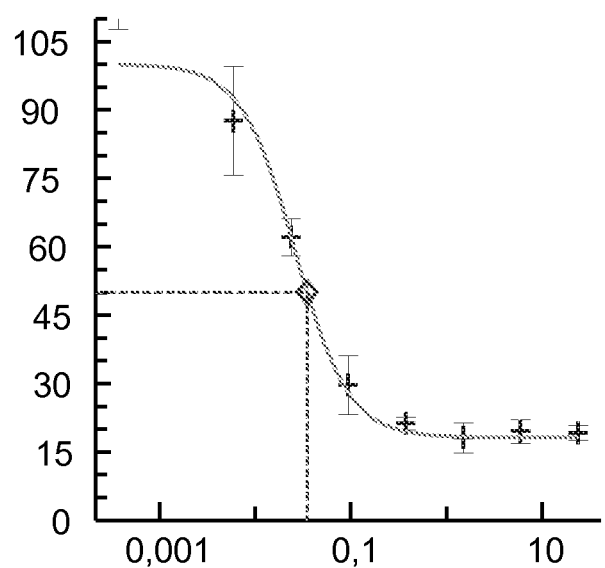
Figure 31:
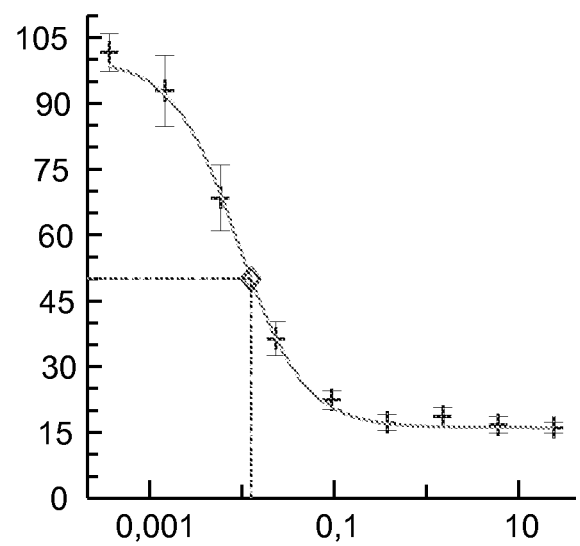
Figure 31:
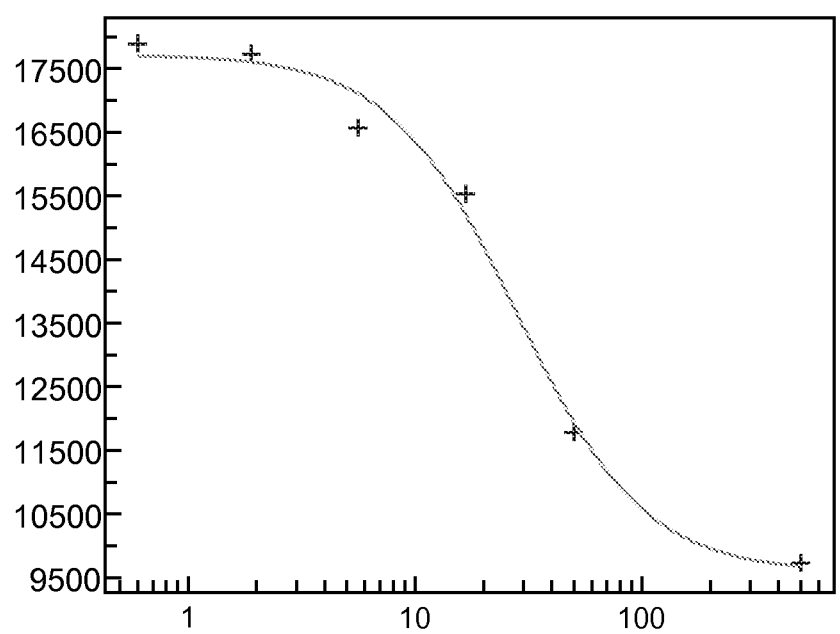
Figure 31:
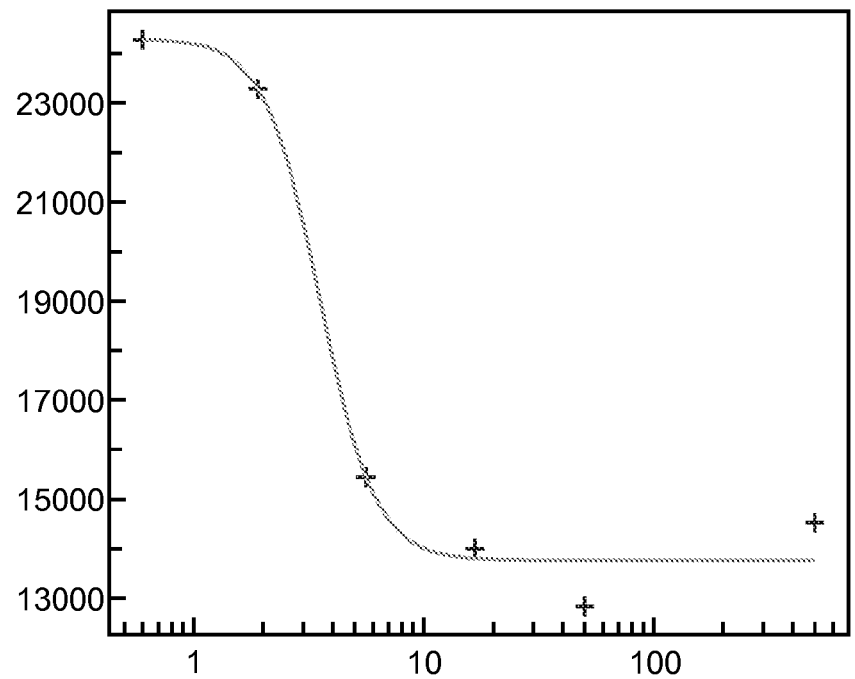
Figure 31:
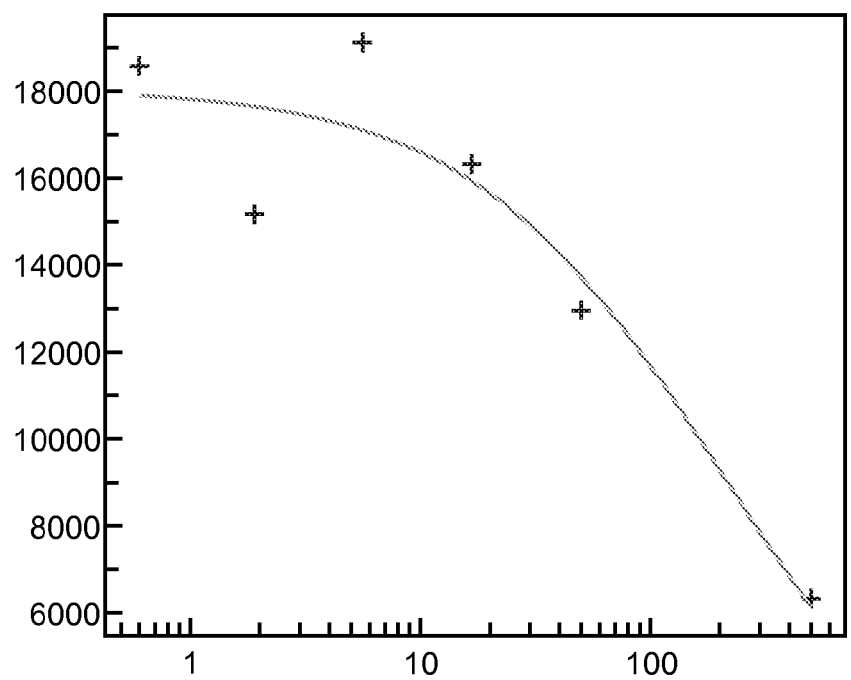
Figure 31:
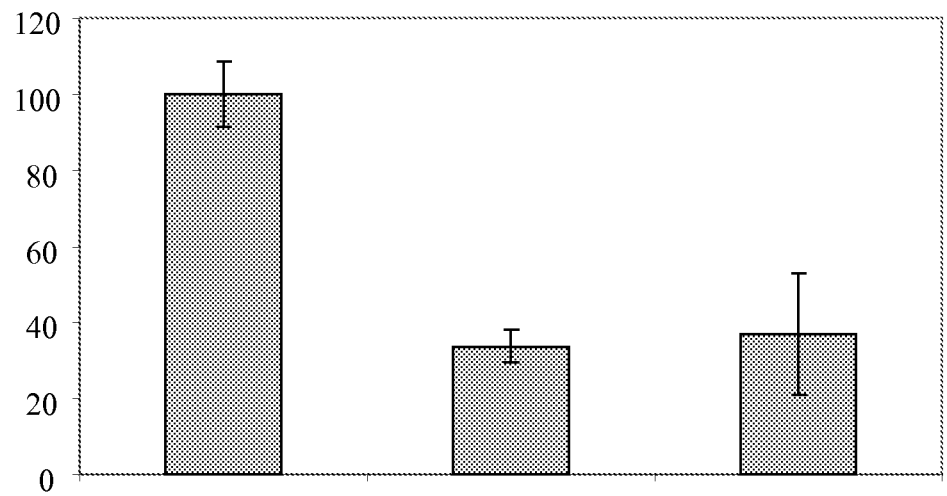

FIG. 31: Biological activity of digoxigenated siRNAs. a) Eg5-siRNA-mediated Eg5 mRNA knockdown, IC50=0.016 nM. Y-axis: % expression, x-axis: siRNA concentration (nM); b) DIG-Eg5-siRNA-mediated Eg5 mRNA knockdown, IC50=0.035 nM. Y-axis: % expression, x-axis: siRNA concentration (nM); c) DIG-Eg5-Cy5-siRNA-mediated Eg5 mRNA knockdown, IC50=0.013 nM. Y-axis: % expression, x-axis: siRNA concentration (nM); d) Eg5 siRNA-mediated cytotoxicity measured in KPL-4 transfected with Eg5siRNA, IC50=28 nM, Y-axis: number of living cells, x-axis: siRNA concentration (nM); e) DIGEg5 siRNA-mediated cytotoxicity measured in KPL-4 transfected with DIG Eg5siRNA, IC50=4 nM, Y-axis: number of living cells, x-axis: siRNA concentration (nM) f) DIG-Eg5-Cy5 siRNA-mediated cytotoxicity measured in KPL-4 transfected with DIG-Eg5-Cy5 siRNA, IC50=215 nM, Y-axis: number of living cells, x-axis: siRNA concentration (nM), g) Eg5 siRNA-mediated Cytotoxicity towards KPL4 cells; KPL4-cells transfected with 50 ng of the respective siRNA, left column: not treated, middle column: Eg5-siRNA, right column DIG-Eg5-siRNA. Shown is the percentage of living cells.

Figure 32:
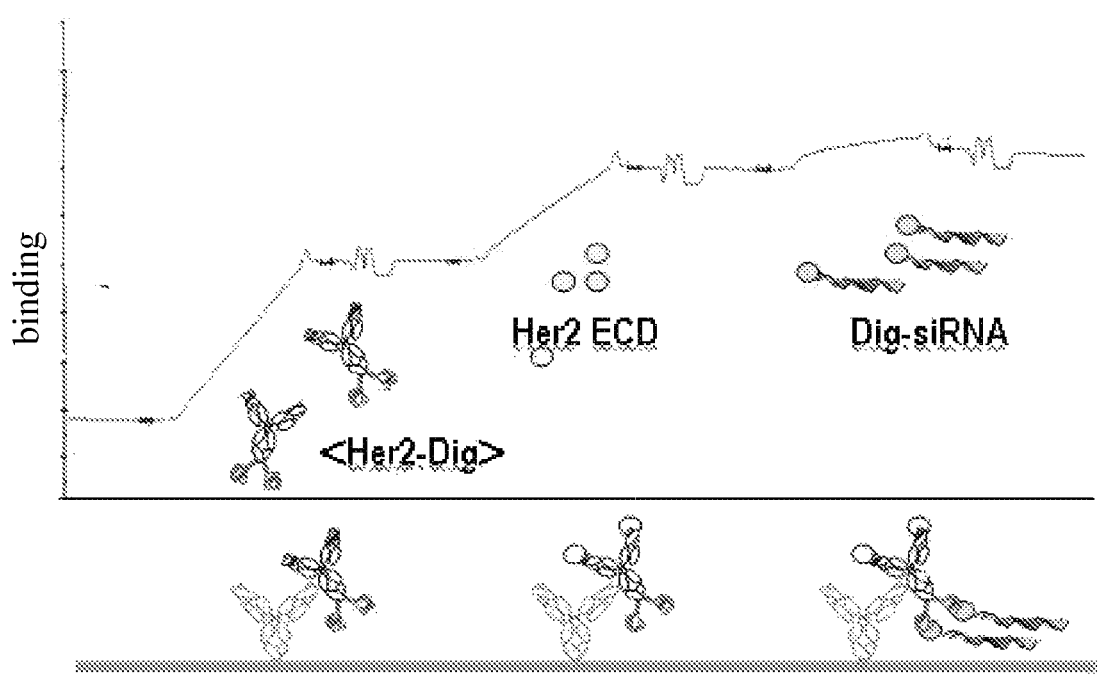

FIG. 32: Simultaneous binding of digoxigenated siRNA and target antigen to bispecific <Her2>-<Dig> antibody. Biacore analysis.

Figure 33:
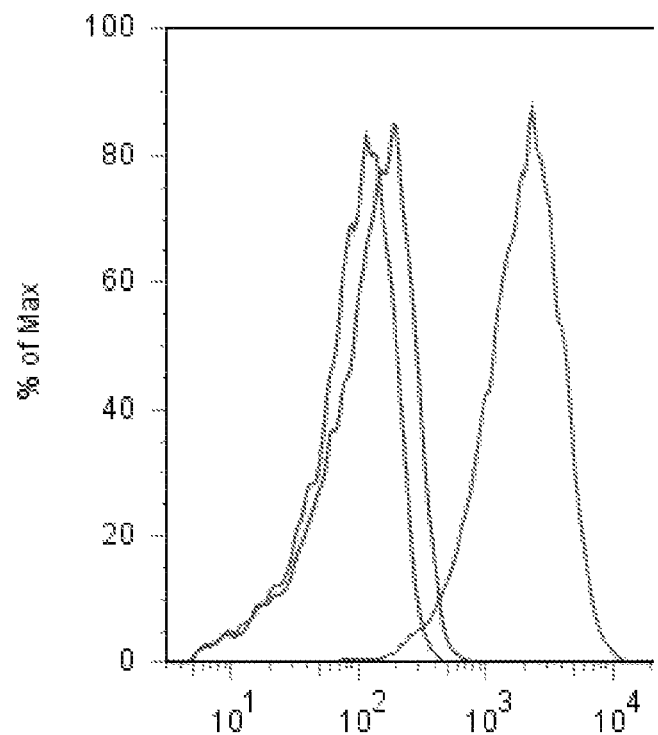
Figure 33:
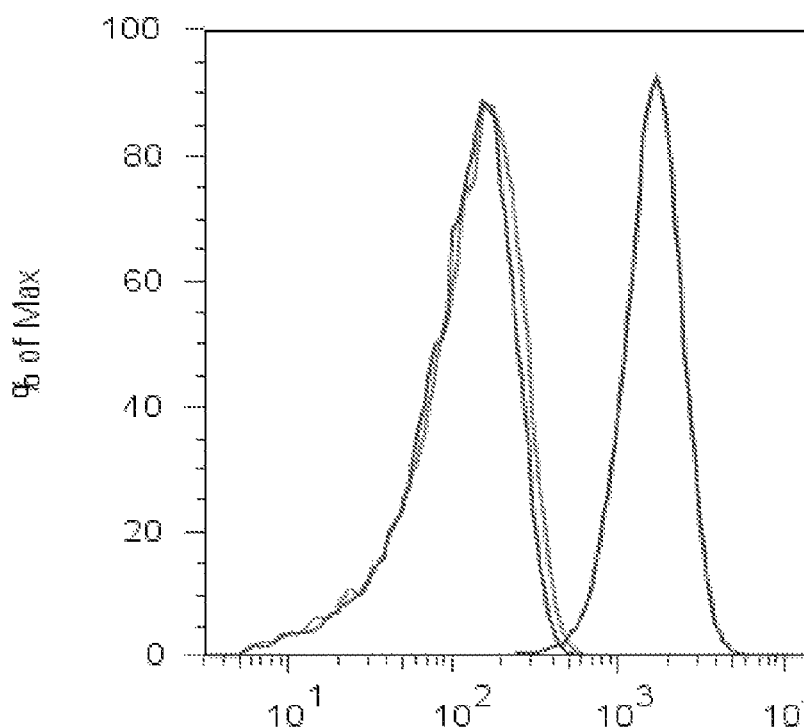

FIG. 33: a) FACS analysis of Raji cells incubated with <CD22>-<Dig> antibody coupled to digoxygenated and Cy5-labeled siRNA. The CD22 WT-DIG antibody on Raji cells in combination with the DIG-siRNA-Cy5 shows a very clear positive signal (single peak at $5 \times 10^3$) in comparison to the DIG-siRNA-Cy5 alone/Raji cells only (double peak at $10^2$). b) FACS analysis of Ramos cells incubated with <CD22>-<Dig> antibody coupled to digoxygenated and Cy5-labeled siRNA. The secondary entity (DIG-siRNA-Cy5) gives no background (double peak together with cells only) while the CD22 WT DIG is positive (single peak).

Figure 34:
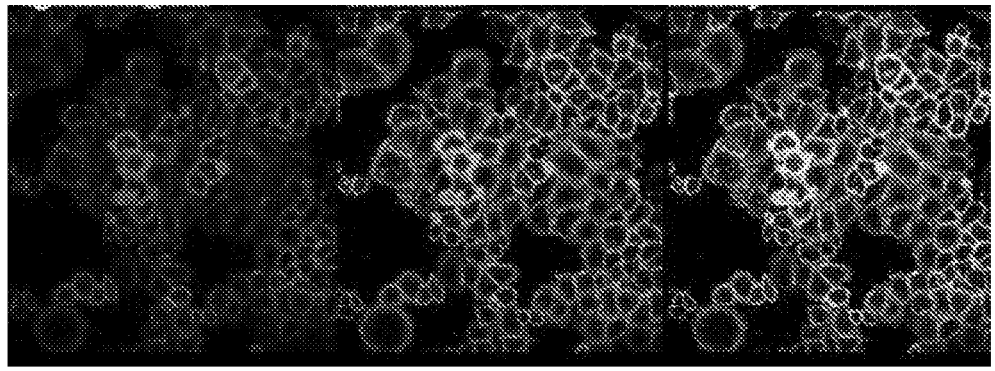
Figure 34:
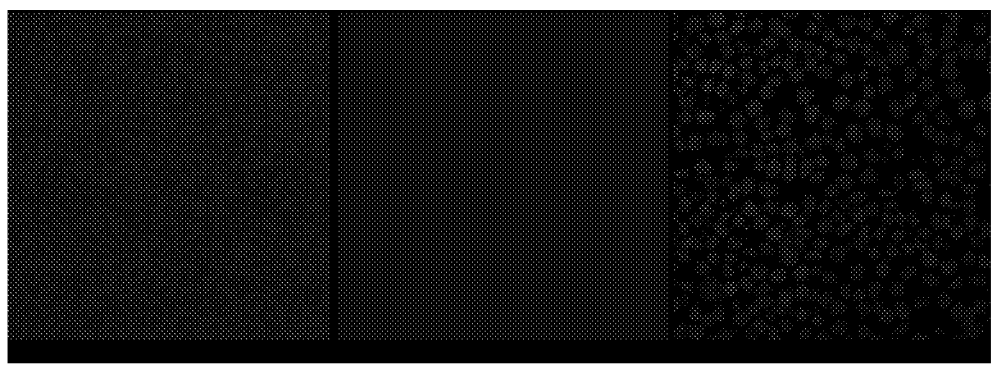
Figure 34:
Figure 34:
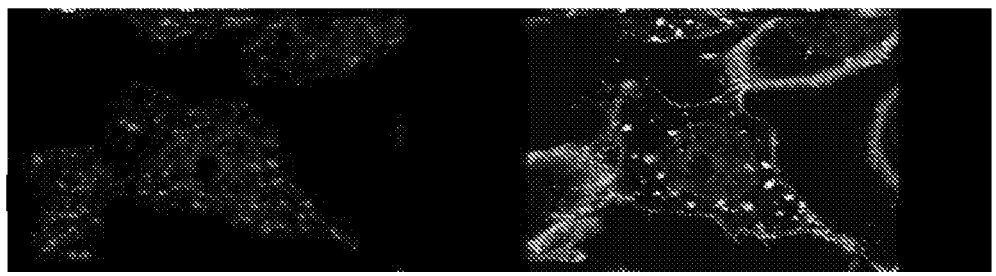

FIG. 34: Specific in vitro targeting of siRNAs coupled to bispecific <Her2>-<Dig> antibodies. Top: Example of surface bound Ab-siRNA complex in KPL4 cells following 30' incubation at 37° C. a) Eg5 siRNA_CY5, b) Herceptin anti-kappa Alexa 488, c) Overlay; Middle: Example of surface bound Ab-siRNA complex in MDAMB468 cells following 30' incubation at 37° C. d) Eg5 siRNA_CY5, e) Herceptin anti-kappa Alexa 488, f) Overlay; Bottom: Example of surface bound Ab-siRNA complex in KPL4 cells following over night incubation at 37° C. g) Eg5 siRNA_CY5, h) Herceptin-DIG_hu2-SS, i) transferrin j) overlay.

Figure 35:
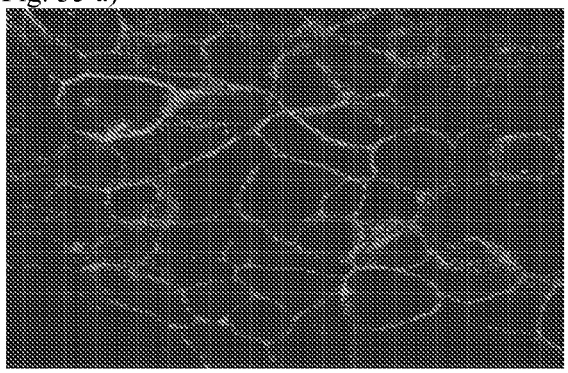
Figure 35:
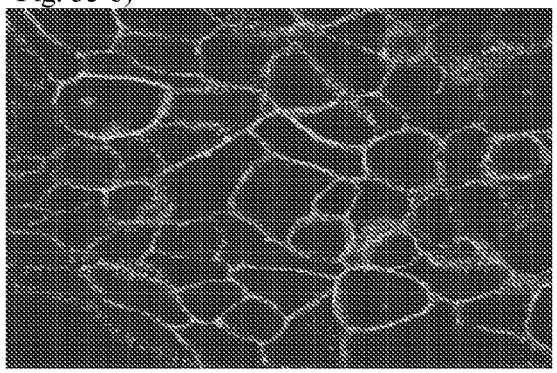
Figure 35:
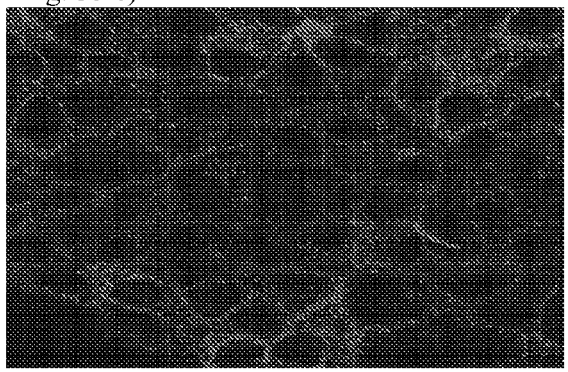
Figure 35:
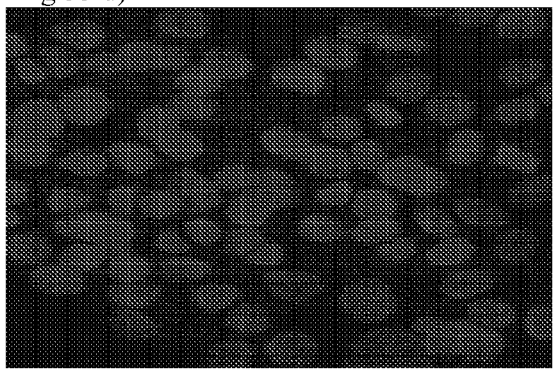
Figure 35:
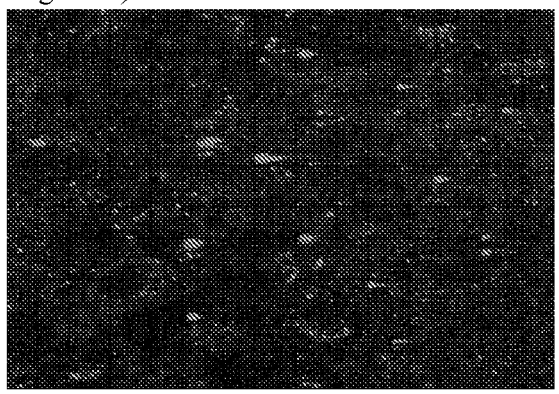
Figure 35:
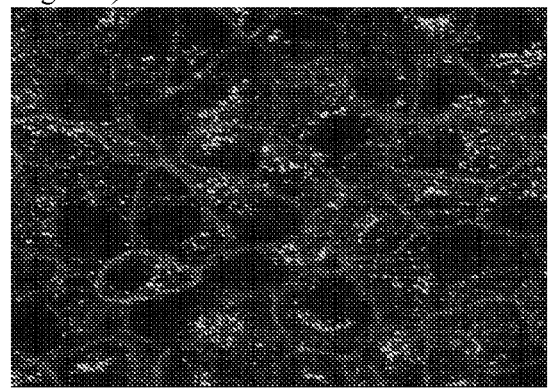
Figure 35:
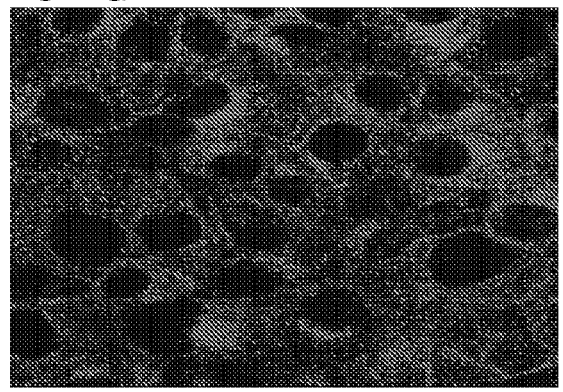
Figure 35:
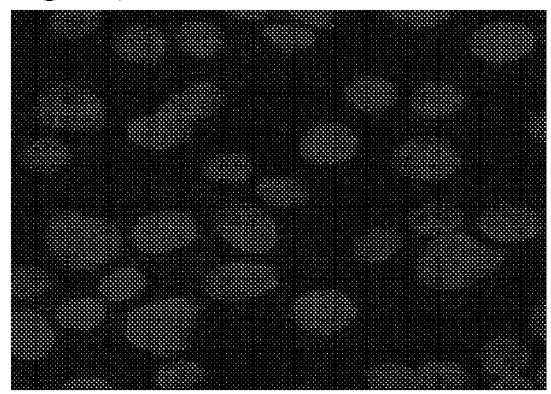

FIG. 35: Specific in vitro targeting of siRNAs coupled to bispecific <IGFR1>-<Dig> antibodies. a)-d): Surface bound Ab-siRNA complex in H322M, 10' incubation @37° C. a) Eg5siRNA detection (cy5), b)<IGF1R>-<DIG> detection (alexa) c) transferrin, d) cell nuclei; e)-h): Internalized Ab-siRNA complex in H322M, 1 h incubation @37° C. e) Eg5siRNA detection (cy5), f)<IGF1R>-<DIG> detection (alexa), g) transferrin, h) cell nuclei.

Figure 36:
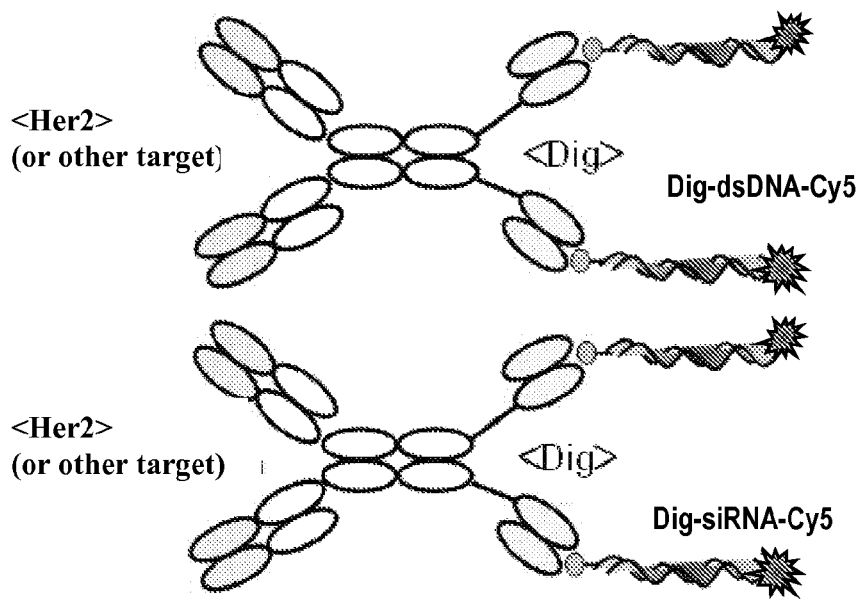
Figure 36:
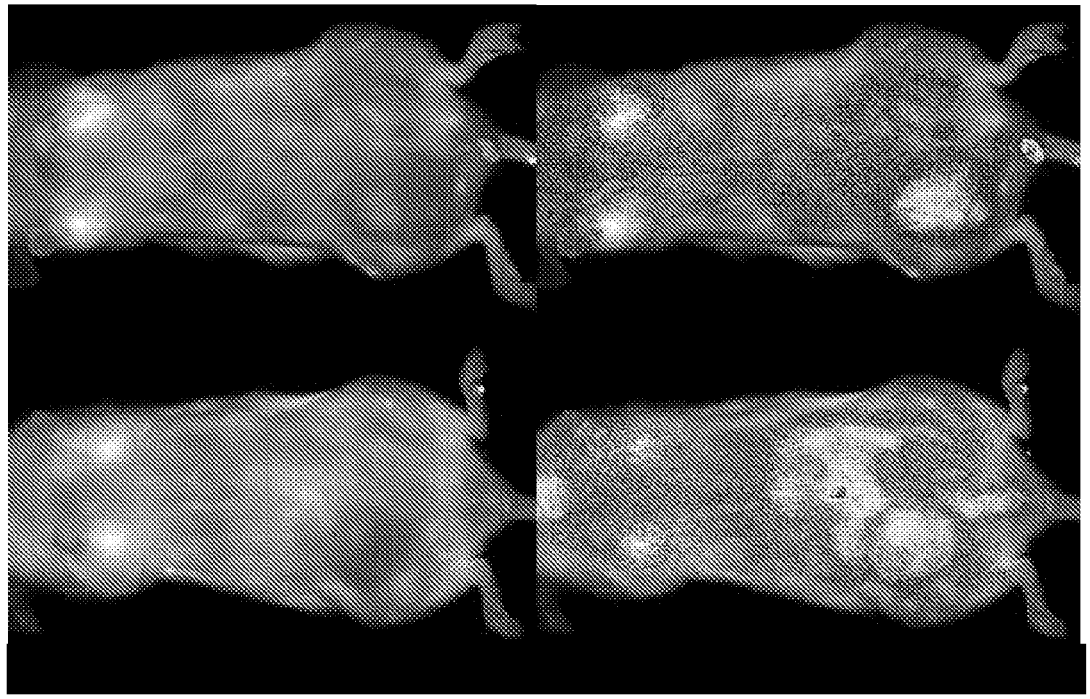

FIG. 36: Specific in vivo targeting of siRNAs coupled to bispecific <Her2>-<Dig> antibodies. a) Schematic structure of bispecific antibodies, b) NIRF image 24 hrs after injection. <Her2Dig>$^{dig}$dsDNA$^{Cy5}$ FIG. 37: Specific in vivo targeting of siRNAs coupled to bispecific <IGFR1>-<Dig> antibodies. a) Schematic structure of bispecific antibody, b) NIRF image FIG. 38: a) Separation of siRNA from targeting modules after internalization. A: <IgG>-<DIG>, B: Eg5siRNA_CY5 C: overlay b) Separation of DIG labeled eGFP from targeting modules after internalization. Upper row: 2 h on ice, lower row: o/n @ 37° C. A: eGFP, B: IgG, C: overlay c) No separation of covalently linked siRNA from targeting modules after internalization. Upper row: 1 h on ice, lower row: o/n @ 37° C. A: siRNA, B: IgG, C: overlay. d) No separation of covalently linked Citrine from targeting modules after internalization. Upper row: 2 h on ice, lower row: o/n @ 37° C. A: citrine B: IgG C: overlay.

Figure 39:
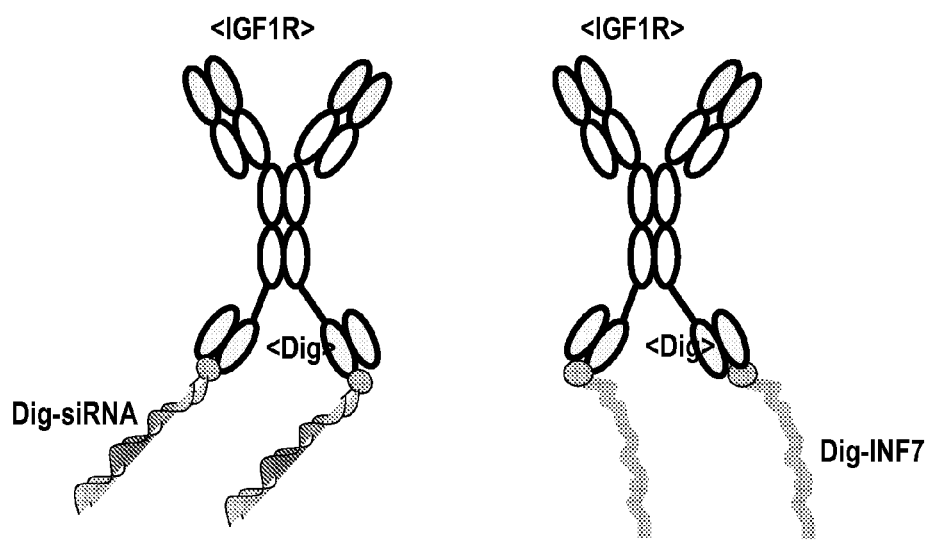
Figure 39:
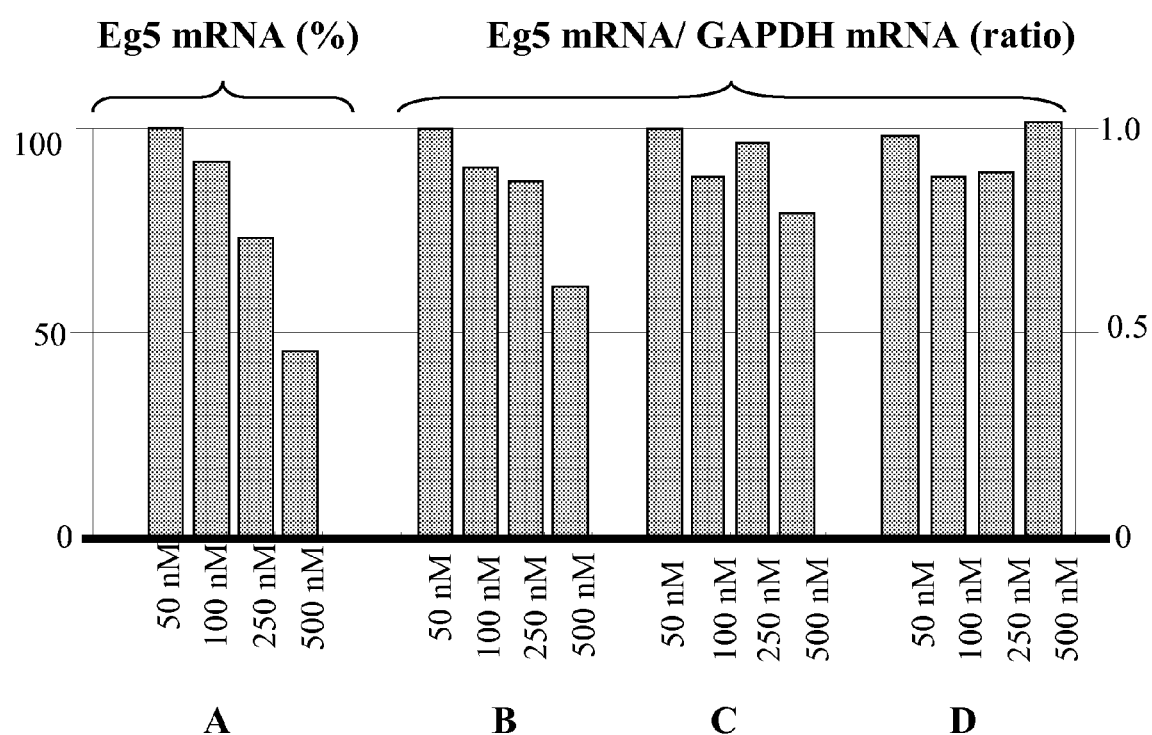

FIG. 39: Specific targeting of siRNA activity to target cells by bispecific <IGFR1>-<Dig> antibody-digoxigenated siRNA complexes. Eg5 mRNA levels in IGF1R expressing H322M cells (% and Eg5/GAPHD ratio). A: 50 nM <IGF1R-Dig> Dig-Eg5siRNA XnM <IGF1R-Dig> Dig-INF7 peptide B: 50 nM <IGF1R-Dig> Dig-Eg5siRNA XnM <IGF1R-Dig> Dig-INF7peptide C: 50 nM <IGF1R-Dig> Dig-LUC-siRNA XnM <IGF1R-Dig> Dig-INF7peptide D: 50 nM <IGF1R-Dig> XnM <IGF1R-Dig> Dig-INF7peptide.

Figure 40:
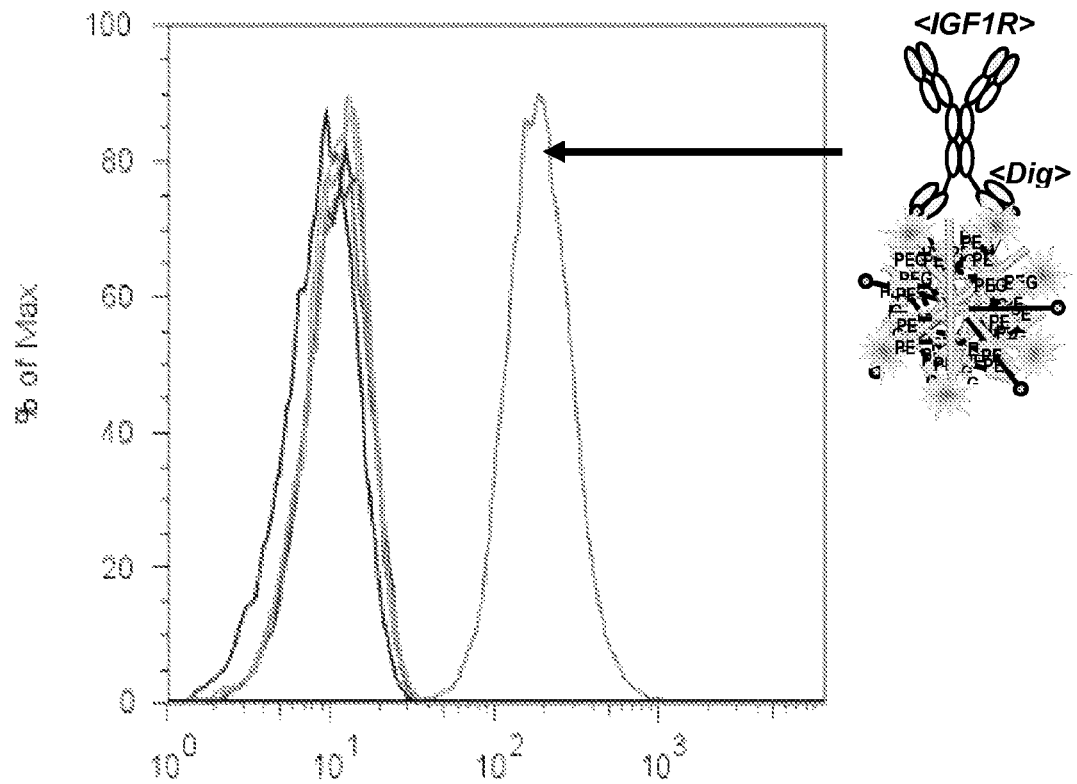
Figure 40:
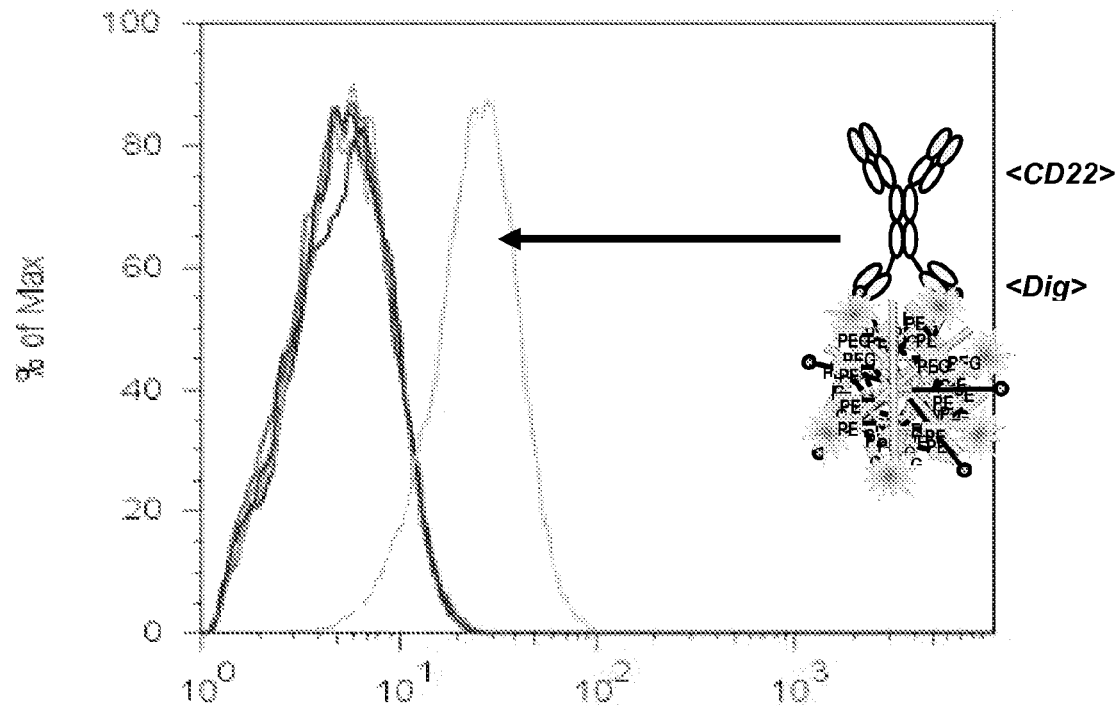

FIG. 40: Antigen functionality of <IGFR1>-<Dig>/<CD22>-<Dig> antibody-digoxigenated DPC complexes. a): H322M, Igf1R positive. Only the H322M conjugate shows a peak at about $2 \times 10^2$. Multiple peaks at $10^1$: <IGFR1>-<Dig> antibody, H322M secondary only, H322<DIG>, H322M isotype and H322M cells only. b): Raji, CD22 positive. Only the Raji conjugate (<CD22>-<Dig>-digoxigenated DPC complex) shows a peak at about $2 \times 10^{1*}$ Multiple peaks: <CD22>-<Dig> antibody, Raji secondary only, Raji <DIG>, Raji isotype and Raji cells only.

Figure 41:
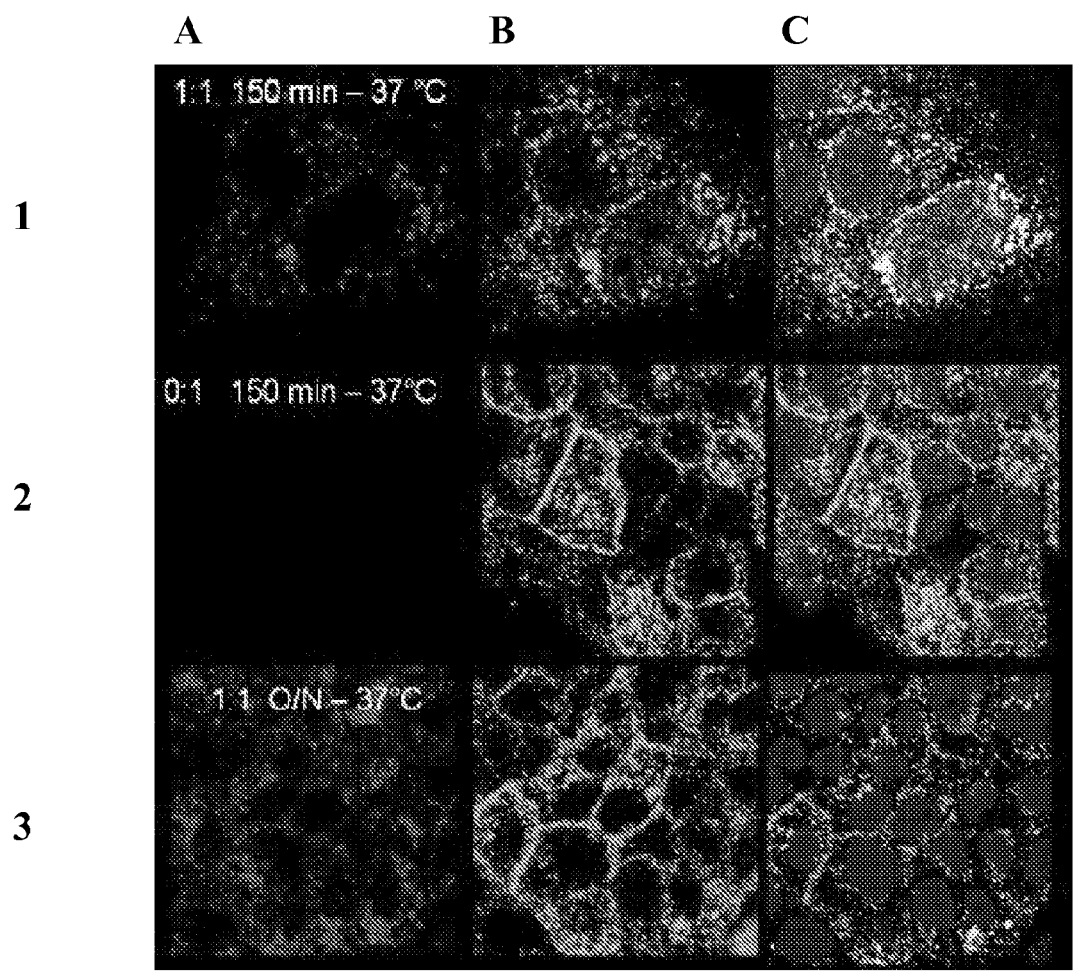

FIG. 41: Specific targeting of <IGFR1>-<Dig> antibody-digoxigenated DPC complexes to target cells. 1: Dig-DPC+<IGFR1>-<Dig> bispec. 2: DPC (no DIG)+<IGFR1>-<Dig> bispec. 3: Dig-DPC+<IGFR1>-<Dig> bispec. A: DPC, B: Antibody C: Antibody DPC Nuclei.

Figure 42:
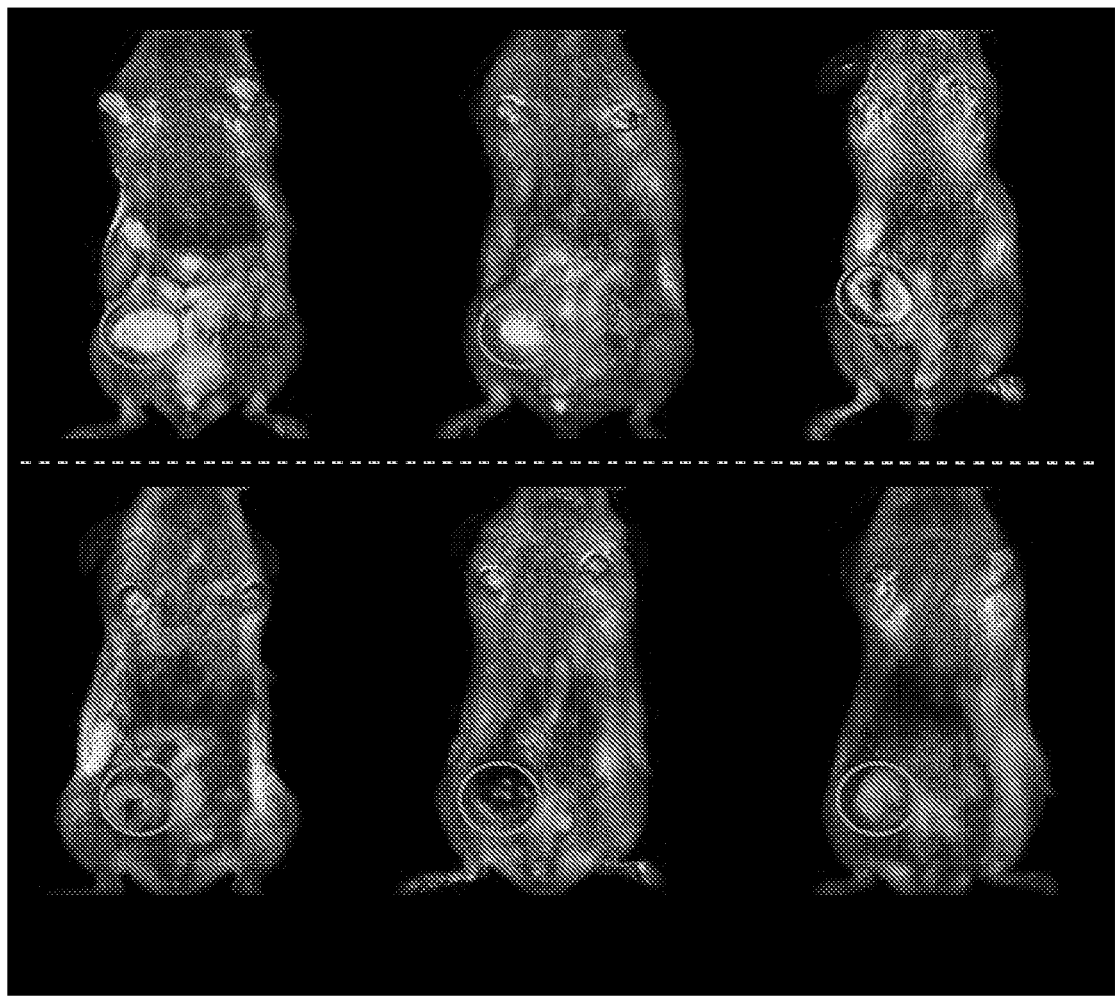

FIG. 42: Specific targeting of <Her2>-<Dig> antibody-digoxigenated DPC complexes to target cells. KPL4 bearing SCID beige mice were injected i.v. with DIG-DPC Cy3<Her2>-<Dig> (upper row) and DIG-DPC Cy3 without antibody (lower row), shown is NIRF after 24 h.

Figure 43:
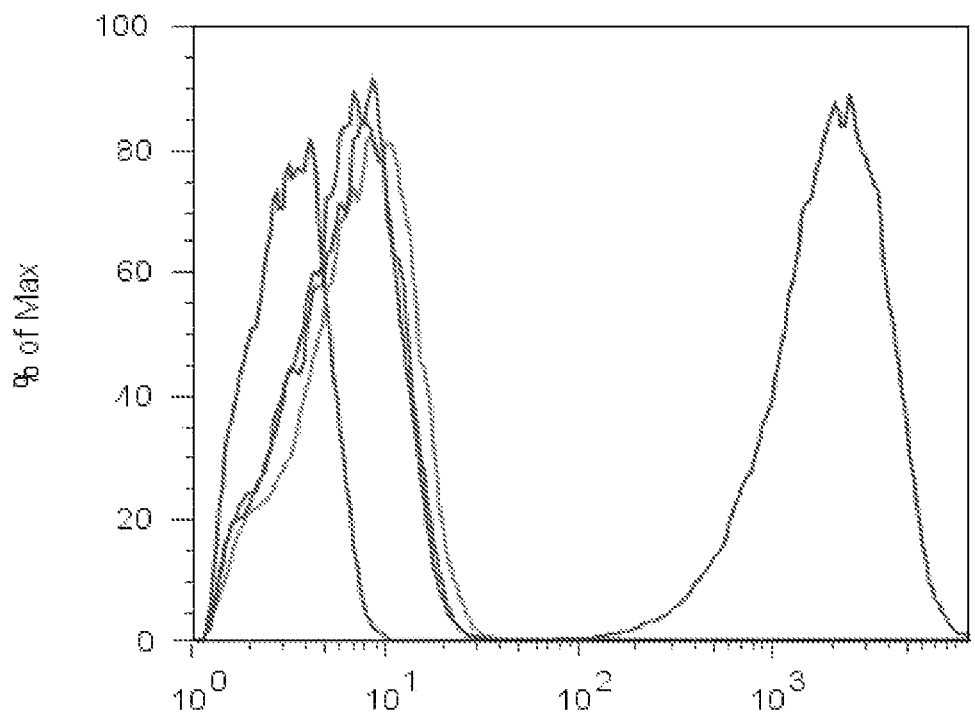
Figure 43:
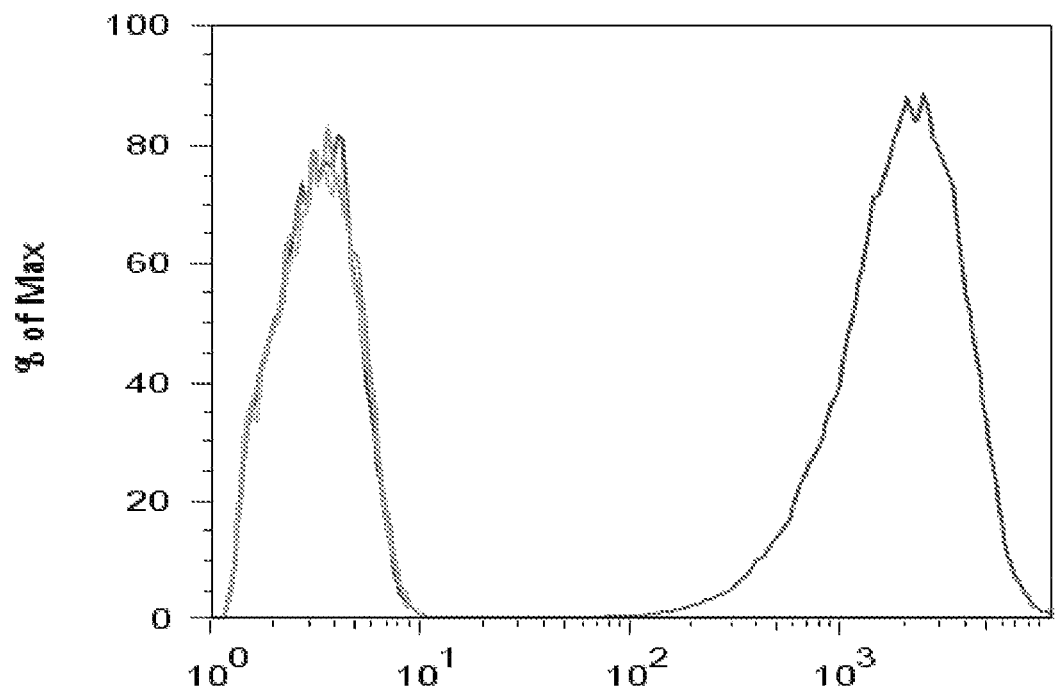

FIG. 43: DIG-eGFP that is complexed with a bispecific antibody is specifically targeted to tumors expressing the cognate antigen. a) Single peak: LeY-DIG bispecific antibody, multiple peaks: DIG only, secondary only, isotype only and cells only. b) Single peak: LeY-DIG bispecific antibody, multiple peaks: 1:3 LeY/DIG-GFP, 1:2 LeY/DIG-GFP and cells only.

Figure 44:
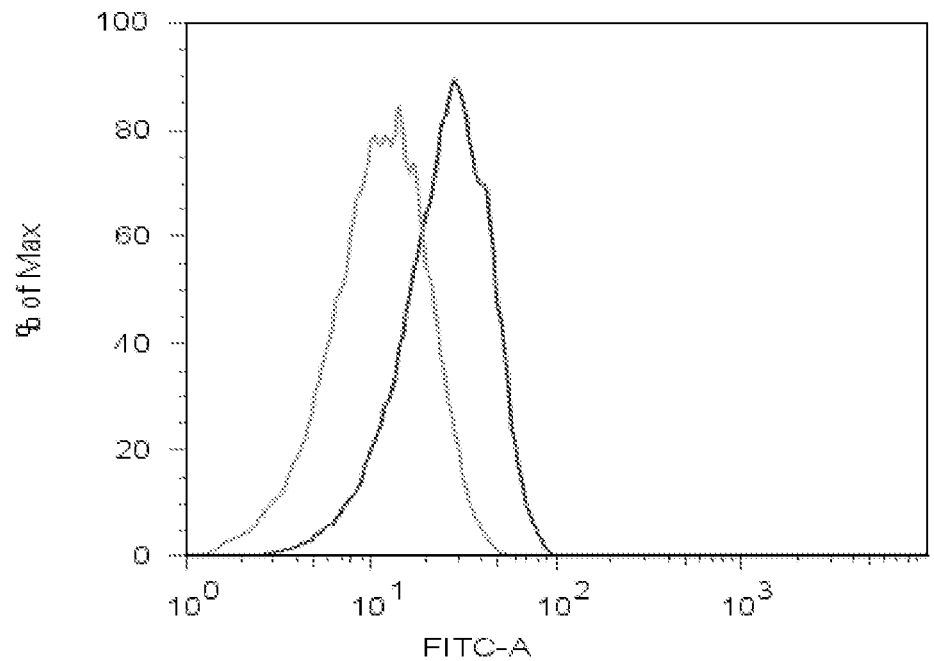
Figure 44:
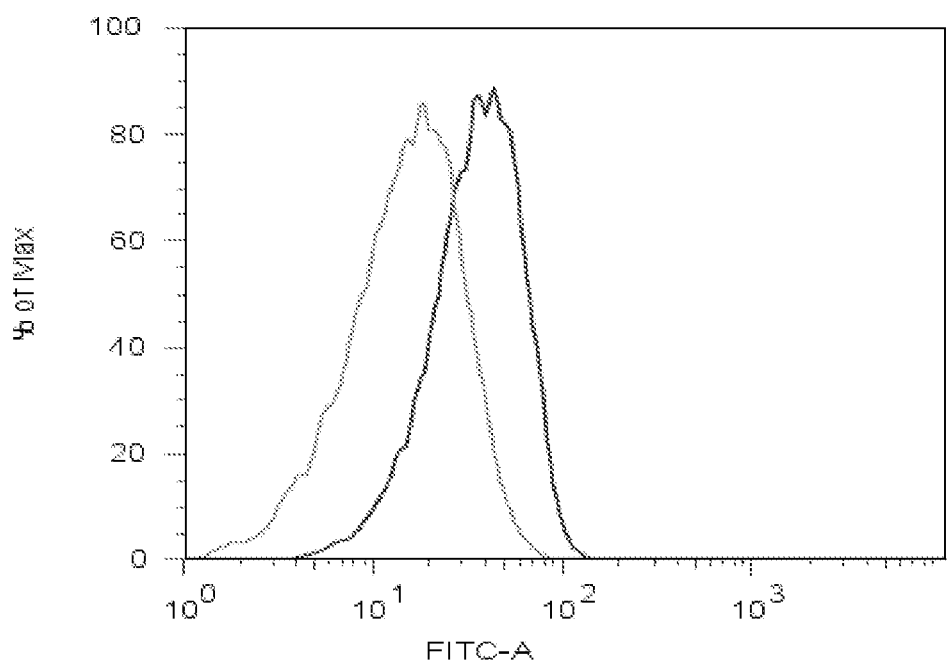

FIG. 44: The DIG labeled protein eGFP can be used to monitor endocytosis of target cell bound bispecific antibody. a) MCF7 1:2 LeY/DIG-GFP grey peak: 37° C., black peak: 4° C. b) MCF7 1:3 LeY/DIG-GFP grey peak: 37° C., black peak: 4° C.

Figure 45:
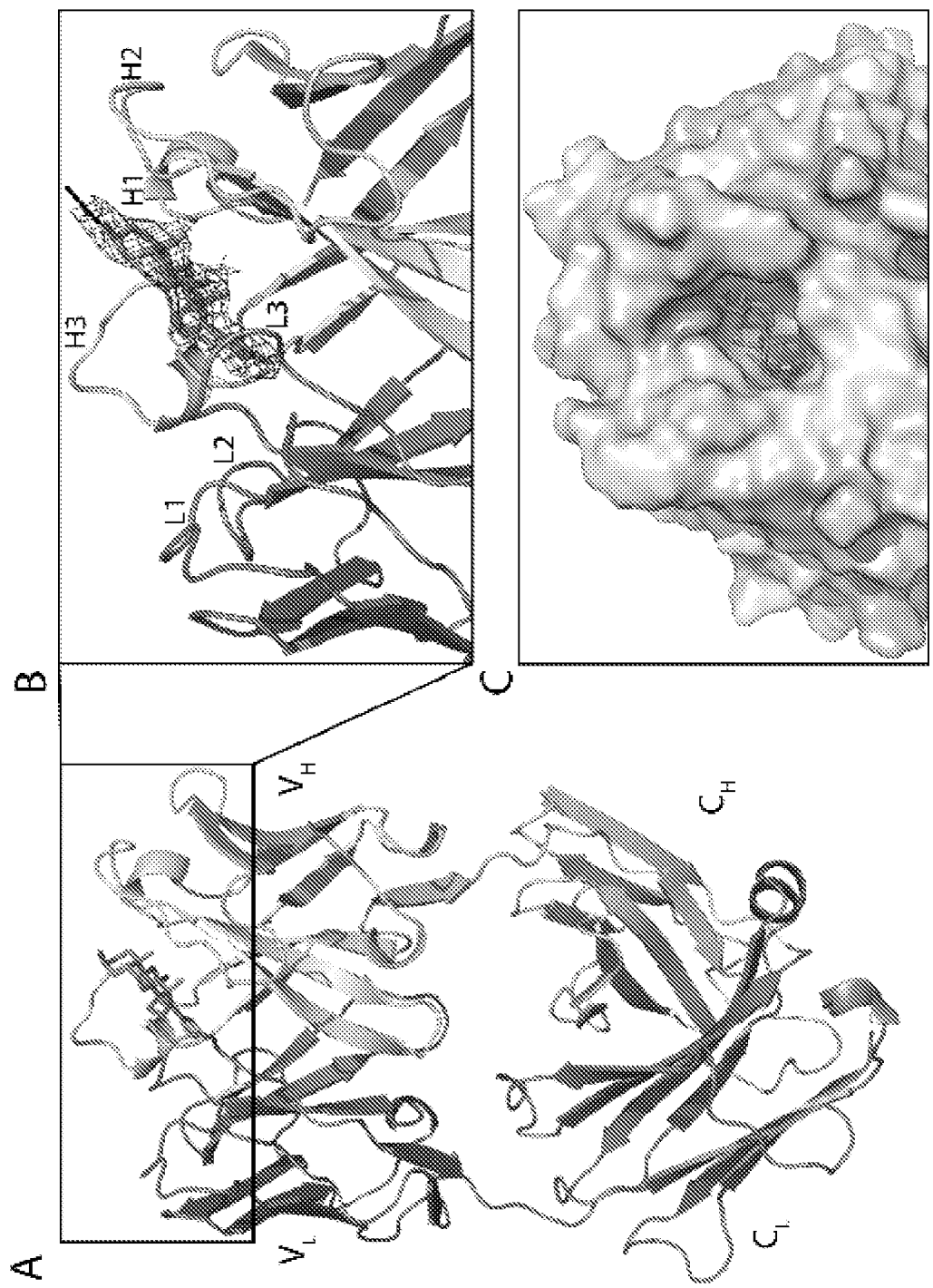
Figure 45:
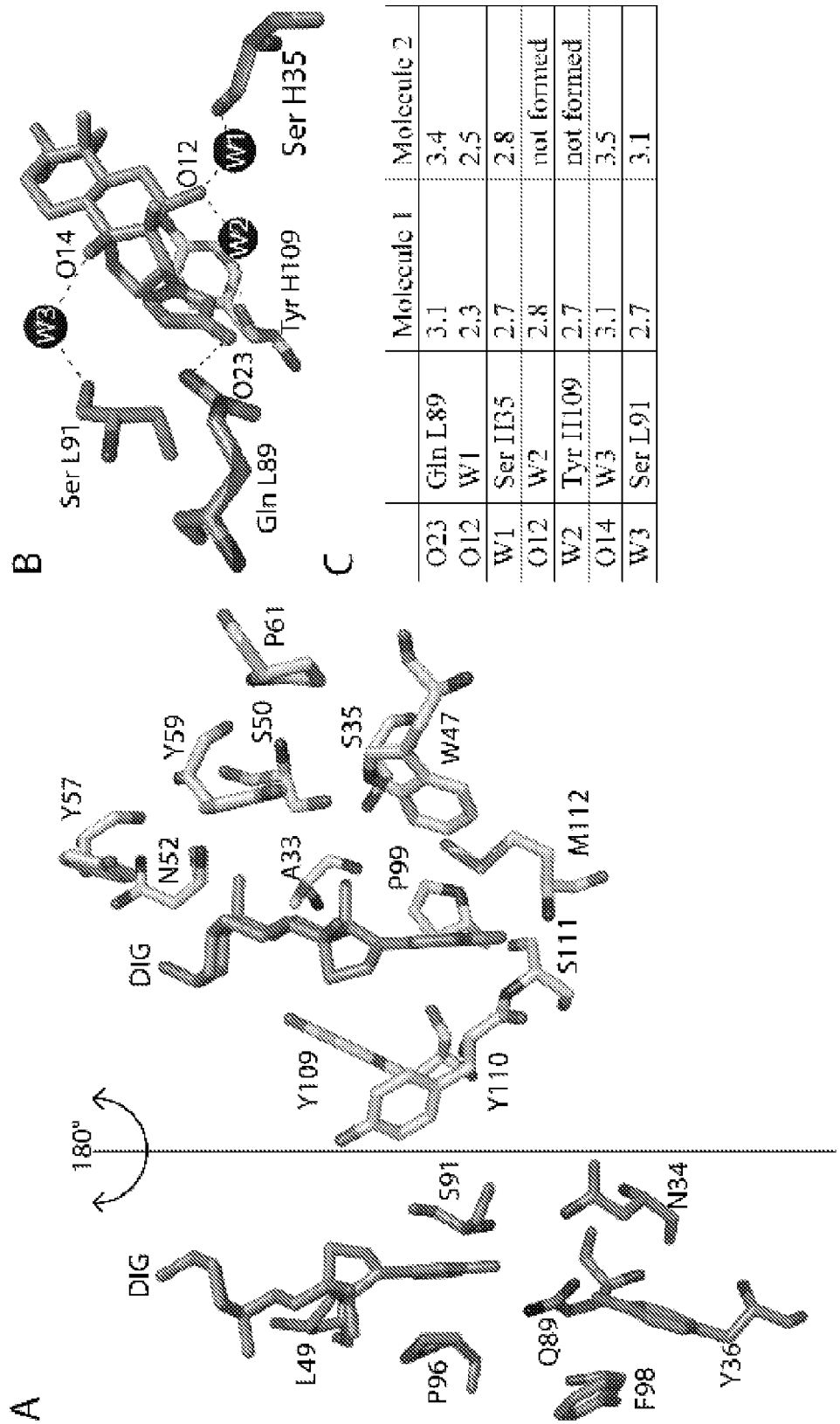

FIG. 45: Crystals of the <Dig> Fab fragment and experimentally determined structure of the Digoxygenin binding region of the murine parent antibody. (a) Crystallographic data collection and model refinement statistics, (b) Complex of the murine anti-DIG Fab in presence of antigen (ribbon representation, chain L in blue, chain H in green) with bound DIG moiety (Panel A:colour-coded stick model). Zoom (panel B) in on CDR with labeled CDR loops. The final $2F_OF_C$ electron density map around DIG moiety is shown as blue mesh countered at 1σ. The dashed line indicates the direction of the linker to Cy5. Panel C shows the electrostatic surface potential of murine Fab with bound DIG. (c) Residues lining the binding pocket are drawn as stick model (Panel A). Residues involved in hydrogen bond interactions with DIG are represented as stick model (Panel B). Table with hydrogen bonds lists partners and distances in Å (Panel C).

Figure 46:
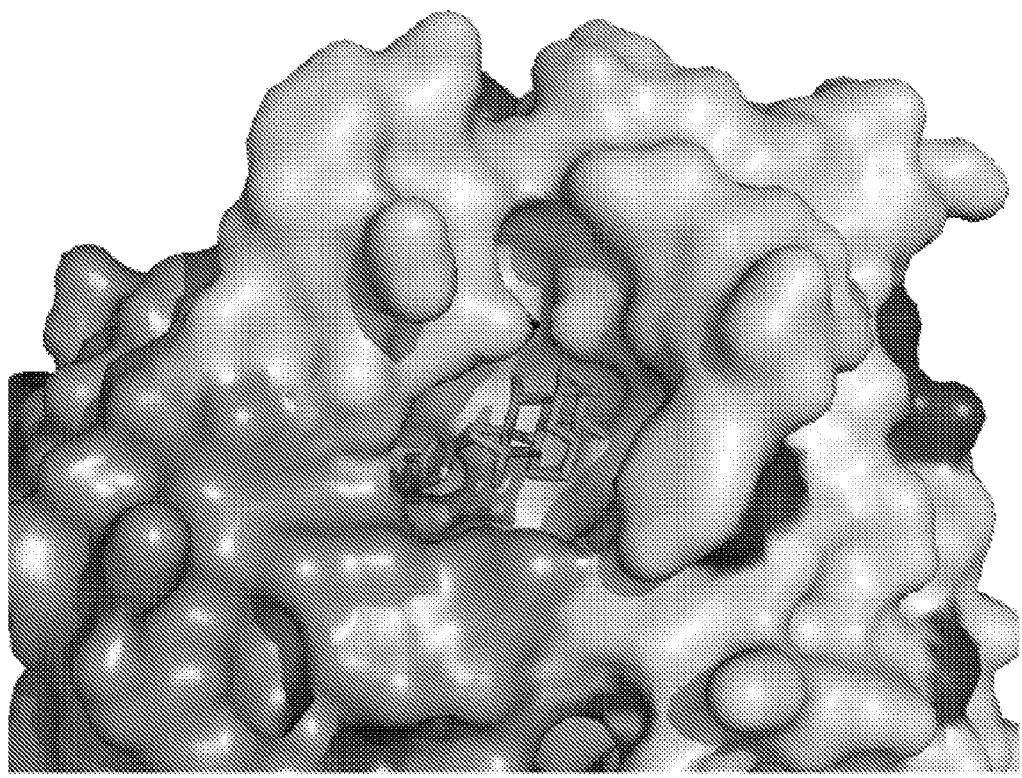
Figure 46:
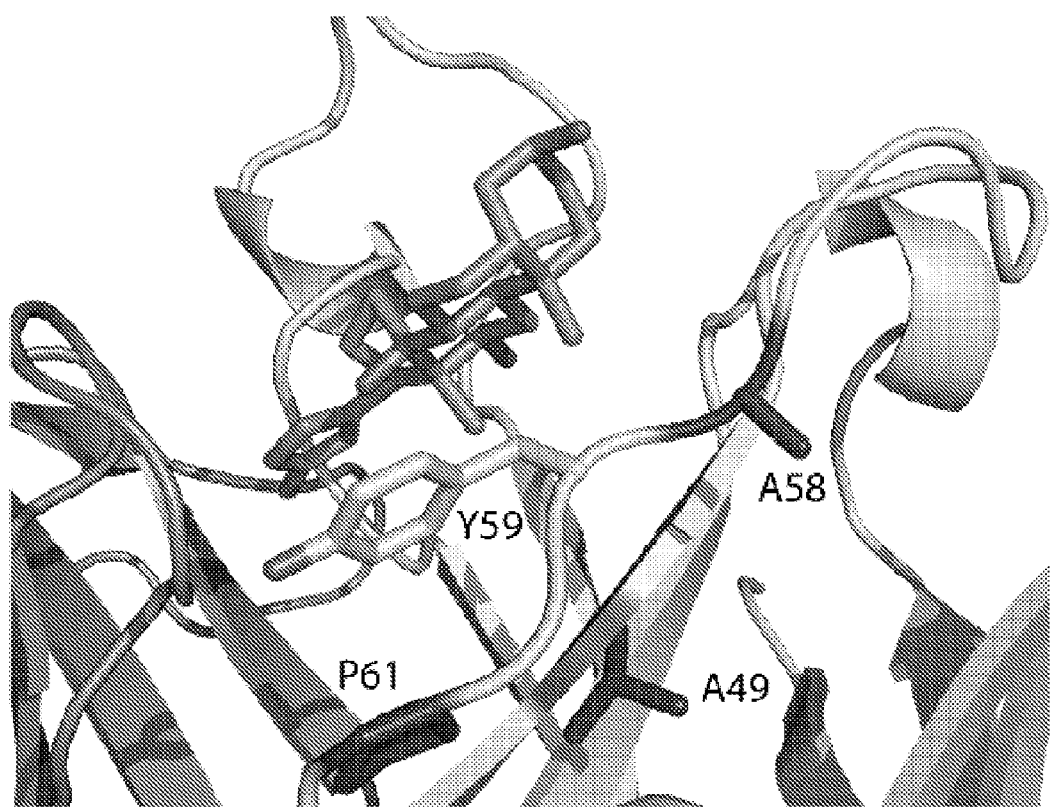
Figure 46:
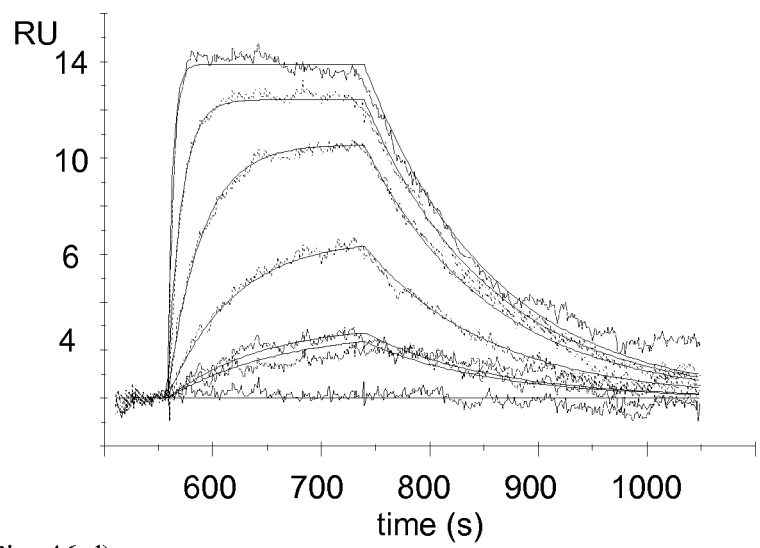
Figure 46:
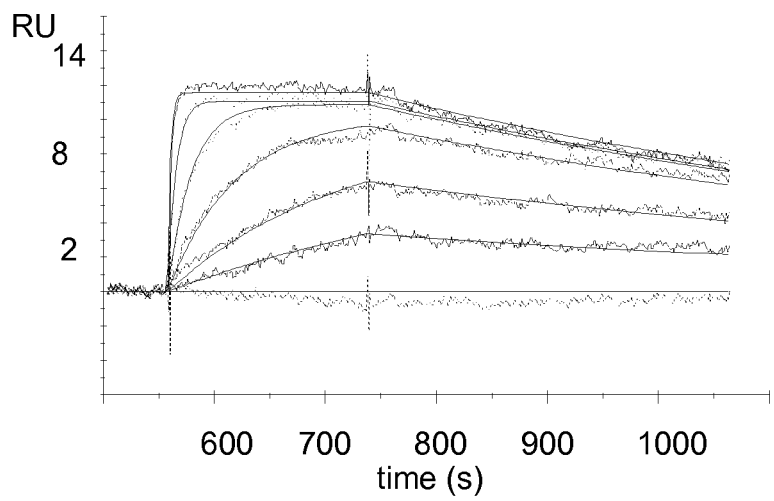

FIG. 46: a) Surface representation of murine anti DIG Fab b) Ribbon representation of murine anti DIG Fabs. c) and d) Surface-Plasmon-Resonance (BiaCore) experiments show binding specificity and improved affinity of sequence-optimized humanized anti-Dig modules. c): <DIG> before optimization, KD=12 nM, d): <DIG> optimized at VH 49, 57, 60 (Kabat). KD=1 nM.

Figure 47:
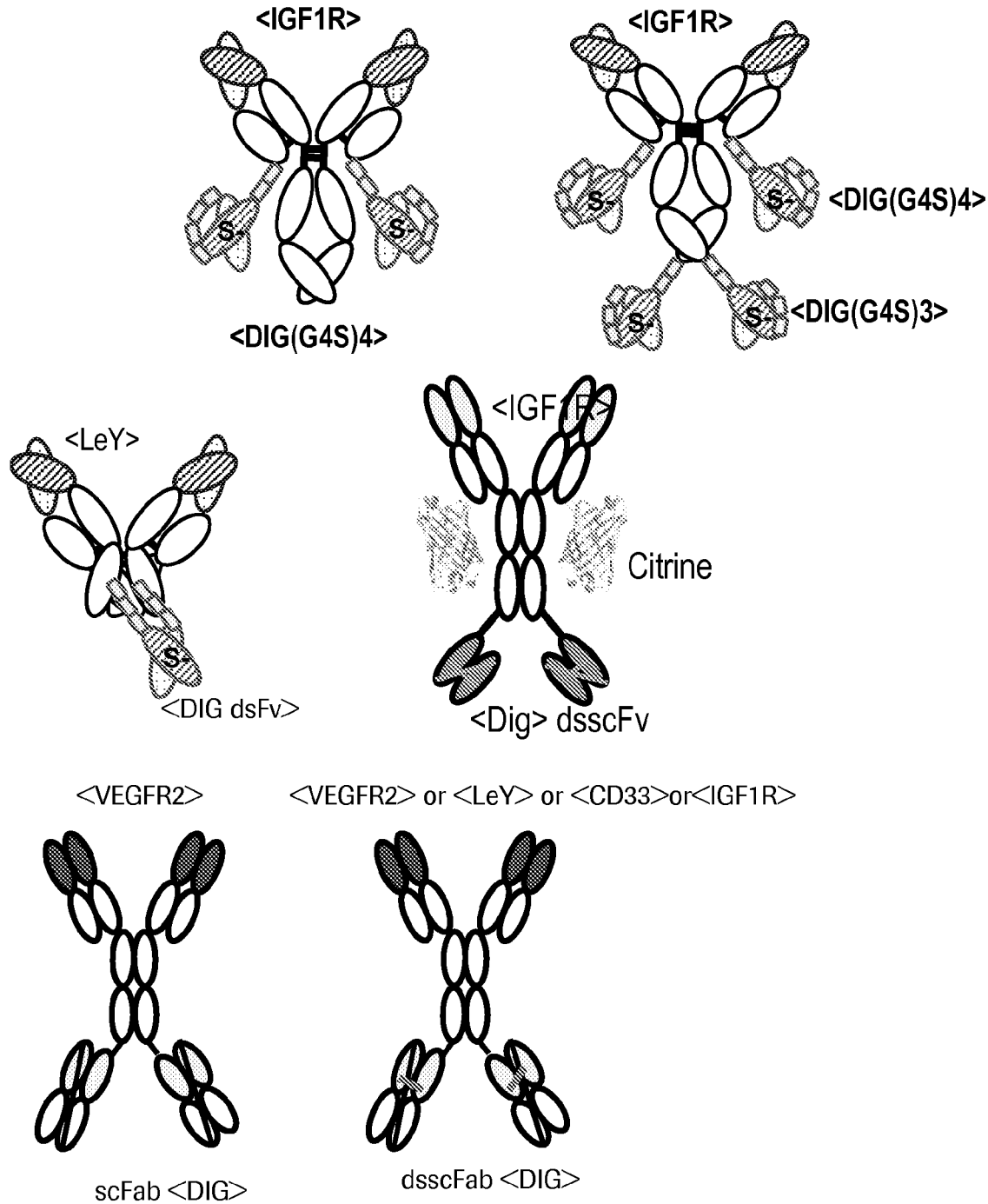
Figure 47:
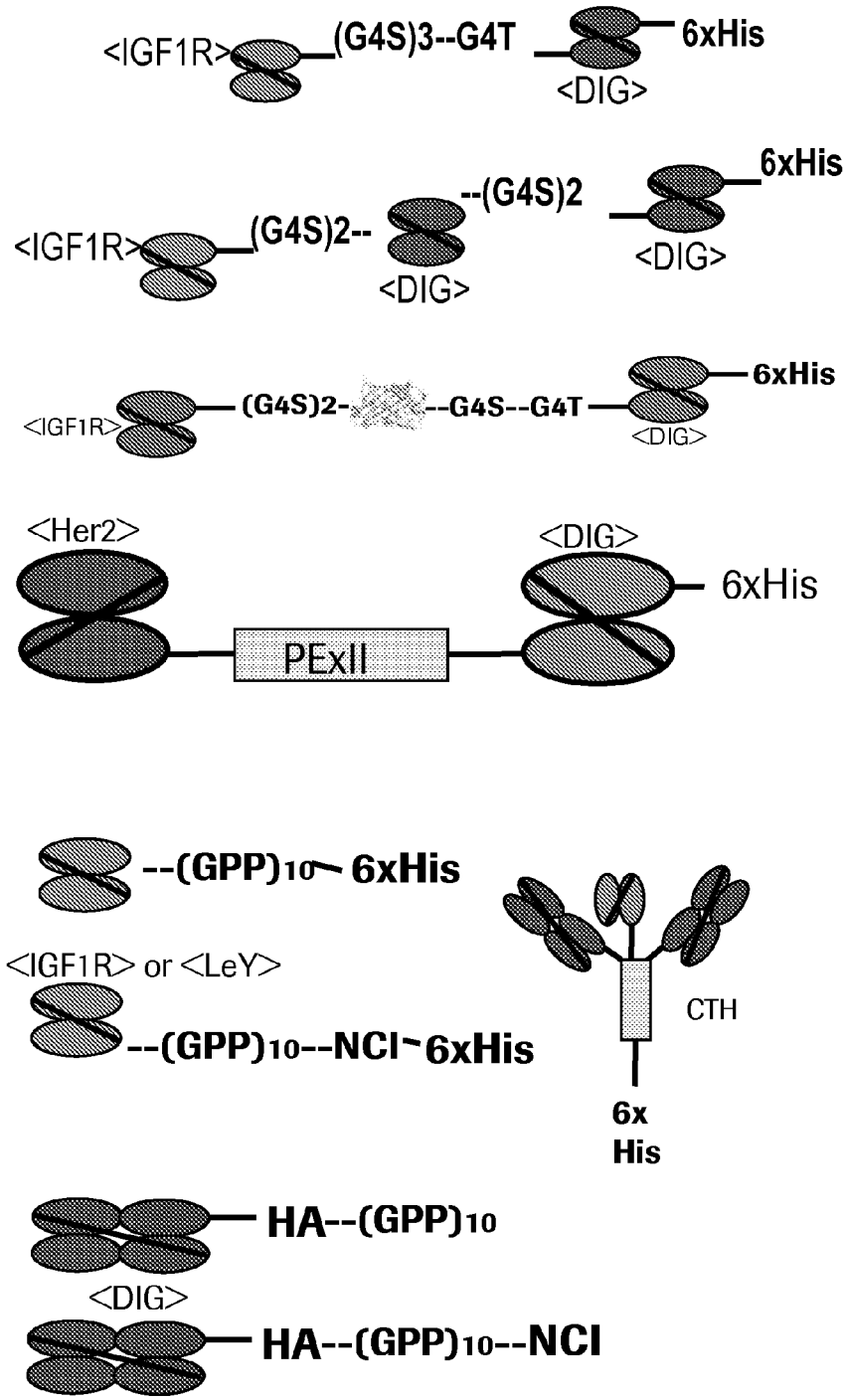
Figure 47:
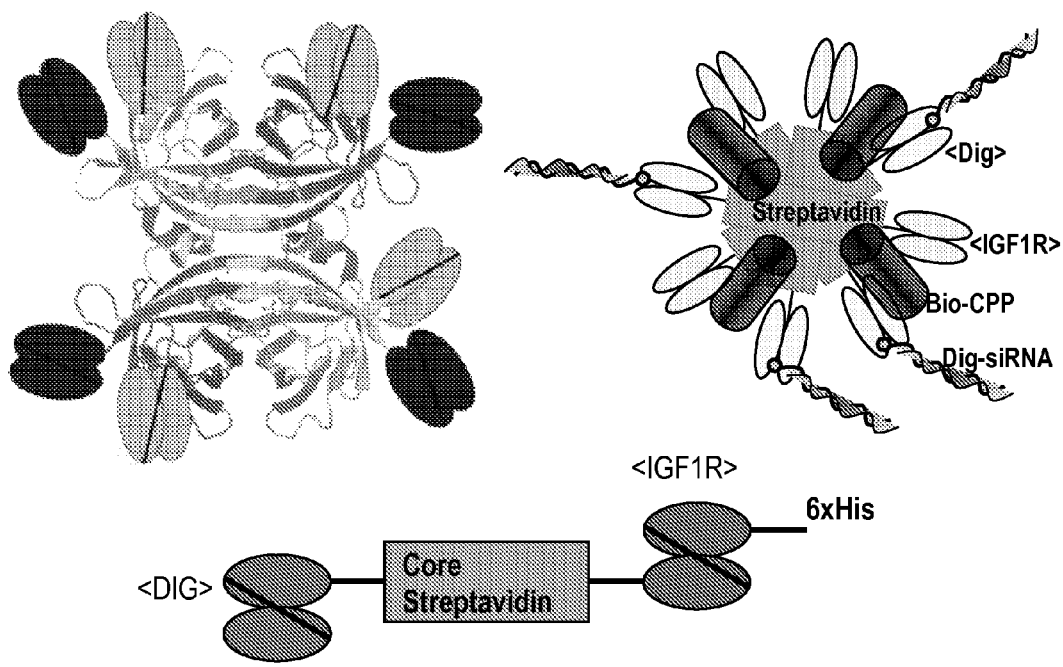
Figure 47:
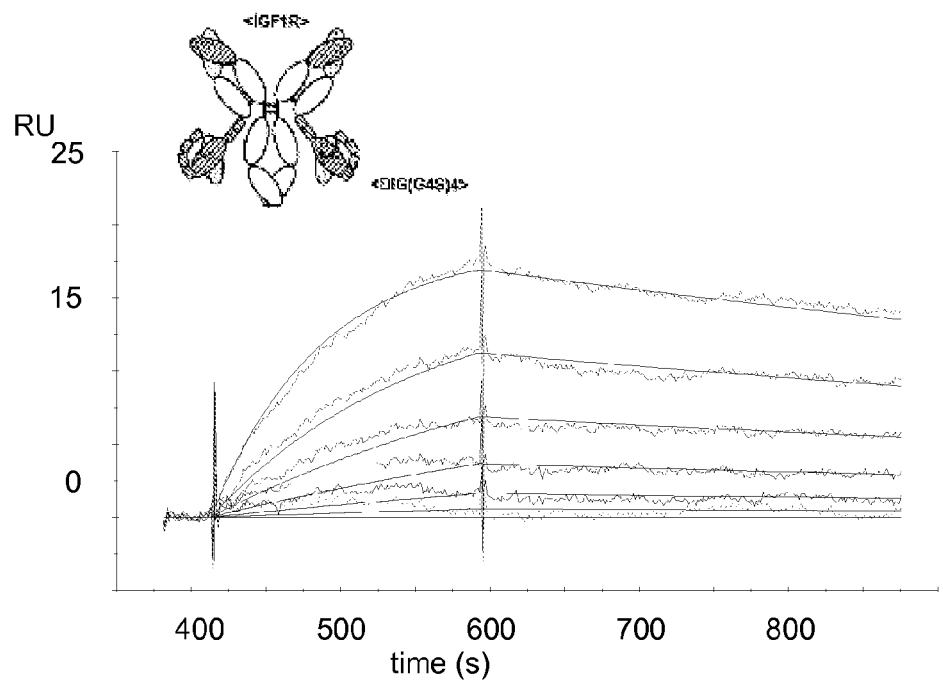
Figure 47:
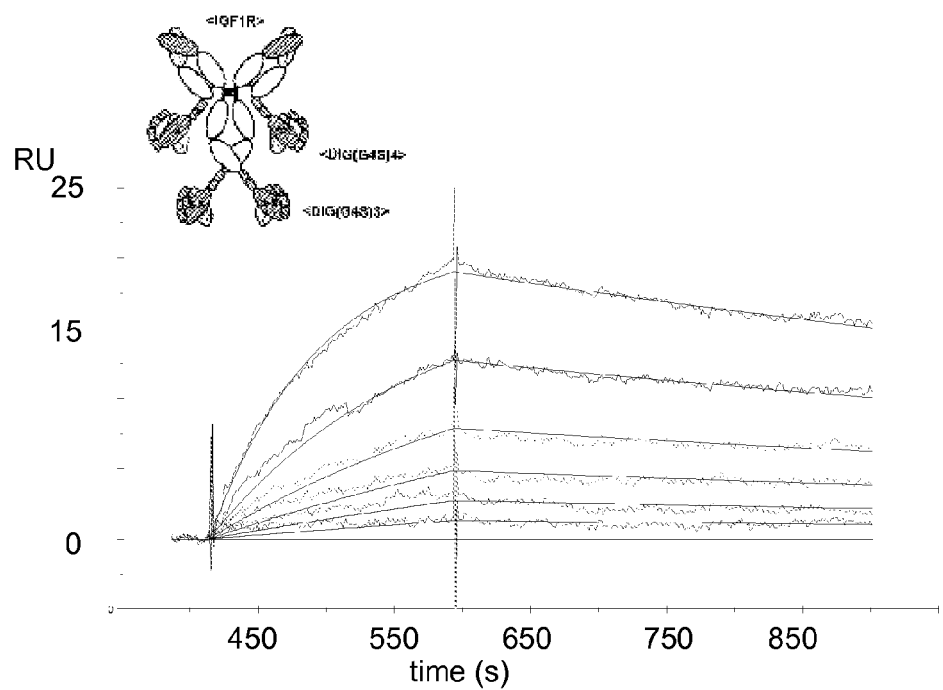
Figure 47:
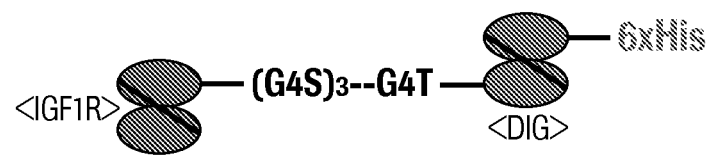
Figure 47:
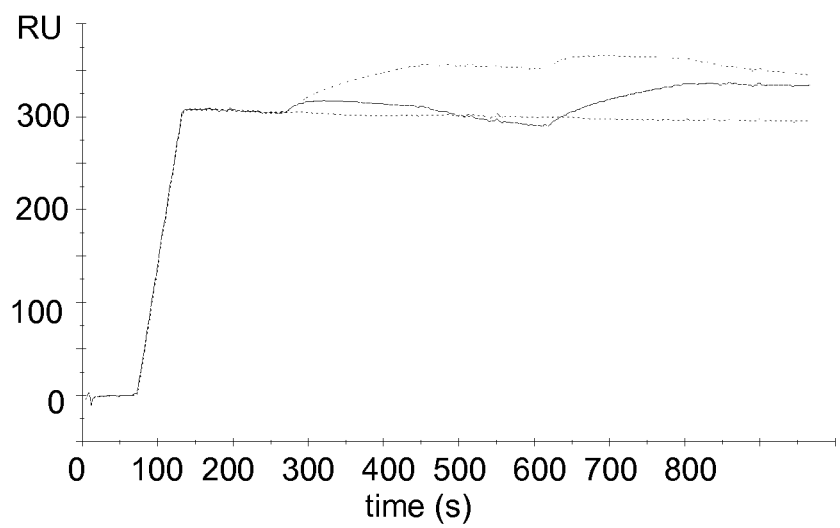
Figure 47:
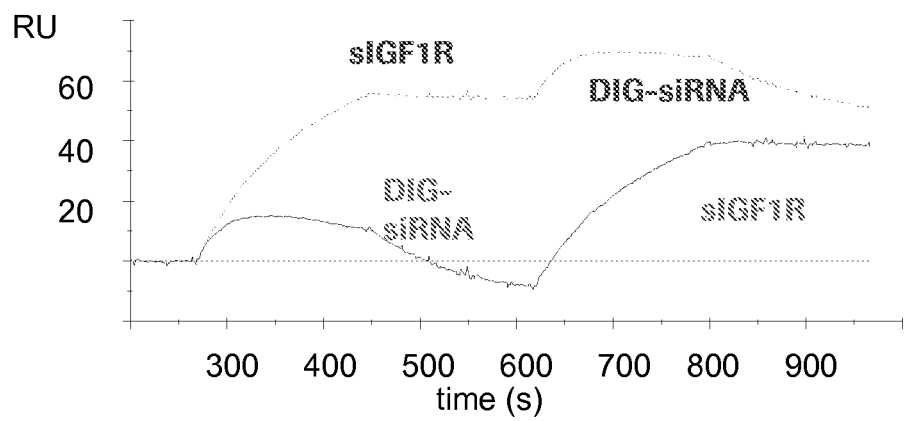
Figure 47:
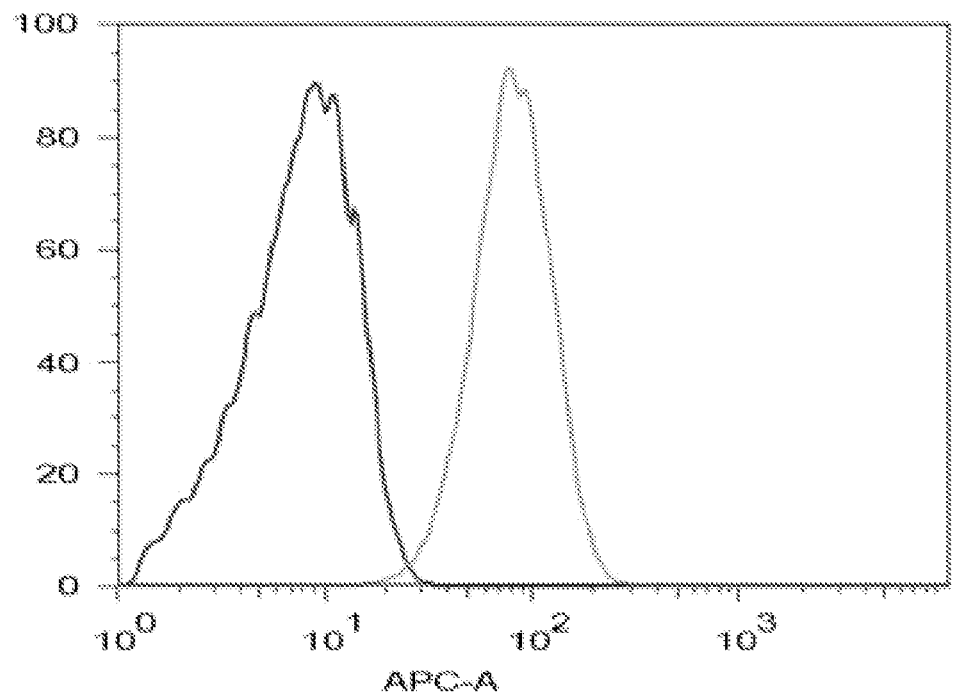
Figure 47:
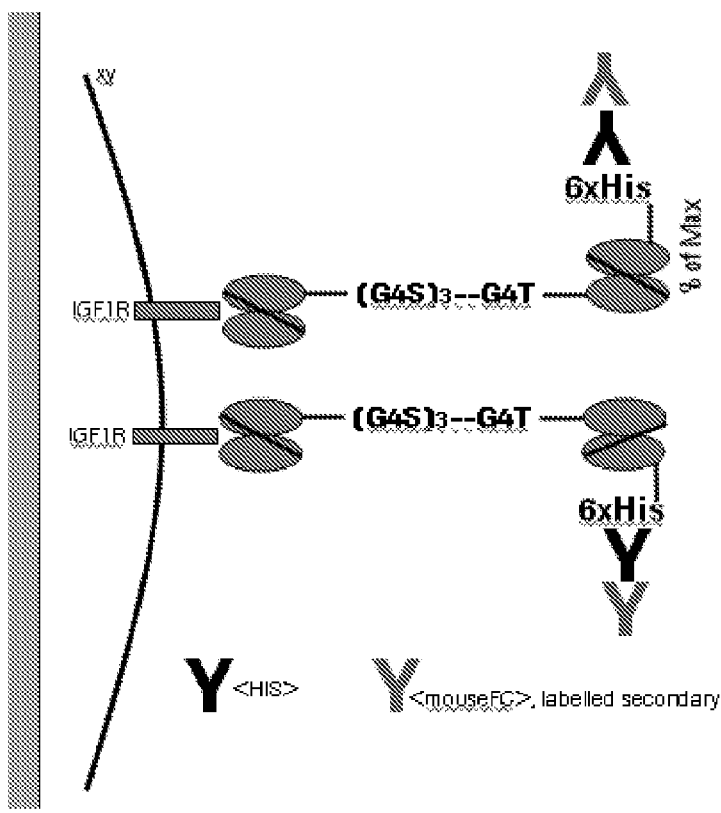
Figure 47:
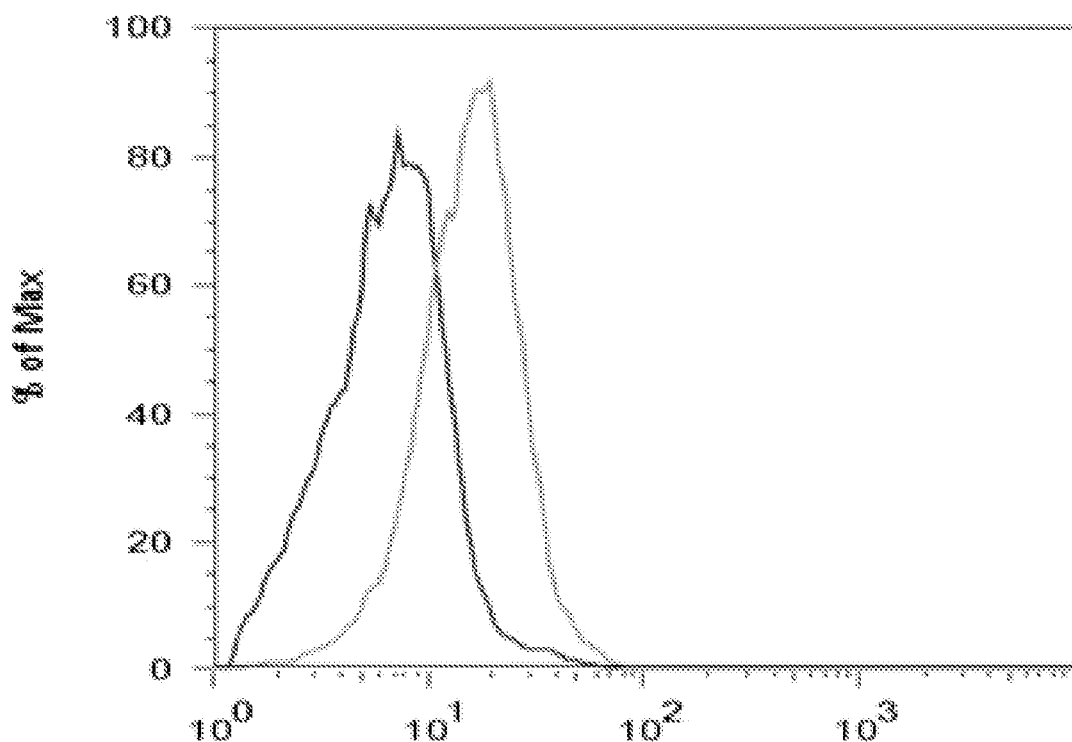
Figure 47:
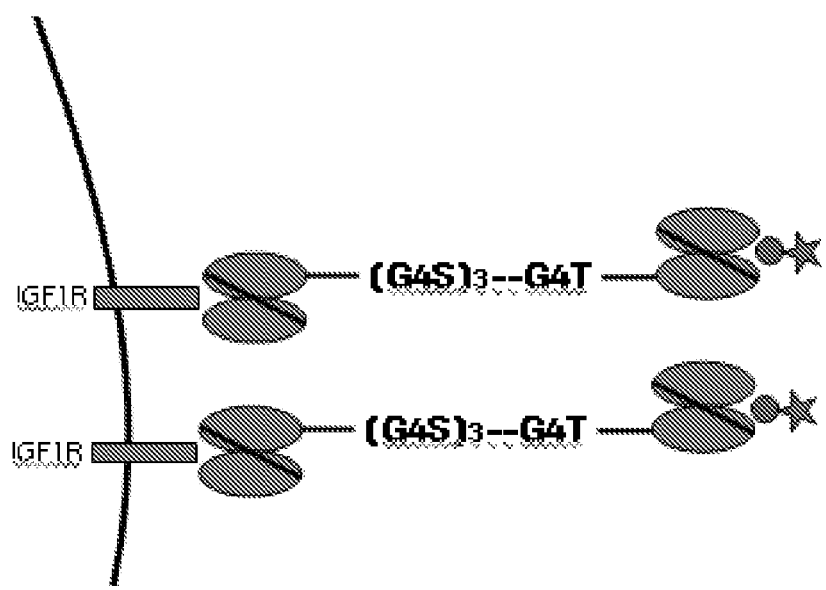
Figure 47:
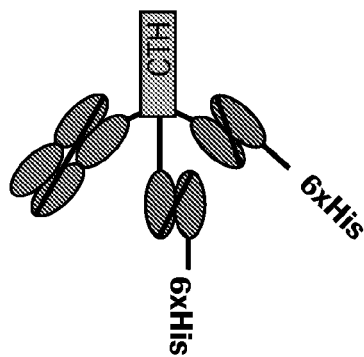
Figure 47:
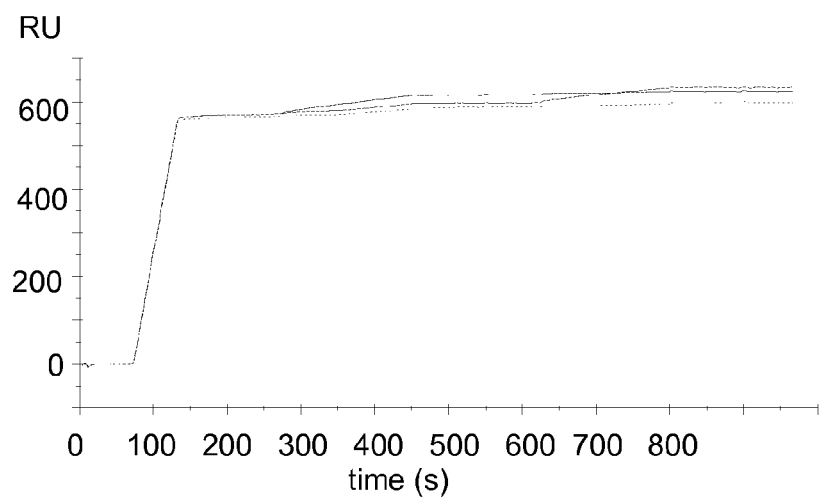
Figure 47:
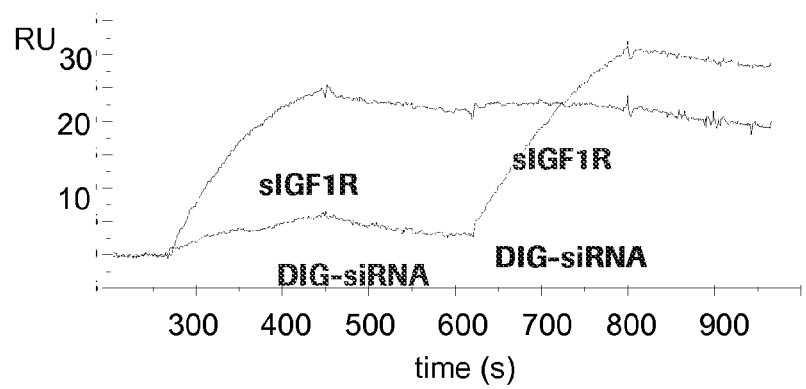
Figure 47:
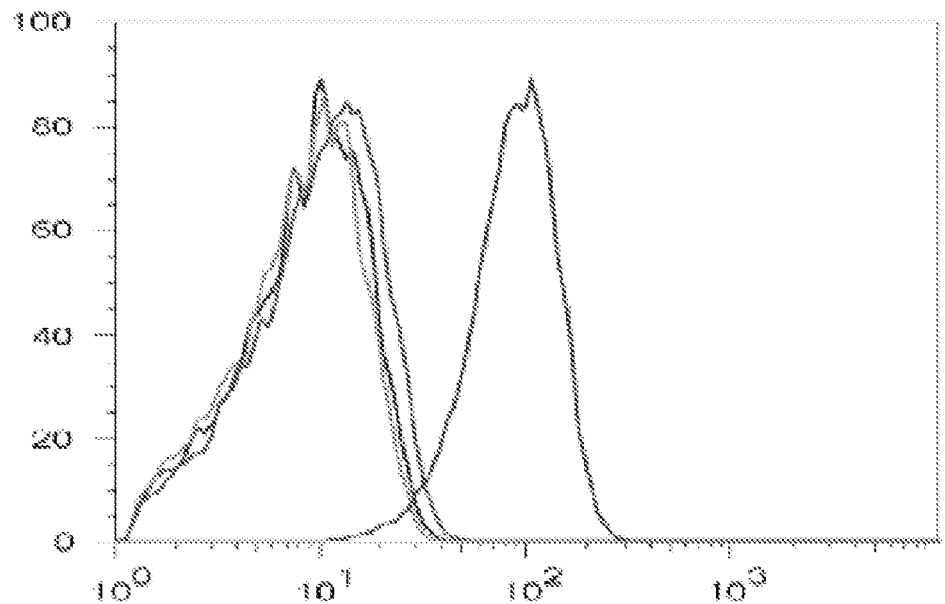
Figure 47:
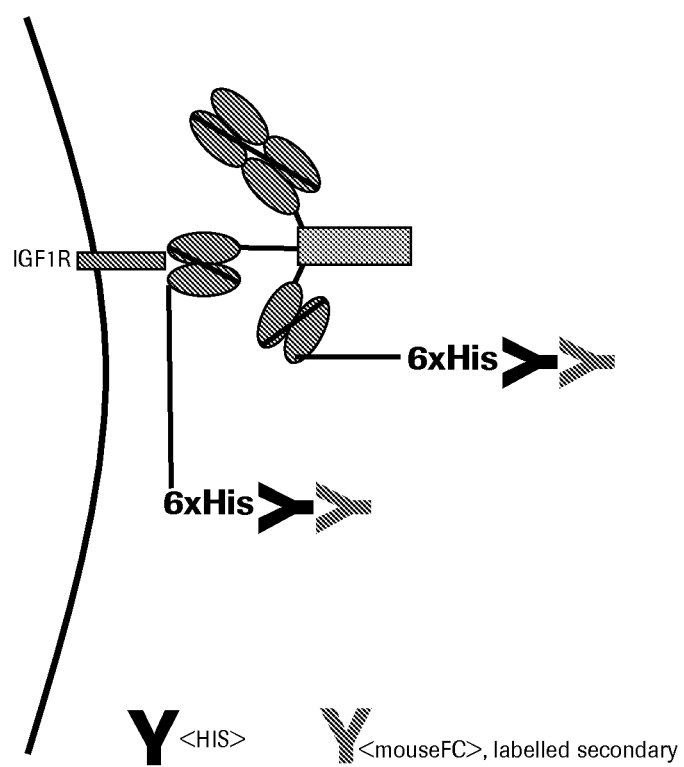
Figure 47:
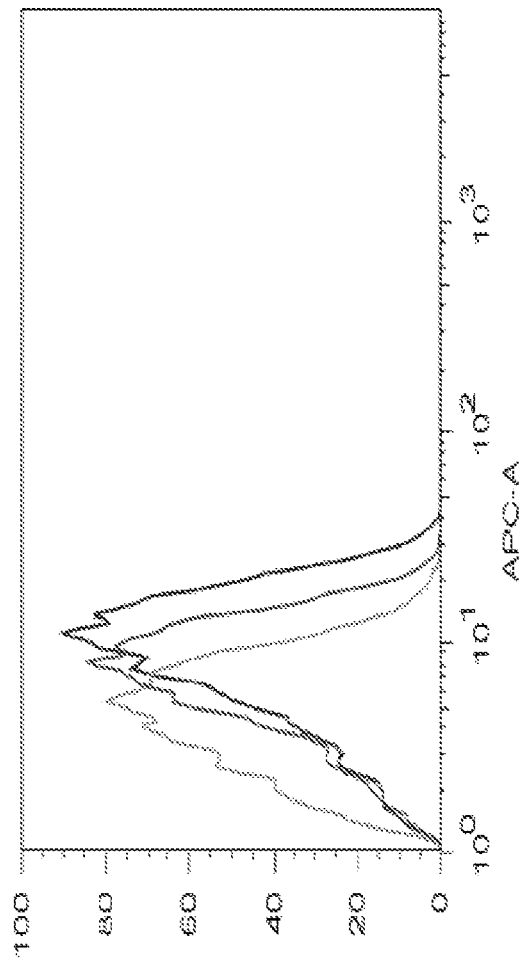
Figure 47:
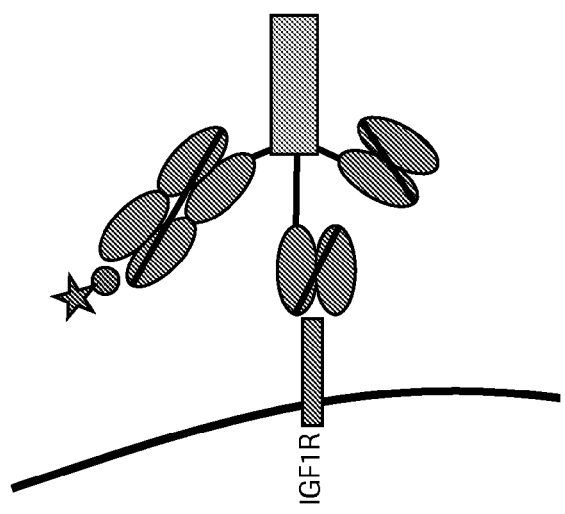
Figure 47:
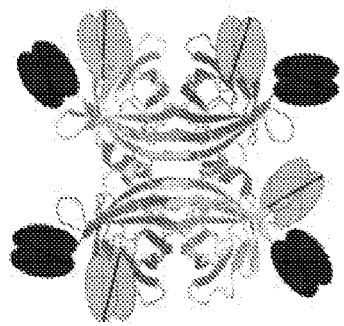
Figure 47:
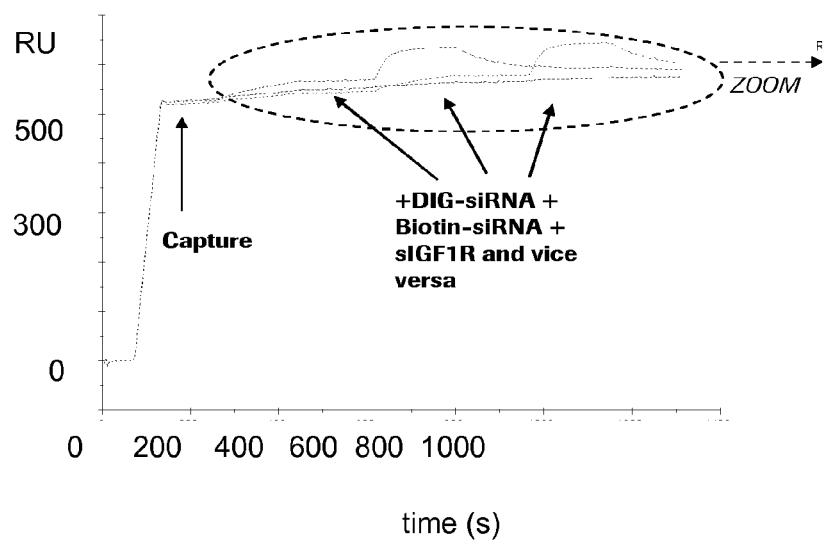
Figure 47:
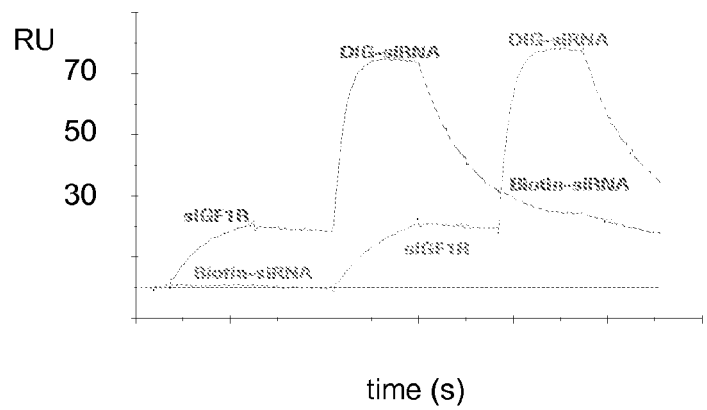
Figure 47:
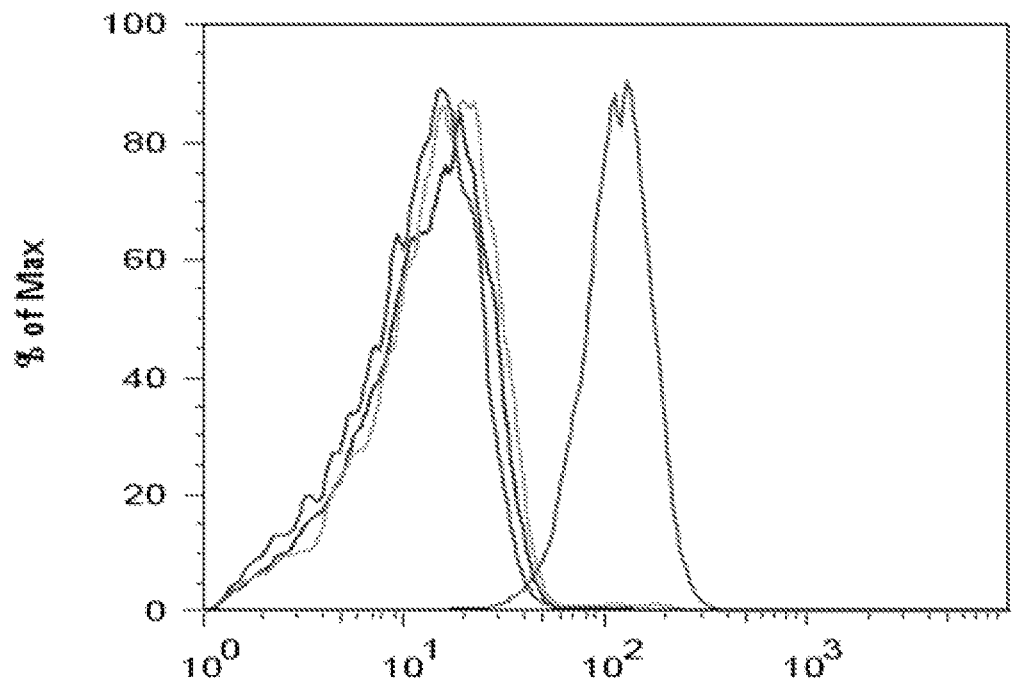
Figure 47:
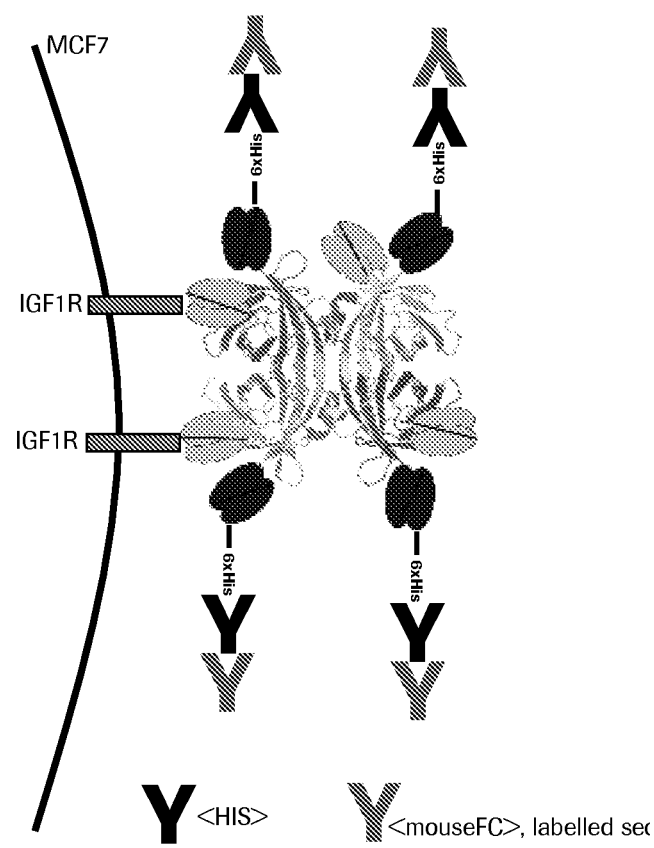
Figure 47:
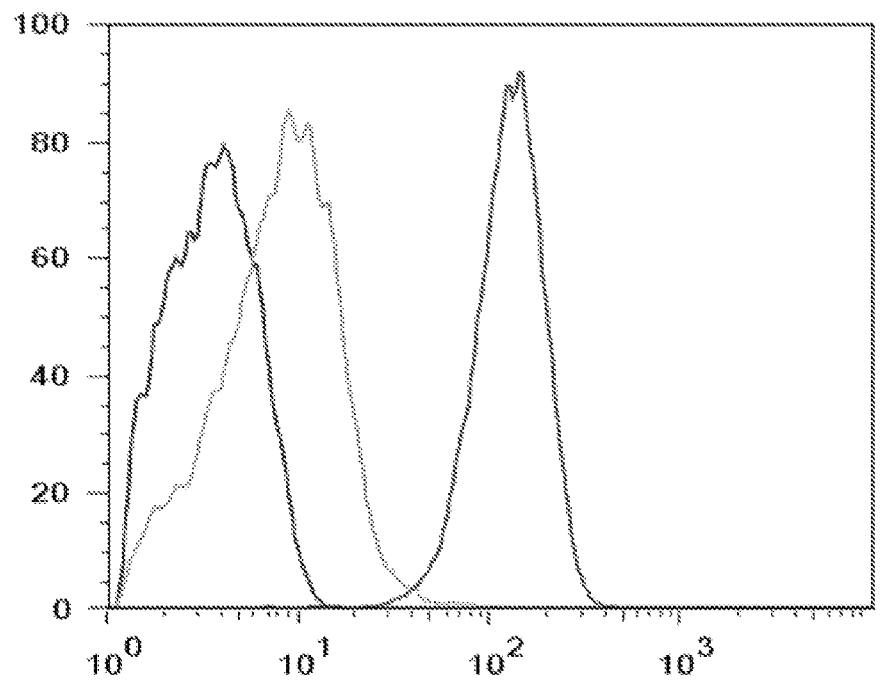
Figure 47:
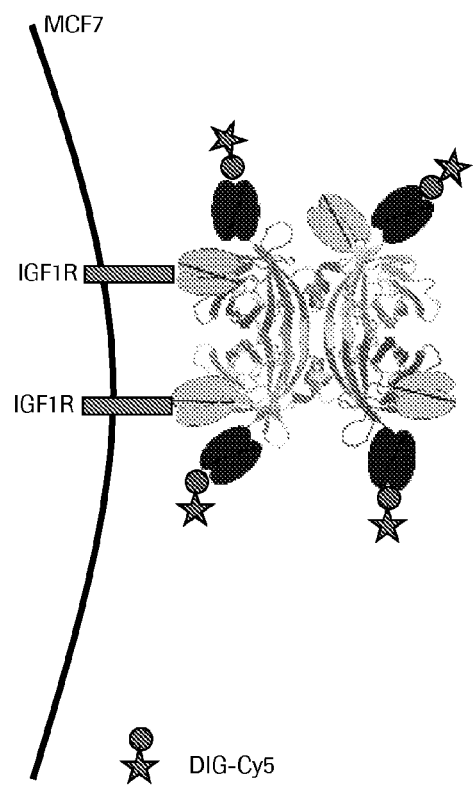
Figure 47:
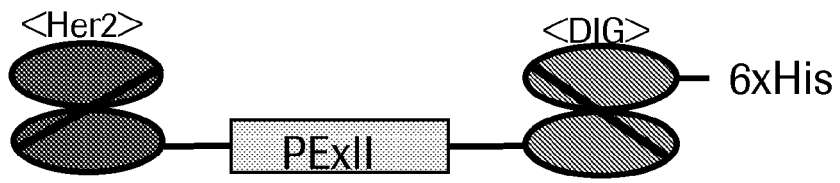
Figure 47:
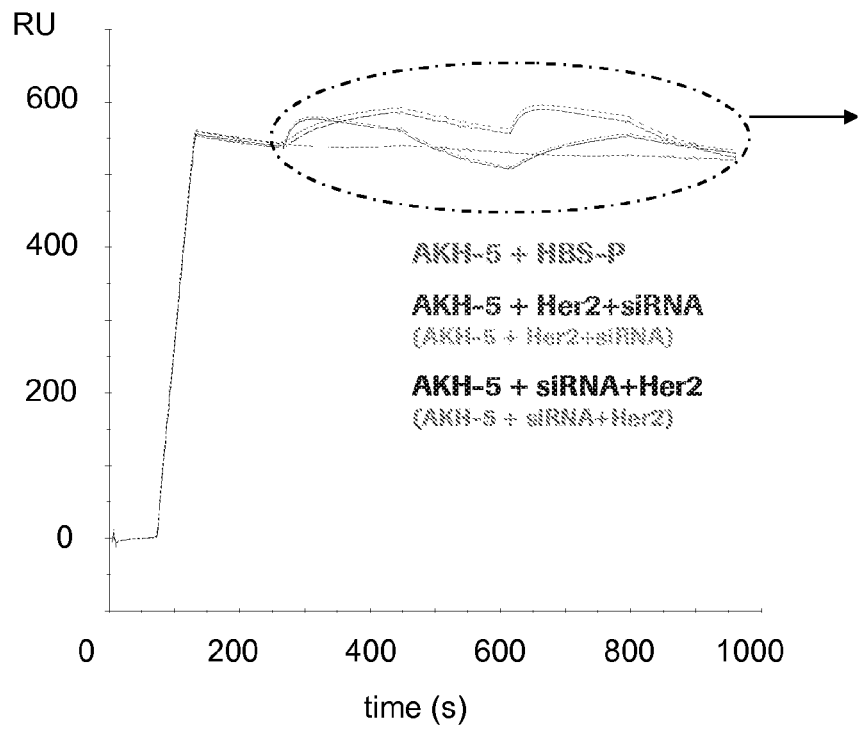
Figure 47:
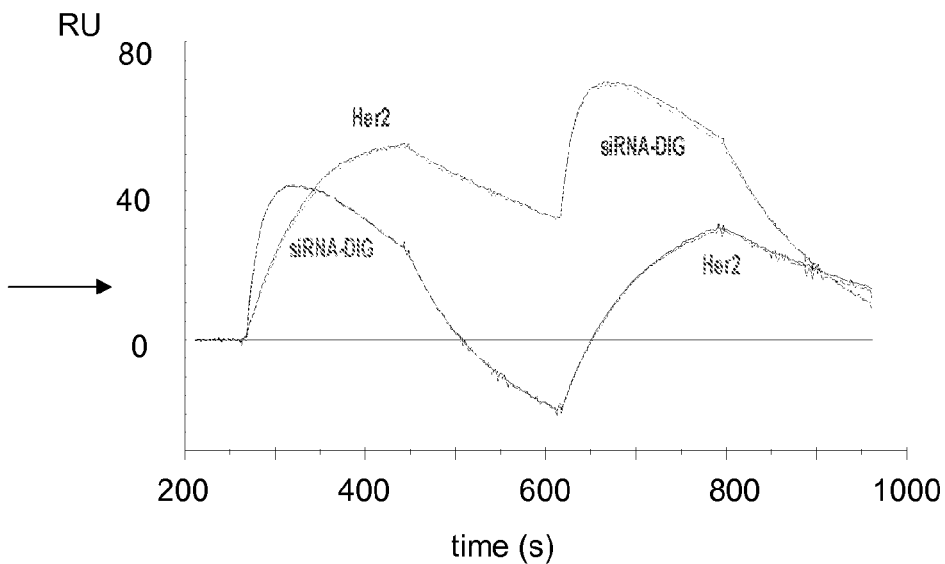

FIG. 47: a) Bi- and multispecific formats that are based on full-length IgGs as 'master molecule.
b) Bi- and multispecific formats that are composed of smaller antibody fragments and protein domains. A synthetic collagen like peptide (GPP) x10 adopts a collagen triple-helix (CTH) conformation and a cystein knot sequence (NCI) can be used to covalently link collagen trimeric constructs
c) target-streptavidin Dig fusion proteins
d)-x): Surface-Plasmon-Resonance (BiaCore) and FACS experiments show full retainment of binding specificity of entities that contain digoxygenin binding modules in different formats.
d) and e) BiaCore analysis of binding of IGF-1R: conc.Series 1.5625; 3.125; 6.25; 12.5; 25; 50 nM. d): <IGF1R-DIG>4421 (30 nM) KD=5 nM. e)<IGF1R-DIG-DIG>2321_4421 (16 nM) KD=2 nM.
f) Summary of binding and affinity of bispecific <DIG> antibodies.
g)-i) BiaCore analysis of binding of <IGF1R> scFv-(G4s)3-G4T-<DIG> scFv-His6 25 nM. g) schematic structure, h): AKH-61 10 nM+DIGsiRNA 50 nM+sIGF1R 25 nM i): DIG-siRNA 50 nM+sIGF1R 25 nM+AKH-61 10 nM
j) FACS analysis of IGF1R binding, grey peak: H322MAKH60+anti-His+anti-mouse, black peak: H322MAKH60+anti-mouse
k) FACS analysis of DIG binding
l)-m) BiaCore analysis of binding of <IGF1R> scFv-His6-<IGF1R> scFv-His6-1-<DIG> scFv-CTH 25 nM. 1) schematic structure. n) AKH-68/66 10 nM+DIGsiRNA 50 nM+sIGF1R 25 nM m): DIGsiRNA 50 nM+sIGF1R 25 nM+AKH-68/66 10 nM
o) FACS analysis of IGF1R binding. Single peak: AKH-68/66+anti-His+anti-mouse, multiple peaks: AKH-68/66+anti-mouse, anti-His (+anti-mouse), mouse isotype y-axis: % of max.
p) FACS analysis of DIG binding. light grey peak: DIG-Cy5, dark grey peak: AKH-68/66+DIG-Cy5, black peak: human isotype y-axis: % of max.
q)-s) BiaCore analysis of binding of target streptavidin Dig Fusion protein. q) schematic structure, r) AKH-42 10 nM+sIGF1R 25 nM+Biotin-siRNA 50 nM. s): sIGF1R 25 nM+DIGsiRNA 50 nM+Biotin-siRNA 50 nM on AKH-42 10 nM
(t) FACS analysis of IGF1R binding. Single peak: AKH-42+anti-His+anti-mouse, multiple peaks: AKH-42+anti-mouse, anti-His (+anti-mouse), mouse secondary y-axis: % of max.
u) FACS analysis of DIG binding. Single peak: AKH-42+anti-His+DIG-Cy5, multiple peaks: DIG-Cy5, cells only.
v)-x) BiaCore analysis of binding of <HER2> scFv-PExII-<DIG> scFv-His6 25 nM. v) schematic structure, w) BiaCore analysis, x) BiaCore analysis, zoom.

Figure 48:
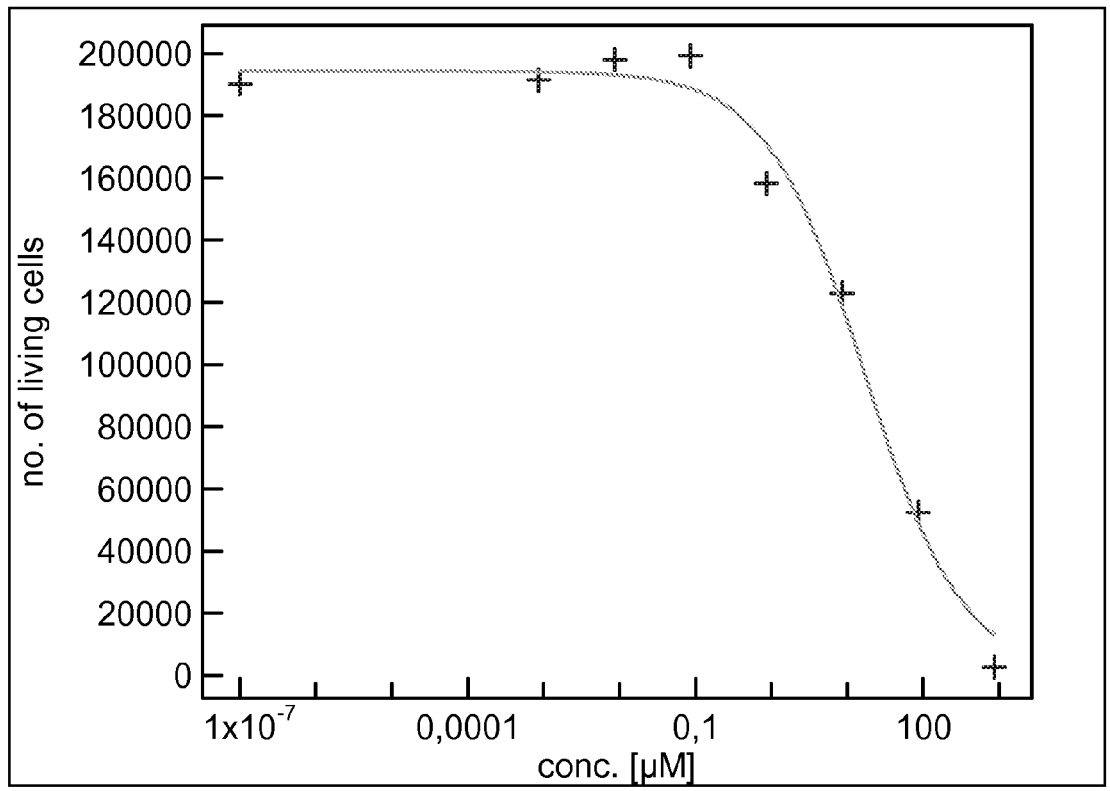
Figure 48:
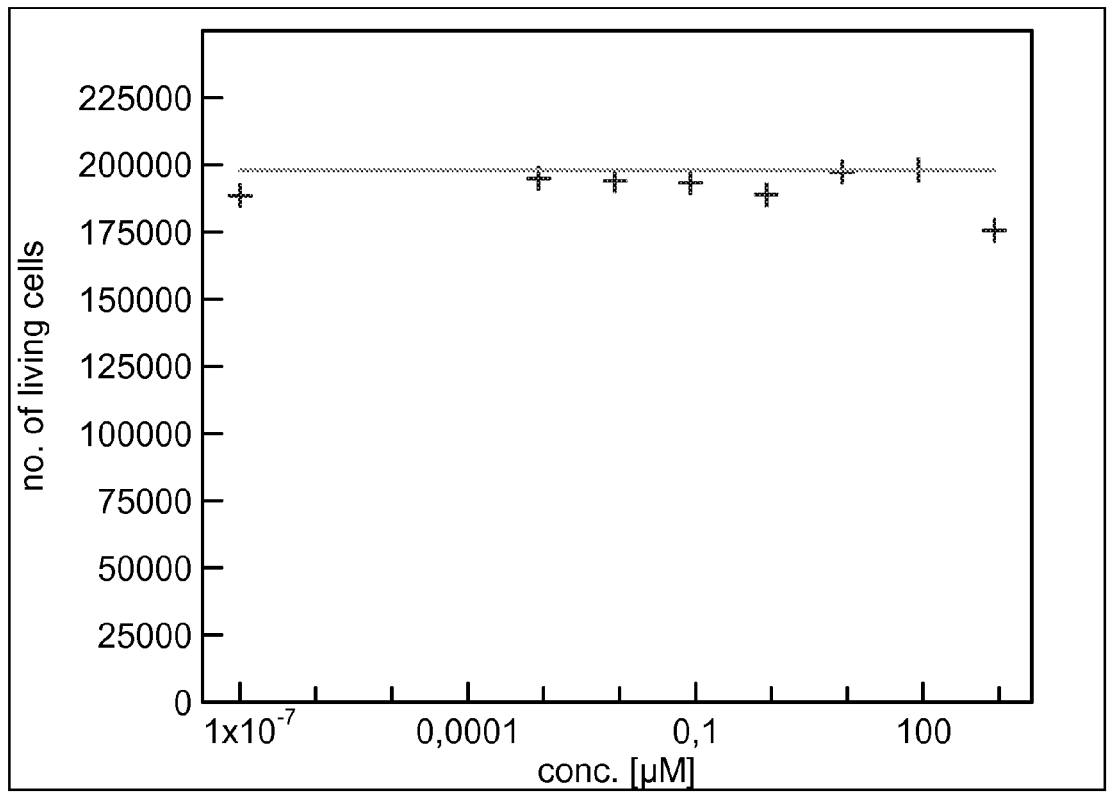
Figure 48:
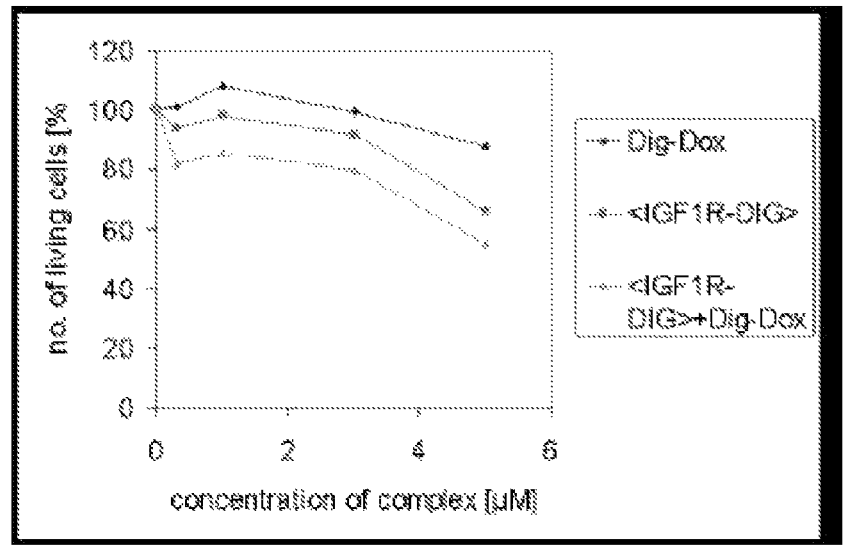
Figure 48:
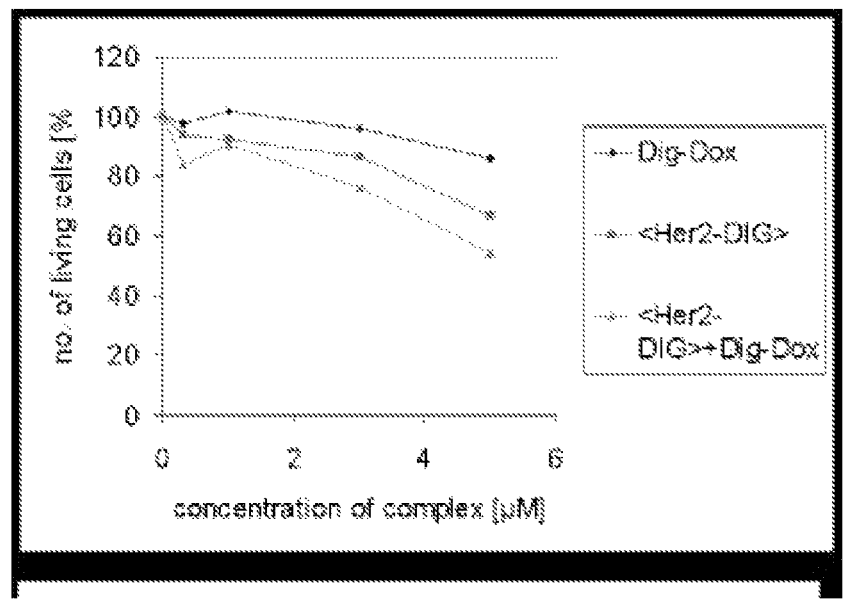
Figure 48:
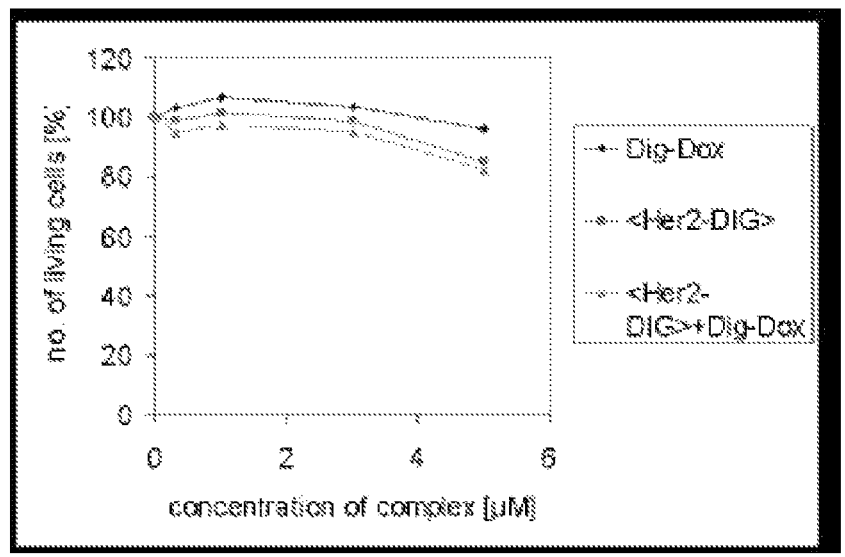

FIG. 48: Targeting experiments of digoxygenated doxorubicin with <Dig> bispecific antibodies.
a) and b): MDA-MB-468 (Her2+/−) cells were treated with doxorubicin (FIG. 48 a)) or digoxygenated doxorubicin (FIG. 48 b)) in the indicated concentrations for 48 hours.
c)-e): H322M (IGF1R+++) (FIG. 48 c)) KPL-4 (Her2+++) (FIG. 48 d)), and MDA-MB-468 (Her2+/−) (FIG. 48 e)) cells were treated with <Her2>-<Dig>-Dig-Dox or <IGF1R>-<Dig>-Dig-Dox complexes for 48 hrs Cell viability was assessed by applying the CellTiter Glo Luminescent Cell Viability Assay (Promega, Madison, Wis.).

Figure 49:
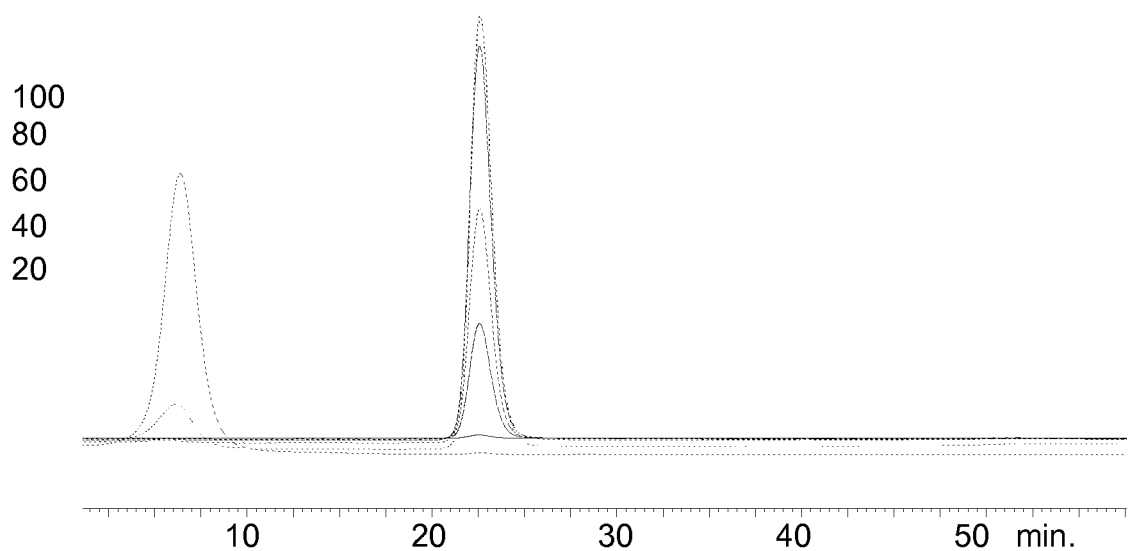
Figure 49:
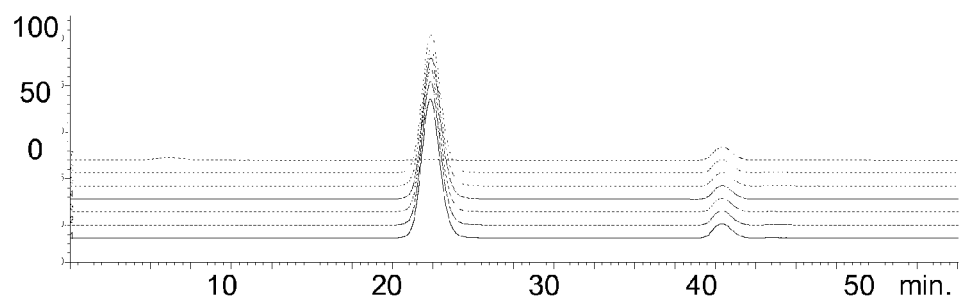
Figure 49:
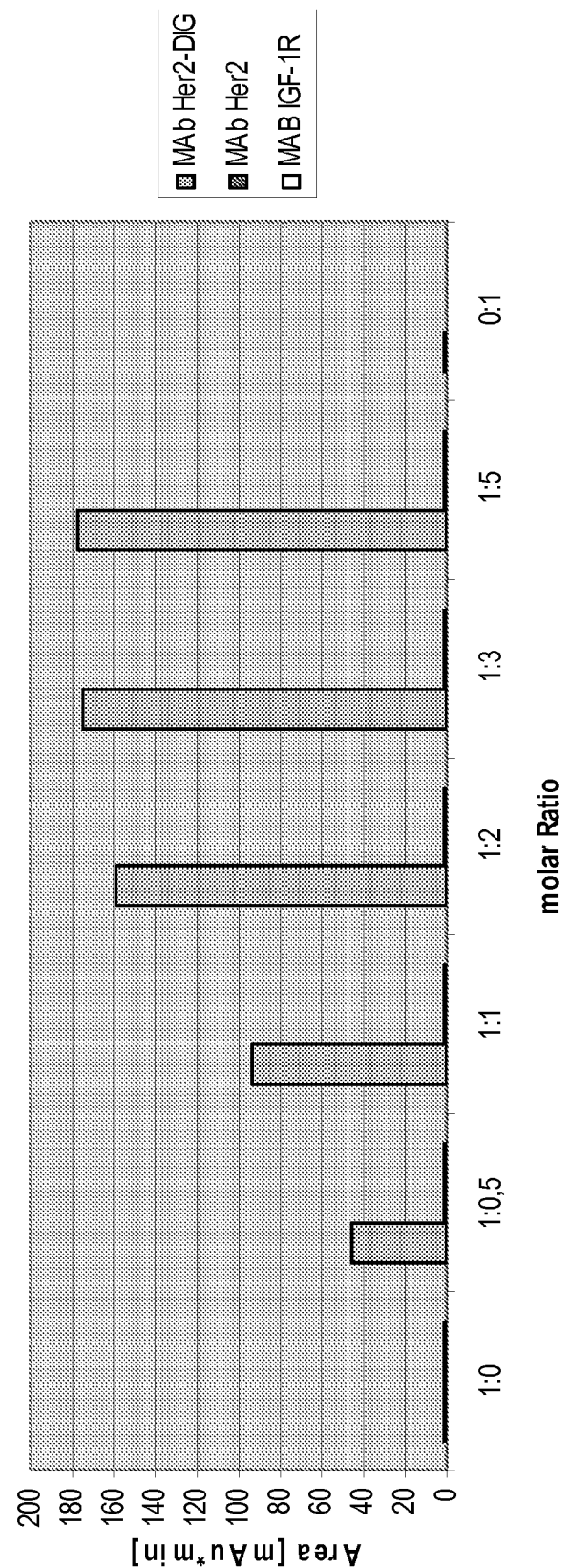

FIG. 49: a) and b) Size exclusion chromatography of digoxygenated Cy5/<Her2>-<Dig> bispecific antibody complex indicates charging ratio of 2:1 (DIG-Cy5: <Her2>-<Dig>) c) and d) Evaluation of SEC FIG. 50: a) Experimental setup and zoom into non-deconvoluted native mass spectra for determination of vehicle to payload charging. Binding of Eg5-siRNA-(2x)Dig (upper panel) and Eg5-siRNA-(1x)Dig (lower panel) to <Her2-Dig> b) Native mass spectroscopy indicates the charging of 2 or less payloads per targeting vehicle. Applying mono-digoxygenated nucleic acids, charged targeting vehicles are observed that contain more than one but no more than two payloads per vehicle. Application of bi-digoxygenated nucleic acids results in increased detection of molecules with lower charging ratios, i.e. most vehicles are charged with one payload. This indicates charging ratios of one Dig per Dig-binding entity.

Figure 51:
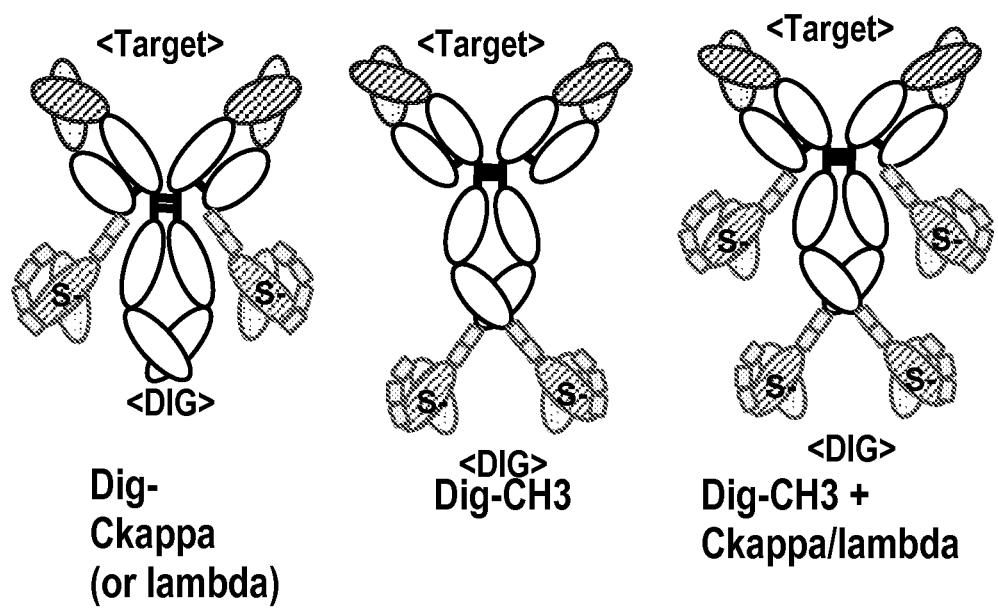
Figure 51:
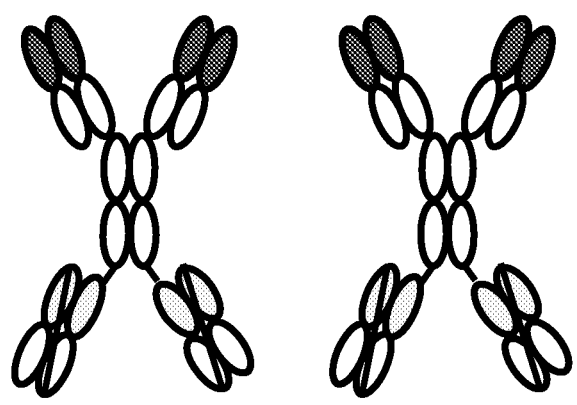
Figure 51:
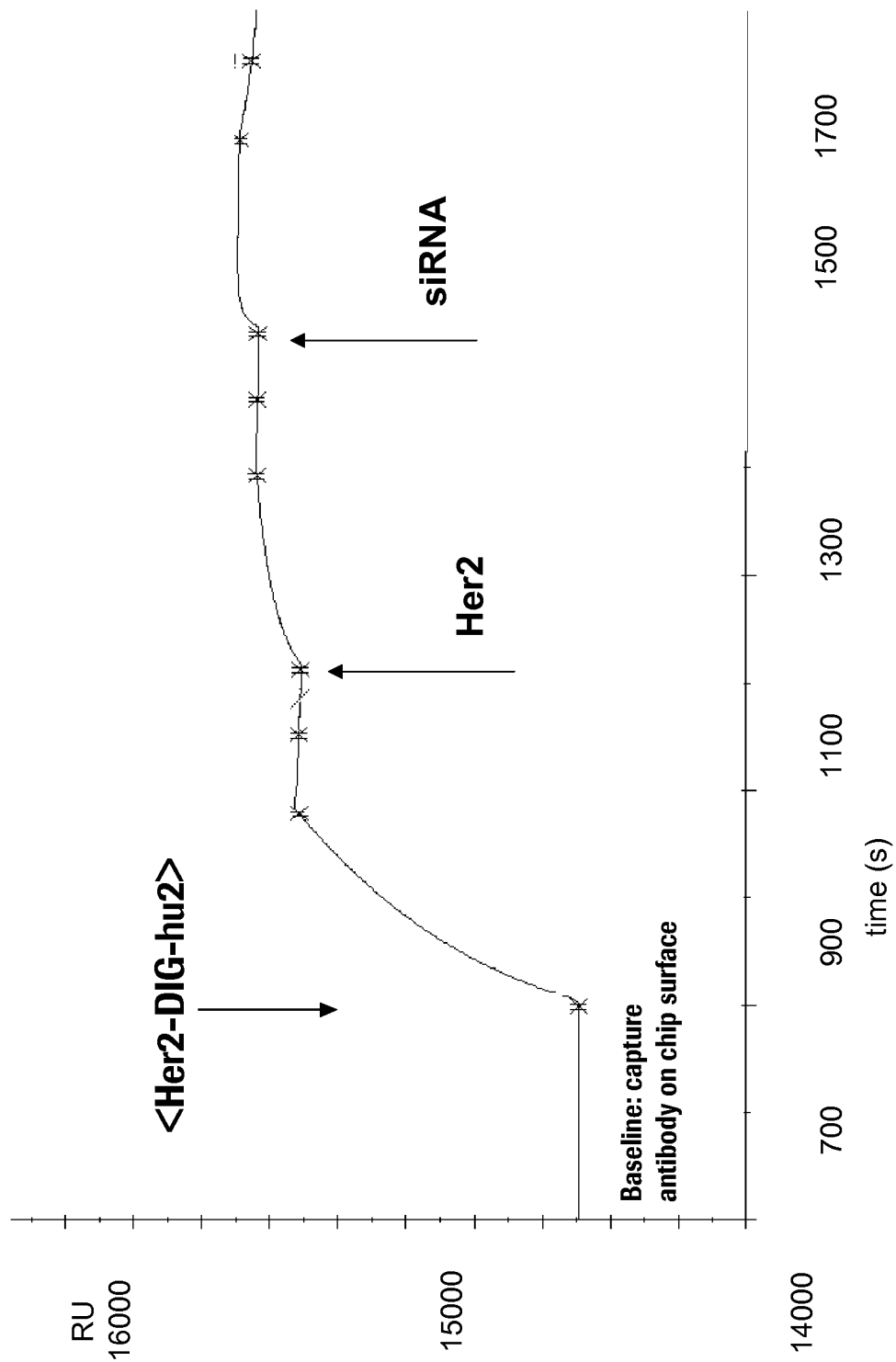
Figure 51:
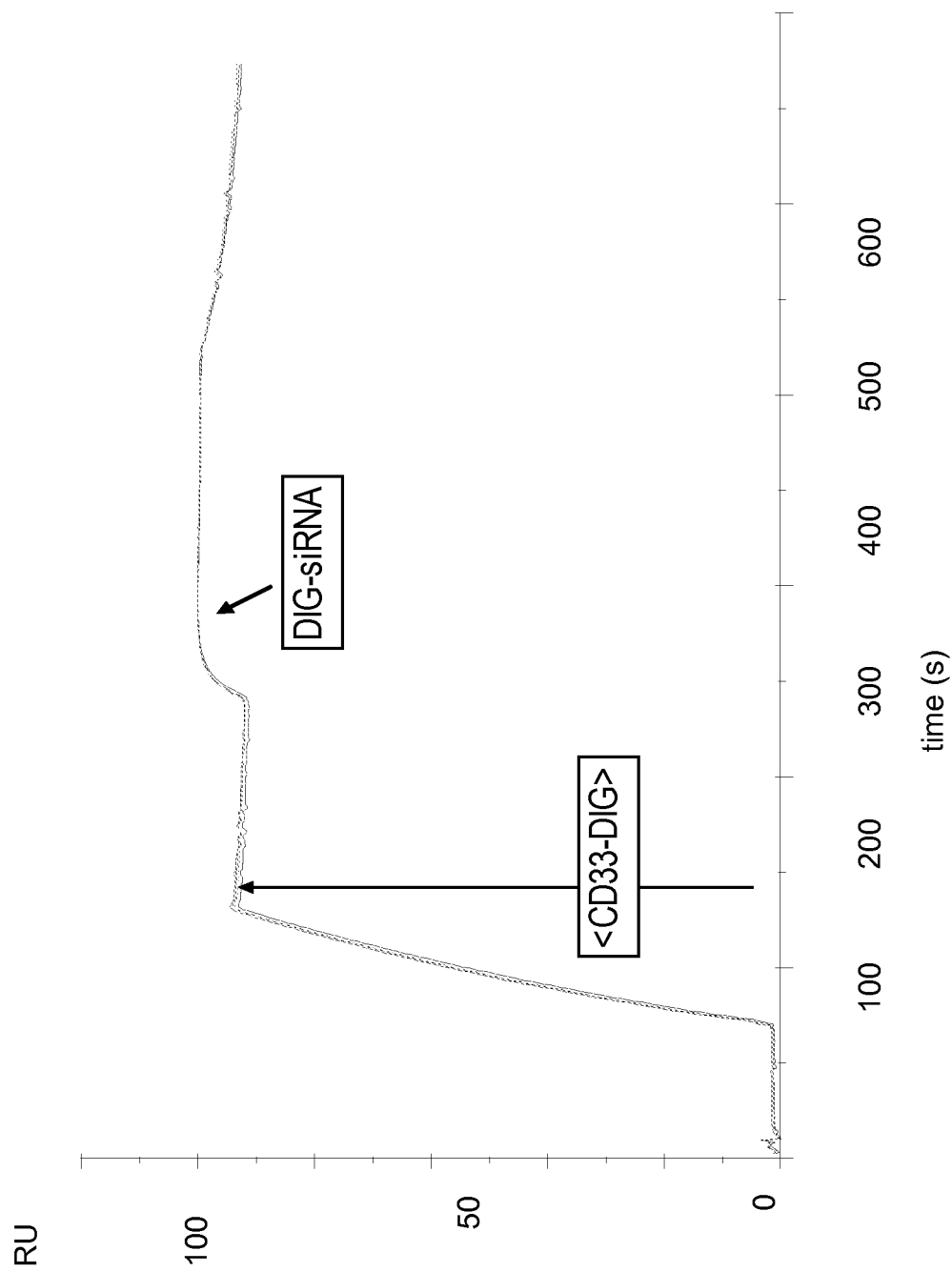
Figure 51:
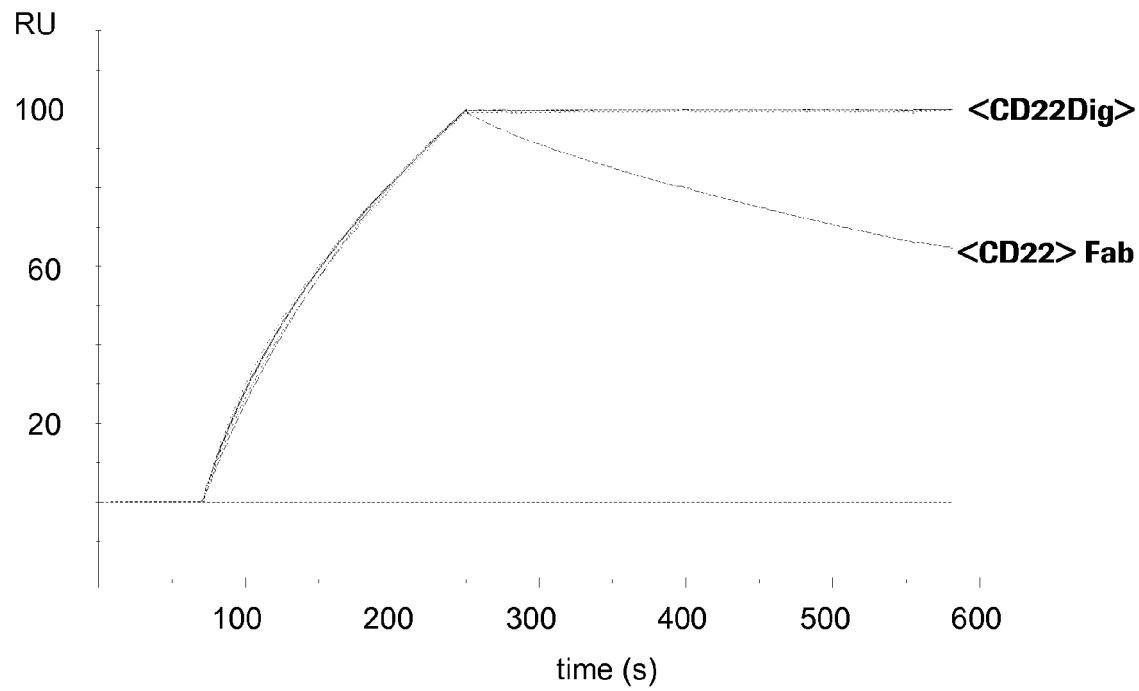
Figure 51:
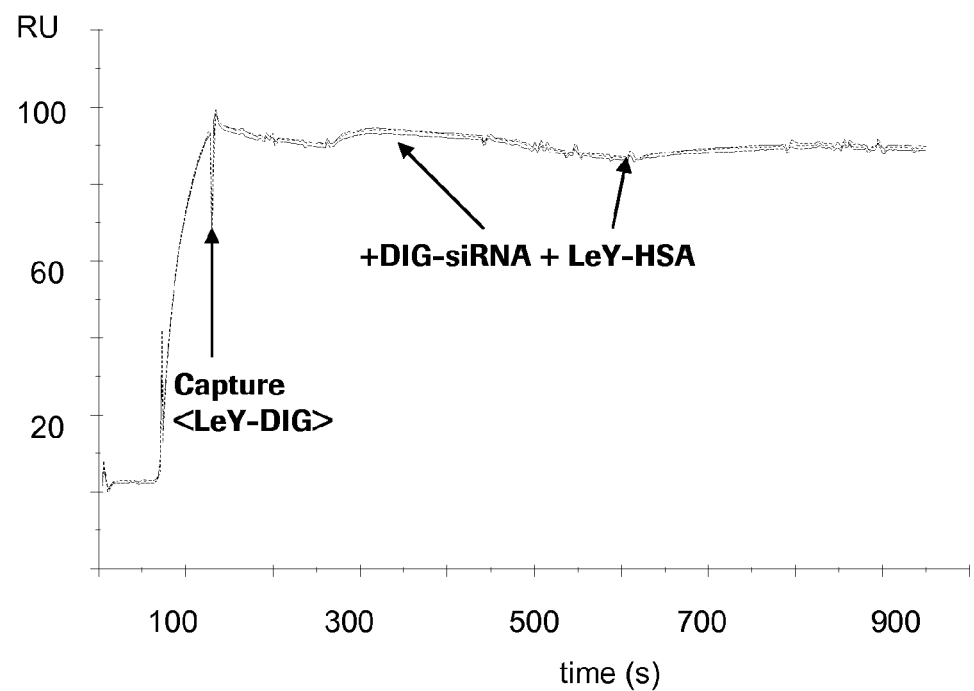
Figure 51:
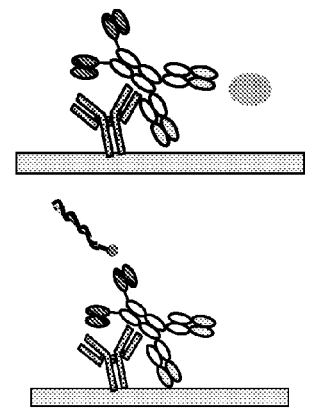

FIG. 51: a) and b) Vehicles for hapten-mediated payload delivery to different cell surface antigens c) vehicles targeting VEGFR2, d) to g): Surface-Plasmon-Resonance experiments show full retainment of binding specificity and affinity of cell-surface targeting and digoxygenin binding modules. d) Binding of Her2 and siRNA to <Her2-DIG-hu2>, e) Binding of <CD33>-<DIG> to human CD33-Fc fusion (ligand) and additional binding of DIG-siRNA f) Binding of anti-CD22 antibodies to immobilized CD22/Fc g) Additive binding of DIG-siRNA and LeY-HAS to <LeY>-<DIG> h) Binding of <CDCP1>-<DIG>.

Figure 52:
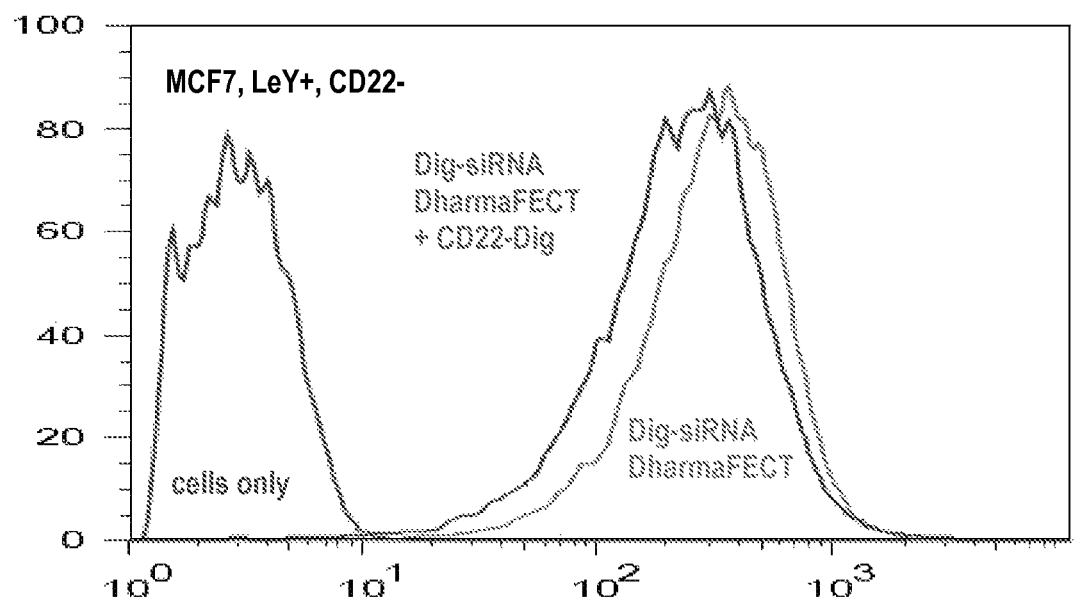
Figure 52:
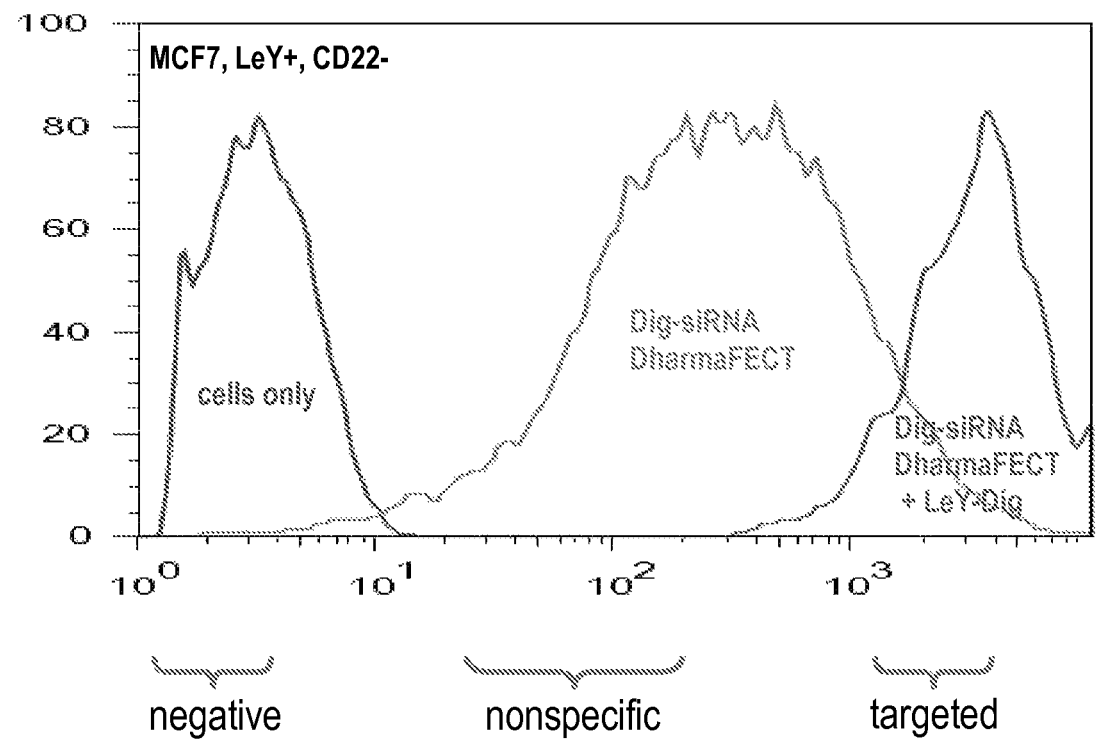
Figure 52:
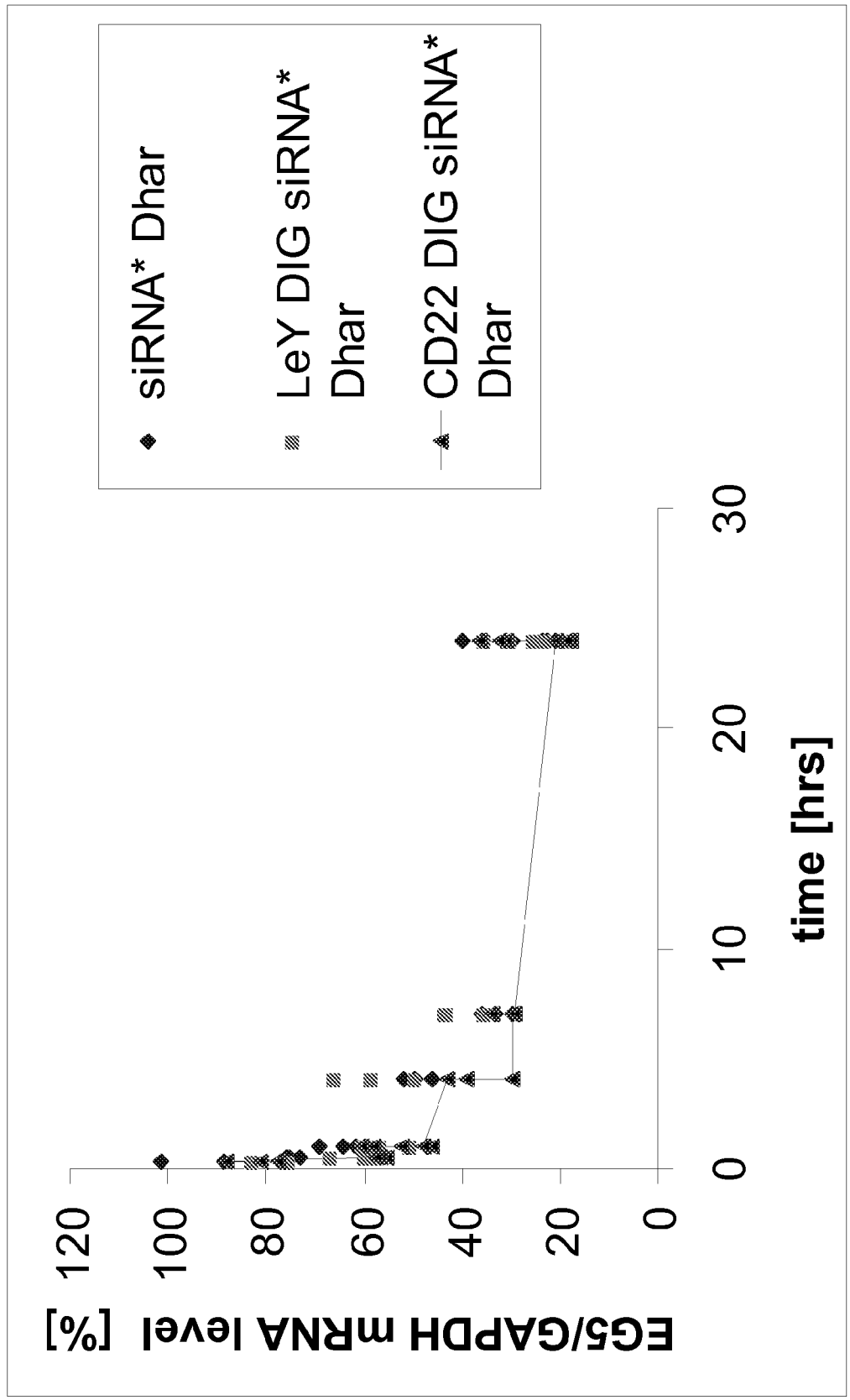

FIG. 52: a) and b) The result of a FACS analysis of MCF7 cells a) treated with the complexes DharmaFECT/DIG-siRNA-Cy5 and CD22-DIG/DharmaFECT/DIG-siRNA-Cy5 b) treated with the complexes DharmaFECT/DIG-siRNA-Cy5 and LeY-DIG/DharmaFECT/DIG-siRNA-Cy5 (lower panel) are shown. LeY-DIG leads to a strong accumulation of DharmaFECT/DIG-siRNA-Cy5 on the target cells. c) Eg5/GAPDH mRNA levels of MCF7 cells treated with DharmaFECT/DIG-siRNA-Cy5, CD22-DIG/DharmaFECT/DIG-siRNA-Cy5 or LeY-DIG/DharmaFECT/DIG-siRNA-Cy5 for the indicated time points are shown. RNAi is visible in all groups, but the unspecific stickiness of DharmaFECT affects the specificity of LeY-DIG.

Figure 53:
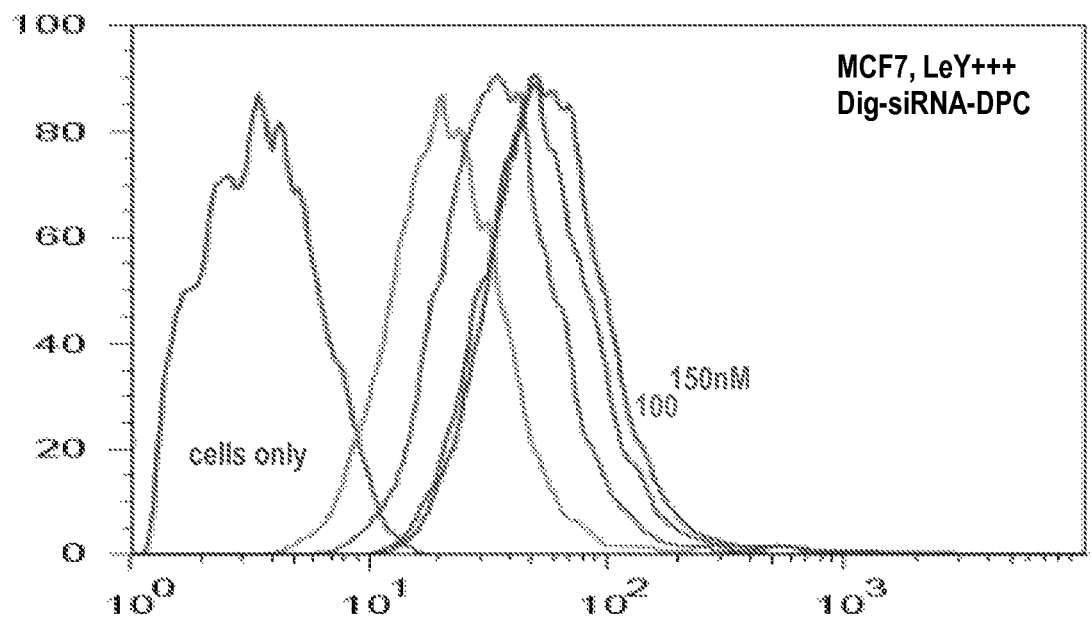
Figure 53:
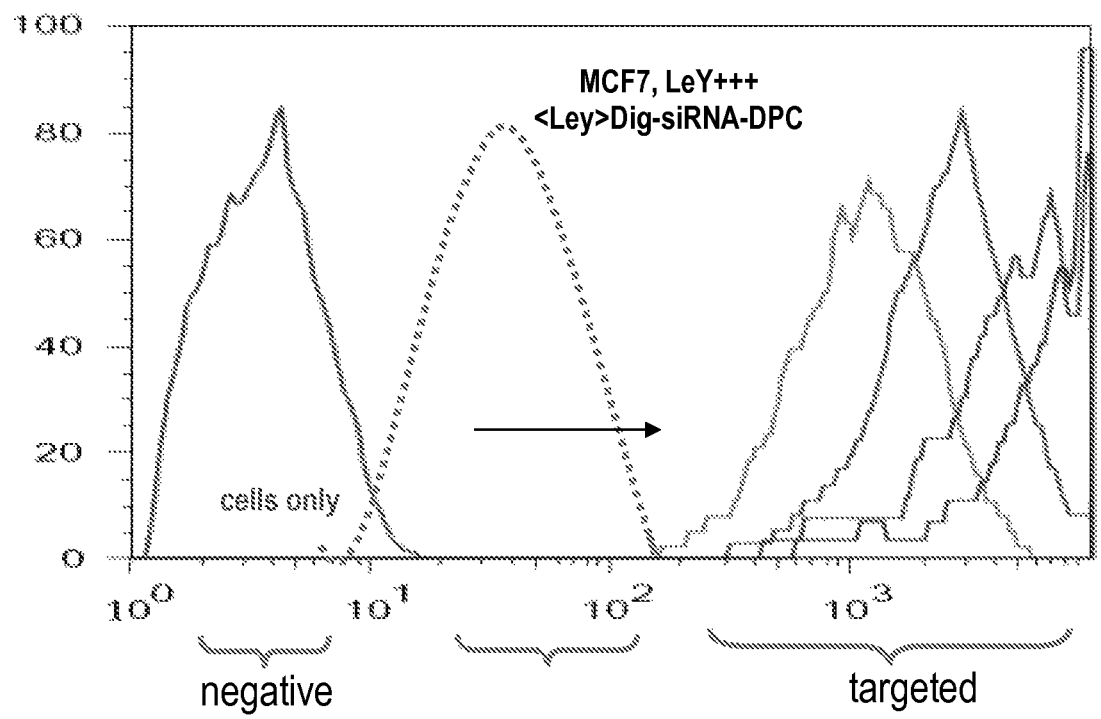
Figure 53:
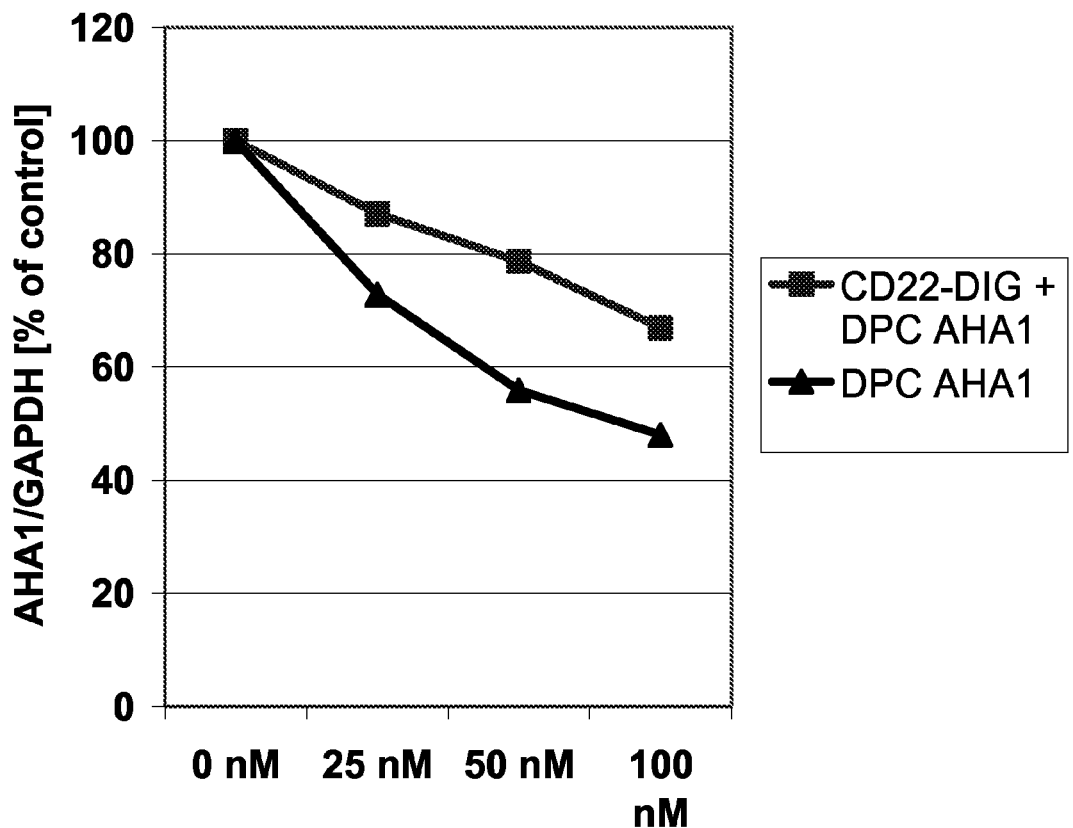
Figure 53:
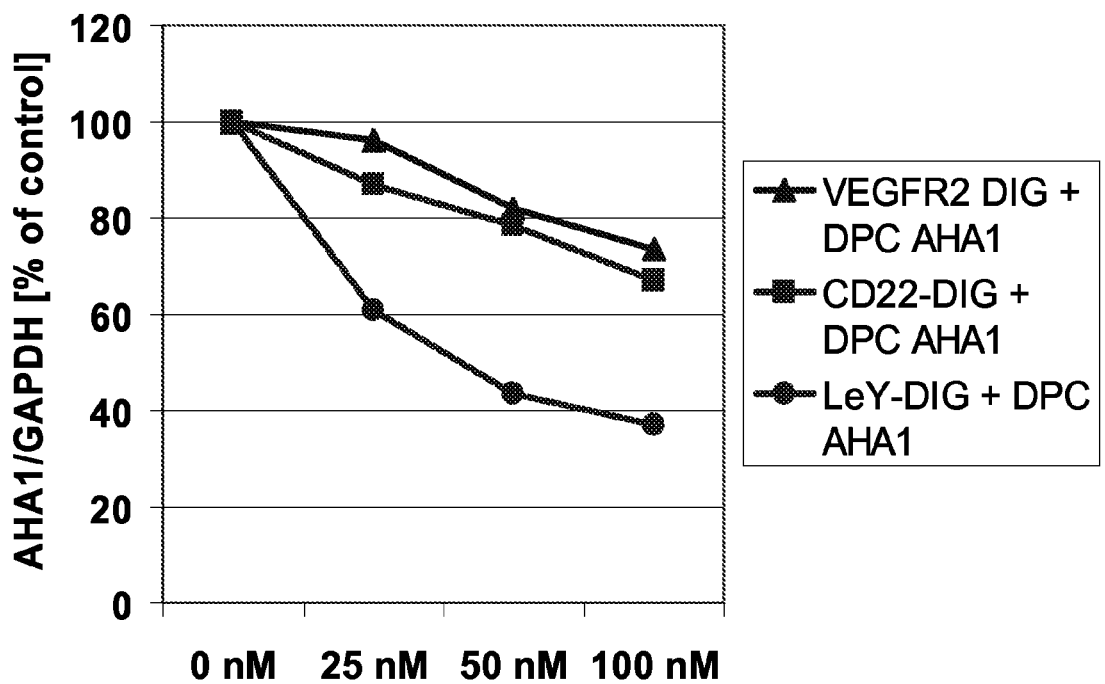
Figure 53:
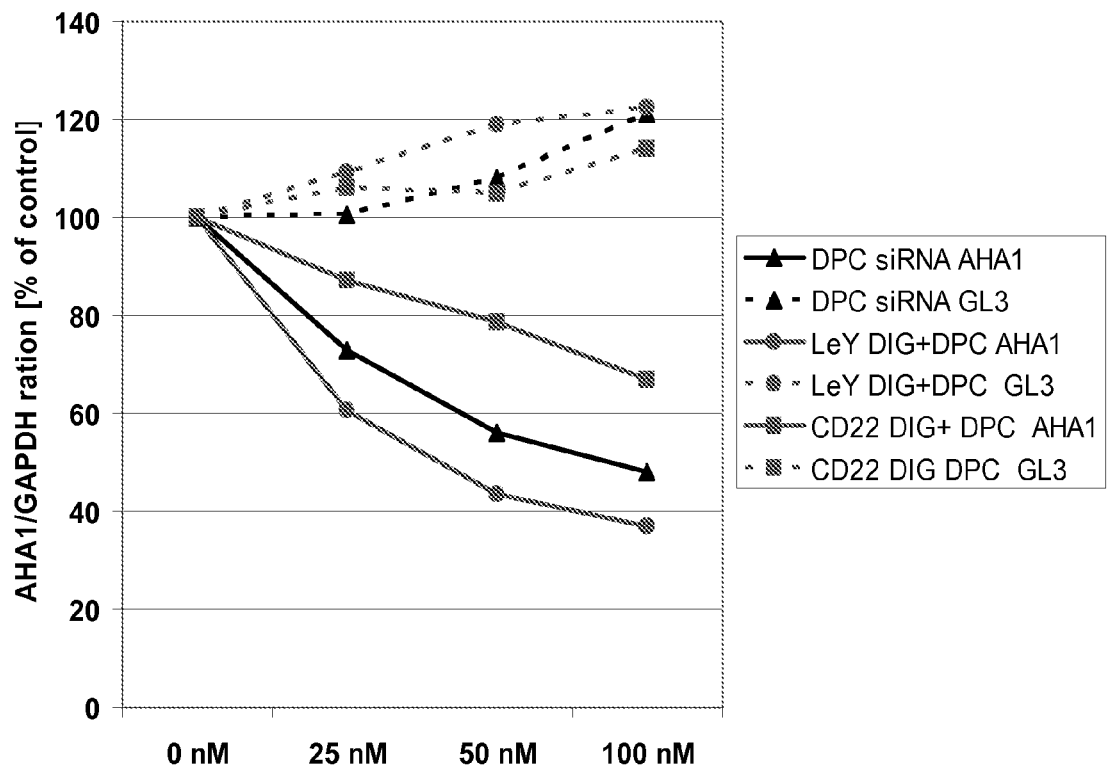
Figure 53:
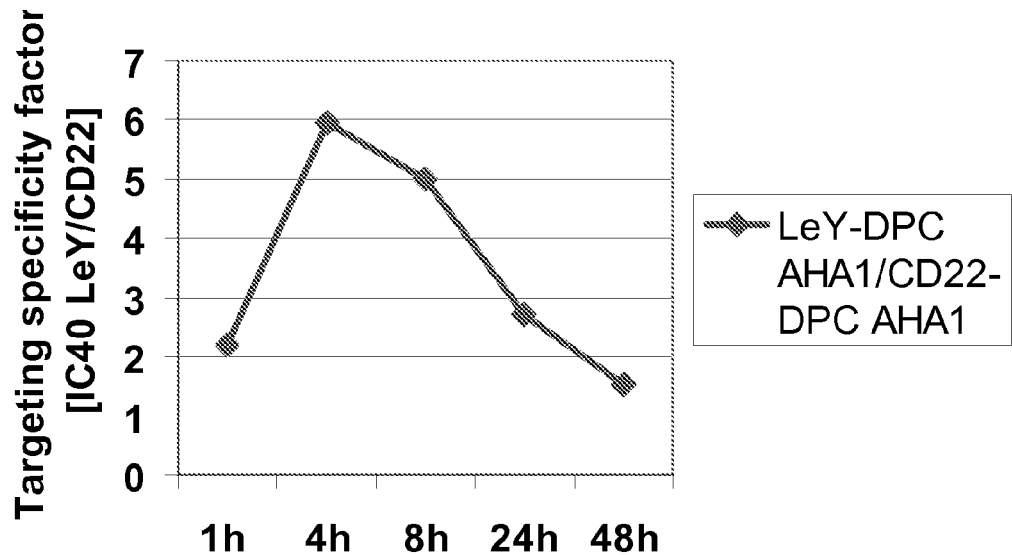

FIG. 53: The result of a FACS analysis of MCF7 cells treated with increasing concentrations of DIG-DPC-siRNA-Cy3 (25, 50, 100, 150 nM, FIG. 53a) or treated with increasing concentrations of the complex LeY-DIG/DIG-DPC-siRNA-Cy3 (25, 50, 100, 150 nM FIG. 53 b) are shown. LeY-DIG leads to a strong accumulation of DIG-DPC-siRNA-Cy3 on the target cells. c) AhaI/GAPDH mRNA levels of MCF7 cells treated with increasing concentrations of DIG-DPC-AhaI or the complex CD22-DIG/DIG-DPC-AhaI is presented. d) AhaI/GAPDH mRNA levels of MCF7 cells treated with increasing concentrations of the complex CD22-DIG/DIG-DPC-AhaI, VEGFR2-DIG/DIG-DPC-AhaI or LeY-DIG/DIG-DPC-AhaI is shown. e) AhaI/GAPDH mRNA levels of MCF7 cells treated with increasing concentrations of DIG-DPC-AhaI or the complex CD22-DIG/DIG-DPC-AhaI or LeY-DIG/DIG-DPC-AhaI in comparison to DIG-DPC-GL3 or the complex CD22-DIG/DIG-DPC-GL3 or LeY-DIG/DIG-DPC-GL3 is presented. f) The targeting specificity factor is plotted against the time, indicating that the highest specificity is reached when treating MCF7 cells for 4-8 hours with LeY-DIG/DIG-DPC-AhaI.

Figure 54:
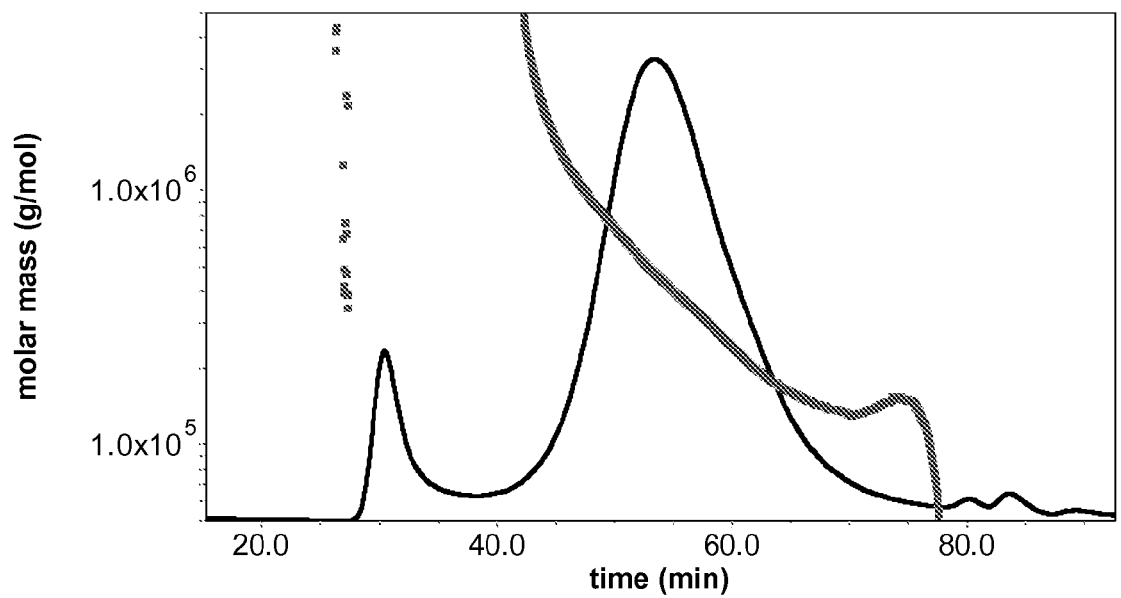
Figure 54:
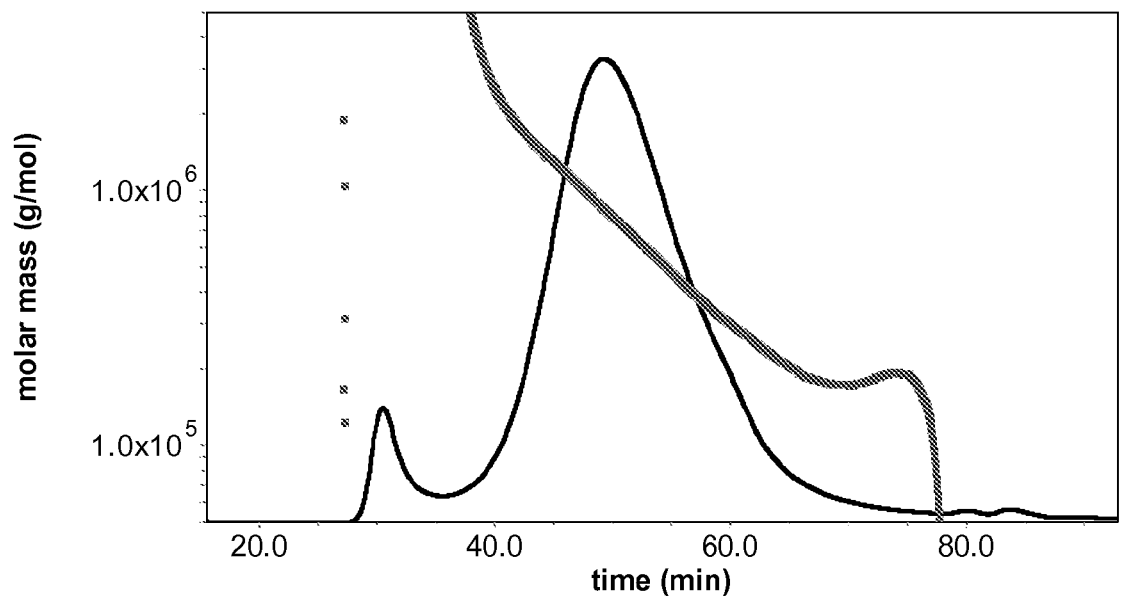
Figure 54:
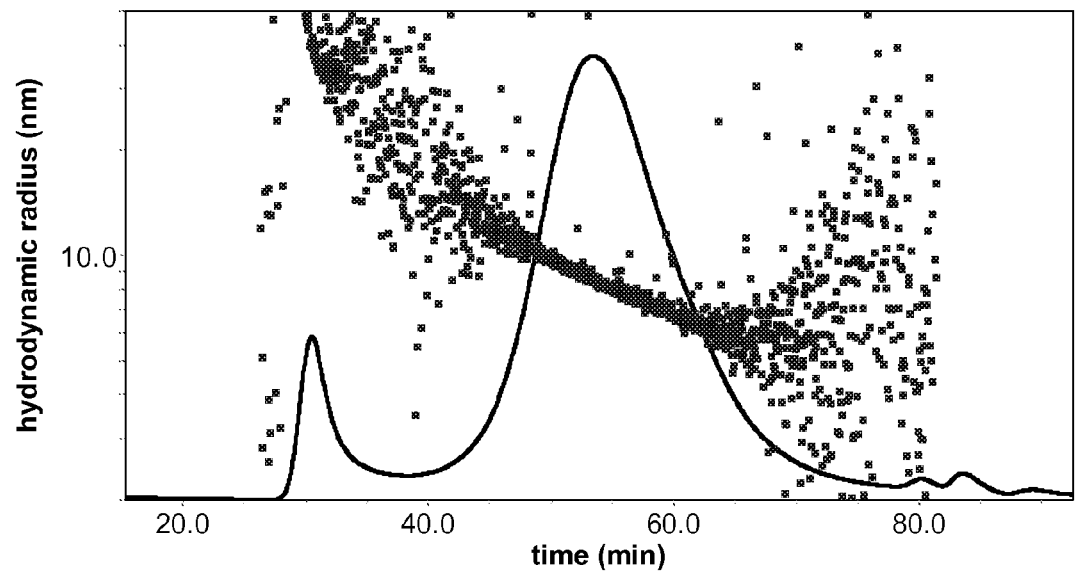
Figure 54:
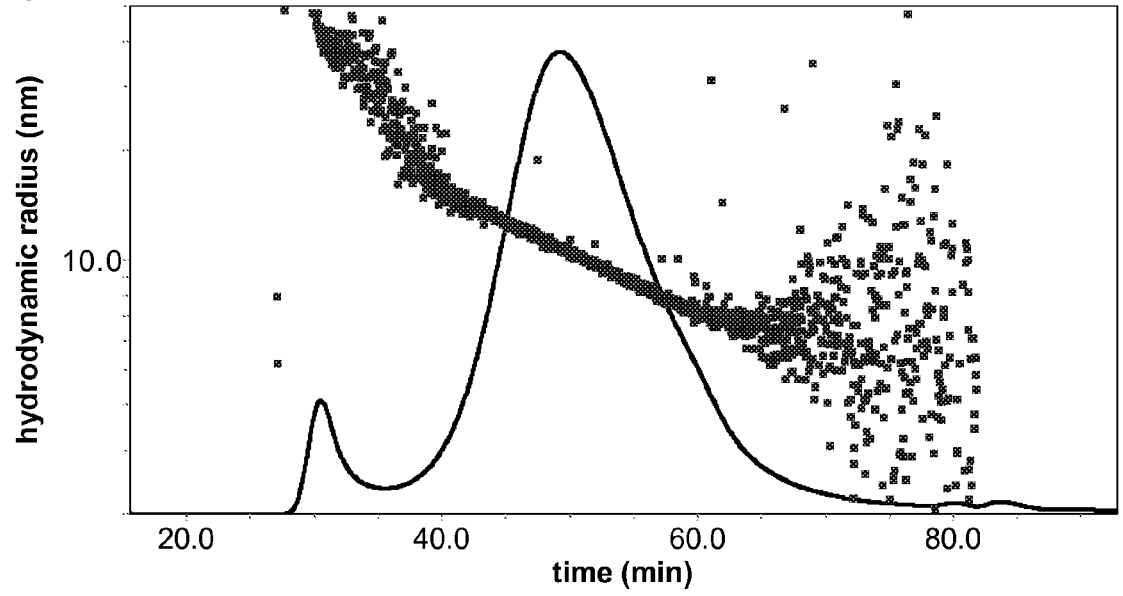

FIG. 54: a) and b): Molecular weight range of DIG-DPC-siRNA AHAI (FIG. 54 a) and LeY-DIG/DIG-DPC-siRNA AHAI (FIG. 54 b) measured by SEC-MALLS. black curve: signal generated by the LS detector; while the grey line: molecular weight generated from the signal of the LS and the RI detector; the generated molecular weight in only an approximation, because the exact dn/dc-value for DIG-DPC-siRNA AHAI is not known and was estimated as 0.146, which is the dn/dc-value for PEG. c) and d): Hydrodynamic radius range of DIG-DPC-siRNA AHAI (FIG. 54 c) and LeY-DIG/DIG-DPC-siRNA AHAI (FIG. 54 d) measured by SEC-MALLS. black curve: signal generated by the LS detector; dotted line: hydrodynamic radius generated from the signal of the QELS detector. Addition of LeY-DIG leads to complex formation of LeY-DIG and DIG-DPC-siRNA AHAI.

Figure 55:
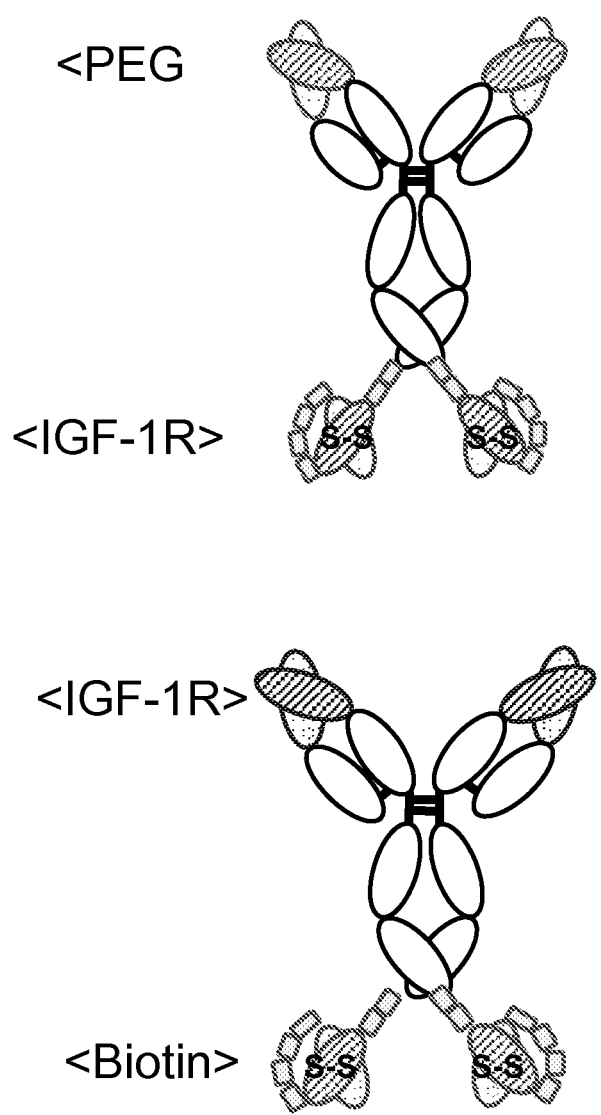
Figure 55:
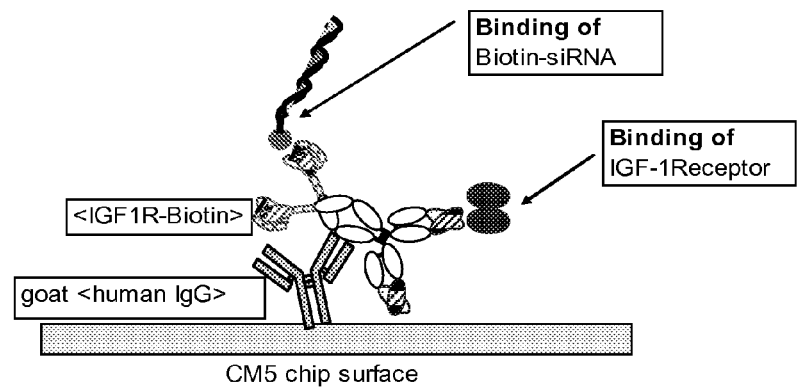
Figure 55:
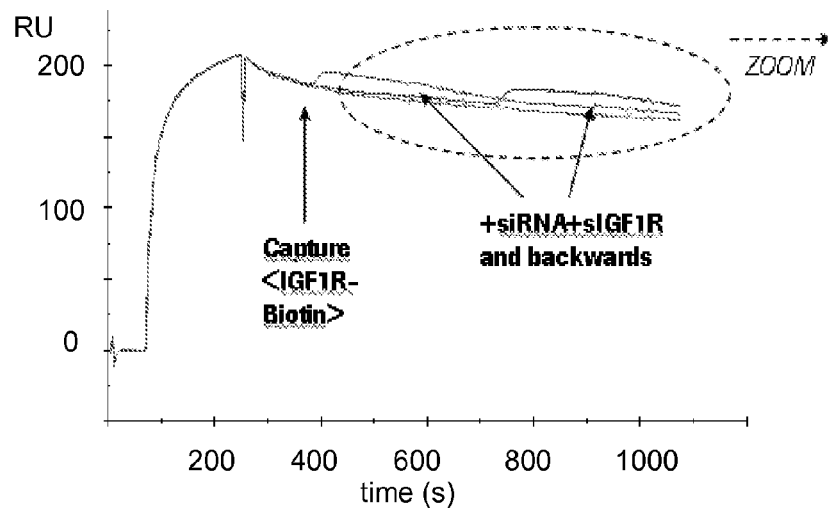
Figure 55:
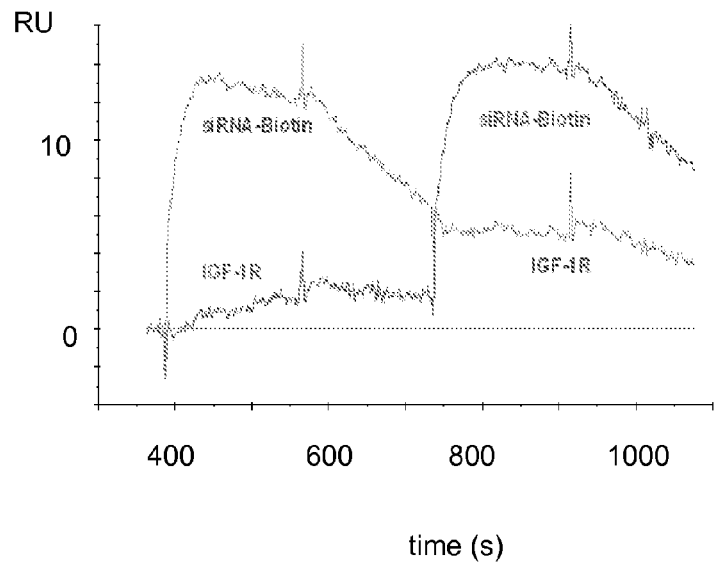

FIG. 55: (a) Vehicles for hapten-mediated payload delivery containing different entities for payload complexation b) to d) Surface-Plasmon-Resonance experiments show retainment of binding specificity and affinity of cell-surface targeting as well as functionality of biotin-binding modules.

Figure 56:
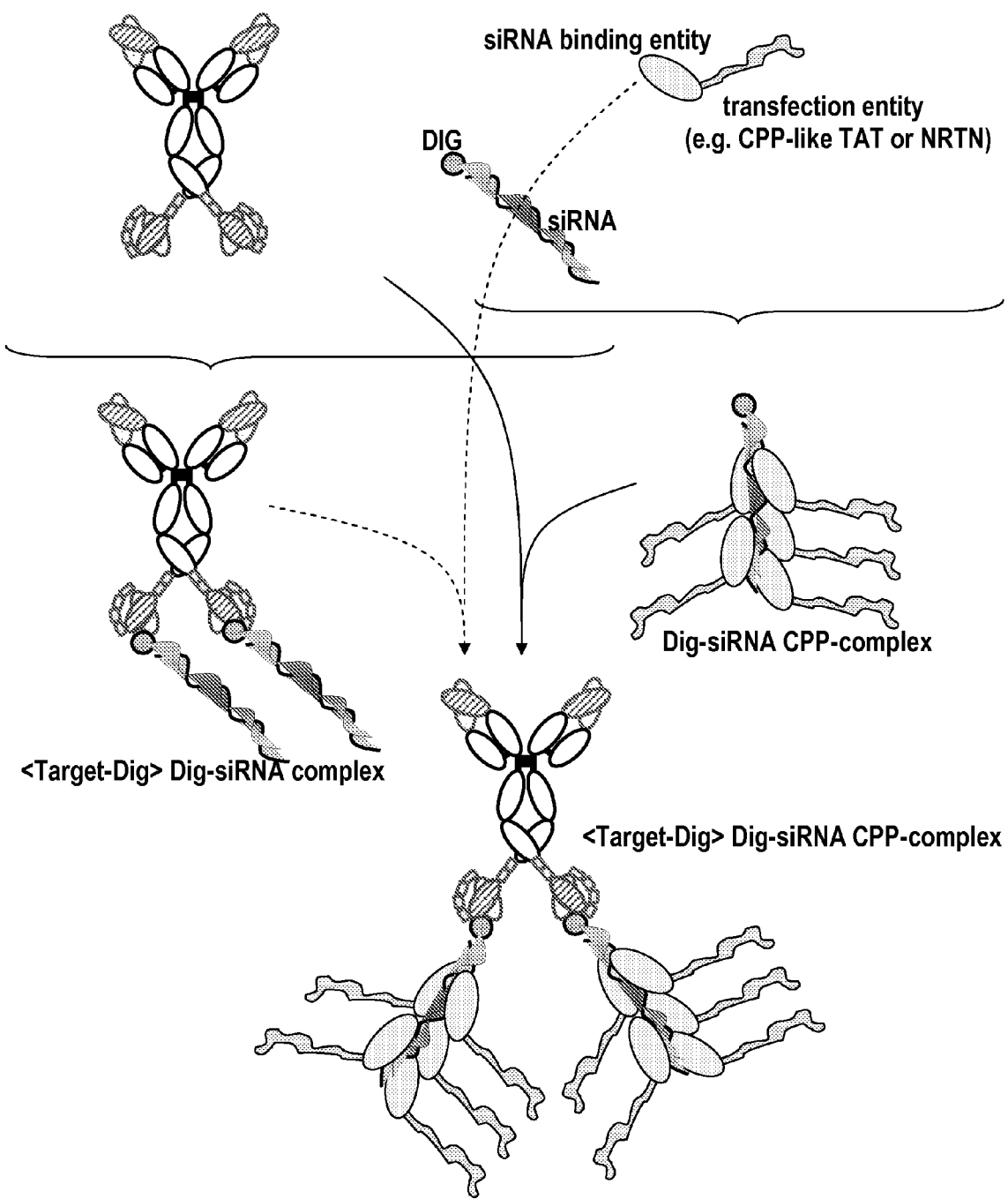
Figure 56:
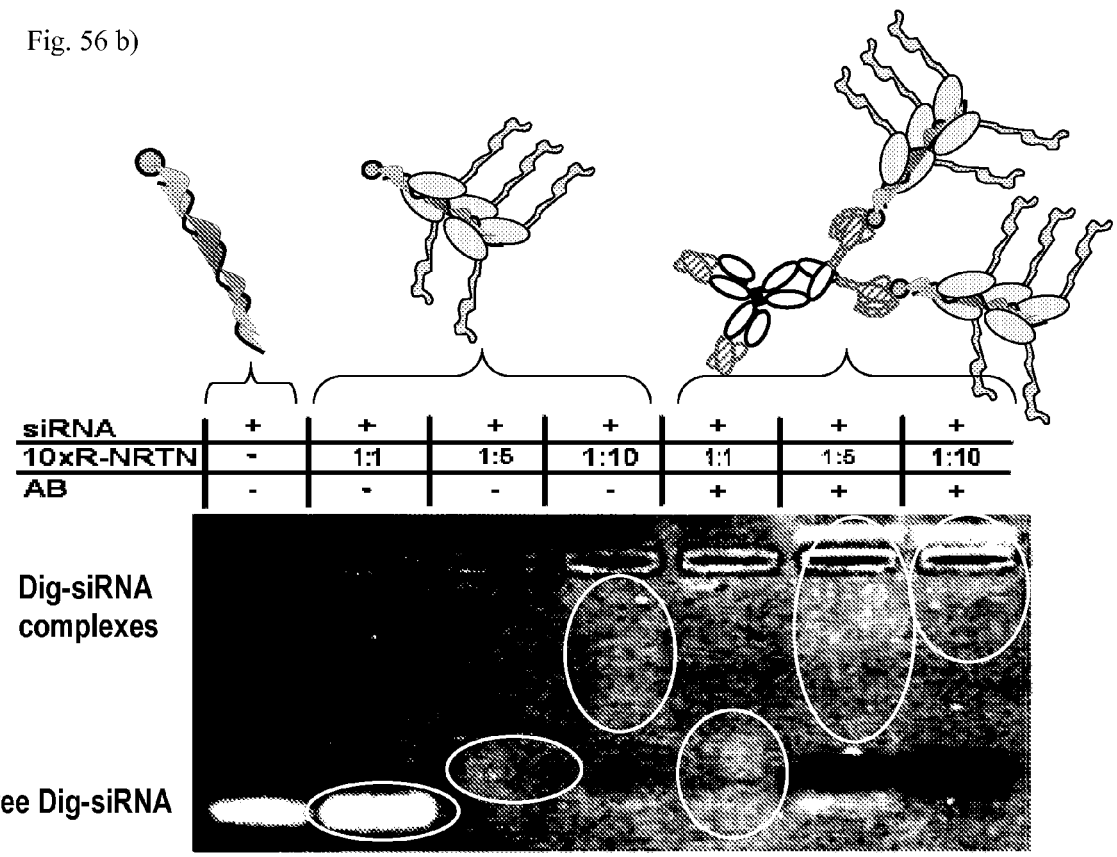
Figure 56:
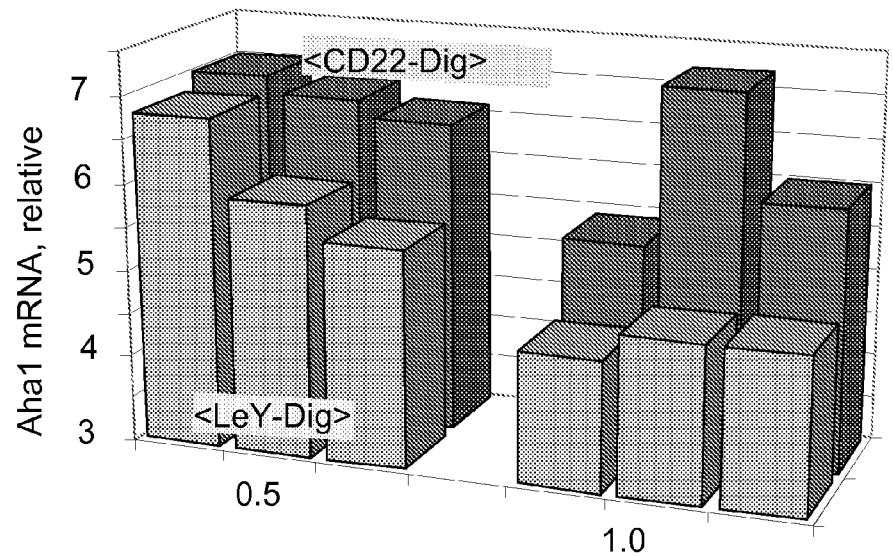

FIG. 56: (a) Complexes composed of <Dig> bispecific antibodies, digoxygenated siRNAs and transfection-aiding entities that contain siRNA binding modules. (b) Gel-shift assays demonstrate complexation of transfection-aiding entities that contain siRNA binding modules to digoxygenated siRNA and formation of 'supercomplexes' with bispecific targeting entities. (c) Specific reduction of AhaI mRNA using targeted delivery aided by peptide/protein modules that bind siRNA and possess transfection functionality.

Figure 57:
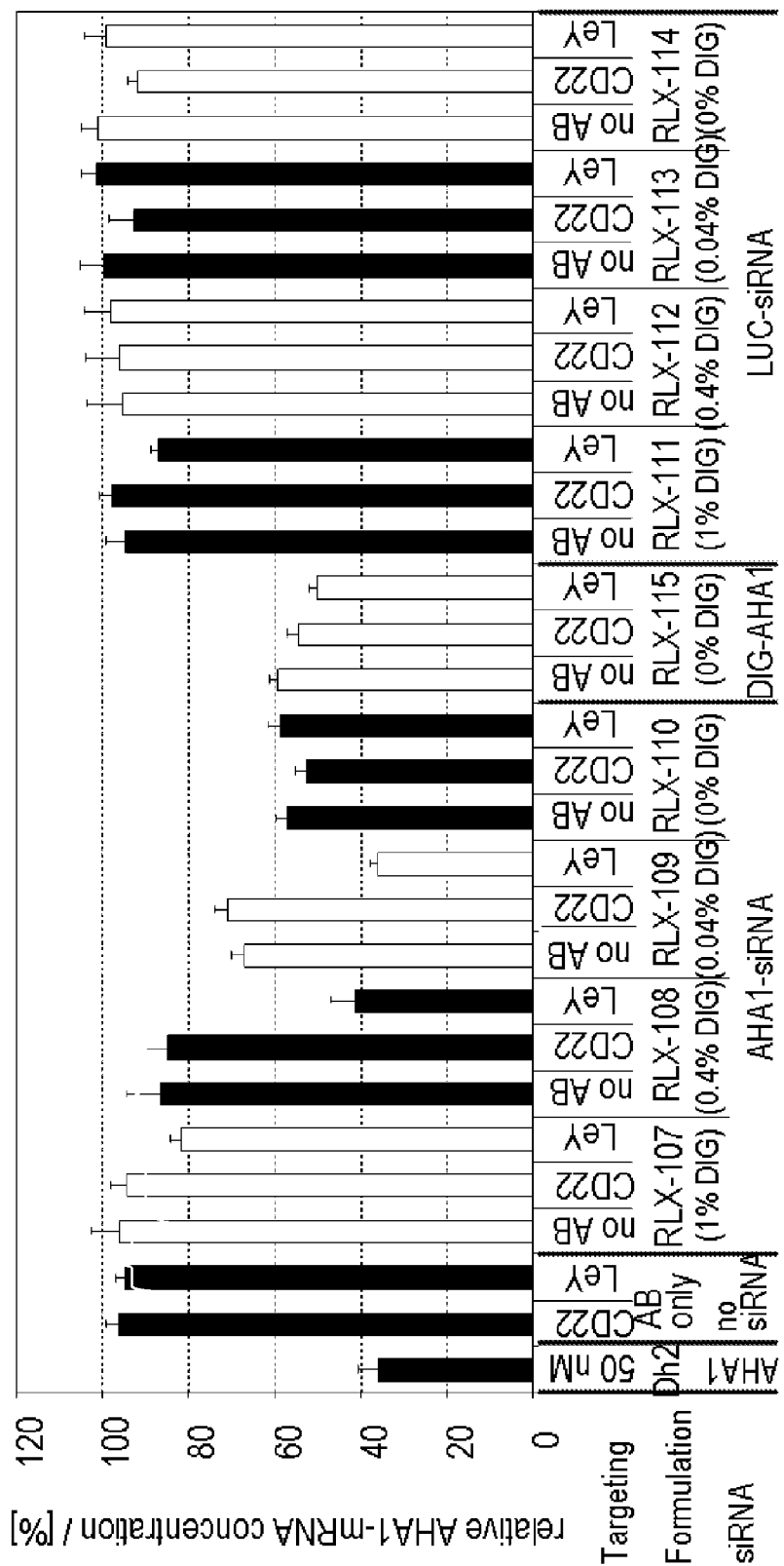

FIG. 57: siRNA mediated mRNA knockdown in MCF-7 cells following treatment with DIG-labeled siRNA-lipid nanoparticles complexed with <Target-Dig> bispecific antibodies. AHA1 mRNA levels (relative to GAPDH) were determined in MCF-7 breast cancer cells expressing the LeY antigen but not CD22 following 12 h incubation with DIG-labeled siRNA-lipid nanoparticles pre-incubated with <Target-DIG> bispecific antibodies. Y-axis: relative AHA1-mRNA concentration/[%]

EXAMPLES

Example 1

Isolation and Characterization of cDNAs Encoding the VH and VL Domains of a Murine <Dig> IgG1 Kappa from Mouse Hybridoma Clone 19-11

A prerequisite for the design, generation, optimization and characterization of recombinant <Dig> antibodies, antibody fragments and -fusion proteins is the availability of protein and (DNA) sequence information. Therefore, this information had to be generated for the VH and VL domains of the 'original' murine <Dig> antibody from the hybridoma clone 19-11. The experimental steps that needed to be performed subsequently were (i) the isolation of RNA from <Dig> producing 19-11 hybridoma cells, (ii) conversion of this RNA into cDNA, then into VH and VL harboring PCR fragments, and (iii) integration of these PCR fragments into plasmids vectors for propagation in E. coli and determination of their DNA (and deduced protein) sequences.

RNA Preparation from 19-11 Hybridoma Cells:

RNA was prepared from 5×10e6 antibody expressing hybridoma cells (clone 19-11) applying the Rneasy-Kit (Qiagen). Briefly, the sedimented cells were washed once in PBS and sedimented and subsequently resuspended for lysis in 500 µl RLT-Puffer (+β-ME). The cells were completely lysed by passing through a Qiashredder (Qiagen) and then subjected to the matrix-mediated purification procedure (ETOH, RNeasy columns) as described in the manufacturers manual. After the last washing step, RNA was recovered from the columns in 50 ul RNase-free water. The concentration of the recovered RNA was determined by quantify A260 and A280 of 1:20 diluted samples. The integrity (quality, degree of degradation) of the isolated RNA samples was analyzed by denaturing RNA gel electrophoresis on Formamide-Agarose gels (see Maniatis Manual). Examples of these RNA gel electrophoreses are shown in FIG. 1. The discrete bands represent the intact 18s and 28 s ribosomal RNAs. Intactness (and approx 2:1 intensity ratios) of these bands indicate a good quality of the RNA preparations. The isolated RNAs from the 19-11 hybridoma were frozen and stored at –80 C in aliquots.

Generation of DNA Fragments Encoding 19-11 VH and VH by RACE PCR.

The cDNA for subsequent (RACE-) PCR reactions were prepared from 19-11 RNA preparations by applying the FirstChoice Kit (Ambion) reagent kit using the described reactions for a standard 5'-RLM RACE protocol. Pwo DNA polymerase was used for the PCR reaction. For that, 10 ug of 19-11 RNA or control RNA (from mouse thymus) was applied, and processed as described to integrate the 5 RACE adapter. We did not need to apply the 'outer PCR' reaction and directly proceeded to the 'inner PCR': This involved combining primer pairs consisting of the 5 'RACE Inner Primer (from the kit) and either C-kappa or CH1 specific primers. The primer sequence for cKappa to amplify the VL region was 5'-TTTTTTGCGGCCGCCctaacactcattcctgttgaagctc-3' (SEQ. ID. No. 15). The primer sequence for CH1 to amplify the VH region was 5'-TTTTTTGCGGCCGCGTAC ATATG-CAAGGCTTACAACCACAATCC-3' (SEQ. ID. No. 16). For these primer combinations, annealing temperatures of 60° C. are suitable and temperatures between 55 and 65 C/(Gradient PCR) have been applied to perform the PCR (94 C 0.5 min, 55-65 C1 min-72 C 1 min, 35 cycles, completion by 10 min extension at 72 C). Successful specific amplification of antibody VH or VL region containing DNA fragments is reflected by occurrence of discrete 600 bp to 800 bp DNA fragments. FIG. 2 shows that these defined DNA fragments that were obtained from 19-11 RNA. These DNA fragments contain the VH and VL encoding sequences of the <Dig> hybridoma 19-11.

Cloning of the DNA Fragments Encoding 19-11 VH and VH into Plasmids and Determination of their DNA- and Protein Sequences The VH and VL-encoding PCR fragments were isolated by agarose gel extraction and subsequent purification by standard molecular biology techniques (Maniatis Manual). The Pwo-generated purified PCR fragments were inserted into the vector pCR bluntII topo by applying the pCR bluntII topo Kit (Invitrogen) exactly following the manufacturers instructions. The Topo-ligation reactions were transformed into E. coli Topo10-one-shot competent cells. Thereafter, E. coli clones that contained vectors with either VL- or VH containing inserts were identified as colonies on LB-Kanamycin agar plates. Plasmids were subsequently prepared from these colonies and the presence of the desired insert in the vector was confirmed by restriction digestion with EcoRI. Because the vector backbone contains EcoRI restriction recognition sites flanking each side of the insert, plasmids harboring inserts were defined by having EcoRi-releasable inserts of approx 800 bp (for VL) or 600 bp (for VH). The DNA sequence and the deduced protein sequence of the 19-11 VL and VH was determined by automated DNA sequencing on multiple clones for VH and VL. The sequence of the VL of <Dig> clone 19-11 is depicted in Seq. ID. NO. 1 and the VH sequence of <Dig> clone 19-11 is depicted in Seq. ID. NO. 2.

Example 2

Humanization of the VH and VL Domains of Mu<Dig>19-11

The objective of humanization of antibody sequences is to generate molecules that retain full functionality of the original antibodies of murine origin, but that harbor no (or only very few or non-relevant) sequences or structures that are recognized as 'foreign' by the human immune system. Different procedures are available and have been published that can address this challenge (Almagro J C, Fransson J Humanization of antibodies. Frontiers in bioscience: a journal and virtual library; 2008 Jan. 1; 13:1619-33, Hwang W Y, Foote J Immunogenicity of engineered antibodies. Methods (San Diego, Calif.); 2005 May; 36(1):3-10).

The functionality of variable regions of antibodies is determined by secondary and tertiary (and quaternary) structures, whose formation however base on the primary sequence of VH and VL (and of adjacent and interacting entities). Because of that, the major challenge of humanization is to (fully) retain structure-defined functionality despite the need to change the primary protein sequence at some positions. Thus, knowledge about the structure of functionally important regions of antibodies (CDR regions) is very important to support humanization. To generate humanized mu<Dig>19-11 derived variants we combined the following experimental wet-lab as well as in-silico procedures. Starting with (i) in silico-predictions of the antigen binding site of mu<Dig>19-11 we were able to (ii) predict in-silico hu<Dig> variants with a high degree of human-likeness as well as high probability to retain full functionality. Finally (iii) we experimentally determined the (X-ray) structure of <Dig> antibody (fragments) with and without antigen to validate and improve upon our in silico model.

In Silico Modeling of the Antigen Binding Site of Mu<Dig>19-11

The basis for our in-silico structure model for the mu<Dig>19-11 Fv region are the protein sequences that were deduced from the experimentally determined VH and VL mRNA sequences (described in Example 1, Seq. ID. NO. 1 and Seq. ID. NO. 2). A structure model of the protein encoded by these sequences was generated in silico by homology modeling of the Fv domain of the murine antibody combined with energy minimization. For that, CDRs and framework sequences to apply for the homology modeling were separately searched for homology over the PDB (Protein Data-Bank). For each CDR and for the frameworks, the more homolog structures were superimposed. A model was subsequently built from the different part for both the light and the heavy chains followed by a (energy) minimization of the complex. The structure model of the mu <Dig>19-11 Fv region that resulted from our homology-modeling procedure is shown in FIG. 3. One rather particular feature of the predicted structure is a prominent cavity that appears to extend deep into the VH-VL interface. The main determinant for formation of this narrow cavity is the long CDR3 loop of VH. The interior of the cavity is lined with a methionine (deeper residue), 2 serines, 2 prolines, an a few tyrosines (flanking walls). It is reasonable to assume that the antigen Digoxygenin that is recognized by this antibody is bound in a hapten-like manner into the deep cavity.

Crystallization and X-Ray Structure Determination of the Binding Region of the Murine Anti-Dig Fv Region in the Presence of Antigen To enable further optimization of the humanized VH and VL sequences of the anti-digoxygenin antibody, we experimentally determined the structure of the parent (murine) antibody. For that, Fab fragments were generated by protease digestion of the purified IgGs, applying well known state of the art methods (papain digestion). Fab fragments were separated from remaining Fc-fragments by protein A chromatography (which removes Fc), thereafter subjected to size exclusion chromatography (Superdex200 HiLoad 120 ml 16/60 gel filtration column, GE Healthcare, Sweden) to remove protein fragments.

For crystallization, purified Fabs in 20 mM His-HCl, 140 mM NaCl, pH 6.0 and Cy5 labeled Digoxigenin (DIG-3-cme-dea-Cy5=DIG-Cy5/powder) were complexed with digoxygenated fluorescent dye Cy5 (Dig-Cy5). Prior to crystal setups the protein solution was concentrated. For complex formation DIG-Cy5 was dissolved in 20 mM His-HCl, 140 mM NaCl, pH 6.0 and added to a final molar ratio of 5:1 to the concentrated protein solution. Crystals of murine Fab in complex with DIG-Cy5 were obtained using the hanging drop vapor diffusion method at 25° C. after mixing 1 µl protein solution (24 mg/ml) with 1 µl reservoir solution containing 60% (v/v) 2-methyl-1,3-propandiol (MPD)/0.1 M sodium acetate pH 4.6/5 mM $CaCl_2$. Crystals were flash frozen in liquid nitrogen crystals without the need of any further cryoprotection.

Diffraction data of murine Fab in complex with DIG-Cy5 were collected at X06SA (SLS, Villingen, Switzerland) on Sep. $11^{th}$ 2009. Data were integrated and scaled with XDS [Kabsch, W., Automatic processing of rotation diffraction data from crystals of initially unknown symmetry and cell constants. J Appl Cryst, 1993. 21: p. 916-24.]. Crystals of the complex belong to space group $P4_22_12$ with a=b=138.01 Å, c=123.696, $\alpha=\beta=\gamma=90°$ and diffracted to a resolution of 2.8 Å.

The structure was solved by molecular replacement using the program BALBES [Long, F., et al., BALBES: a molecular-replacement pipeline. Acta Crystallogr D Biol Crystallogr, 2008. 64(Pt 1): p. 125-32.] by generating a search model based on structures with PDB ID 3cfd, 2a6d, 2a6j [Debler, E. W., et al., Deeply inverted electron-hole recombination in a luminescent antibody-stilbene complex. Science, 2008. 319 (5867): p. 1232-5., Sethi, D. K., et al., Differential epitope positioning within the germline antibody paratope enhances promiscuity in the primary immune response. Immunity, 2006. 24(Sethi, D. K., et al., Differential epitope positioning within the germline antibody paratope enhances promiscuity in the primary immune response. Immunity, 2006. 24(4): p. 429-38): p. 429-38.]. In total 2 Fab molecules could be located in the asymmetric unit. The initial models were completed and refined by manual model building with the program COOT [Emsley, P. and K. Cowtan, Coot: model-building tools for molecular graphics. Acta Crystallogr D Biol Crystallogr, 2004. 60(Pt 12 Pt 1): p. 2126-32.] and refinement using the program PHENIX [Zwart, P. H., et al., Automated structure solution with the PHENIX suite. Methods Mol Biol, 2008. 426: p. 419-35.]. After first rounds of refinement a difference electron density for the DIG moiety of DIG-Cy5 appeared. A model for DIG was obtained from PDB ID 1lke [Korndorfer, I. P., S. Schlehuber, and A. Skerra, Structural mechanism of specific ligand recognition by a lipocalin tailored for the complexation of digoxigenin. J Mol Biol, 2003. 330(2): p. 385-96.] and refinement parameters for DIG were generated by the online tool PRODRG [Schuttelkopf, A. W.

and D. M. van Aalten, PRODRG: a tool for high-throughput crystallography of protein-ligand complexes. Acta Crystallogr D Biol Crystallogr, 2004. 60(Pt 8): p. 1355-63.]. The model of DIG was placed in the electron density for final refinement steps. For refinement statistics see FIG. 45*a*. Figures were prepared with the program PYMOL [DeLano, W. L., The PyMOL Molecular Graphics System. 2008.].

The results of the experimental structure determination are shown in FIG. 45*b*: The obtained crystal form contained two independent DIG-Cy5:anti-DIG Fab complexes in the asymmetric unit and atomic models for both complexes could be build. The DIG moiety of DIG-Cy5 is well ordered in both Fab molecules in the asymmetric unit although it appears to be bound in one molecule of the asymmetric unit more tightly than in the other one. DIG is bound in a pocket located at the interface of chain L and chain H in the middle of the CDR. Atom O32 of DIG is pointing towards the bottom of the pocket and the linker with Cy5 is located outside and points into the solvent. In addition to DIG, a clear $2F_O$-$F_C$ electron density is visible for the first C atom of the linker to Cy5 (panel B in FIG. 45*b*). Due to the flexibility of the linker neither the remainder of the linker nor Cy5 are visible in the electron density map. This disorder indicates that the linker is not attached to the protein and long enough to allow attachment of molecules of different nature and size such as dyes, siRNA and others to DIG without influencing the recognition of DIG by the antibody.

Interestingly the binding pocket is not completely hydrophobic as expected for a hydrophobic molecule as DIG but contains some positive charge potential (Panel C in FIG. 45*b*). The binding pocket is lined by four Tyrosin residues (57, 59, 109, 110) as well as A33, W47, P61, P99 and M112 of the heavy chain. From the light chain residues Q89, S91, L94, P96 and F98 are involved in pocket formation. The possible hydrogen bonding partners N35 and Y36 of the light chain form the bottom of the pocket but are not reached by the DIG (Panel A in FIG. 45*c*).

Only one direct hydrogen bond is involved in DIG binding and is formed between O32 of DIG and Q89 of the light chain. Two more hydrogen bonds are not direct but mediated through water molecules. O12 is interacting with the carbonyl oxygen of Y109 and the side chain of S35 of the heavy chain (Panel B in FIG. 45*c*). A fourth hydrogen bond is formed between O14 and backbone carbonyl oxygen of S91 (chain L) but again mediated by a water molecule. Comparisons of the number and the lengths of the hydrogen bonds in both molecules of the asymmetric unit indicate that in the second complex DIG is not able to fully enter the pocket. In one molecule the DIG moiety immerses relatively deep into the pocket and forms four hydrogen bonds. The second DIG is bound more loosely bound, it does not enter the pocket as deep as in the other molecule and forms only three hydrogen bonds that are weaker than in the other molecule (Panel C in FIG. 45*c*).

The results of the experimental determination of the binding region at a resolution of 2.8 Å enables the characterization of the binding mode of the ligand to its antibody. It further confirms that structure is generally similar to the structure model that we predicted by in-silico analyses of the primary sequence (see above). The availability of the in silico modeled structure as well as of experimentally determined 'real' structure of the variable region of the parent antibody is a prerequisite for detailed modeling and further improvement via protein engineering of recombinant digoxigenin binding modules.

Definition of Mu<Dig>19-11 Humanized Variants which Retain Full Functionality

Amino acid sequences that represent desired humanized VH and VL domains were defined by applying a procedure which is based on CDR-grafting and introduction of additional mutations which modulate binding specificity and affinity. The basic principle underlying this procedure is the attribution of a 'score value' for each amino acid that differs from the mouse sequence among the human germlines. This score is defined by its putative influence of the amino acid change on the antigen recognition capability or on the stability of the complex. Human germline are selected based on their lower score and their relative high usage. TEPITOPE analyses (predicting T-cell epitopes) are included in this humanization procedure with the objective to have few to no t-cell epitopes in the resulting humanized molecule. The 'human' sequences initially defined by this procedure may need to be replaced by the (original) murine ones when the score is too high (indicating high probability of negative interference). This is most frequently required for amino acid changes in the CDR or in the surrounding region of the CDR sequences. In some instances, 'back-mutations' to murine residues are required not only in the CDRs but also within the framework to retain stability and functionality.

The resulting hu<Dig> variant that we chose is based on the human Framework VH3_11 and VL1_39 combination, and has a high degree of human-likeliness. For VL, it was not necessary to integrate any backmutation in the framework of the human VK1_39 and the human j element of IGKJ4-01/02 germlines. This lead to a high human character and a relatively low number of TEPITOPE alerts. The VH variant is originated from the human VH3_23 germline and the human J IGHJ6-01-2. The variant J is built on the human VH3_11 germline. Moreover, using our scoring methodology, we were able to introduce one human amino acid within CDRS in order to increase the human character and decrease the number of TEPITOPE alerts. The protein sequence of the humanized VH (and Fd-Fragment) is depicted in Seq. ID. NO. 3 and Seq. ID. NO. 4 and the protein sequence of the humanized VL (and L-chain) is shown in depicted in Seq. ID. NO.5 and Seq. ID. NO.6. Despite careful application of our established procedure, there still exists the possibility that the sequence alterations that are part of the humanized VH ad VL could interfere with structural integrity of the Fv region. Because of that, we generated a further <Dig> structure mode by applying the same in-silico procedure as described above to the humanized Fv sequence. This structure is shown in FIG. 4. A comparison of the mu<Dig> structure (FIG. 3) and the hu<Dig> structure (FIG. 4) indicate that the antigen binding site is not affected by the amino-acid changes that were introduced within the course of humanization.

Generation of Digoxygenin Binding Modules with Increased Affinity

Further optimization of the humanized VH and VL sequences of the anti-digoxygenin antibody was applied to generate modules with even higher affinity towards digoxygenin. Based upon the experimentally determined as well as in-silico calculated predicted structures (see above, based upon structure modeling without experimental structure determination), we identified three positions in which alterations might affect affinity. These were located at (Kabat positions) Ser49, Ile57 and Ala60 of the VH domain (FIG. 46). Replacement of the amino acid VHSer49 with Ala, VHIle57 with Ala and of VHAla60 with Pro generated antibody derivatives with sequences that are listed as SEQ ID NO 36 and SEQ ID NO 37. Binding entitiesthat are composed of this sequence could be expressed and purified with standard Protein-A and size exclusion technologies (see Example 3 'Composition, expression and purification of recombinant humanized <Dig> antibodies, -fragments and bispecific-fusion proteins). The resulting molecules were fully functional and displayed improved affinity towards digoxygenin compared to the humanized parent molecule. This was demonstrated by Surface-Plasmon-Resonance (BiaCore) experiments (see example 4 'Binding of recombinant <Dig> antibodies, -fragments and bispecific-fusion proteins to digoxygenated antigens' for details). The results of these experiments are shown in FIG. 46 and prove that the affinity towards digoxygenin is improved approximately 10-fold by introducing VH49, VH57 and VH60 mutations. The relevance of these positions was thereafter confirmed by inspecting the experimentally determined structure of the dig-binding variable region. The digoxygenin binding module with improved affinity can be applied as hapten-binding entity for various bi- and multispecific antibody derivatives.

Example 3

Composition, Expression and Purification of Recombinant Humanized <Dig> Antibodies, -Fragments and Bispecific-Fusion Proteins For more detailed characterization, murine and humanized <Dig> modules were combined with constant regions of human antibodies, either to form humanized IgG's or to generate bispecific fusion proteins with other antibody sequences. The generation of humanized <Dig> IgGs, and bispecific derivatives that bind Dig as well as other targets (e.g. receptor tyrosine kinases Her2 or IGF1R) required (i) design and definition of amino- and nucleotide sequences for such molecules, (ii) expression of these molecules in transfected cultured mammalian cells, and (iii) purification of these molecules from the supernatants of transfected cells.

Design and Definition of Amino- and Nucleotide Sequences of <Dig> IgG and Bispecific Antibody Derivatives that Bind Digoxygenin as Well as Her2 or IGF To generate a humanized IgG that harbors the binding specificity of the (original) murine mu<Dig>19-11 Fv region, we fused the above defined humanized VH sequence in frame to the N-terminus of CH1-CH2-CH3 of IgG1. Similarly, we fused the above defined humanized VL sequence in frame to the N-terminus of Ckappa. The amino acid-sequences of the resulting hu<her2> <Dig> IgG H- and L-chains are depicted in Seq. ID. NO. 7, Seq. ID. NO. 8 and Seq. ID. NO. 9. To generate bispecific antibody derivatives that contain the binding specificity of hu<Dig> as well as specificities to the receptor tyrosine kinase Her2, we fused the <Dig> single-chain Fv module defined by humanized VH and VL sequences in frame to the C-terminus of the H-chain of a previously described <Her2> antibody (e.g. U.S. Pat. No. 5,772,997). This <Dig> scFv module was further stabilized by introduction of a VH44-VL100 disulfide bond which has been previously described (e.g. Reiter Y, Brinkmann U, Lee B, Pastan I Engineering antibody Fv fragments. for cancer detection and therapy: disulfide-stabilized Fv fragments. Nature biotechnology; 1996 October; 14(10): 1239-45). The amino acid and sequences of the resulting bispecific antibody derivatives that bind Her2 as well as Digoxygenin are depicted in Seq. ID. NO.7, Seq. ID. NO.8 and Seq. ID. NO.9

To generate bispecific antibody derivatives that contain the binding specificity of hu<Dig> as well as specificities to the receptor tyrosine kinase IGF1R, we fused the <Dig> single-chain Fv module defined by humanized VH and VL sequences in frame to the C-terminus of the H-chain of a previously described <IGF1R> antibody. This <Dig> scFv module was further stabilized by introduction of a VH44-VL100 disulfide bond which has been previously described (e.g. Reiter Y, Brinkmann U, Lee B, Pastan I Engineering antibody Fv fragments. for cancer detection and therapy: disulfide-stabilized Fv fragments. Nature biotechnology; 1996 October; 14(10):1239-45). The amino acid and nucleotide-sequences of the resulting bispecific antibody derivatives that bind IGF1R as well as Digoxygenin are listed in Seq. ID. NO.10, Seq. ID. NO.11 and Seq. ID. NO.12.

Expression of <Dig> IgG and of Bispecific Antibody Derivatives that Bind Digoxygenin as Well as her2 or IGF The <Dig> IgG and the bispecific antibody derivatives were expressed by transient transfection of human embryonic kidney 293-F cells using the FreeStyle™ 293 Expression System according to the manufacturer's instruction (Invitrogen, USA). For that, light and heavy chains of the corresponding bispecific antibodies were constructed in expression vectors carrying pro- and eukaryotic selection markers. These plasmids were amplified in *E. coli*, purified, and subsequently applied for transient transfections. Standard cell culture techniques were used for handling of the cells as described in Current Protocols in Cell Biology (2000), Bonifacino, J. S., Dasso, M., Harford, J. B., Lippincott-Schwartz, J. and Yamada, K. M. (eds.), John Wiley & Sons, Inc. The suspension FreeStyle™ 293-F cells were cultivated in FreeStyle™ 293 Expression medium at 37° C./8% CO2 and the cells were seeded in fresh medium at a density of 1–2×106 viable cells/ml on the day of transfection. The DNA-293Fectin™ complexes were prepared in Opti-MEM I medium (Invitrogen, USA) using 333 µl of 293Fectin™ (Invitrogen, Germany) and 250 µg of heavy and light chain plasmid DNA in a 1:1 molar ratio for a 250 ml final transfection volume. The IgG or bispecific antibody containing cell culture supernatants were clarified 7 days after transfection by centrifugation at 14000 g for 30 minutes and filtration through a sterile filter (0.22 µm). Supernatants were stored at −20° C. until purification.

To determine the concentration of antibodies and derivatives in the cell culture supernatants, affinity HPLC chromatography was applied. For that, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an UltiMate 3000 HPLC system (Dionex). The eluted protein was quantified by UV absorbance and integration of peak areas. A purified standard IgG1 antibody served as a standard.

Purification of <Dig> IgG and of Bispecific Antibody Derivatives that Bind Digoxygenin as Well as her2 or IGF1R 7 days after transfection of the expression plasmids, the HEK 293 cell supernatants were harvested. The recombinant antibody (-derivatives) contained therein were purified from the supernatant in two steps by affinity chromatography using Protein A-Sepharose™ (GE Healthcare, Sweden) and Superdex200 size exclusion chromatography. Briefly, the bispecific and trispecific antibody containing clarified culture supernatants were applied on a HiTrap ProteinA HP (5 ml) column equilibrated with PBS buffer (10 mM Na2HPO4, 1 mM KH2PO4, 137 mM NaCl and 2.7 mM KCl, pH 7.4). Unbound proteins were washed out with equilibration buffer. The bispecific antibodies were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. The protein concentration of purified antibodies and derivatives was determined by determining the optical density (OD) at 280 nm with the OD at 320 nm as the background correction, using the molar extinction coefficient calculated on the basis of the amino acid sequence according to Pace et. al., Protein Science, 1995, 4, 2411-1423. Monomeric antibody fractions were pooled, snap-frozen and stored at −80° C. Part of the samples were provided for subsequent protein analytics and characterization.

The homogeneity of the DIGHu2 antibody construct and the bispecific DIG constructs were confirmed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-20% Tris-Glycine gels).

Under reducing conditions (FIG. 5-7), polypeptide chains related to the IgG and also C-1-terminal scFv fusions showed upon SDS-PAGE at apparent molecular sizes analogous to the calculated molecular weights. Expression levels of all constructs were analysed by Protein A HPLC and were similar to expression yields of 'standard' IgGs or in the case of IGF-1RDIGHu2-2321 lower. Average protein yields were between 6 and 35 mg of purified protein per liter of cell-culture supernatant in such non-optimized transient expression experiments (FIG. 8).

The aggregate content of bispecific antibody samples was analyzed by high-performance SEC on an UltiMate 3000 HPLC system (Dionex) using a Superdex 200 analytical size-exclusion column (GE Healthcare, Sweden) in 200 mM KH2PO4, 250 mM KCl, pH 7.0 running buffer at 25° C. 25 µg protein were injected on the column at a flow rate of 0.5 ml/min and eluted isocratic over 50 minutes. For stability analysis, concentrations of 0.1 mg/ml, 1 mg/ml and 3 mg/ml of purified proteins were prepared and incubated at 4° C., 37° C. for 7 days and then evaluated by high-performance SEC. The integrity of the amino acid backbone of reduced bispecific antibody light and heavy chains was verified by Nano-Electrospray Q-TOF mass spectrometry after removal of N-glycans by enzymatic treatment with Peptide-N-Glycosidase F (Roche Molecular Biochemicals). The aggregate-analyses by HP-Size exclusion chromatography analysis of the purified proteins showed (compared to 'normal' IgGs) a greatly increased tendency to aggregate for molecules that contained scFvs that were not stabilized by interchain disulfides between VH and VL. To address the problems with aggregation of such bispecific antibodies, disulfide-stabilization of the scFv moieties was applied. For that we introduced single cysteine replacements within VH and VL of the scFv at defined positions (positions VH44/VL100 according to the Kabat numbering scheme). These mutations enable the formation of stable interchain disulfides between VH and VL, which in turn stabilize the resulting disulfide-stabilized scFv module. Introduction of the VH44/VL100 disulphides in scFvs at the N- and C-terminus of the Fv lead to a significant improvement in protein expression levels for all constructs (FIG. 9). Her2DIGHu2-2320 had a final yield after purification of 1 mg whereas Her2DIGHu2-2321 had a final yield of approximately 32 mg.

Example 4

Binding of Recombinant Humanized <Dig> Antibodies, -Fragments and -Fusion Proteins to Digoxygenated Antigens The analyses that are described below were performed to evaluate if the humanization procedure resulted in <Dig> derivatives that had retained full binding activity. For that, binding properties of the recombinant <Dig> derivatives were analyzed by surface plasmon resonance (SPR) technology using a Biacore T100 or Biacore 3000 instrument (GE Healthcare Bio-Sciences AB, Uppsala). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases. To perform the binding studies capturing anti-human IgG antibody was immobilized on the surface of a CM5 biosensor chip using amine-coupling chemistry. Flow cells were activated with a 1:1 mixture of 0.1 M N-hydroxysuccinimide and 0.1 M 3-(N,N-dimethylamino)propyl-N-ethylcarbodiimide at a flow rate of 5 µl/min. If not described elsewise, anti-human IgG antibody was injected in sodium acetate, pH 5.0 at 10 µg/ml, which resulted in a surface density of approximately 12000 RU. A reference control flow cell was treated in the same way but with vehicle buffers only instead of the capturing antibody. Surfaces were blocked with an injection of 1 M ethanolamine/HCl pH 8.5. To compare the binding of the humanized protein variants with that of the murine <Dig> IgG from the original hybridoma 19-11, capturing anti-mouse IgG antibody was immobilized on the surface of a CM5 biosensor chip in the same fashion as described above for the anti-human IgG antibody. To evaluate the functionality of the recombinant <Dig> derivatives, binding of the recombinant hu<Dig> modules, incl. (i) humanized IgG, (ii) fusion proteins harboring hu<Dig> scFv or (iii) disulfide-stabilized scFvs was assayed with different digoxygenated antigens The resulting binding affinities were compared to the binding of the murine 'wildtype' DIG-IgG from which the recombinant humanized modules were derived.

Comparison of Hybridoma-Derived Murine <Dig>19-11 with Humanized <Dig> IgG

Anti-mouse IgG antibody was immobilized on the surface of a CM5 biosensor chip in the same fashion as described above. Anti-human IgG antibody was injected at 2 µg/ml, which resulted in a surface density of approximately 600 RU. The regeneration was carried out by injecting 0.85% $H_3PO_4$ for 60 s at 5 µl/min and then injecting 5 mM NaOH for 60 s at 5 µl/min to remove any non-covalently bound protein after each binding cycle. The samples to be analyzed were diluted in HBS-P (10 mM HEPES, pH 7.4, 150 mM NaCl, 0.005% Surfactant P20) and injected at a flow rate of 5 µl/min. The contact time (association phase) was 3 min for the antibodies at a concentration between 1 and 5 nM. In order to measure binding affinities different digoxygenated antigens were injected at increasing concentrations, that were 0.3125, 0.625, 1.25, 2.5, 5 and 10 nM for DIG-BP4, and between 0.018 and 300 nM for DIG-siRNA. The contact time (association phase) was 3 min, the dissociation time (washing with running buffer) 5 min for each molecule at a flow rate of 30 µl/min. All interactions were performed at 25° C. (standard temperature). In case of the murine <DIG>19_11 the regeneration solution of 10 mM Glycine/HCl pH 1.5 was injected for 60 s at 30 µl/min flow to remove any non-covalently bound protein after each binding cycle. In case of the humanized <DIG> IgG the regeneration was carried out by injecting 0.85% H$_3$PO$_4$ for 60 s at 5 µl/min and then injecting 5 mM NaOH for 60 s at 5 µl/min. Signals were detected at a rate of one signal per second.

The results of these analyses, exemplarily shown in FIG. 10 and summarized in Table 3, indicate that the recombinant humanized <Dig> binds digoxygenated proteins and nucleic acids with the same functionality and high affinity as the murine parent antibody. The Kd of murine antibody towards digoxygenated protein (Dig-BP4, European Patent EP 1545623 B1) was found to be 33 pM, and that of the humanized antibody was <76 pM. Similarly, the Kd of murine antibody towards digoxygenated nucleic acids (siRNA-Dig, see Example 11) was found to be 269 pM, and that of the humanized antibody was 12 nM. Thus, we conclude that the functionality of the <Dig> antibody was retained in its humanized variant (which is defined by the sequences as depicted in Seq. ID. NO. 3, Seq. ID. NO. 4, Seq. ID. NO. 5 and Seq. ID. NO. 6).

Comparison of Hybridoma-Derived Murine <Dig>19-11 with Recombinant Humanized <Dig>-Single-Chain Fv-Fusion Proteins Anti-mouse and anti-human IgG antibodies were immobilized on the surface of a CM5 biosensor chip in the same fashion as described in the introduction of example 4. The samples to be analyzed were diluted in HBS-P and injected at a flow rate of 5 µl/min. The contact time (association phase) was 3 min for the antibodies at a concentration between 1 and 5 nM. In order to measure binding affinities different digoxygenated antigens were injected at increasing concentrations, that were 0.3125, 0.625, 1.25, 2.5, 5 and 10 nM for DIG-BP4, and between 0.018 and 120 nM for DIG-siRNA. The contact time (association phase) was 3 min, the dissociation time (washing with running buffer) 5 min for each molecule at a flow rate of 30 µl/min. All interactions were performed at 25° C. (standard temperature). The regeneration solution of 10 mM Glycine/HCl pH 1.5 was injected for 60 s at 30 µl/min flow to remove any non-covalently bound protein after each binding cycle. When RNAses were used as ligands the regeneration was carried out by injecting 0.85% H$_3$PO$_4$ for 60 s at 5 µl/min and then injecting 5 mM NaOH for 60 s at 5 µl/min. Signals were detected at a rate of one signal per second.

The results of these analyses, exemplarily shown in FIG. 11 (results of murine <Dig>19-11 in FIG. 10) and summarized in Table 3, indicate that the recombinant humanized <Dig> scFv module that is present in the applied bispecific fusion protein (Her2-Dig, see example 3) binds digoxygenated proteins and nucleic acids with the same functionality and high affinity as the murine parent antibody. The Kd of murine antibody towards digoxygenated protein (Dig-BP4) was found to be 33 pM, and that of the humanized single-chain Fv was 68 pM. Similarly, the Kd of murine antibody towards digoxygenated nucleic acids (siRNA-Dig, see Example 11) was found to be 269 pM, and that of the humanized single-chain Fv was 35 nM. Thus, we conclude that the functionality of the wild-type antibody is also retained in the recombinant humanized <Dig> scFv module that is present in bispecific fusion protein (Her2-Dig, see example 3).

Comparison of Hybridoma-Derived Murine <Dig>19-11 with Recombinant Humanized <Dig>-Disulfide-Stabilized Single-Chain Fv-Fusion Proteins Anti-mouse and anti-human IgG antibodies were immobilized on the surface of a CM5 biosensor chip in the same fashion as described in the introduction of example 4. In those assays where DIG-RNAses were added as ligand, anti-human IgG antibodies were immobilized on the chip surface by injecting 2 µg/ml, which resulted in a surface density of approximately 600 RU. The samples to be analyzed were diluted in HBS-P and injected at a flow rate of 5 µl/min. The contact time (association phase) was 3 min for the antibodies at a concentration between 1 and 10 nM. In order to measure binding affinities different digoxygenated antigens were injected at increasing concentrations, that were between 0.018 and 120 nM for DIG-siRNA. In order to visualize binding the different digoxygenated RNAses (human and bovine) were injected in two replicates in a concentration of 50 nM for each Raze. The contact time (association phase) was 3 min, the dissociation time (washing with running buffer) 5 min for each molecule at a flow rate of 30 µl/min. All interactions were performed at 25° C. (standard temperature). The regeneration solution of 10 mM Glycine/HCl pH 1.5 was injected for 60 s at 30 µl/min flow to remove any non-covalently bound protein after each binding cycle. Signals were detected at a rate of one signal per second.

The results of these analyses, exemplarily shown in FIG. 12 (results of murine <Dig>19-11 in FIG. 10) and summarized in Table 3, indicate that the recombinant disulfide-stabilized humanized <Dig> scFv module that is present in the applied bispecific fusion protein (Her2-Dig, see example 3) binds digoxygenated nucleic acids with the same functionality and high affinity as the murine parent antibody. The Kd of murine antibody towards digoxygenated nucleic acids (siRNA-Dig, see Example 11) was found to be 269 pM, and that of the disulfide-stabilized humanized <Dig> scFv module was 32 nM. Thus, we conclude that the functionality of the wild-type antibody is also retained in the recombinant disulfide-stabilized humanized <Dig> scFv module that is present in bispecific fusion protein (Her2-Dig, see example 3).

Comparison of Hybridoma-Derived Murine <Dig>19-11 with Recombinant Murine <Dig>-Disulfide-Stabilized Single-Chain Fv-Fusion Proteins The samples to be analyzed were diluted in HBS-P and injected at a flow rate of 5 µl/min. The contact time (association phase) was 3 min for the antibodies at a concentration between 1 and 5 nM. In order to measure binding affinities different digoxygenated antigens were injected at increasing concentrations, that were 0.3125, 0.625, 1.25, 2.5, 5 and 10 nM for DIG-BP4, and between 0.018 and 120 nM for DIG-siRNA. The contact time (association phase) was 3 min, the dissociation time (washing with running buffer) 5 min for each molecule at a flow rate of 30 µl/min. All interactions were performed at 25° C. (standard temperature). The regeneration solution of 10 mM Glycine/HCl pH 1.5 was injected for 60 s at 30 µl/min flow to remove any non-covalently bound protein after each binding cycle. Signals were detected at a rate of one signal per second.

The results of these analyses, exemplarily shown in FIG. 13 (results of murine <Dig>19-11 in FIG. 10) and summarized in Table 3, indicate that the recombinant murine disulfide-stabilized <Dig> scFv module that is present in the applied bispecific fusion protein (Her2-Dig, see example 3) binds digoxygenated nucleic acids with the same functionality and high affinity as the murine parent antibody. The Kd of murine antibody towards digoxygenated nucleic acids (siRNA-Dig, see Example 11) was found to be 269 pM, and that of the disulfide-stabilized murine <Dig> scFv module was 467 pM. Thus, we conclude that the functionality of the wild-type antibody is also retained in the recombinant murine disulfide-stabilized <Dig> scFv module that is present in bispecific fusion protein (Her2-Dig, see example 3).

TABLE 3

Binding affinities of the murine 'wildtype' DIG-IgG and recombinant <Dig> derivatives to different digoxygenated antigens

|  | siRNA-DIG | siRNA-(2x)DIG |
| --- | --- | --- |
| DIG-BP4 | | |
| murine DIG-IgG 19-11 | 33 pM | 269 pM | 17 pM |
| humanized DIG-IgG | <76 pM | 12 nM | 8 pM |
| humanized <Dig>- single-chain Fv-fusion proteins | 68 pM | 35 nM | 162 pM |
| DIG-RNAse (human or bovine) | | |
| humanized <Dig>- disulfide-stabilized single-chain Fv-fusion proteins | about 1-2 nM | 32 nM | 246 pM |
| murine <Dig>- disulfide-stabilized single-chain Fv-fusion proteins | n.d. | 467 nM | 40 pM |

Note: The first data row is shown above with columns: Antibody | siRNA-DIG | siRNA-(2x)DIG. The DIG-BP4 and DIG-RNAse labels are section headers within the antibody column spanning the whole table.

Another SPR study was performed in which the binding affinity of <DIG>-hu2, IGF1R-DIG and <DIG> M-19-11 was compared in terms of binding to the mono-digoxygenated protein DIG-myoglobin. The binding affinities of <DIG>-hu2 and the disulfide-stabilized <DIG> scFv to DIG-Myo are comparable (~15-25 nM) and the affinity of the murine <DIG> M-19-11 was about a hundred fold better as also described for the binding of mono-digoxygenated nucleic acid (see above). The much higher affinities of <DIG>-hu2 to DIG-BP4 (<76 pM, see table 3) and the disulfide-stabilized <DIG> scFv to DIG-BP4 (68 pM, see table 3) in comparison to their affinities to DIG-Myoglobin (see Table 3a) are most likely due to an avidity effect of binding to DIG-BP4, because the protein DIG-BP4 carries more than one DIG molecule on its surface.

TABLE 3a)

| Antibody | Analyte | ka (1/Ms) | kd (1/s) | KD (M) |
| --- | --- | --- | --- | --- |
| <DIG>hu2 | DIG-Myoglobin | 6.20E+05 | 9.82E−03 | 1.58E−08 |
| | Repl. | 7.49E+05 | 8.81E−03 | 1.18E−08 |
| <DIG>hu2 | DIG-siRNA2349 | 6.45E+05 | 9.37E−03 | 1.45E−08 |
| | Repl. | 6.28E+05 | 9.80E−03 | 1.56E−08 |
| <IGF1R-DIG>2321 | DIG-Myoglobin | 3.92E+05 | 1.05E−02 | 2.69E−08 |
| | Repl. | 4.40E+05 | 1.07E−02 | 2.43E−08 |
| <IGF1R-DIG>2321 | DIG-siRNA2349 | 4.29E+05 | 1.17E−02 | 2.73E−08 |
| | Repl. | 4.93E+05 | 1.23E−02 | 2.51E−08 |
| <DIG>M-19-11 | DIG-Myoglobin | 1.75E+06 | 6.76E−04 | 3.86E−10 |
| | Repl. | 2.28E+06 | 6.75E−04 | 2.95E−10 |
| <DIG>M-19-11 | DIG-siRNA2349 | 3.27E+06 | 9.03E−04 | 2.76E−10 |
| | Repl. | 2.26E+06 | 8.38E−04 | 3.71E−10 |

Bi- and Multispecific Digoxygenin Binding Entities can be Generated with Different Formats The digoxygenin binding modules can be connected to cell targeting entities in a variety of formats. For example, not only 'classical' antibody fragments and antibody derived modules such as Fabs or Fvs can be applied for that, but also single-domain antibody-like entities which have previously been described in the literature. In addition to C-terminal fusions to the H-chain (exemplarily depicted in FIG. 6 and used as example for many analyses), additional formats have been produced in our lab and were functionally evaluated. FIG. 47 a displays a selection of molecules, based on the full length IgGs as master molecule, that were generated to achieve hapten-mediated payload delivery to antigen-expressing target cells. These include as examples fusions of (disulfide-stabilized) scFvs to the C-terminus of the L-chains of IgG's, fusions of single-chain Fabs to C-termini of either CH3 or C-kappa, fusions of scFvs (and/or scFabs) to L-chains as well as H-chains to generate hexavalent molecules. Furthermore, trivalent entities inclusive trivalents that contain disulfide-stabilized Fvs without single-chain linkers were successfully produced and can be applied for hapten-mediated payload delivery. Also, bispecific entities that contained fused fluorescent proteins were generated. The amino acid sequences that were applied to generate the different formats are listed as SEQ ID NO 38-SEQ ID NO 45. All molecules could be expressed in mammalian cells and purified with good yields with standard Protein-A and size exclusion technologies (see Example 3 'Composition, expression and purification of recombinant humanized <Dig> antibodies, -fragments and bispecific-fusion proteins).

FIGS. 47b and c display a selection of molecules of smaller size than those that are based on the full length IgGs as master molecule. These molecules are composed of smaller antibody fragments but were also generated to achieve hapten-mediated payload delivery to antigen-expressing target cells. Smaller modules may have better tissue and tumor penetration properties and have a different pharmacokinetics compared to IgG derived entities. Modular composition of smaller molecules furthermore permits the addition and recombinant expression of additional modules, e.g. for binding of Biotin (e.g. Straptavidin or avidin), or of entities that may facilitate entry into cells (e.g. translocation domains of pathogens). The amino acid sequences that were applied to generate the different formats are listed as SEQ ID NO 46-SEQ ID NO 50. All these molecules could be expressed and purified via affinity chromatography and size exclusion technologies for further characterization.

FIGS. 47c)-47 o) shows that all these molecules of the different formats fully retained targeting specificity as well as digoxygenin binding competency as a prerequisite for payload delivery: This was demonstrated by Surface-Plasmon-Resonance (BiaCore) experiments (see example 4 'Binding of recombinant <Dig> antibodies, -fragments and bispecific-fusion proteins to digoxygenated antigens' for details) and FACS analysis (see example 10 'Digoxygenated Cy5 and complexes with <Target>-<Dig> bispecific antibodies retain target specific binding and fluorescence features that can be used for in vitro and in vivo imaging' for details). The results of these experiments are shown in FIGS. 47c) to 47 o) and prove that the binding ability towards digoxygenin is comparable to the parent digoxygenin binding moieties that were applied as recombinant modules. Furthermore, specificity for recognition of the targeting antigen remained also uncompromised in the various formats. Thus, many different formats can be applied as vehicles for hapten-mediated targeted payload delivery.

Example 5

Generation of Defined Complexes of Digoxygenated Peptides with Bispecific <Her2>-<Dig> and <IGF1R>-<Dig>

Complexes of digoxygenated peptides with bispecific antibody derivatives containing recombinant Dig-binding modules may confer benign biophysical behaviour and improved PK parameters to peptides. Furthermore, such complexes are capable to target the peptides to cells which display the antigen that is recognized by the bispecific antibody variant. These complexes are composed of one humanized <Target>-<Dig> IgG which binds at its two high affinity Dig-binding sites two (one each site) digoxygenated peptides. It is desired that the peptides retain good biological activity despite being digoxygenated, as well as while being complexed to the antibody. It is also desired that the cell surface target binding site of the bispecific antibody derivative retains its binding specificity and affinity in the presence of complexed digoxygenated Peptides.

The peptides that we have used as examples to evaluate this technology are Melittin, INF7, FALLLv1, FALLv2 and Fam5b. The latter three peptides have been identified in a screen for bioactive peptides of human origin (to be described separately). The biological activity of the peptides can be assessed in vitro by determining their cytotoxic effects towards human tumor cell lines in vitro.

The amino acid sequences of these peptides are as follows:

```
Melittin:
                                   (Seq. ID. NO. 17)
GIGAVLKVLTTGLPALISWIKRKRQQ FALLv1:
                                   (Seq. ID. NO. 18)
FALLGDFFRKSKEKIGKEFKRIVQRIKDFLRNLVPRTES FALLv2:
                                   (Seq. ID. NO. 19)
NKRFALLGDFFRKSKEKIGKEFKRIVQRIKDFLRNLVPR Fam5b:
                                   (Seq. ID. NO. 20)
QHRYQQLGAGLKVLFKKTHRILRRLFNLAK INF7:
                                   (SEQ. ID. NO. 21)
GLFEAIEGFIENGWEGMIDGWYG
```

Bispecific complexes of digoxygenated peptides with bispecific <Target>-<Dig> antibody variants can be applied to target the peptides specifically to cells that express the target antigen. Thereby, the cells that are recognized by surface antigens will be selectively addressed by the peptides, peptide mediated cytotoxicity should be enhanced on antigen-expressing cells.

For the generation of such bispecific antibody complexes for selective targeting, it is necessary to (i) couple digoxygenin via suitable linkers to the peptide in a manner that allows the peptide to retain its activity; (ii) generate and characterize complexes of digoxygenated peptides with the bispecific <Target>-<Dig> IgG. These complexes shall be formed in a defined manner (2 Dig-peptides bind to 1<Dig> IgG). (iii) assure that these complexes retain activity of the peptide as well as specificity and affinity of the targeting antibody, to mediate increased (specific) peptide mediated biological activity on cells that express the targeting antigen.

Generation of Peptides with Amino-Terminal Cystein for Digoxigenin Conjugation

Peptide syntheses were performed according to established protocols (FastMoc 0.25 mmol) in an automated Applied Biosystems ABI 433A peptide synthesizer using Fmoc chemistry. In iterative cycles the peptide sequences were assembled by sequential coupling of the corresponding Fmoc-amino acids. In every coupling step, the N-terminal Fmoc-group was removed by treatment of the resin (3×2.5 min) with 20% piperidine in N-methylpyrrolidone. Couplings were carried out employing Fmoc-protected amino acids (1 mmol) activated by HBTU/HOBt (1 mmol each) and DIPEA (2 mmol) in DMF (45-60 min vortex). After every coupling step, unreacted amino groups were capped by treatment with a mixture of Ac2O (0.5 M), DIPEA (0.125 M) and HOBt (0.015 M) in NMP (10 min vortex). Between each step, the resin was extensively washed with N-methylpyrrolidone and DMF. Incorporation of sterically hindered amino acids was accomplished in automated double couplings. For this purpose, the resin was treated twice with 1 mmol of the activated building block without a capping step in between coupling cycles. Upon completion of the target sequences, Fmoc-12-amino-4,7,10-trioxadodecanoic acid (TEG-spacer) was coupled to the FAM5B and INF7 peptides using standard amino acid coupling conditions. Subsequently, Fmoc-Cys (Trt)-OH was attached to the amino terminus of all peptide sequences (FAM5B and INF7 with spacer, Melittin, FALLv1 and FALLv2 without spacer). After final Fmoc deprotection, the peptide resin was placed into a filter frit and treated with a mixture of trifluoroacetic acid, water and triisopropylsilane (19 mL: 0.5 mL: 0.5 mL) for 2.5 h. The cleavage solution was filtered and the peptides were precipitated by addition of cold (0° C.) diisopropyl ether (300 mL) to furnish a colorless solid, which was repeatedly washed with diisopropyl ether. The crude product was re-dissolved in a mixture of acetic acid/water, lyophilized and subsequently purified by preparative reversed phase HPLC employing an acetonitrile/water gradient containing 0.1% TFA (Merck Cromolith prep RP-18e column, 100×25 mm).

Coupling of Peptides with Amino Terminal Cystein to Digoxigenin

To a solution of the corresponding cysteine-modified peptide (6-20 mg) in a 0.1 M $KPO_4$ buffer (1 mL) was added an equimolar quantity of Digoxigenin-3-carboxy-methyl-ethylamido maleimide dissolved in 100 µL DMF. The reaction mixture was gently tumbled for 2-20 h at ambient temperature, filtered, and the target compound was isolated by preparative reversed phase HPLC employing an acetonitrile/water gradient containing 0.1% TFA (Merck Cromolith prep RP-18e column, 100×25 mm). After lyophilization the Digoxigenin-peptide conjugate was obtained as a colorless solid.

The molecular weight of the peptide Melittin is 2949.64, the molecular weight of the resulting peptide-Dig conjugate is 3520.33. The molecular weight of the peptide FALLv1 is 4710.59, the molecular weight of the resulting peptide-Dig conjugate is 5384.43. The molecular weight of the peptide FALLv2 is 4791.76, the molecular weight of the resulting peptide-Dig conjugate is 5465.59. The molecular weight of the peptide Fam5b is 3634.37, the molecular weight of the resulting peptide-Dig conjugate is 5410.47. The molecular weight of the peptide INF7 is 2896.25, the molecular weight of the resulting peptide-Dig conjugate is 3466.94. Until the point of complexation to the antibody, we stored the conjugate in aliquots dissolved in H2O at −20° C. FIG. 14 represents schematically the composition of the peptide-digoxygenin complexes.

Complexation of Digoxygenated Peptides with Recombinant <Target>-<Dig> Bispecific Antibodies Recombinant <IGF1R>-<Dig> bispecific antibodies and <Her2>-<Dig> bispecific antibodies were used as protein components of the coupling reaction. The composition and purification of these molecules has been described in example 1.

For the generation of complexes of digoxygenated peptides with <IGF1R>-<Dig> and <Her2>-<Dig> bispecific antibodies, we dissolved the (Melittin, INF7, FALLv1, FALLv2, Fam5b) peptide-Dig conjugate in $H_2O$ to a final concentration of 1 mg/ml. The bispecific antibody was brought to a concentration of 1 mg/ml (4.85 µM) in 20 mM Histidine, 140 mM NaCl, pH=6.0 buffer. Peptide and bispecific antibody were mixed to a 2:1 molar ratio (peptide to antibody) by pipetting up and down and incubated for 15 minutes at RT.

Then, the complex was used in vitro assays without further modification. Dilutions of the complex for these assays were carried out in Opti-MEM 1 (Invitrogen Madison, Wis.).

The resulting complex was defined as monomeric IgG-like molecule, carrying 2 Dig-peptides per one antibody derivative. The defined composition (and 2:1 peptide to protein ratio) of these bispecific peptide complexes was confirmed by size exclusion chromatography and charging/competition experiments.

Example 6

Digoxygenated Peptides and Complexes with <Target>-<Dig> Bispecific Antibodies Retain Target Specific Binding and Biological Activity One very important topic that needs to be addressed for any technology aimed at specific targeting of bioactive compounds is that the biological activity of the compound should be retained. Furthermore, the specificity and activity of the targeting module should not be affected by attachment of the payload. The bispecific antibody technology that we describe carries two modulation steps for bioactive peptides, one of which also modifies the targeting module. In a first step we covalently couple digoxygenin to the bioactive peptide. In a second step, this digoxygenated peptide is complexed with the bispecific antibody derivative, which is a large protein. To retain activity of the peptide it is important to assure activity of modified peptide for both steps: activity assays need to show that (i) functionality of the peptide is retained after digoxygenation, and (ii) functionality is retained after complexation of digoxygenated peptide to the murine or humanized <Dig>. Finally, it is necessary to show that (iii) the binding specificity and affinity of the targeting module is still retained in the final complex.

Comparison of the Biological Activities of Unmodified and Digoxygenated Cytotoxic Peptides To evaluate whether additions or alterations of the peptide Melittin, FALLv1 and FALLv2 by digoxygenin alters its biological activity, we performed in vitro assays. As these peptides are cytotoxic, their biological activity can easily be analyzed by monitoring the number of dead cells. To measure this number, the CytoTox-Glo assay (Promega Madison, Wis.) was used.

FIG. 15 shows the results of these CytoTox-Glo-assays that were performed to assess the biological activity of the Melittin, Fallv1 and Fallv2 peptides and their DIG-modified variants. For these assays, H322M cells were seeded at a density of 15.000 cells per well in 96 well plates. The cells were incubated for 24 hours at 37° C., 5% CO2 and 85% humidity in RPMI with 10% FCS, Na+Pyrovate, L-Glutamine and NEAA mix. The peptide and it's DIG-modified variant were then added to the cells in the concentrations indicated. The cells were incubated for further 48 hours. After this period, the cells were treated with the CytoTox-Glo-assay reagent according to the manufacturers instructions. In brief, this assay detects dead cells via the presence of a protease in the medium that cleaves a fluorogenic peptide in the reagent. The luminescence of this assay therefore represents dead cells. The 96 well plates were then analyzed in a InfiniteF200 luminescence reader (Tecan Austria, Gröding).

The results of these assays (FIG. 15, summarized in Table 4) show that the digoxygenated peptides retain their biological activities when compared to non-modified peptides. The IC50 value of the CytoTox-Glo assay was 3.28 μM for unmodified peptide and 3.98 μM for the digoxygenated peptide Melittin. The activities of Fallv1 and Fallv2 was similarly retained upon conjugation to digoxygenin (Table 4). Thus, digoxygenation did not interfere with the biological activity. We conclude that digoxygenation of the Melittin, FALLv1 and FALLv2 peptides does not interfere with their biological activity.

Specific Targeting of the Biological Activities of Digoxygenated-Antibody Complexed Peptides to Antigen Expressing Tumor Cells Not only covalent coupling to haptens, but also complexation of peptides to large bispecific antibody molecules may influence their biological activity. Because IgG-derived bispecific molecules are large proteins (10-40 fold the size of peptides), it cannot a priori be excluded that such molecules may sterically hinder accessibility of peptide and therefore interfere with biological activity. Vice versa, it may be possible that peptide complexation may interfere with the specific antigen binding functionality of the targeting modules in the bispecific antibody derivative. To address these topics, we analyzed the specific antigen binding functionality of the antibody-peptide complexes, as well as the in vitro activity of peptide-antibody complexes towards antigen expressing tumor cell lines.

For determining the antigen binding functionality of the complex, we applied surface plasmon resonance. Due to the low molecular weight of the peptides higher surface density is required to reach valuable signal heights during binding. Therefore, a special Chip surface was created to evaluate the functionality of the recombinant <Dig> derivatives with Dig-Peptides. Flow cells were activated with a 1:1 mixture of 0.1 M N-hydroxysuccinimide and 0.1 M 3-(N,N-dimethylamino)propyl-N-ethylcarbodiimide at a flow rate of 5 μl/min. Anti-human IgG antibody was injected in sodium acetate, pH 5.0 at 5 μg/ml, to aim a surface density of approximately 2000 RU. A reference control flow cell was treated equally omitting the capturing antibody. Surfaces were blocked with an injection of 1 M ethanolamine/HCl pH 8.5.

Additive Binding of Antigen and Digoxygenated Peptides to <Target> <DIG> Bispecific Antibodies For these Biacore experiments, recombinantly produced soluble extracellular domains of the RTK IGF1R was applied to characterize the <IGF1R>-<Dig>-Dig-Peptide complexes. To show additive binding to digoxygenated peptides, digoxygenated INF7 (SEQ. ID. NO. 21) and FALLv1 (SEQ. ID. NO. 18) were used. The antibody was diluted in HBS-P (10 mM HEPES, pH 7.4, 150 mM NaCl, 0.005% Surfactant P20) including 0.1% BSA and was injected at a flow rate of 10 μl/min. The contact time (association phase) was 1 min for the antibody at a concentration of 50 nM. Digoxygenated INF7 was used at a concentration of 50 nM for DIG-INF7, digoxygenated FALLv1 was used at a concentration of 90 nM. The soluble IGF1R fragment was used at a concentration of 50 nM. The digoxygenated peptides and sIGF1R were diluted in HBS-P (10 mM HEPES, pH 7.4, 150 mM NaCl, 0.005% Surfactant P20) and injected additively at a flow rate of 10 μl/min. The contact time (association phase) was 3 min, the dissociation time (washing with running buffer) 3 min for each molecule. The regeneration solution of 0.85% H3PO4 was injected for 120 s at 10 μl/min flow, followed by an injection of 10 mM NaOH for 120s at 10 μl/min flow to remove any non-covalently bound protein after each binding cycle. Signals were detected at a rate of one signal per second. All interactions were performed at 25° C. The results of these assays (FIG. 16) show that the IgG complexes with digoxygenated peptides retain binding specificity and affinity towards the cell surface antigens, independent of the order of binding.

To analyze whether the <Her2>-<Dig>-Dig-Peptide complexes, and <IGF1R>-<Dig>-Dig-Peptide complexes mediate specific targeting of their payload towards antigen expressing cells, we made use of the fact that the FALLv1 and Fam5b peptides are cytotoxic. By monitoring the number of dead cells we are therefore able to compare the biological activity of the DIG-peptides and the targeted DIG-peptide-<Her2>-<Dig> complexes. To measure the number of dead cells, the CytoTox-Glo assay (Promega Madison, Wis.) was used. To analyze the specificity of the targeting, two cell lines were used: H322M which have low levels of surface Her2 and KPL4 which have high levels of surface Her2.

For these assays, H322M cells were seeded at a density of 15.000 cells per well in 96 well plates. The cells were incubated for 24 hours at 37° C., 5% CO2 and 85% humidity in RPMI with 10% FCS, Na+Pyrovate, L-Glutamine and NEAA mix. KPL4 cells were seeded at a density of 7.000 cells per well in 96 well plates. The cells were incubated for 24 hours at 37° C., 5% CO2 and 85% humidity in RPMI with 10% FCS, and L-Glutamine. The DIG-peptides and the DIG-peptide-<Her2>-<Dig> complexes were then added to the cells in the concentrations indicated. The cells were incubated for further 48 hours. After this period, the cells were treated with the CytoTox-Glo-assay reagent according to the manufacturers instructions. In brief, this assay detects dead cells via the presence of a protease in the medium that cleaves a fluorogenic peptide in the reagent. The luminescence of this assay therefore represents dead cells. The 96 well plates were then analyzed in a InfiniteF200 luminescence reader (Tecan Austria, Gröding).

The results of these assays (FIG. 17) show that the IgG complexes with digoxygenated peptides confers cytotoxicity to antigen expressing cells: When the cytotoxicity of DIG-FALLv1 delivered by the <Her2>-<Dig> bispecific antibody to H322M and KPL4 cells is compared, it is consistently found to be more toxic to cells expressing higher levels of surface antigen. The cytotoxicity of the DIG-Fam5b peptide delivered by the <Her2>-<Dig> bispecific antibody also correlates with the levels of surface antigen. These findings show that the cytotoxic peptides are specifically enriched on antigen expressing cells when delivered by the appropriate bispecific antibody.

When the cytotoxicity of the DIG peptides was compared to the cytotoxicity of DIG peptides delivered to antigen expressing cells by the appropriate DIG bispecific AB (FIG. 18), the delivered peptides were consistently found to confer higher toxicity: the cytotoxicity of the <Her2>-<Dig> complex towards antigen expressing target cells is higher for the FALLv1 peptide compared to application of the non-complexed peptide. The cytotoxicity of the Fam5b peptide is also higher when it is delivered to antigen positive target cells compared to the non-delivered control peptide. This shows that the peptide complexes are specifically enriched on (and therefore mediate higher biological activity towards) antigen expressing target cells.

TABLE 4

| Molecule | IC50 unmodified peptide | IC50 Dig-peptide |
|----------|------------------------|------------------|
| Melittin | 3.3 uM | 4.0 uM |
| FALLv2 | 9.3 uM | 7.6 uM |
| FALLv1 | 7.4 uM | 6.4 uM |

Example 7

Generation of Defined Complexes of Digoxygenated Small Compounds with Bispecific <her2>-<Dig> and <IGF1R>-<Dig>

Complexes of digoxygenated small compounds with bispecific antibody derivatives containing recombinant Dig-binding modules may confer benign biophysical behaviour and improved PK parameters to the small compounds. Furthermore, such complexes are capable to target the compounds to cells which display the antigen that is recognized by the bispecific antibody variant. These complexes are composed of one humanized <Target>-<Dig> IgG which binds at its two high affinity Dig-binding sites two (one each site) digoxygenated compounds. It is desired that the compounds retain biological activity despite being digoxygenated, as well as while being complexed to the antibody. It is also desired that the cell surface target binding site of the bispecific antibody derivative retains its binding specificity and affinity in the presence of complexed Dig-Compounds. The small compound that we have used as example to evaluate this technology is Doxorubicin. The biological activity of Doxorubicin and digoxygenated Doxorubicin (=Dig-Dox) can be assessed by determining cytotoxic effects towards human tumor cell lines in vitro.

Bispecific complexes of digoxygenated doxorubicin with bispecific <Target>-<Dig> antibody variants can be applied to target Doxorubicin specifically to cells that express the target antigen. Thereby, the cells that are recognized by surface antigens will be addressed by doxorubicin. Because of that, doxorubicin mediated cytotoxicity should be enhanced on antigen-expressing cells.

For the generation of such bispecific antibody complexes for selective targeting, it is necessary to (i) couple digoxygenin via suitable linkers to doxorubicin in a manner that allows the doxorubicin to retain its activity; (ii) generate and characterize complexes of digoxygenated doxorubicin with the bispecific <Target>-<Dig> IgG. These complexes shall be formed in a defined manner (2 Dig-doxorubicin bind to 1<Dig> IgG). (iii) assure that these complexes retain activity of doxorubicin as well as specificity and affinity of the targeting antibody, to mediate specific doxorubicin mediated biological activity on cells that express the targeting antigen.

Generation of Digoxygenated Doxorubicin

Doxorubicin was obtained from Sigma-Aldrich. To couple digoxygenin to doxorubicin, we performed the following procedure: To a solution of Digoxigenin-3-O-methylcarbonyl-epsilon-aminocaproic acid-N-hydroxysuccinimide ester (20 mg, 30.4 µmol) in DMF (500 µL) was added triethylamine (8.4 µL, 60.8 µmol) and the resulting mixture was transferred immediately to a solution of Doxorubicin-HCl (16.6 mg, 30.4 µmol) in DMF (500 µL). The reaction mixture was tumbled for 2 h at ambient temperature, filtered, and the target compound was isolated by preparative reversed phase HPLC employing an acetonitrile/water gradient containing 0.1% TFA (Merck Cromolith prep RP-18e column, 100×25 mm). After lyophilization the Doxorubicin-Digoxigenin conjugate was obtained as a colorless solid (25.2 mg, 76%). Analytical HPLC: tR=13.9 min (Merck Chromolith Performance RP-18e, 100×4.6 mm, water+0.1% TFA acetonitrile/water+0.1% TFA 80:20, 25 min); ESI-MS (positive ion mode): m/z: calcd for $C_{58}H_{75}N_2O_{18}$: 1087.5; found: 1087.6 [M+H]+. The molecular weight of doxorubicin is 579.98 Da. The molecular weight of the resulting Doxorubicin-Dig conjugate is 1087.24 Da. Until the point of complexation to the antibody, we stored the conjugate in aliquots in DMSO at −20° C. FIG. 18 shows the structure of Doxorubicin-digoxygenin conjugate.

Complexation of Digoxygenated Doxorubicin with Recombinant <Target-Dig> Bispecific Antibodies Recombinant <IGF1R>-<Dig> bispecific antibodies and <Her2>-<Dig> bispecific antibodies were used as protein components of the coupling reaction. The composition and purification of these molecules has been described in example 1.

For the generation of complexes of digoxygenated doxorubicin with <IGF1R>-<Dig> and <Her2>-<Dig> bispecific antibodies, we dissolved the doxorubicin-Dig conjugate in OptiMEM (Invitrogen) containing 1% Acetonitrile and 0.1% DMSO to a final concentration of 0.1 mg/ml. The bispecific antibody was used in a concentration of 1 mg/ml (5 µM) in a buffer composed of 20 mM Histidin and 140 mM NaCl, pH 6. Digoxygenated doxorubicin and bispecific antibody were mixed to a 2:1 molar ratio (digoxygenated doxorubicin to antibody). This procedure resulted in a homogenous preparation of complexes of defined composition. Subsequently, this preparation was applied in the cell viability assays that are described below.

FIG. 19 shows the size exclusion profile of the complex of digoxygenated doxorubicin with <Her2>-<Dig>. Increased charging (signal at the size of the protein complex) is revealed by increasing fluorescence signals up to a ratio of at least one DIG-dox molecule per one protein molecule. Thereafter, addition of more DIG-dox molecules does not increase the signal at the position of protein in a linear manner, but there neither appears a signal where the unbound DIG-dox would be expected possibly due to unspecific association with the column material. We conclude from these experiments that the complex of Dig-dox and the bispecific antibody was composed of molecules that contained at least one LMW compound per protein.

Further characterization of the complex by applying surface plasmon resonance studies (Biacore, see example 4 above) provided additional evidence that the complexation reaction generated defined molecules that completely retained the specific binding affinity of the bispecific antibody module.

Example 8

Digoxygenated Doxorubicin and Complexes with <Target-Dig> Bispecific Antibodies Retain Target Specific Binding and Biological Activity One very important topic that needs to be addressed for any technology aimed at specific targeting of bioactive compounds is that the biological activity of the compound should be retained. Furthermore, the specificity and activity of the targeting module should not be affected by attachment of the payload. The bispecific antibody technology that we describe carries two modulation steps for bioactive compounds, one of which also modifies the targeting module. In a first step we covalently couple digoxygenin to doxorubicin. In a second step, this digoxygenated doxorubicin is complexed with the bispecific antibody derivative, which is a large protein. To retain activity of doxorubicin it is important to assure activity of modified doxorubicin for both steps: activity assays need to show that (i) functionality of the doxorubicin can be retained after digoxygenation, and (ii) the binding specificity and affinity of the targeting module is still retained in the final complex.

Comparison of the Biological Activities of Unmodified and Digoxygenated Doxorubicin To evaluate whether digoxygenation of doxorubicin alters its biological activity, we performed bioassays with different cell lines that were grown in presence of doxorubicin or digoxygenated doxorubicin. Afterwards the cell viability was analysed. FIGS. 20, 21 and 48a show the results of these cell viability assays that were performed to assess the biological activity of doxorubicin and digoxygenated doxorubicin. For these assays, we seeded KPL-4, H322M or MDA-MB-468 cells and let them attach to the plates over night. The next day they were treated with doxorubicin or digoxygenated doxorubicin in the indicated concentrations for 48 hours. Then, the cells were lysed and the cell viability was assessed by applying the CellTiter Glo Luminescent Cell Viability Assay (Promega, Madison, Wis.). The results of these assays (FIGS. 20 21 and 48a) show that digoxygenated doxorubicin retains some of its biological activity when incubated on H322M cells. The KPL-4 cells do not show any effect after exposure with digoxygenated doxorubicin in the used concentrations. The IC50 value of the cell viability assay was 25 µM for unmodified doxorubicin and >1000 µM for digoxygenated doxorubicin when incubated with H322M cells. In the case of KPL-4 cells, the IC50 value of the cell viability assay was 2.6 µM for unmodified doxorubicin and >1000 µM for digoxygenated doxorubicin The IC50 value of the cell viability assay was 17 µM for unmodified doxorubicin and >1000 µM for digoxygenated doxorubicin when incubated with MDA-MB-468 cells. This indicates a significant loss of activity of doxorubicin upon modification with digoxygenin. The reason for this reduced activity is not the loss of functionality but limitations in cell membrane penetration of the digoxygenated doxorubicin. This molecule is much larger than the original doxorubicin and therefore cannot easily penetrate biological membranes. This limitation is experimentally shown in FIG. 22: Immunofluorescence shows that doxorubicin penetrates membranes and accumulates at its site of action in the nucleus. In contrast, the bulk of digoxygenated doxorubicin accumulates upon exposure of cells in endosomes, thus it does not reach its site of action within the cell. Nevertheless, the molecular functionality of digoxygenated doxorubicin is still retained. This can be demonstrated by the co-application of endosome-escape reagents, which permit digoxygenated doxorubicin to enter the cytoplasm and nuclei and in consequence lead to greatly increased cytotoxicity (see below).

Specific Targeting of the Biological Activities of Digoxygenated-Antibody Complexed Doxorubicin to Antigen Expressing Tumor Cells To analyze if the specific antigen binding functionality of the antibody-complexes can be utilized to specifically deliver payload-activity to tumor cells, we performed immunofluorescence studies followed by in vitro cytotoxicity assays to determine biological activity of targeted doxorubicin. Dig-Dox can be visualized by immunofluorescence by excitation with a 514 nm laser, while the emission is detected between a wavelength of 520 and 560 nm. Because of that we were able to visualize optically targeting and accumulation of dig-dox complexed to <IGF1R>-<DIG> on cells. FIG. 22 shows IF-analyses of IGF1R-expressing MCF7 cells with the complex of IGF1R-DIG and Dig-Dox accumulated on the cell surface. Results of these studies indicate that dig-dox is specifically delivered to target cells by targeting moieties of the bispecific antibody.

To further analyze whether the <Her2>-<Dig>-Dig-Dox complexes, and <IGF1R>-<Dig>-Dig-Dox complexes mediate specific targeting of their (cytotoxic) payload towards antigen expressing cells, we seeded defined numbers of KPL-4 (Her2+++), H322M (IGF1R+++) and MDA-MB-468 (Her2+/−) cells and let them attach to the plates over night. The next day they were treated with <Her2>-<Dig>-Dig-Dox or <IGF1R>-<Dig>-Dig-Dox complexes in the indicated concentrations for 48 hours. Then, cell viability was assessed by applying the CellTiter Glo Luminescent Cell Viability Assay (Promega, Madison, Wis.).

The results of these assays (FIGS. 20, 21 and 48b) show that the IgG complexes with digoxygenated Doxorubicin confer cytotoxicity to antigen expressing cells: The IC50 value of the Dig-Dox/<Her2>-<Dig> complex toward Her2 expressing Kpl-4 target cells was 5.9 µM, while for the target negative MDA-MB-468 cells, the complex of Dig-Dox and <Her2>-<Dig> did not confer much more cytotoxicity than <Her2>-<Dig> without any payload. Similarly, the IC50 value of the Dig-Dox/<IGF1R>-<Dig> complex toward IGF1R expressing H322M target cells was 5.8 µM. For both target cell lines (KPL-4 and H322M) it was shown that the targeting antibody loaded with Dig-Dox had a stronger cytotoxicity than the non-loaded antibody applied in the same concentrations. We conclude that <Target>-<Dig> bispecific antibody derivatives are capable to specifically deliver cytotoxic payloads to cells which are recognized by the targeting modules.

FIG. 48 shows the results of additional targeting experiments of digoxygenated doxorubicin with >Dig> bispecific antibodies. These experiments included an additional breast tumor cell line MDA-MB-468. For these assays, we propagated and plated KPL-4, H322M or MDA-MB-468 cells as described above and treated them with doxorubicin or digoxygenated doxorubicin in the indicated concentrations for 48 hours. Cell viability determination with the CellTiter Glo Luminescent Cell Viability Assay (Promega, Madison, Wis.) (FIGS. 48a and b) confirmed that digoxygenated doxorubicin loses most of its biological activity when incubated on MDA-MB468 cells. This phenotype is very similar to that observed for KPL-4 and H322M cells (see above). The IC50 value on MDA-MB-468 cells was 17 µM for unmodified doxorubicin and >1000 µM for digoxygenated doxorubicin. Additional experiments that address the possibility to deliver digoxygenated doxorubicine complexed to bispecific targeting modules are shown in FIG. 48 c to e: KPL-4 (Her2+++), H322M (IGF1R+++) and MDA-MB-468 (Her2+/−) cells were treated with <Her2>-<Dig>-Dig-Dox or <IGF1R>-<Dig>-Dig-Dox complexes for 48 hrs as described above. Thereafter, cell viability was assessed by applying the CellTiter Glo Luminescent Cell Viability Assay (Promega, Madison, Wis.). The results of these assays confirms that the IgG complexes with digoxygenated Doxorubicin confer cytotoxicity to antigen expressing cells. For both target cell lines (KPL-4 and H322M) that express either her2 or IGF1R it was shown that the targeting antibody loaded with Dig-Dox had a stronger cytotoxicity than the non-loaded antibody applied in the same concentrations. In contrast, for the target negative MDA-MB-468 cells, the complex of Dig-Dox and <Her2>-<Dig> did not confer much more cytotoxicity than <Her2>-<Dig> without any payload. We conclude that <Target>-<Dig> bispecific antibody derivatives are capable to specifically deliver cytotoxic payloads to cells which are recognized by the targeting modules.

Example 9

Generation of Defined Complexes of Digoxygenated Fluorescent Substrates with Bispecific <Her2>-<Dig> and <IGF1R>-<Dig>

Complexes of digoxygenated fluorescent substrates with bispecific antibody derivatives containing recombinant Dig-binding modules can be applied for specific imaging of tissues or cells that carry the target antigen. These complexes are composed of one humanized <Target>-<Dig> IgG which binds at its two high affinity Dig-binding sites two (one each site) digoxygenated substrates that can be visualized by imaging technologies. It is necessary that the imaging compounds retain their properties (fluorescence) despite being digoxygenated, as well as while being complexed to the antibody. It is also desired that the cell surface target binding site of the bispecific antibody derivative retains its binding specificity and affinity in the presence of complexed Dig-Compounds.

The imaging compound that we have used as example to evaluate this technology is Cy5. Cy5 is a fluorescence substrate that is excited by a wavelength between 575-633 nm and upon excitement it emits light in the near infrared spectrum at a wavelength of 670 nM. Because of that, the presence of Cy5 and digoxygenated Cy5 (=Dig-Cy5) can be assessed by fluorescence microscopy as well as by in vivo imaging technologies. Bispecific complexes of digoxygenated Cy5 with bispecific <Target>-<Dig> antibody variants can be applied to target Cy5 specifically to cells that express the target antigen. Thereby, the cells that are recognized by surface antigens can be visualized by Cy5, and thus be distinguished from cells that do not carry the target antigen.

For the generation of such bispecific antibody complexes for selective targeting of imaging reagents, it is necessary to (i) couple digoxygenin via suitable linkers to Cy5 in a manner that allows the Cy5 to retain its fluorescence features; (ii) generate and characterize complexes of digoxygenated Cy5 with the bispecific <Target>-<Dig> IgG. These complexes shall be formed in a defined manner (2 Dig-Cy5 bind to 1<Dig> IgG). (iii) assure that these complexes retain activity of Cy5 as well as specificity and affinity of the targeting antibody, to mediate specific Cy5-visualization of cells that express the targeting antigen.

Generation of Digoxygenated Cy5

For the generation of digoxygenated Cy5 DIG-Carboxymethyl-NHS ester (DE 3836656) was transformed with monobac ethylendiamine. Afterwards boc was removed and the released amine was allowed to react with Cy5-NHS ester (GE Healthcare, PA15106). In order to purify DIG-Cy5 a HPLC using a RP 18 column was carried out. Eluent A was H2O containing 0.1% TFA, eluent B was acetonitrile containing 0.1% TFA. During the elution that was run over 60 min the concentration of eluent B was increased from 0% to 100%.

The molecular weight of Cy5 is 791.99 Da. The molecular weight of the resulting Cy5-Dig conjugate is 1167.55 Da. Until the point of complexation to the antibody, we stored the conjugate in aliquots in PBS at −20° C. FIG. 23 shows the structure of Cy5-digoxygenin conjugate.

Complexation of Digoxygenated Cy5 with Recombinant <Target-Dig> Bispecific Antibodies Recombinant <IGF1R>-<Dig> bispecific antibodies and <Her2>-<Dig> bispecific antibodies were used as protein components of the coupling reaction. The composition and purification of these molecules has been described in example 1.

For the generation of complexes of digoxygenated Cy5 with <IGF1R>-<Dig> and <Her2>-<Dig> bispecific antibodies, we dissolved the Cy5-Dig conjugate in PBS to a final concentration of 0.5 mg/ml. The bispecific antibody was used in a concentration of 1 mg/ml (5 µM) in a buffer composed of 20 mM Histidin and 140 mM NaCl, pH 6. Digoxygenated Cy5 and bispecific antibody were mixed to a 2:1 molar ratio (digoxygenated Cy5 to antibody). This procedure resulted in a homogenous preparation of complexes of defined composition. Subsequently, this preparation was applied in the in vitro and in vivo imaging studies that are described below.

FIG. 24 shows the size exclusion profile of the complex of digoxygenated Cy5 with <Her2>-<Dig>. Increased charging (signal at the size of the protein complex) is revealed by increasing fluorescence signals up to a ratio of two DIG-Cy5 molecules per one protein molecule. If charging is increased up to a ratio of five DIG-Cy5 molecules per protein the fluorescent signal does not increase anymore indicating that the two DIG-binding sites are saturated at a ratio of 2:1 (DIG-Cy5: <Her2>-<Dig>). In contrast antibodies directed against <Her2> or <IGF1R> without a <Dig> binding part do not bind DIG-Cy5 at all (FIG. 49b) indicating that DIG-Cy5 does not bind unspecifically to those antibodies. We conclude from these experiments that the complex of Dig-Cy5 and the bispecific antibody was composed of molecules that contained two Dig-Cy5 compounds per protein.

Characterization of the complex by applying surface Plasmon resonance studies (Biacore, see example above) provided additional evidence that the complexation reaction generated defined molecules that completely retained the specific binding affinity of the bispecific antibody module.

Further refinement of the experimental conditions showed more clearly that the binding ratio between <Her2>-<Dig> and DIG-Cy5 is 1:2. FIGS. 49a and b show the size exclusion profile and the evaluation of the SEC of the complex of digoxygenated Cy5 with <Her2>-<Dig> after refinement of the experimental setup. Increased charging (signal at the size of the protein complex) is revealed by increasing fluorescence signals up to a ratio of two DIG-Cy5 molecules per one protein molecule. If charging is increased up to a ratio of five DIG-Cy5 molecules per protein the fluorescent signal does not increase anymore indicating that the two DIG-binding sites are saturated at a ratio of 2:1 (DIG-Cy5: <Her2>-<Dig>). In contrast antibodies directed against <Her2> or <IGF1R> without a <Dig> binding part do not bind DIG-Cy5 at all (FIG. 49b) indicating that DIG-Cy5 does not bind unspecifically to those antibodies. We conclude from these experiments that the complex of Dig-Cy5 and the bispecific antibody was composed of molecules that contained two Dig-Cy5 compounds per protein.

Example 10

Digoxygenated Cy5 and Complexes with <Target>-<Dig> Bispecific Antibodies Retain Target Specific Binding and Fluorescence Features that can be Used for in Vitro and In Vivo Imaging One very important topic that needs to be addressed for any technology aimed at specific targeting of bioactive compounds is that the biological activity of the compound should be retained. Furthermore, the specificity and activity of the targeting module should not be affected by attachment of the payload. The bispecific antibody technology that we describe carries two modulation steps for bioactive compounds, one of which also modifies the targeting module. In a first step we covalently couple digoxygenin to Cy5. In a second step, this digoxygenated Cy5 is complexed with the bispecific antibody derivative, which is a large protein. To retain activity of Cy5 it is important to assure activity of modified Cy5 for both steps: it needs to be shown that (i) fluorescence functionality of the Cy5 can be retained after digoxygenation, and (ii) the binding specificity and affinity of the targeting module is still retained in the final complex.

Fluorescence Activities of Unmodified and Digoxygenated Cy5

To evaluate whether digoxygenation of Cy5 alters its fluorescence features, we compared the excitation and emission spectra of Cy5 and compared it with the spectra of the newly generated Dig-Cy5 and with Dig-Cy5 within a complex with bispecific antibodies. Table 4 summarizes the results of these analyses: Conjugation of Cy5 to digoxygenin, as well as complexation of Dig-Cy5 to antibodies does not interfere with the fluorescence features of Cy5. We conclude that Dig-Cy5 and -complexes can be applied for antibody-mediated targeting and in vivo imaging.

Binding Activity of Dig-Cy5 Complexed Targeting Modules

To evaluate whether complexation of digoxygenated Cy5 alters the binding features of the bispecific targeting modules, we applied surface resonance analyses. The extracellular domain of Her2 (as well as IGF1R) were used as antigens to determine antibody affinities. Details of these analyses have been described in example 4. Table 5 summarizes the results of these analyses: Complexation of Dig-Cy5 to antibodies does not interfere with the binding affinity of the targeting modules.

TABLE 5

| Molecule | Cy5 | Dig-Cy5 | <Her2Dig> | <Her2Dig> Dig-Cy5 |
|---|---|---|---|---|
| Excitation wavelength | 575-605 nm | 575-605 nm | n.a. | 575-605 nm |
| Emission wavelength | max. nm at 670 | max. nm at 670 | n.a. | max. nm at 670 |
| affinity Her2ECD | n.a. | n.a. | tbd | tbd |

Further characterization of the complex by applying FACS analysis provided additional evidence that complexation of Dig-Cy5 to antibodies does not interfere with the binding of the targeting modules. For these analyses we used CD22 positive Raji and Ramos cells and the bispecific <CD22>-<DIG> antibody. $3 \times 10^5$ cells per well of a 96-well-plate were incubated with 5 µg/ml of the <CD22>-<DIG> antibody in FACS buffer (PBS containing 5% FCS). After washing the cells were incubated with DIG-Cy5 in a final concentration of 66.4 nM. After another washing step cells were analysed with the FACS canto II (BD Biosciences).

The result of this analyses is shown in FIG. 25. The complex of <CD22>-<DIG> and DIG-Cy5 clearly binds to the Raji or Ramos cells while DIG-Cy5 alone shows hardly any binding. We therefore conclude that Dig-Cy5 complexes with bispecific antibodies can be applied for antibody-mediated targeting and in vivo imaging.

Specific Targeting of Digoxygenated-Antibody Complexed Cy5 to Antigen Expressing Tumor Cells In Vivo To analyze if the specific antigen binding functionality of the antibody-complexes can be utilized to specifically deliver imaging reagents to tumor cells, we performed Near Infrared Fluorescence Imaging Studies (NIRF) in vivo. For these studies, 50 µg of either <Her2>-<Dig>-Dig-Cy5 or <IGF1R>-<Dig> Dig-Cy5 complexes were injected intravenously into immunodeficient mice which carried subcutaneous tumor xenografts. These xenografts were either expressing the antigen Her2 (KPL4 cells) or the antigen IGF1R (H322M cells). Subsequently NIRF imaging was performed by using the Maestro system from CRI. Animals were placed in a measuring chamber and the fluorescence was measured over a defined spectral wavelength array, depending on the dye.

Spectral information of each pixel of the obtained image was analyzed by a special software which allows to separate different pre-defined spectra, e.g. autofluorescence and the signal of the dye. Theses separated specific signals were quantified by the Maestro software in order to compare different samples.

The results of these assays (FIGS. 26 and 27) show that the Dig-Cy5 that is complexed with bispecific antibodies is specifically targeted to tumors which express the cognate antigen. Her2 expressing KPL4 tumors can be visualized by NIRF with <Her2>-<Dig> Dig-Cy5 complexes 24 hours after injection. In a similar manner, IGF1R expressing tumors can be specifically visualized by NIRF 30 min after applying the complex of the bispecific antibody derivative <IGF1R>-<Dig> with Dig-Cy5. In contrast to the antibody complexes, which show fluorescence of the targeted tumor, Dig-Cy that is not complexed with antibody shows no tumor specific fluorescence (but instead some accumulation in the liver, as indicated by circles in FIG. 29).

Figure 28:
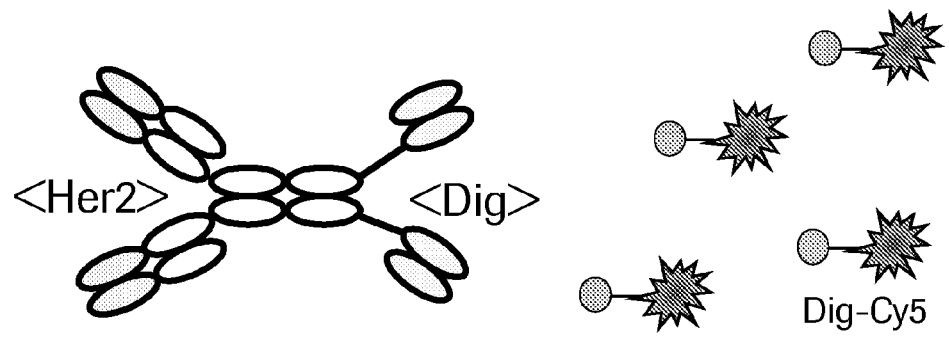
Figure 28:
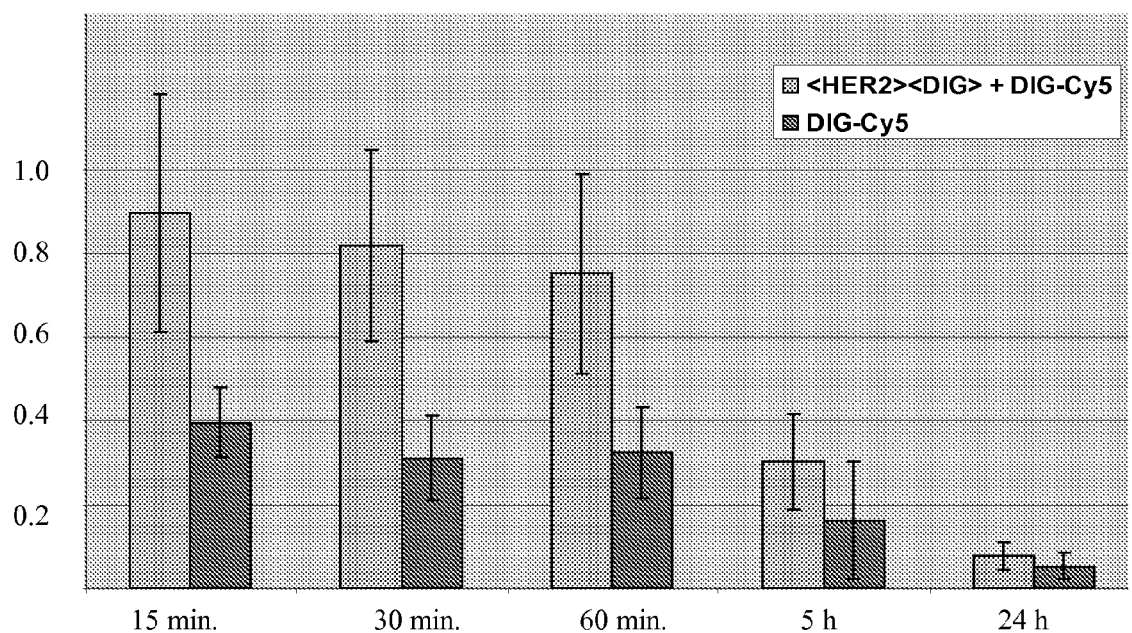

One further imaging approach that makes use of <Target>-<Dig> bispecific antibodies combined with digoxygenated imaging substrates is shown in FIG. 28: In this experiment, we have not pre-formed the complex of proteinous targeting modules with digoxygenated payload before injection into tumor bearing animals. Instead, we have injected the bispecific antibody and waited 48 hrs before subsequent injection of the digoxygenated imaging substrate. This procedure gives the targeting module time for tumor/tissue penetration and accumulation on tumors. Thereafter, the imaging reagent is given which due to its small size has rapid tumor penetration and accumulates on the target tissue where it forms the <Target>-<Dig> Dig-Cy5 complex in vivo. This method has the advantage that the time for opening the imaging window is rather short because any uncomplexed imaging reagent is rapidly cleared. Furthermore, this approach may be particularly useful for radioactive imaging (or therapeutic) agents which should give only limited systemic exposure to patients.

We conclude from these experiments that complexes of bispecific <Target>-<Dig> antibodies with digoxygenated imaging reagents can be used for specific in vivo imaging purposes.

Example 11

Generation of Defined Complexes of Digoxygenated Nucleic Acids with Bispecific <her2>-<Dig> and <IGF1R>-<Dig>

Complexes of digoxygenated nucleic acids, such as siRNAs with bispecific antibody derivatives containing recombinant Dig-binding modules can be applied for specific targeting of nucleic acids to antigen expressing cells. Such complexes are capable to target the peptides to cells which display the antigen that is recognized by the bispecific antibody variant. These complexes are composed of one humanized <Target>-<Dig> IgG which binds at its two high affinity Dig-binding sites two (one each site) digoxygenated nucleic acids. It is desired that the nucleic acids retain their functionality despite being digoxygenated, as well as while being complexed to the antibody. It is also desired that the cell surface target binding site of the bispecific antibody derivative retains its binding specificity and affinity in the presence of complexed digoxygenated nucleic acids.

The nucleic acids that we have used as examples to evaluate this technology are either DNA fragments or siRNAs. We applied siRNAs targeting Eg5 or luciferase as an example which inactivate the respective mRNA within the cytoplasm of cells DNAs and siRNAs were generated as nucleic acids that were digoxygenated. Furthermore, selected molecules were digoxygenated as well as coupled to fluorescent dyes (incl. Cy5, see examples 9 and 10). The specific targeting and localization of fluorescent nucleic acids can be visualized by imaging technologies as described above. Furthermore, the biological activity of the siRNAs can be assessed in vitro by determining their mRNA down-regulation effects in human tumor cell lines in vitro.

TABLE 6

| Small caps: cuu = 2'O-Methyl modification, 2'F: 2'F on ribose instead of 2'OH | | | | |
|---|---|---|---|---|
| Molecule (→ Seq 5 - 3') | sense sequence | Seq. ID NO. | antisense sequence | Seq. ID NO. | molecular weight duplex |
| Luciferase | cuu AcG cuG AGu Acu ucG ATsT | 22 | UCGAAGuACUc AGCGu AAG TsT | 29 | 13530.7 |
| Dig-Luciferase | cuu AcG cuG AGu Acu ucG ATsT(C6NH)(Dig) | 23 | UCG AAGu ACU cAG CGu AAG TsT | 30 | 14237 |
| Eg5 | CUG AAG ACC UGA AGA CAA uuu | 24 | AUU GUC UUC AGG UCU UCA GUU | 31 | 13295.1 |
| Dig-Eg5 | cuG AAG Acc uGA AGA cAA uuu(C6NH)(Dig) | 25 | AUU GUC UUC AGG UCU UCA GUU | 32 | 14177.3 |
| Dig-Eg5-Dig | cuG AAG Acc uGA AGA cAA uuu(C6NH)(Dig) | 26 | AUfUfGUfCf UfUfCf AGG UfCfUf UfCfA GUfUf(C6NH2)(DIG) | 33 | 14895.3 |
| Dig-Eg5-Cy5 | (Cy5)CUG AAG ACC UGA AGA CAA UUU (C6NH2)(DI | 27 | AUU GUC UUC AGG UCU UCA GUU | 34 | 14552.1 |

TABLE 6-continued

Small caps: cuu = 2'O-Methyl modification, 2'F: 2'F on ribose instead of 2'OH

| Molecule (→ Seq 5 - 3') | sense sequence | Seq. ID NO. | antisense sequence | Seq. ID NO. | molecular weight duplex |
|---|---|---|---|---|---|
| Dig-Eg5-Dig-Cy5 | (CY5)cuG AAG Acc uGA AGA cAA | 28 | AUfUfGUfCf UfUfCf AGG UfCfUf UfCfA | 35 | 15428 |

The composition of the nucleic acids that we have applied for these examples are shown in Table 6.

Bispecific complexes of digoxygenated nucleic acids with bispecific <Target-Dig> antibody variants can be applied to target the nucleic acids specifically to cells that express the target antigen. Thereby, the cells that are recognized by surface antigens will be selectively addressed by the nucleic acids, activities caused by nucleic acids, e.g. RNAi or other nucleic acid mediated cytotoxicity should be enhanced on antigen-expressing cells.

For the generation of such bispecific antibody complexes for selective targeting, it is necessary to (i) couple digoxygenin via suitable linkers to the nucleic acid in a manner that allows the nucleic acid to retain its activity; (ii) generate and characterize complexes of digoxygenated nucleic acids with the bispecific <Target>-<Dig> IgG. These complexes shall be formed in a defined manner (2 Dig-nucleic acids bind to 1<Dig> IgG). (iii) assure that these complexes retain activity of the nucleic acid as well as specificity and affinity of the targeting antibody, to mediate increased (specific) nucleic acid mediated biological activity on cells that express the targeting antigen.

Generation of Digoxygenated Nucleic Acids

1. Oligoribonucleotide Synthesis and Purification:

Oligoribonucleotides were synthesized according to the phosphoramidite technology on solid phase employing an ABI 394 synthesizer (Applied Biosystems) at the 10 μmol scale. Syntheses were performed on a solid support made of controlled pore glass (CPG, 520 Å, with a loading of 75 μmol/g, obtained from Prime Synthesis, Aston, Pa., USA or 3'-PT-Amino-Mod. C6 CPG, with a loading of 37 μmol/g, from Glen Research, Sterling, Va., USA). Regular RNA phosphoramidites, 2'-O-Methylphosphoramidites, and 2'-F phosphoramidites as well as ancillary reagents were purchased from Proligo (Hamburg, Germany). Without any modification of the synthesis cycle the Cy5 fluorescent dye was attached to the 5'-end using the corresponding phosphoramidite (obtained from GE Healthcare, Munich Germany). After finalization of the solid phase synthesis, cleavage and deprotection of the support bound oligomer was carried out. Then the crude oligomers were purified by Anion exchange (AEX) HPLC using a Source 15Q, SPSC-150, 150×8 mm column (Bischoff, Leonberg, Germany) on an AKTA Explorer system (GE Healthcare).

2. DIG Labeling of the Amino Modified RNA

Digoxigenin-3-O-methyl carbonyl-ε-aminocaproicacid-N-hydroxysuccinimide (Roche, Basel, Switzerland) was dissolved in Dimethylsulfoxide (DMSO) (Fluka, Buchs, Switzerland). This solution was added to the purified amino modified RNA dissolved in buffer (0.1 M Na-Borate in 0.1 M KCl, pH 8.5). The reaction was controlled by AEX HPLC. In case of quantitative reaction the conjugated RNA was isolated by precipitation with 3M NaOAc, pH=5.2 and Ethanol (1:32). If the reaction was not quantitative a purification step was performed. In this case the oligomers were purified by AEX HPLC using a DNAPac PA-100 22×250 mm (Dionex, Idstein, Germany) on an AKTA Explorer system (GE Healthcare). Buffer A was 6 M Urea, 10 mM NaClO$_4$, 20 mMTris, 1 mM EDTA; pH 7.4, 20% ACN and, buffer B 6 M Urea 500 mM NaClO$_4$, 20 mM Tris, 1 mM EDTA; pH 7.4, 20% ACN. A flow rate of 4.5 mL/min (at 60° C.) was employed. UV traces at 260, 280 and in case of Cy5 643 nm were recorded. A gradient of 25% B to 55% B within 55 min was employed. Appropriate fractions were pooled and precipitated with 3M NaOAc, pH=5.2 and Ethanol (1:32). After centrifugation the pellet was dissolved in water.

The concentration of the solution was determined by absorbance measurement at 260 nm in a UV photometer (Beckman Coulter, Krefeld, Germany). Until annealing the individual strands were stored as frozen solutions at −20° C.

3. Annealing of Oligoribonucleotides to Generate siRNA

Complementary strands were annealed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 95° C. which was cooled to rt within 3 h.

The molecular weight of the nucleic acids as well as of the siRNA heteroduplexes are listed in Table 6. Until the point of complexation to the antibody, we stored the nucleic acid conjugates in aliquots dissolved in 0.1 M NaCl, 20 mM NaH2PO4×H2O/Na$_2$HPO4×2H2O, pH 6.8 at −20° C. FIG. 29 represents schematically the composition of digoxygenin coupled nucleic acids.

Complexation of Digoxygenated Nucleic Acids with Recombinant <Target-Dig> Bispecific Antibodies Recombinant <IGF1R>-<Dig> bispecific antibodies and <Her2>-<Dig> bispecific antibodies were used as protein components of the coupling reaction. The composition and purification of these molecules has been described in example 1.

For the generation of complexes of digoxygenated nucleic acids with <IGF1R>-<Dig> and <Her2>-<Dig> bispecific antibodies, we dissolved the Nucleic Acid-Dig conjugate in 0.1 M NaCl, 20 mM NaH$_2$PO$_4$×H2O/Na$_2$HPO$_{4×2}$H2O, pH 6.8 to a final concentration of 100 μM. The bispecific antibody was brought to a concentration of 1 mg/ml (5 μM) in 20 mM Histidine, 140 mM NaCl, pH=6.0 buffer. Nucleic acid and bispecific antibody were mixed to a 2:1 molar ratio (nucleic acid to antibody) by pipetting up and down and incubated for 15 minutes at RT. Then, the complex was used in in vitro assays or in vivo applications without further modification. Dilutions of the complex for these assays were carried out in Opti-MEM 1 (Invitrogen Madison, Wis.). The resulting complex was defined as monomeric IgG-like molecule, carrying 2 Dig-siRNAs per one antibody derivative. The defined composition (and 2:1 nucleic acid to protein ratio) of these bispecific complexes was confirmed by size exclusion chromatography and charging/competition experiments. The results of these size exclusion chromatography analyses with bispecific targeting modules and fluorescently labeled nucleic acids are shown in FIG. 30: Increased charging (signal at the size of the larger protein complex) is revealed by increasing fluorescence signals up to a ratio of two nucleic acids per one protein molecule. Thereafter, addition of more labeled nucleic acids does not increase the signal at the position of protein but instead at a position that reflects lower molecular weight molecules of the size of the nucleic acids. The 2:1 siRNA-protein complexes do not show any evidence of dissociation. We conclude from these experiments that the Protein-Dig-siRNA complex consists of defined molecules harboring 2 siRNAs per one protein.

Application of Native Mass Spectrometry to Analyze Payload Charging of Delivery Vehicles Native mass spectrometry can be applied to determine the molecular mass of protein complexes. This technology, which in contrast to denaturing mass spectrometry is performed using aqueous volatile solvents at neutral pH, is optimized in a manner that minimizes dissociation or destruction of non-covalent protein complexes during the mass spectrometric analysis (Sharon M, Robinson C V (2007), The role of mass spectrometry in structure elucidation of dynamic protein complexes, Annu Rev Biochem. 2007; 76:167-93.; Heck A J (2008), Native mass spectrometry: a bridge between interactomics and structural biology, Nat. Methods. 5(11): 927-33.) Nevertheless, a certain stability of the analyzed protein complex is still a prerequisite for native mass spectrometry to prevent complex dissociation during sample preparation and mass spectra acquisition.

To determine the payload charging of <Dig> bispecifics with digoxygenated payloads—in particular Dig-siRNA or Dig-peptides—, we subjected <Her2-Dig> bispecific antibodies as well as the parent bivalent <Dig> antibody to native mass spectrometry. Payloads that were attached to these binding modules were mono-digoxygenated and bi-digoxygenated siRNAs and a mono-digoxygenated peptide.

Prior to the mass spectrometric analysis, the antibodies were deglycosylated using PNGase-F in order to decrease spectral complexity and facilitate data interpretation. To bring the molecules into solutions compatible with native MS, the initial sample buffer was sequentially exchanged to 50 mM aqueous ammonium acetate (pH 7.5) by using centrifugal filter units with a cutoff of 10 kDa (Millipore, England). Thereafter, the antibodies were mixed with the respective payloads in a ratio of 1:2 (mol/mol), and the final sample concentration used for the mass spectrometric measurements was adjusted to ~10 µM. The mixed samples were subsequently analyzed on a LCT electrospray time-of-flight instrument (Waters, Manchester, UK). Nanospray glass capillaries were used to introduce the samples into the Z-spray source. The source pressure was increased up to ~9 mbar to create increased collisional cooling. The source temperature was set to 80° C., and the sample cone voltage varied from 125 to 175 V. The needle voltage was set to ~1200 V providing a stable spray and proper desolvation without leading to fragmentation of the protein and payload molecules. The cone voltage was varied between 100 and 200 V in order to reach optimal resolution. The mass spectra were acquired with scan durations of 2 seconds and interpreted using the Mass Lynx software (Waters, Manchester, UK).

The results of these analyses, exemplarily shown in FIG. 50a, indicate that complexes of <Dig> vehicle and digoxygenated siRNAs or digoxygenated peptides can be detected by native mass spectrometry. Antibody complexes that contain one or two dig-siRNAs or dig-peptides can be detected. This proves that the payload complexes form in the aqueous buffer used for the native mass spectrometry and have a sufficient stability to 'survive' the pre-treatment, desolvation and mass spectrometric procedure as intact complexes, even though they are not covalently linked.

FIG. 50b summarizes and compares the composition of complexes that were detectable upon completion of the procedure: All spectra contained signals indicating free uncomplexed antibody and, at the low m/z range of the spectra, free uncomplexed payload molecules (not shown in depicted zoom spectra). However, in all samples that contained digoxygenated payloads, the majority of signals could be assigned to complexes that contained one or two payloads. The maximum number of payloads observed per vehicle was two or less, which is in full agreement with the presence of two Dig-capture modules per protein.

When applying siRNAs or peptides that contained one digoxygenin into a complexation reaction with the bispecific Dig-targeting vehicle, the predominant fraction of complexes contained two payloads per antibody. This was observed to the same extent for mono-digoxygenated siRNAs and for mono-digoxygenated peptides. This observation is in agreement with a 2 (payload) to one (vehicle) complex stoichiometry.

In contrast, upon application of a siRNAs that contained two digoxygenins into a complexation reaction with the bispecific Dig-targeting vehicle, 1:1 complexes between (double-Dig)payload and the dig-bispecific appeared as predominant signals. This may indicate that one payload binds at both ends via digoxygenin to one <Dig> module. In this case, the 2:1 Dig- to vehicle stoichiometry becomes converted to a 1:1 stoichiometry because the payload contains two digoxygenins. These experimental data indicate the formation of defined and rather stable complexes between digoxygenated payloads and <Dig> containing targeting vehicles. Furthermore, our results indicate that native mass spectrometry may be a valuable tool to analyze charging stoichiometries and compositions of vehicle-payload complexes.

Example 12

Digoxygenated siRNA and Complexes with <Target>-<Dig> Bispecific Antibodies Retain Biologic Activity of the siRNAs, as Well as Target Specific Binding of the Protein Module One very important topic that needs to be addressed for any technology aimed at specific targeting of bioactive compounds is that the biological activity of the compound should be retained. Furthermore, the specificity and activity of the targeting module should not be affected by attachment of the payload. The bispecific antibody technology that we describe carries two modulation steps for bioactive nucleic acids, one of which also modifies the targeting module. In a first step we covalently couple digoxygenin to the bioactive nucleic acid, e.g. siRNA. In a second step, this digoxygenated nucleic acid (siRNA) is complexed with the bispecific antibody derivative, which is a large protein. To retain activity of the nucleic acid, it is important to assure activity of modified nucleic acid for both steps: activity assays need to show that (i) functionality of the nucleic acid is retained after digoxygenation, and (ii) functionality is retained after complexation of digoxygenated nucleic acid to the <Dig> containing targeting module. Finally, it is necessary to show that (iii) the binding specificity and affinity of the targeting module is still retained in the final complex.

Comparison of the Biological Activities of Unmodified and Digoxygenated siRNAs

To evaluate whether additions or alterations of siRNAs by digoxygenin alters its biological activity, we performed in vitro assays in cell culture. For that, we chose to assess the activity of siRNA that inactivates the mRNA of Eg5. The direct effect of Eg5 siRNA activity is down-regulation of its cognate mRNA. This can be quantified by bDNA (branched DNA) assays, which detect the amount of specific mRNAs in cells (Burris et al., 1999, Molecular Endocrinology). To perform these assays, we seeded a defined number of the respective cell type into 96-well plates and allowed them to attach over night. The next day cells were transfected with desired amounts of a certain siRNA or treated with the agent whose effect on the mRNA-level should be analysed. After 24 hours the QuantiGene kit protocol was followed according to the instructions of the manufacturer (Affymetrix) in order to quantify the mRNA levels. Briefly, the cell lysates were transferred to a capture plate in the presence of a gene-specific probe set and then incubated at 53° C. over night. Wells were washed. They were then incubated at 53° C. sequentially with an Amplifier and an alkaline phosphatase-linked label probe with a wash between the incubations. After a final wash, the luminescent alkaline phosphatase substrate dioxitane was added and was incubated for 30 min at 53° C. The luminescence was detected using a InfiniteF200 luminescence reader (Tecan Austria, Gröding). The biological activity of siRNAs that target Eg5 can not only be determined by bDNA analyses, but also by the phenotype that is caused by Eg5 mRNA depletion in growing cells. Eg5 is a motor protein that belongs to the kinesin-like protein family. Eg5, also known as KSP (kinesin spindle protein), is essential for the formation of the bipolar mitotic spindle and is required for the proper separation of the spindle poles. Depletion of Eg5 leads to the formation of characteristic monoaster spindles and activates the spindle checkpoint. This causes a mitotic arrest that ultimately leads to apoptosis (Tao et. al., Molecular and cellular biology. 2007 January; 27(2):689-98) (Tao W. et. al., *Cancer Cell.* 2005; 8:49-59.) Because of that, inactivation of Eg5 by siRNA mediates in many cases a cytotoxic phenotype to cultured cells. Therefore, the biological activity of Eg5 siRNA can be analyzed by monitoring the number of living cells.

To measure the number of living cells the CellTiter-Glo Luminescent Cell Viability Assay (Promega Madison, Wis.) assay was applied according to the protocol supplied by the manufacturer. In this assay the cells are lysed and a luminescent signal proportional to the ATP amount is generated. The ATP amount is directly proportional to the number of living cells. The 96 well plates were then analyzed in a InfiniteF200 luminescence reader (Tecan Austria, Gröding).

Table 7 summarizes the results of the bDNA and cytotox assays that we performed to compare the biological activities of transfected siRNAs with that of their transfected digoxygenated counterparts. For the bDNA assays, we seeded HeLa-S3 cells into 96-well plates and allowed them to attach over night. The next day cells were transfected with the indicated amounts of siRNA using the Lipofectamine™ 2000 transfection reagent according to the instructions of the manufacturer (Invitrogen). After 24 hours the QuantiGene kit protocol was followed according to the instructions of the manufacturer (Affymetrix) in order to quantify the mRNA levels of the Eg5 mRNA. The results of these assays are shown in FIG. 31.

For the cytotox assays, KPL-4 cells were seeded at a density of 7000 cells per well in 96 well plates. The cells were incubated for 24 hours at 37° C., 5% CO2 and 85% humidity in RPMI with 10% FCS and L-Glutamine. The next day cells were transfected with the indicated amounts of siRNA using the Dharmafect transfection reagent according to the instructions of the manufacturer (Dharmacon). After 48 hours the cells were treated with the CellTiter-Glo-assay reagent according to the manufacturers instructions. The results of these assays are shown in FIG. 33.

TABLE 7

| Molecule | IC50 Cytotox assay [nM] | IC50 Eg5 bDNA assay [nM] |
|---|---|---|
| Luciferase siRNA | n.a. | >100 |
| Dig-Luciferase siRNA | n.a. | >100 |
| Eg5 siRNA | 28 | 0.016 |
| Dig-Eg5 siRNA | 4 | 0.035 |
| Dig-Eg5-Cy5 siRNA | 215 | 0.013 |

The IC50 value of the CellTiter-Glo assay was 28 nM for unmodified Eg5 siRNA and 4 nM for the digoxygenated siRNA. The corresponding IC50 values of bDNA assays were 0.016 nM for unmodified Eg5 siRNA and 0.035 nM for the digoxygenated siRNA.

A further example of the results of our cytotox assays with unmodified and Dig-modified Eg5 siRNA is given in FIG. 31. We conclude from these analyses that siRNAs can be digoxygenated without interfering with their biological activity.

Bi- and Multispecific Digoxygenin Binding Entities can be Generated that Recognize Different Target Antigens The digoxygenin binding modules can be connected to different cell targeting entities in a variety of formats. In addition to C-terminal fusions to antibodies that recognize human IGF1-receptor or Her2, various other antibodies that recognize different cell surface antigens were converted to vehicles for hapten-mediated payload delivery. Examples that were produced, purified and characterized include <Dig>-containing delivery vehicles that recognize human CD22 antigen, human CD33 antigen, the Lewis Y cancer associated carbohydrate antigen, human and murine VEGF receptor 2 or the receptor CDCP1. Applying the formats or format combinations that are described in FIG. 47, even molecules that recognize two (or more) separate targets or separate epitopes on one surface target molecule can be combined with Dig-targeting entities. FIGS. 51*a* and *b* display a selection of molecules that were generated to achieve hapten-mediated payload delivery to antigen-expressing target cells that express different surface target molecules. The amino acid sequences that were applied to generate vehicles for targeted payload delivery that address different cell surface antigens are listed as SEQ ID NO 51-SEQ ID NO 60. The amino acid sequences that were used to generate CDCP1-recognizing bispecific targeting entities are described in the application EP 09011046.1. All molecules could be expressed in mammalian cells and purified with good yields with standard Protein-A and size exclusion technologies (see Example 3 'Composition, expression and purification of recombinant humanized <Dig> antibodies, -fragments and bispecific-fusion proteins). FIGS. 51 *c-g* show that all these molecules of the different formats recognizing different target antigens fully retained targeting specificity as well as digoxygenin binding competency and affinity as a prerequisite for payload delivery: This was demonstrated by Surface-Plasmon-Resonance (BiaCore) experiments (see example 4 'Binding of recombinant <Dig> antibodies, -fragments and bispecific-fusion proteins to digoxygenated antigens' for details), as well as by FACS analyses (data not shown). For FACS analyses, Target-Dig Bispecifics were incubated with the cells, followed by separate incubation of fluorescently labeled Digoxygenin. The results of these experiments are summarized FIG. 51 *c-g*. The data prove that the binding specificity and affinity towards cell surface target antigen as well as towards digoxygenin is unchanged compared to the parent antibodies or digoxygenin binding moieties. Thus, many different formats and modules that recognize many different target antigens can be applied as vehicles for hapten-mediated targeted payload delivery. Some of these targeting vehicles, especially those that recognize internalized antigens of high density on tumor cells, may be particularly suited for targeted payload delivery. For example, bispecific molecules that recognize the LeY carbohydrate antigen that is abundant on tumor cells are very effective carriers for delivery of nucleic acids and other payloads into tumor cells (see below Example 15, Ley-mediated targeting of DPCs).

Example 13

Specific Targeting of Digoxygenated-Antibody Complexed siRNA to Antigen Expressing Tumor Cells Because siRNAs have a considerable size and are highly charged, it may be possible that complexation of the bispecific targeting module with siRNA may interfere with the specific antigen binding functionality of the targeting modules. To address this topic, we analyzed (i) the specific antigen binding functionality of the antibody-siRNA complexes, as well as (ii) the capability of these complexes to target siRNAs to antigen expressing target cells in vitro. Finally, we also confirmed the functionality of the antibody-siRNA complexes by (iii) NIRF imaging of siRNA targeting in tumor xenograft models in vivo.

Specific Antigen Binding of Antibody-siRNA-Complexes

For determining the antigen binding functionality of the <Target>-<Dig> Dig-siRNA complex, we applied surface plasmon resonance, utilizing the same experimental setup as described in example 4, for <Her2>-<Dig>. For <IGF1R>-<Dig> the following alterations of the method described in example 4, were applied: anti-human IgG antibody was injected in sodium acetate, pH 5.0 at 2 μg/ml, which resulted in a surface density of approximately 600 RU. The regeneration was carried out by injecting 0.85% H3PO4 for 60 s at 5 μl/min and then injecting 5 mM NaOH for 60 s at 5 μl/min to remove any non-covalently bound protein after each binding cycle. For these Biacore experiments, recombinantly produced soluble extracellular domains of the RTK Her2 was used to characterize the <Her2>-<Dig>-Dig-siRNA complexes, and recombinantly produced soluble extracellular domain of the RTK IGF1R was applied to characterize the <IGF1R>-<Dig>-Dig-siRNA complexes. The results of these assays (summarized in Table 8) show that the IgG complexes with digoxygenated siRNAs retain binding specificity and affinity towards the cell surface antigens. This table also shows the affinities of the digoxygenated siRNAs towards the <Her2>-<Dig> or <IGF1R>-<Dig> bispecific targeting modules.

TABLE 8

| Molecule | antigen | ka [1/mol × s] | kd [1/s] | KD [nM] |
|---|---|---|---|---|
| <IGF1R> | IGF1R-ECD | 2.00E05 | 1.01E−03 | 5 |
| <IGF1R>-<Dig> | IGF1R-ECD | 2.03E05 | 1.09E−03 | 5 |
| <IGF1R>-<Dig> | Dig-siRNA | 4.82E05 | 9.81E−03 | 20 |
| <IGF1R>-<Dig> | Dig-siRNA-Dig-Cy5 | 3.94E06 | 3.54E−04 | 0.09 |
| <Her2> | Her2-ECD | n.d. | n.d. | n.d. |
| <Her2>-<Dig> | Her2-ECD | n.d. | n.d. | n.d. |
| <Her2>-<Dig> | Dig-siRNA | 3.77E05 | 1.20E−02 | 32 |
| <Her2>-<Dig> | Dig-siRNA-Dig-Cy5 | 2.31E06 | 5.64E−04 | 0.246 |

A further example that demonstrates simultaneous binding of the cell surface antigen as well as the digoxygenated siRNA to the bispecific molecules is shown in FIG. 32: For this experiment, we applied Biacore experiments as described in example 4, but with the following modification: The samples to be analyzed were diluted in HBS-P and injected at a flow rate of 5 μl/min. The antibody <Her2>-<Dig>, the Her2-ECD and the DIG-siRNA were sequentially injected at a concentration of 5 μg/ml each. The contact time (association phase) was 3 min for each molecule.

We conclude from the results of our binding studies (Table 8 and FIG. 32) that the bispecific modules simultaneously bind Dig-siRNA as well as target antigen. Furthermore, we conclude that target antigen binding is not affected by the presence of siRNA in the antibody complex.

Specific Targeting of Digoxygenated-Antibody Complexed siRNA to Antigen Expressing Tumor Cells In Vitro To analyze whether the <Her2>-<Dig>-Dig-siRNA complexes, and <IGF1R>-<Dig>-Dig-siRNA complexes mediate specific targeting of their payload towards antigen expressing cells, we made use of the fact that siRNAs can simultaneously be labeled with Dig as well as with fluorescence labels. Thereby, it is possible to visualize the localization of siRNAs by microscopy or other imaging technologies.

Characterization by FACS analysis provided evidence that complexation of Dig-siRNA-Cy5 to antibodies does not interfere with the binding of the targeting modules. For these analyses we used CD22 positive Raji and Ramos cells and the bispecific <CD22>-<DIG> antibody. $3 \times 10^5$ cells per well of a 96-well-plate were incubated with 5 μg/ml of the <CD22>-<DIG> antibody in FACS buffer (PBS containing 5% FCS). After washing the cells were incubated with DIG-siRNA-Cy5 in a final concentration of 66.4 nM. After another washing step cells were analysed with the FACS canto II (BD Biosciences).

The result of this analyses is shown in FIG. 35. The complex of <CD22>-<DIG> and DIG-siRNA-Cy5 clearly binds to the Raji or Ramos cells while DIG-siRNA-Cy5 alone shows hardly any binding. Thus we conclude, that complexation of Dig-siRNA-Cy5 to bispecific antibodies does not interfere with the binding of the targeting modules. FIG. 34 shows the results of in vitro imaging analyses by confocal microscopy, for which we have exposed antigen expressing cells as well as cells which had no (or only weak) antigen expression to complexes of <Her2>-<Dig> modules with digoxygenated Cy5-labeled siRNAs. FIG. 35 shows the results of in vitro imaging analyses by confocal microscopy, for which we have exposed antigen expressing cells as well as cells which had no (or only weak) antigen expression to complexes of <IGF1R>-<Dig> modules with digoxygenated Cy5-labeled siRNAs.

For these experiments, KPL-4, MDA-MB-468 or H322M cells were grown on glass coverslips to a density of about 50-70%. Then they were treated with the <Her2>-<Dig>-Dig-siRNA-Cy5 or <IGF1R>-<Dig>-Dig-siRNA-Cy5 complex in a concentration of 5 nM for the indicated times.

Afterwards cells were fixed with paraformaldehyde. For the staining of the bispecific antibody the fixed cells were washed, incubated with the blocking reagent GSDB and incubated with a rabbit anti-human kappa-light chains antibody (DAKO) at a concentration of 6.5 µg/ml for 1.5 to 2 hours in a humidity chamber. After another wash, the cells were incubated with an Alexa-fluor 488-labeled goat anti rabbit antibody (Molecular Probes) in a concentration of 28.6 µg/ml for 1.5 hours in a humidity chamber. Then cells were washed. Next the DNA was labeled with DAPI (Roche) at a concentration of 10 µg/ml for 2-3 min, washed again and covered with mounting medium. The cells were analysed with a Leica SP20 confocal microscope.

The results of these analyses (FIGS. 34 and 35, summarized in Table 9) demonstrate that the complexes of Dig-siRNAs are specifically delivered to antigen expressing cells by the bispecific <Her2>-<Dig> or <IGF1R>-<Dig> targeting modules. This delivery is specific for and dependent on the targeting antigen that is recognized by the complex because siRNA is not delivered to antigen negative cells. Further evidence for specific delivery mediated by the antigen binding module is the fact that the siRNA delivery can be competed by application of excess (competitor-) IgG of the same antibody that is part of the bispecific module (but that does not bind siRNA). Incubation of cells with antibody siRNA complexes at 37° C. gives clear evidence for internalization of antibodies as well as coupled Dig-siRNAs (FIGS. 34 and 35). We conclude that the siRNAs are not only specifically delivered to antigen expressing cells, but they also become internalized into those cells.

TABLE 9

| Molecule | tumor xenograft | surface antigen | cy5 staining (siRNA) | Alexa staining (protein) |
|---|---|---|---|---|
| <Her2>-<Dig> Dig-siRNA-Cy5 | KPL-4 | Her2 | + | + |
| <Her2>-<Dig> Dig-siRNA-Cy5 | MDA-MB468 | EGF1R | − | − |
| <IGF1R>-<Dig> Dig-siRNA-Cy5 | H322M | IGF1R | + | + |
| <Her2>-<Dig> Dig-siRNA-Cy5 + <Her2> competition | KPL-4 | Her2 | − | + |
| Dig-siRNA-Cy5 | KPL4 | Her2 | − | − |
| Dig-siRNA-Cy5 | H322M | IGF1R | − | − |

Specific Targeting of Digoxygenated-Antibody Complexed siRNA to Antigen Expressing Tumor Cells In Vivo To analyze whether the <Her2>-<Dig>-Dig-siRNA complexes, and <IGF1R>-<Dig>-Dig-siRNA complexes mediate specific targeting of their payload towards antigen expressing cells not only in cell culture experiments but also in live animals, we made use of the fact that siRNAs can simultaneously be labeled with Dig as well as with fluorescence labels. Thereby, it is possible to visualize the localization of siRNAs by imaging technologies in living animals. The technology that we've applied for this task is Near Infrared Fluorescence Imaging (NIRF) in vivo. For these studies, 50 ug of either <Her2>-<Dig>-Dig-siRNA-Cy5 or <IGF1R>-<Dig> Dig-siRNA-Cy5 complexes were injected intravenously into immunodeficient mice which carried subcutaneous tumor xenografts. These xenografts were either expressing the antigen Her2 (KPL-4 cells) or the antigen IGF1R(H322M cells). Subsequently NIRF imaging was performed by using the Maestro system as described in example 10.

TABLE 10

| Molecule | tumor xenograft | surface antigen | tumor accumulation 30 min | tumor accumulation 24 hrs |
|---|---|---|---|---|
| <Her2>-<Dig> Dig-siRNA-Cy5 | KPL-4 | Her2 | + | + |
| <IGF1R>-<Dig> Dig-siRNA-Cy5 | H322M | IGF1R | + | − |
| Dig-siRNA-Cy5 | KPL-4 | Her2 | n.d. | n.d. |
| Dig-siRNA-Cy5 | H322M | IGF1R | − | − |

Figure 37:
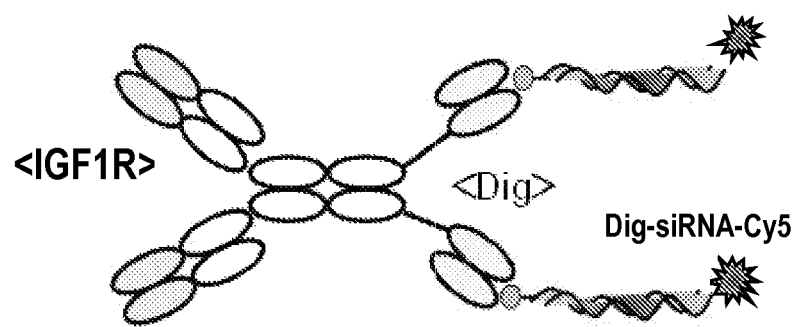
Figure 37:
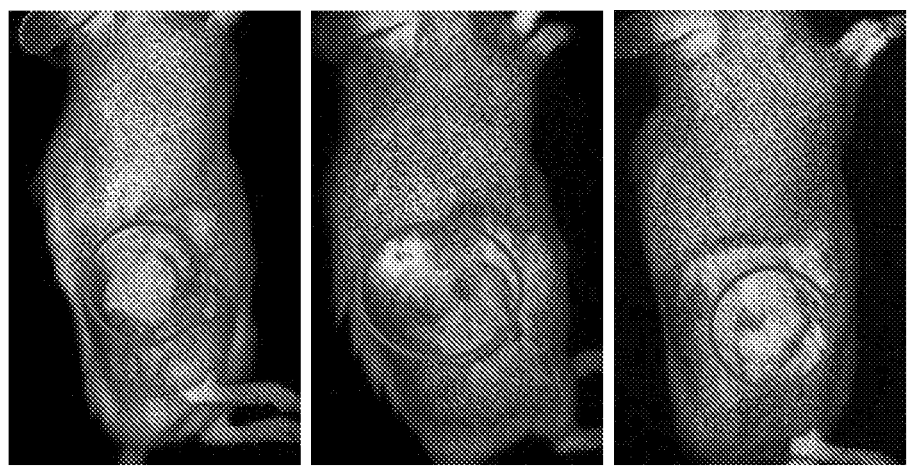
Figure 38:
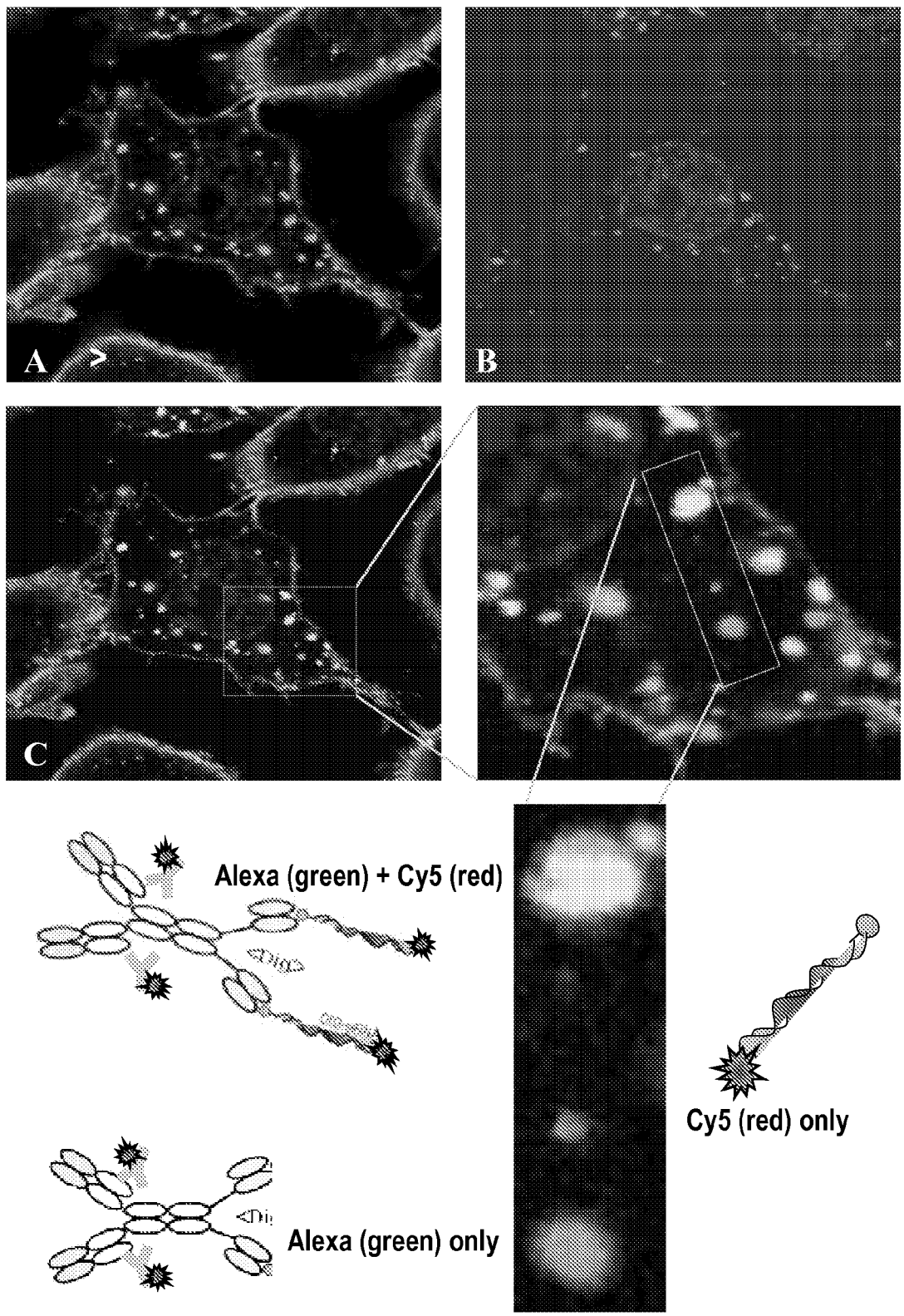
Figure 38:
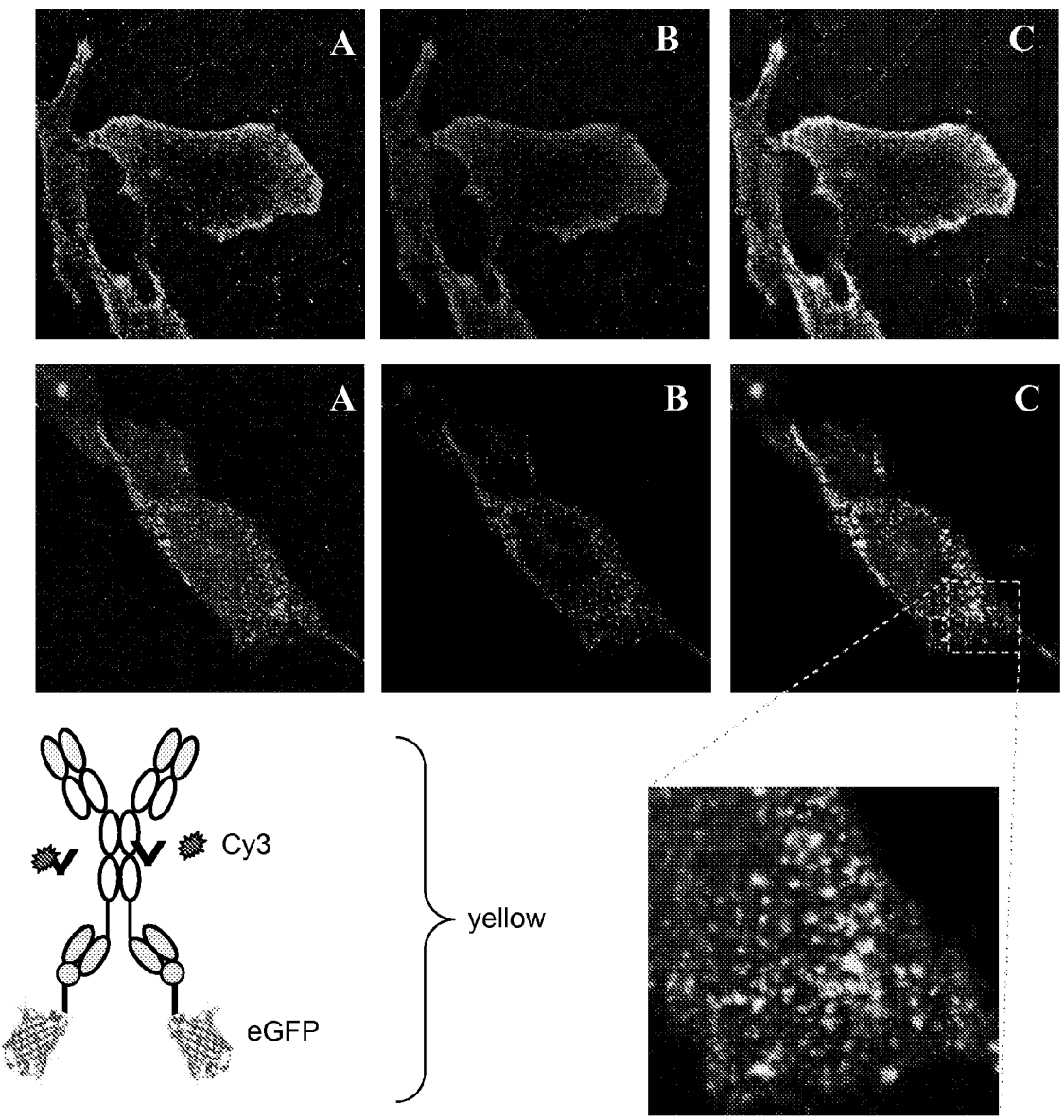
Figure 38:
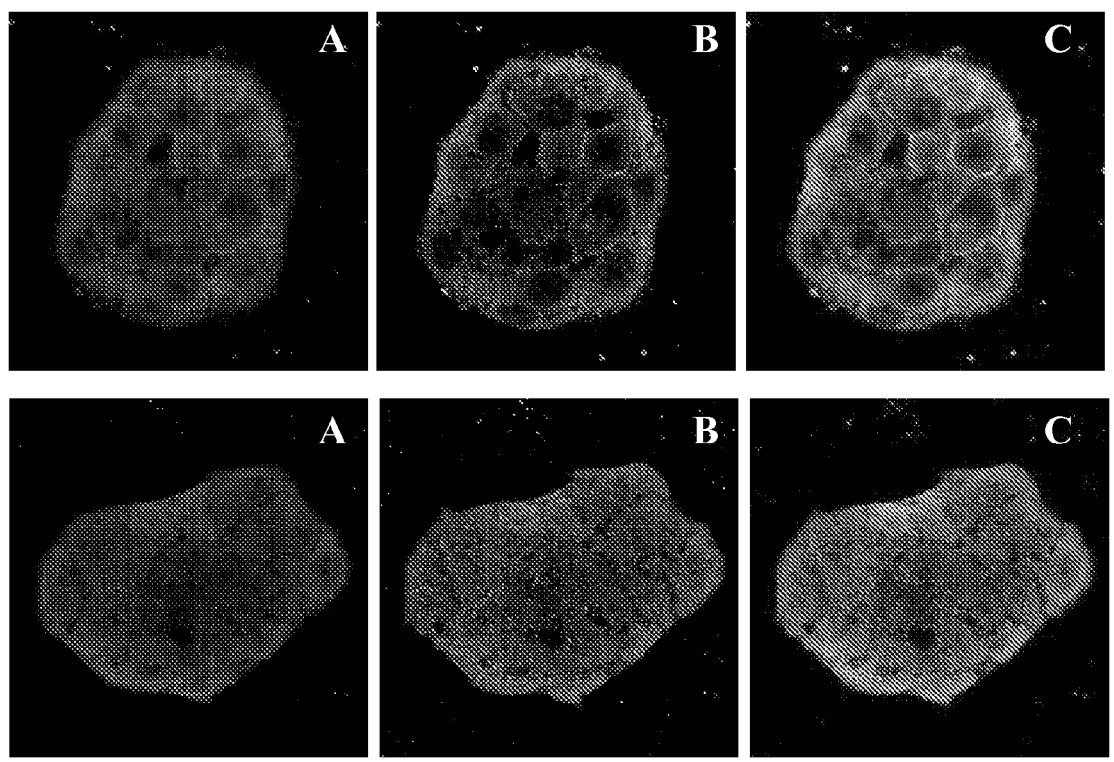
Figure 38:
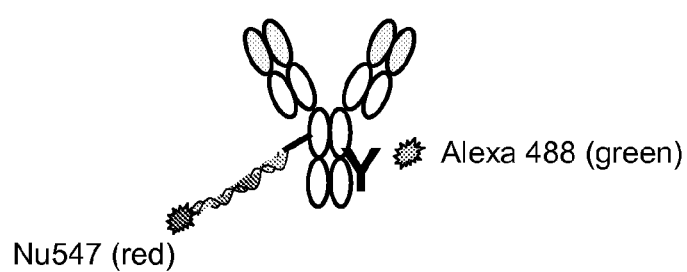
Figure 38:
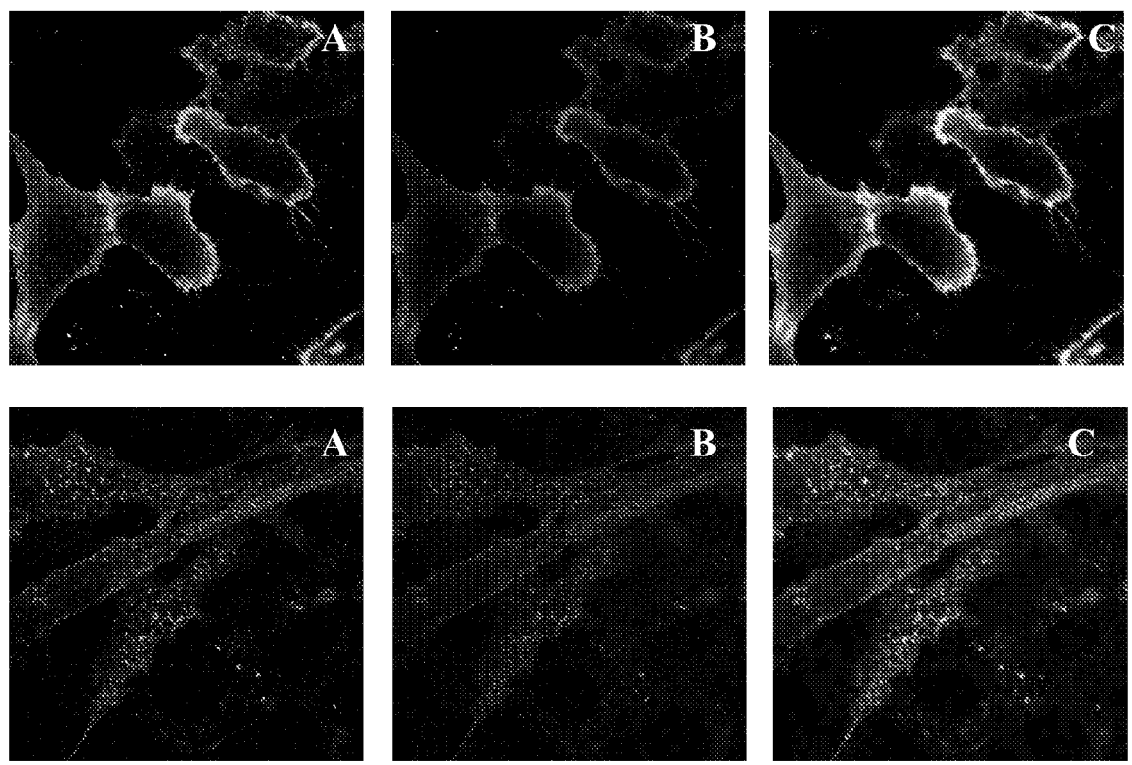
Figure 38:
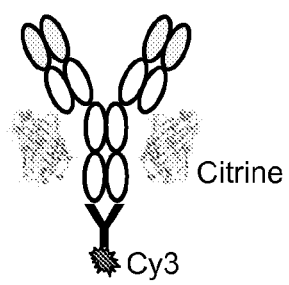

The results of these assays (FIGS. 36 and 37) show that the Dig-siRNA that is complexed with bispecific antibodies is specifically targeted to tumors which express the cognate antigen. These data are summarized in Table 10: Her2 expressing KPL4 tumors can be visualized by NIRF with <Her2>-<Dig> Dig-siRNA complexes (FIG. 36). In the same manner, IGF1R expressing tumors can be specifically visualized by NIRF when applying the complex of the bispecific antibody derivative <IGF1R>-<Dig> with Dig-siRNA (FIG. 37). We conclude from these experiments that complexes of bispecific <Target-Dig> antibodies with digoxygenated siRNAs specifically accumulate at tissues or cells that express the target antigen in vivo.

Example 14 siRNA Activity in Antigen Expressing Tumor Cells that are Targeted by Digoxygenated-Antibody Complexed siRNA To mediate specific destruction of mRNAs, siRNAs have to access the cytoplasm of their target cells. Thus, one important factor for delivery of specific siRNA activity is that the molecules are not only delivered to cells (which has been demonstrated in examples 12 and 13), but also that sufficient amounts of siRNA has to be transferred into the cytoplasm of these cells. For that, these molecules have to penetrate a biological membrane at least once. Since biologics do not pass easily across membranes, this process is a bottleneck that must be overcome for effective delivery of siRNA activity. Means to overcome this bottleneck can be membrane penetration, protein translocation across membranes, or endosome-escape or vesicular-escape mechanisms that may involve membrane disrupting processes. One factor that may aid in processes that get siRNAs to the cytoplasm is (i) the potential to release the siRNA payload from the bispecific targeting moiety after internalization (internalization of siRNA payload has been shown in Example 13). This may facilitate entry into the cytoplasm because the entity that needs to be transferred is smaller (just Dig-siRNA) than the whole siRNA targeting complex. Another principle that may facilitate siRNA transfer to the cytoplasm of target cells is (ii) the combination of targeting complexes with modulators of endosome functionality, or with endosome escape/disruption modules.

Dig-siRNA Payload is Released from the Bispecific Antibody Moiety after Internalization The complex of digoxygenated siRNA with <Target>-<Dig> bispecific targeting modules is defined and stable because of sufficient affinity of the <Dig> module. On the other hand, the connection between Dig-siRNA and the protein is not covalent, but instead consists of an antibody-hapten interaction. To analyze whether the non-covalent coupling mode of the complexes can mediate payload release after internalization, we performed fluorescence microscopy experiments with double labeled siRNA complexes. For these experiments, we applied Cy5-labeled Dig-siRNA to locate the position of the siRNA within cells. To visualize the protein moiety of the targeting complex a rabbit anti-human kappa-light chains antibody was applied followed by an incubation with a Alexa-fluor 488-labeled goat anti rabbit antibody. Both entities could be visualized microscopically at different excitation and emission channels. Overlayed visualization of signals from both channels opens the opportunity to simultaneously follow the routes of protein and siRNA after application to antigen expressing cells. The experimental details of the visualization and microscopy technology have been described in example 12. FIGS. 33 and 34 shows the results of these co-staining experiments. Her2 expressing KPL4-cells were exposed to <Her2>-<Dig> Dig-siRNA-Cy5 complexes at 37° C. and subsequently analyzed microscopically (FIG. 37). In the same manner, IGF1R expressing H322M-cells were exposed to <IGF1R>-<Dig> Dig-siRNA-Cy5 complexes at 37° C. and subsequently analyzed microscopically (FIG. 40). In both examples, binding of the complex to cell surfaces and subsequent internalization were observed. At early time points protein and siRNA signals co-localized on the cell surface and in endosomes. This indicates binding to and internalization into target cells of the complete complex. At later time points, we observed separation of protein-associated signals from siRNA associated signals. This separation was observed in KPL4-cells with <Her2>-<Dig> Dig-siRNA-Cy5, as well as in H322M-cells exposed to <IGF1R>-<Dig> Dig-siRNA-Cy5.

To confirm our results about the separation of the DIG labeled payload from the DIG bispecific AB, LeY expressing MCF7 cells were exposed <LeY>-<DIG> loaded with DIG labeled recombinant eGFP. binding of the complex to cell surfaces and subsequent internalization were observed. These data are shown in FIGS. 38c-d. At early time points antibody and eGFP signals co-localized on the cell surface and in endosomes. This indicates binding to and internalization into target cells of the complete complex. At later time points, we observed separation of antibody-associated signals from eGFP associated signals. This finding indicates that different cargo molecules are separated from the targeting DIG bispecific antibodies. To show that the observed separation is based on the DIG system, comparable experiments were conducted with either Nu457 labeled siRNA covalently linked to an <IGF1R> antibody via a SMCC linker or an in-line fusion protein of an <IGF1R> antibody with the fluorescent protein citrine. In none of these cases, a significant separation of the payload from the targeting antibody was observed.

We conclude from these experiments that intact <Target>-<Dig> Dig-siRNA complexes bind to target cell surfaces and become internalized, and subsequently release the siRNA payload from the antibody entity.

Targeted siRNA Activity in Antigen Expressing Cells.

To mediate specific destruction of mRNAs sufficient amounts of siRNA has to be transferred into the cytoplasm of these cells. where components of the RNAi machinery specifically recognize the siRNA duplex and incorporate the antisense siRNA strand into a protein complex termed the RNA-induced silencing complex. The antisense strand then pairs with the respective mRNA resulting in cleavage of the mRNA by the RISC thereby mediating specific mRNA destruction.

To analyze whether targeted Dig-siRNAs are capable to escape from endosomes and subsequently mediate mRNA knockdown, we applied <IGF1R>-<Dig> Dig-siRNA complexes to IGF1R expressing H322M tumor cells. Furthermore, we applied <Her2>-<Dig> Dig-siRNA complexes to Her2 expressing tumor cells. To facilitate endosome escape of targeted siRNA's, we also co-applied targeted endosome escape modules. The module used in these experiments is the digoxygenated INF7 peptide described in example 5.

Upon application of targeted siRNAs and targeted peptides to cells, siRNA mediated mRNA knockdown was assayed, as well as siRNA mediated phenotypes. The molecules that we applied for these experiments was Eg5-siRNA, which mediates a cytotoxic phenotype towards cells provided a sufficient Eg5 knockdown can be achieved. The Eg5 siRNAs and the assays to quantitate Eg5 mRNA levels (bDNA assays) and phenotypes (cytotox assays) have been described in detail in Example 12 and Table 7.

The results of these analyses are shown in FIG. 34 and summarized in Table 11: For these experiments H322M cells were seeded at a density of 15.000 cells per well in 96 well plates. The cells were incubated for 24 hours at 37° C., 5% $CO_2$ and 85% humidity in RPMI with 10% FCS, Na+Pyrovate, L-Glutamine and NEAA mix. (KPL4 cells were seeded at a density of 7.000 cells per well in 96 well plates.) The cells were incubated for 24 hours at 37° C., 5% $CO_2$ and 85% humidity in RPMI with 10% FCS, and L-Glutamine. For the generation of complexes of digoxygenated peptides with <IGF1R>-<Dig> and <Her2>-<Dig> bispecific antibodies, we dissolved peptide-Dig conjugate in $H_2O$ to a final concentration of 1 mg/ml. The bispecific antibody was brought to a concentration of 1 mg/ml (4.85 µM) in 20 mM Histidine, 140 mM NaCl, pH=6.0 buffer. Peptide and bispecific antibody were mixed to a 2:1 molar ratio (peptide to antibody) by pipetting up and down and incubated for 15 minutes at RT. Eg5 and luciferase control siRNA molecules were added independently to bispecific antibodies in a 1:2 (AB to siRNA) ratio and mixed by pipetting up and down. The three mixes were incubated for 15 minutes at RT. Then, the complexes were added to the cells in the concentrations indicated. The cells were incubated for further 24 hours and lysed for bDNA analysis as previously described.

By co-application of <Target>-<Dig>-Dig-siRNA with <Target-Dig>-Dig-INF7 (an endosome escape mediating peptide (Esbjörner et al., 2007, Biochemistry), we were able to observe mRNA knockdown in cells that are targeted by the siRNA-Protein complex. IGF1R expressing cells showed reduction of Eg5 mRNA with the <IGF1R>-<Dig>-Dig siRNA modules in a dose dependent manner (dose dependence shown for the INF peptide in FIG. 35). Control experiments in which we applied Dig-siRNAs without targeting modules, or targeted INF7-peptides without siRNAs, did not cause any mRNA depletion. This indicates that the complete siRNA-targeting complex that recognizes the cell surface antigen is required to mediate siRNA knockdown. The dose-dependent correlation of siRNA activity with targeted INF7 peptide indicates that added endosome modulators can increase the efficacy of specific targeting of siRNA by <Target>-<Dig> bispecific antibody derivatives.

We conclude from these experiments that <Target>-<Dig> bispecific molecules can specifically target siRNA activity to antigen expressing cells. We furthermore conclude that this activity can be increased by additionally applying targeted endosome modulating agents.

TABLE 11

| Molecule | cell line | surface antigen | Eg5 mRNA | GapDH mRNA | Eg5/ GapDH |
|---|---|---|---|---|---|
| <IGF1R>-<Dig> Dig-Eg5siRNA (50 nM-siRNA, 500 nM Dig-INF7) | H322M | IGF1R | 44% | 71% | 0.6 |
| <IGF1R>-<Dig> Dig-LucsiRNA (50 nM-siRNA, 500 nM Dig-INF7) | H322M | IGF1R | 61% | 71% | 0.9 |
| <IGF1R>-<Dig> Dig-INF7 (0 nM-siRNA, 500 nM Dig-INF7) | H322M | IGF1R | 87% | 92% | 0.9 |
| <IGF1R>-<Dig> (0 nM-siRNA, 0 nM Dig-INF7) | H322M | IGF1R | 97% | 85% | 1.1 |

<DIG> Bispecific Antibodies in Complex with Dharma-FECT-DIG-siRNA Mediate RNAi

The capability of Lipid-based transfection reagents to help endosomal escape of specifically targeted siRNAs by <DIG> bispecific antibodies was investigated. Therefore the commercially available Lipid-based transfection reagent DharmaFECT (provided by Dharmacon) was used.

To analyze complex formation of DIG-siRNA, DharmaFECT and bispecific <DIG> antibody and accumulation on target cells FACS analysis was performed using MCF7 cells (LeY-positive, CD22-negative). LeY-DIG was used as targeting antibody and CD22-DIG as non-targeting control antibody, in addition a Cy5-labeled DIG-siRNA was used. DharmaFECT was incubated with DIG-siRNA-Cy5 according to the manufacturer's instruction to allow complex formation. Afterwards, the DharmaFECT/DIG-siRNA-Cy5 complex was incubated with LeY-DIG or CD22-DIG antibodies. MCF7 cells were suspended in PBS and incubated for 30 min on ice with either the complex of DIG-siRNA-Cy and DharmaFECT or the complex of LeY-DIG/DharmaFECT/DIG-siRNA-Cy5 or CD22-DIG/DharmaFECT/DIG-siRNA-Cy5. Before measuring the samples on BD FACS Canto II, the cells were washed. Signals were detected at the wavelength that is suitable to detect Cy5.

FIGS. 52a and b shows the results of this FACS analysis. In the upper panel, a similar binding behavior of DharmaFECT/DIG-siRNA-Cy and CD22-DIG/DharmaFECT/DIG-siRNA-Cy5 to MCF7 is visible. Both complexes bind to MCF7 cells due to the unspecific stickiness of DharmaFECT which is an inherent property of a transfection reagent. In contrast, in the lower panel, a stronger accumulation of LeY-DIG/DharmaFECT/DIG-siRNA-Cy5 complexes in comparison to DharmaFECT/DIG-siRNA-Cy5 is clearly visible indication specific targeting of DharmaFECT/DIG-siRNA-Cy5 by LeY-DIG to MCF7 cells.

Next, the capability of the complexes DharmaFECT/DIG-siRNA, CD22-DIG/DharmaFECT/DIG-siRNA and LeY-DIG/DharmaFECT/DIG-siRNA to mediate specific RNAi in MCF7 cells was analyzed. Therefore, a siRNA targeting EG5 was used. A defined number of MCF7 cells was seeded into 96-well plates and allowed to attach over night. The next day cells were treated with desired amounts of DharmaFECT/DIG-siRNA, CD22-DIG/DharmaFECT/DIG-siRNA and LeY-DIG/DharmaFECT/DIG-siRNA for 24 hours. The down-regulation of Eg5-mRNA-levels was analyzed by bDNA assay (see example 12 for description) and normalized to GAPDH-mRNA-levels.

FIG. 52 c shows the results of this bDNA assay. The transfection activity of DharmaFECT/DIG-siRNA is retained when complexing LeY-DIG/DharmaFECT/DIG-siRNA with LeY-DIG and CD22-DIG. Downregulation of the Eg5-mRNA is mediated by the complex LeY-DIG/DharmaFECT/DIG-siRNA which is targeted to those cells (see FIG. 52a). However, a downregulation is also observed with the complex CD22-DIG/DharmaFECT/DIG-siRNA. The targeted accumulation of DharmaFECT/DIG-siRNA on MCF7 cells mediated by LeY-DIG only marginally increases the RNAi. The accumulation of DharmaFECT/DIG-siRNA mediated by the stickiness of DharmaFECT is already sufficient to obtain transfection and subsequent RNAi. In conclusion, targeting of Lipid-based transfection reagents complexed with siRNA as endosomal escape modules is possible. However, in cases where transfection reagents have a strong cell attachment capability by themselves, antibody-mediated targeting specificity may become affected.

Example 15

Digoxygenated DPCs Complexed with <Target>-<Dig> Bispecific Antibodies can be Utilized to Targeted siRNA Delivery with Targeted Endosomolytic Activity One very important topic that needs to be addressed for any technology aimed at specific targeting of siRNAs is that the nucleic acids have to reach the cytoplasm of the target cell for biological activity. Because nucleic acids are highly charged and per se not easily getting across membranes, release of targeted (and internalized) siRNAs into the cytoplasm of cells is a mayor bottleneck for siRNA delivery.

The bottleneck 'endosome escape of siRNAs' can be overcome by application of Dynamic Poly Conjugates (DPCs), chemical entities that upon cell binding and internalization cause endosome escape of siRNAs (Rozema D B et. al., Dynamic PolyConjugates for targeted in vivo delivery of siRNA to hepatocytes. Proceedings of the National Academy of Sciences of the United States of America; 2007 Aug. 7; 104(32):12982-7 PMID:17652171, and, inter alia in WO2008/0022309, US publication No. US2008-0152661A1, US2008-0287630, US2008-0281074A1, US2008-0287628A1, US2008-0269450A1, U.S. Pat. Nos. 7,098,032, 7,019,113, 6,919,091). Such DPCs are composed of PBAVE scaffolds to which PEG molecules are attached reversibly using a bifunctional maleamate linkage. For the latter, carboxylated dimethyl maleic acid (CDM) can be applied. The PEG units are used to shield the endosomolytic positive charges of the PBAVE. Also linked to the PBAVE is the siRNA cargo (e.g. via a reversible disulfide linkage). The resulting delivery vehicles are called siRNA Dynamic Poly-Conjugates because siRNA, shielding groups (and additional targeting ligands) are conjugated to a polymer in a reversible manner. The endosomolytic properties of such DPCs which cause the cytoplasmic delivery of siRNA is induced by its chemical environment: The decrease in pH within maturing endolysomes induces release of the CDM-PEG, exposing positive charges of PBAVE which in turn mediates endosmolysis.

To combine the endosomolytic features of DPCs with the specific targeting properties of the bispecific Digoxygenin or hapten system, the following procedure was applied. In a first step (i) DPCs need to be generated that are conjugated to Digoxygenin in a manner that Digoxygenin is accessible to anti-Dig antibodies. Furthermore, (ii) Dig-DPCs need to be complexed with Target-Dig bispecific antibodies in a manner that binding specificity and affinity of the cell surface targeting moiety of the bispecific antibody is retained. Finally, it is necessary to show that (iii) the Antibody-DPC complex that is held together by the Dig-hapten forms a defined composition that is stable enough to confer specific targeting in vitro as well as in vivo.

Generation of Digoxygenated DPCs and Bispecific DPC Complexes

To generate digoxygenated DPCs, procedures were applied that have been described elsewhere (Rozema D B et. al., Dynamic PolyConjugates for targeted in vivo delivery of siRNA to hepatocytes. Proceedings of the National Academy of Sciences of the United States of America; 2007 Aug. 7; 104(32):12982-7 PMID:17652171, and, inter alia in WO2008/0022309, US publication No. US2008-0152661A1, US2008-0287630, US2008-0281074A1, US2008-0287628A1, US2008-0269450A1, U.S. Pat. Nos. 7,098,032, 7,019,113, 6,919,091), with the modification that NHS-digoxygenin was added to the PBAVE-CDM-PEG reaction mix at different ratios. Briefly, for generation of digoxygenated DPCs, a 2.5 µM solution of poly butyl amino vinyl ether (PBAVE) in Hepes-buffer (500 mM, pH 8) is mixed with a 0.07 M solution of N-hydroxysuccinimide NHS-DIG (in Isotonic glucose buffer or in 1× Phosphate buffered saline PBS). The mixture is incubated for 30 min at room temperature. The ratio of PBAVE to NHS-Dig that can be applied for that includes molar ratios 1:1 or various other ratios. After the 30 min incubation step, a CDM-PEG550 solution (0.11 M) is added to the PBAVE-DIG complex at a 1 to 35 ratio (Dig-PBAVE to CDM-PEG) and incubated for another 60 min at room temperature. Thereafter, any excess of uncoupled CDM-PEG are removed by applying a 1.3 ml Sephadex G-50 spin column. The attachment of NHS-Dig and CDM-PEG to the PBAVE scaffold results in the formation of the pH sensitive carboxy dimethylmaleic anhydride CDM bonds.

To analyze if these digoxygenated DPCs have their digoxygenins exposed enough so that they can be complexed with Dig-bispecific antibodies, SEC-MALLS analyses were performed. This technology analyzes not only sizes of proteins or protein complexes but gives also evidence about the radius, i.e. shape, of molecules. The results of SEC-MALLS analyses performed with complexes of bispecific antibodies and digoxygenated DPCs indicate that the digoxygenated DPCs become bound by the bispecific Dig-targeting modules in a rather stable manner. We conclude that digoxygenated DPCs can be applied to form stable complexes with bispecific antibody modules that harbor Dig-binding units.

Bispecific Anti-Dig Antibody-Digoxygenated DPC Complexes Deliver DPCs to Cultured Target Cells and Internalize DPCs For determining the antigen binding functionality of the <Target>-<Dig> Dig-DPC complex, we applied FACS assays. For these assays, <IGF1R-Dig>-DPC complexes were applied to H322M cells which express the IGF1R. FACS analyses were performed on H322M and Raji cell lines as shown in FIG. 40. Suspended in a PBS+5% FCS the cells received an antibody or complex molarity of 7.5 nM and a secondary antibody concentration (when needed, i.e. controls) of 30 nM. The primary antibody was incubated for 30 min on ice and after a washing step, the secondary antibody was added for 30 min on ice. Before measuring the samples on BD FACS Canto II, the cells were washed. Signals were detected at the appropriate wavelengths that are suitable to detect APC (controls) or Cy3 (DPC containing samples). For H322M, IGF1R is expressed giving a signal for the IGF1R-DIG bispecific antibody coupled to the conjugate. The Raji cell line is expressing CD22 and this cell line have a positive signal for the CD22-DIG+conjugate. Both cell lines show a moderate background signal which is caused by the rather high secondary antibody concentration. However, since the bispecific antibody coupled to the conjugate does not have a secondary antibody in the assay, all signals detected in these samples are due to specific antigen binding. Our experimental analyses demonstrated that the IGF1R.Dig:: Dig-DPC complex binds to H322M cells which express the IGF1R. In contrast, this molecule does not bind to Raji or Ramos cells which do not express the IGF1R. This proves that binding and specificity is retained for DPC coupled bispecific antibodies. Further experiments demonstrate that Ramos and Raji cells which express the CD22 antigen bind DPCs that are complexed to Dig-bispecifics that recognize the CD22 antigen. This confirms that binding and specificity is retained for DPC coupled bispecific antibodies.

Confocal microscopy was further applied to demonstrate specific binding and subsequent internalization of targeted DPCs. For these experiments, H322M cells that express the IGF1R were treated with <IGF1R-Dig>-Dig DPC complexes. The DPC part of these complexes were labeled with the fluorescence substrate Cy3 to visualize the whereabouts of the DPCs after antigen binding. FIG. 41 shows that targeted DPCs bind to the surface of antigen expressing H322M cells and become internalized. At early time points after binding and internalization, antibody and DPC co-localize in endosomes. Thereafter, antibody detection and DPC detection indicate a separation of the complex within the cell. This indicates that the Dig-complexed DPCs dissociates from the antibody targeting moiety within the cell, for mediation of unrestricted endosomolytic activity.

Bispecific Anti-Dig Antibody-Digoxygenated DPC Complexes Deliver DPCs to Tumor Xenografts In Vivo To address the question whether antibody-DPC complexes are stable enough to target DPCs to tumors in vivo, animal experiments were performed. For these experiments, Cy3 labeled Her2-Dig bispecific antibodies complexed to Cy3 labeled digoxygenated DPCs were injected into animals that carried Her2 expressing KPL4-tumor xenografts. Accumulation of the DPC in the tumor was detected by Near Infrared Fluorescence Imaging (NIRF) at different time points and compared to accumulation of non-targeted Cy3-labeled Dig-DPCs (that were not complexed with bispecific antibody). FIG. 42 shows the results of this analysis: DPCs that are not targeted show only poor to no accumulation in the antigen positive tumor. In contrast, DPCs that become targeted via the bispecific Dig-antibodies show clear evidence of accumulation in the tumor. We conclude that Dig.Bispecifics can be used to target DPCs to desired target sites in vivo.

siRNA Targeting with LeY-DIG and DIG-DPCs

LeY is a carbohydrate antigen of the LeY family that is found on the surface of many mucinous carcinomas of the colon, stomach, ovaries, breast and lung as well as some epidermal carcinomas. For targeting this antigen, a bispecific LeY-DIG antibody was constructed in which the <LeY> sequence was derived from the monoclonal antibody B3, a murine antibody directed against the LeY antigen. (Pastan, et al., 1991, Cancer research). Since B3 reacts with only a limited number of normal tissues, it is an ideal candidate for the treatment of cancer (Brinkmann et al., 1991, PNAS). In addition, because the LeY antigen has a very high density on cells derived from the above mentioned carcinomas, upon binding to the antigen, the complex of LeY and <LeY> displays a high internalization rate.

FACS analysis was performed to investigate the capability of LeY-DIG to target DIG-DPC-siRNA to LeY-expressing MCF7 breast cancer cells (FIGS. 53a and b). FACS analysis was carried out as described above. In FIG. 53a DIG-DPC-siRNA was added to MCF7 cells in increasing concentrations (25 nM, 50 nM, 100 nM and 150 nM) resulting in an concentration-dependent unspecific binding of DIG-DPC-siRNA to the surface of the MCF7 cells. In FIG. 53 b, the complex of LeY-DIG and DIG-DPC-siRNA was incubated on the cells in increasing concentrations (25 nM, 50 nM, 100 nM and 150 nM). A concentration-dependent targeting of LeY-DIG to MCF7 cells was observed which much more exceeds the degree of unspecific binding of DIG-DPC-siRNA alone. Taken together, LeY-DIG is capable to strongly target DIG-DPC-siRNA to LeY-expressing MCF7 cells.

Next, bioassays using MCF7 cells were performed in order to analyze whether targeting of DIG-DPC-siRNA by LeY-DIG results in a down regulation of the cognate mRNA, that is higher than mRNA down regulation in cells treated with DIG-DPC-siRNA alone or in complex with a non-targeting antibody.

FIG. 53 c) shows the result of a bDNA assay (described above) of MCF7 cells treated for 24 hours with an increasing concentration of DIG-DPC-siRNA alone or in complex with the non-targeting antibody CD22-DIG. In this experiment a siRNA targeting AhaI was bound to the DPCs. Aha I (activator of the Hsp90 ATPase) is a regulator for Hsp90 chaperones (Panaretou et al., 2002, Molecular Cell). The treatment of MCF7 cells with DIG-DPC-AhaI alone results in a concentration-dependent decrease of the ratio of AhaI/GAPDH mRNA, indicating that the unspecific binding of DIG-DPC-AhaI to MCF7 cells also results in some mRNA knock-down of the target mRNA. In addition, the mRNA of the housekeeper GAPDH is also slightly decreased when using higher concentrations of DIG-DPC-AhaI. However, surprisingly, incubating MCF7 cells with a complex of CD22-DIG/DIG-DPC-AhaI in a concentration-dependent manner partially reverts the unspecific DPC-mediated knockdown of AhaI-mRNA. This probably reflects a shielding effect of the non-targeting antibody once connected to the Dig-siRNA DPC complex.

In FIG. 53 d) a mRNA analysis of MCF7 cells treated with DIG-DPC-AHAI in complex with VEGFR2-DIG, another non-targeting antibody, in a concentration-dependent manner is shown. Again, binding to VEGFR2-DIG leads to a decrease of non-specific transfection of DIG-DPC-AhaI. In conclusion, DIG-DPC-AhaI in complex with non-targeting antibodies have less non-specific activity than DIG-DPC-AhaI alone.

Targeted treatment of MCF7 cells with a complex of LeY-DIG and DIG-DPC-AhaI in a concentration-dependent manner leads to a strong increase of the mRNA-downregulation of AhaI (normalized to GAPDH). This indicates that specific targeting of LeY-DIG (FIG. 54a) also results in increased bioactivity of DIG-DPC-AhaI.

FIG. 53e shows the mRNA analysis of MCF7 cells treated with DIG-DPC-AHAI alone or in complex with LeY-DIG or CD22-DIG in comparison to cells treated with DIG-DPC-GL3 alone or in complex with LeY-DIG or CD22-DIG. The siRNA GL3 is directed against luciferase, a target mRNA usually not present in cancer cells. Treatment with DIG-DPC-GL3 alone or in complex with LeY-DIG or CD22-DIG does not lead to a decrease of the AhaI/GAPDH ratio in contrast to treatment with DIG-DPC-AhaI alone or in complex with LeY-DIG or CD22-DIG. This result indicates that the decrease of the AhaI/GAPDH ratio indicted by DIG-DPC-AhaI is a specific siRNA-mediated effect.

Next, MCF7 cells were treated with LeY-DIG/DIG-DPC-AhaI and CD22-DIG/DIG-DPC-AHAI in a time dependent manner (1, 4, 8, 24 or 48 hours) and again the ratio of mRNA levels of AhaI over GAPDH was assessed by bDNA assay. From those experiments IC40 values were calculated and a targeting specificity factor was generated by dividing the IC40 values of MCF7 cells treated with LeY-DIG/DIG-DPC-AhaI by the IC40 values of MCF7 cells treated with CD22-DIG/DIG-DPC-AhaI (abbreviated IC40 LeY/CD22). In FIG. 53 f the targeting specificity factor is plotted against the time, indicating that the highest specificity is reached when treating MCF7 cells for 4-8 hours with LeY-DIG/DIG-DPC-AhaI.

SEC-MALLS can be Used for the Analysis of DIG-PBAVE-siRNA and Complexes of LeY-DIG DIG-PBAVE-siRNA SEC-MALLS (size-exclusion chromatography multi-angle laser light scattering) is an analytical technique by which biomolecules are separated over a gel filtration column and delivered to three detection systems: UV/Visible, Refractive Index (RI) and Light Scattering (LS). The detectors for UV/Visible and RI provide information about the concentration of the sample. LS is a non-invasive technique for characterizing macromolecules and a wide range of particles in solution. In contrast to most methods for characterization, it does not require outside calibration standards. In this sense it is an absolute technique. The Wyatt Technology instruments used here make two different types of light scattering measurements for absolute molecular characterization:

Classical Light Scattering/Static Light Scattering: Here, the intensity of the scattered light is measured as a function of angle and can yield the molar mass, rms radius, and second virial coefficient (A2). For certain classes of particles, classical light scattering can yield the size, shape, and structure.

Quasi-elastic Light Scattering (QELS) or Dynamic Light Scattering (DLS): In a QELS measurement, time-dependent fluctuations in the scattered light signal are measured using a fast photon counter. QELS measurements can determine the hydrodynamic radius of macromolecules or particles.

Static and Dynamic light scatter methods collect different types of information, providing complimentary data for a more complete characterization of biomolecules.

DIG-DPC-siRNA AHAI and the complex of LeY-DIG and DIG-DPC-siRNA AHAI were analysed by Size Exclusion Chromatography in combination with Multiple Angle Laser Light Scattering (SEC-MALLS) and Quasi Elastic Light Scattering (QELS). The SEC part consisted of a HPLC pump, a degasser and an autosampler from the Dionex Ultimate 3000-Series. 190 µl of a 5 mg/ml solution of DIG-DPC-siRNA AHAI or 190 µl of a 3.3 mg/ml solution of the complex of LeY-DIG and DIG-DPC-siRNA AHAI was applied to a Superose 6 10/300 GL SEC column from GE Healthcare Bio-Sciences (Uppsala, Sweden). 1×PBS as eluent and a flow rate of 0.25 mL/min was used. The samples were detected by a differential refractive index (RI) detector (Optilab rEx), an 3 angle laser light scattering detector (miniDAWN Treos, GaAs laser 658 nm, 50 mW, K5 cell) and a dynamic light scattering detector (WyattQELS) from Wyatt Technology (Santa Barbara, Calif., USA). The calculation of the molecular weights using Zimm plots and hydrodynamic radii were done by ASTRA for Windows Software, Version 5.3.4.13.

The results of the SEC-MALLS analysis of DIG-DPC-siRNA AHAI and the complex of LeY-DIG and DIG-DPC-siRNA AHAI are shown in FIG. 54.

In FIG. 54a and b, the analysis of the molecular weight of DIG-DPC-siRNA AHAI (left panel) and LeY-DIG/DIG-DPC-siRNA AHAI (right panel) is presented. The black curve indicates the signal generated by the LS detector while the red line represents the molecular weight generated from the signal of the LS and the RI detector. The given molecular weight in only an approximation, because the exact dn/dc-value for DIG-DPC-siRNA AHAI is not known and was estimated as 0.146, which is the dn/dc-value for PEG. As shown in FIG. 54a, DIG-DPC-siRNA AHAI display a polydisperse solution with molecules of an estimated molecular weight of ~300 to ~720 kD. Addition of LeY-DIG results also in a polydisperse solution but with molecules of an estimated molecular weight of ~500 to ~1100 kD. The size increase indicates a complex formation between LeY-DIG and DIG-DPC-siRNA AHAI.

In FIG. 54 c) and d), the analysis of the hydrodynamic radius of DIG-DPC-siRNA AHAI (left panel) and LeY-DIG/DIG-DPC-siRNA AHAI (right panel) is presented. The black curve indicates the signal generated by the LS detector while the blue dotted lines represent the hydrodynamic radius generated from the signal of the QELS detector. DIG-DPC-siRNA AHAI contains molecules ranging from a hydrodynamic radius from ~7 nm-~10 nm, LeY-DIG/DIG-DPC-siRNA AHAI contains molecules ranging from a hydrodynamic radius from ~9 nm-~12.5 nm. Again, addition of LeY-DIG leads to an increase in size again indicating complex formation of LeY-DIG and DIG-DPC-siRNA AHAI Example 16

Measurement of Internalisation of <LeY> <DIG> Bispecific Antibodies Using DIG labeled GFP <Target>-<Dig> bispecific antibodies can be used to specifically deliver DIG labeled cargo to cells (Example 6). One question arising is whether the <Target>-<Dig> bispecific antibodies can also be used to target DIG labeled proteins to cells. To answer this question we conjugated the DIG moiety to enhanced green fluorescent protein (eGFP) as previously described. eGFP is a mutant form of GFP derived from *Aequorea Victoria* with improved spectral characteristics, increased fluorescence, photostability and a shift of the major excitation to 488 nm (Heim R, Cubitt A, Tsien R (1995). *Nature* 373 (6516): 663-4.)

<LeY>-<DIG> Bispecific Antibodies can be Used to Target the DIG Labeled Protein eGFP to Target Cells To analyse whether <LeY>-<DIG> bispecific antibodies can be used to bring the DIG labeled protein eGFP to target cells we used FACS analysis. As eGFP is fluorescent (major excitation 488 nm, major emission 509 nm), the presence of the protein can be detected by commonly available FITC filter sets. We generated two variants of eGFP coupled to either two [1:2] or three [1:3] DIG moieties.

For these analyses we used LeY positive MCF7 cells and the bispecific <LeY>-<DIG> antibody. 3×10⁵ cells were seeded per well of a 96-well-plate and used immediately. 3.43 nM of the <LeY>-<DIG> bispecific antibody in FACS buffer (PBS containing 5% FCS) was added to the wells. A <DIG> antibody at the same concentration was used as a non-targeting control. For detection of bound antibodies, a secondary Cy5 labeled antibody (Jackson Immunoresearch 709-176-1490; Cy5 F(ab')2 Donkey anti-human IgG (H+L)) was added to a final concentration of 3.43 nM. After washing in FACS buffer the cells were incubated for one hour at 4° C. and then analyzed with the FACS canto II (BD Biosciences). To show <LeY>-<DIG> bispecific antibody mediated eGFP delivery to cells, 3.43 nM of the <LeY>-<DIG> bispecific antibody in FACS buffer (PBS containing 5% FCS) pre-incubated with a twofold molar amount of both [1:2] and [1:3] DIG-eGFP were added to the wells. After washing in FACS buffer the cells were analyzed with the FACS canto II (BD Biosciences).

The results of these assays (FIG. 43) show that the DIG-eGFP that is complexed with a bispecific antibody is specifically targeted to tumors expressing the cognate antigen. A weak background binding of the <DIG> control antibody was observed. This signal was also observed with the secondary antibody only and is thus a artifact of this secondary antibody. On the other hand, the <LeY>-<DIG> bispecific antibody shows clear binding to the LeY expressing MCF7 cells as detected by the specific secondary antibody. None of these antibodies generated a significant signal in the FITC channel. When the <LeY>-<DIG> bispecific antibody was loaded with either [1:2] or [1:3] DIG-eGFP, these complexes did not generate a significant signal when analyzed for a Cy5 signal as compared to a non-loaded antibody detected with the Cy5 coupled secondary antibody (FIG. 43). When the same complexes were analyzed in the FITC channel, significant signals were obtained for both [1:2] and [1:3] DIG-eGFP, but no signal was observed for the <LeY>-<DIG> bispecific antibody (FIG. 43, 4). These data show that DIG coupled eGFP as a model protein can be recruited specifically to target positive cells by a <Target>-<DIG> bispecific antibody.

The DIG Labeled Protein eGFP can be Used to Monitor Endocytosis of Target Cell Bound Bispecific Antibody Antibodies targeting cell surface associated receptors often become internalized upon binding. After internalization, the antibodies bound to the target are trafficked to the endosomal compartments. These compartments a successively acidified. With the help of a pH dependent fluorophore such as eGFP, the internalization of a antibody can be monitored.

The chromophore of eGFP that is responsible for absorption and fluorescence consists of a p-hydroxybenzylideneimidazolidinone inside a cylinder of b-sheets. The chromophore can either exist in a neutral phenol form or a anionic phenolate form. Both forms exhibit distinct absorbance and fluorescence characteristics. The equilibrium between these forms depends on pH of the surrounding medium (Nakabayashi T, Wang H P, Kinjo M, Ohta N. Photochemical & photobiological sciences: Official journal of the European Photochemistry Association and the European Society for Photobiology; 2008 June; 7(6):668-70.). The different fluorescence characteristics of both forms of the chromphore have been used in various assays (Puckett L G, Lewis J C, Bachas L G, Daunert S. Analytical biochemistry; 2002 Oct. 15; 309(2):224-31) (Kneen M, Farinas J, Li Y, Verkman A S. Biophysical journal; 1998 March; 74(3):1591-9).

To analyze the ability of DIG-eGFP to monitor internalization, we performed FACS experiments. For these analyses we used LeY positive MCF7 cells and the bispecific <LeY>-<DIG> antibody. 3×10⁵ cells were seeded per well of a 96-well-plate and used immediately. 3.43 nM of the <LeY>-<DIG> bispecific antibody in FACS buffer (PBS containing 5% FCS) pre-incubated with a twofold molar amount of both [1:2] and [1:3] DIG-eGFP was added to the wells. After washing in FACS buffer the cells were incubated for one hour at either 4° C. or at 37° C. The cells were then analyzed with the FACS canto II (BD Biosciences).

The results of these experiments (FIG. 44) show that the fluorescence of DIG-eGFP is significantly reduced after internalization of the <LeY>-<DIG> bispecific antibody. At 4° C. the complex can bind to the cell surface localized LeY antigen, but cannot be internalized. After one hour, the fluorescence is fully retained (FIG. 44). One hour of incubation at 37° C. however is sufficient to initiate the internalization of the DIG-eGFP <LeY>-<DIG> bispecific antibody complex. The signal measured shows that there is still eGFP in these cells, but in comparison to the 4° C. control cells, a significant reduction of the fluorescence signal is observed (FIG. 44, 1,2). These data show that a pH dependent fluorophore can be utilized to measure endocytosis dependent acidification of endosomes and thus track the trafficking of a endocytosed bispecific antibody.

Bi- and Multispecific Targeting Entities can be Generated that Bind Different Haptens The application of digoxygenin binding modules to couple digoxygenated payloads to targeting vehicles is one technical possibility by which hapten-mediated payload delivery can be realized. However, the concept can be expanded to different haptens or other entities that capture payloads and connect them to the targeting module. For example, for siRNA delivery, bispecific antibodies and antibody derivatives that bind nucleic acids can be applied to connect siRNAs to the targeting vehicle.

Prerequisites for application as payload capturing modules are (i) that coupling of payloads to hapten does not interfere with payload activity and (ii) the possibility of effective binding/complexation of targeting vehicles to 'haptenylated' payloads. This example describes two further modules that can be utilized for payload delivery: biotin binding entities (antibodies) and PEG binding entities.

Biotin is a small molecule which is stable and for which robust state of the art coupling technologies are widely available. Biotin can be coupled to proteins, peptides, low molecular weight compounds or nucleic acids and other substances. Like digoxygenin, coupling via standard methods can be done without affecting the activity of payloads.

Quite different from standard 'hapten' binders are antibodies that recognize polyethyleneglycol (PEG). PEG is a polymer and hence can not be considered as a standard 'hapten'. Nevertheless, PEG-binding entities may be a good choice to use as payload capturing entity because PEG is already used as attachment for recombinant proteins. Robust technologies and optimized procedures for PEGylation of proteins, peptides and other substances are available; furthermore, PEG is a component of many siRNA delivery vehicles such as nanoparticles. Thus, having PEG-binding moieties for payload capture in targeting vehicles allows complexation by simple combination with already existing modules. These may include PEGylated compounds, PEGylated protein or nucleic acids, PEG-liposomes or other PEGylated nanoparticles.

Delivery vehicles that utilize biotin- or PEGbinding moieties for payload complexation can be generated based upon the same formats or format combinations that are described in FIG. 47. These molecules, which are shown in FIG. 55 can be generated by replacing digoxygenin binding entities of bispecific antibodies with antibody derivatives that bind biotin or polyethyleneglycol. The cell surface targeting moieties that we applied for the generation of biotin-binding bispecific antibodiesin this example were derived from an antibody that recognizes the human IGF1-receptor. The biotin binding sequences were isolated from mRNA from murine hybridomas that produced anti-Biotin antibodies (in a similar manner as described in Example 1 for the anti-Dig module). In the same manner PEG binding sequences can be isolated from mRNA from hybridomas that produce anti-PEG antibodies (in a similar manner as described in Example 1 for the anti-Dig module). Anti-PEG antibodies that can be applied for that have previously been described (Wunderlich et al., Hybridoma 26(3): 168-172, 2007; Chenget al., Bioconj. Chem. 16:1225-31, 2005; Tsai et al., Biotechniques 30: 396-402, 2001).

The amino acid sequences that were applied to generate vehicles for targeted payload delivery that contain anti-biotin modules are listed as SEQ ID NO 61 and SEQ ID NO 62. Roche Hybridoma <IGF1R-Biotin> could be expressed in mammalian cells and purified to homogeneity with standard Protein-A and size exclusion technologies (see Example 3 'Composition, expression and purification of recombinant humanized <Dig> antibodies, -fragments and bispecific-fusion proteins). FIG. 55b to d) shows that the anti-biotin containing molecules fully retained targeting specificity as well as biotin-binding competency as a prerequisite for payload delivery: This was demonstrated by Surface-Plasmon-Resonance (BiaCore) experiments (see example 4 'Binding of recombinant <Dig> antibodies, -fragments and bispecific-fusion proteins to digoxygenated antigens' for details). The data that are shown in this figure prove that the binding specificity and affinity towards cell surface target antigen as well as towards biotin is retained. Thus, in addition to digoxygenin, other substances with hapten (-like) properties or with direct payload binding competencies can be utilized to generate vehicles for targeted payload delivery.

Bi-Specific Digoxygenin Binding Entities can be Used to Deliver Protein- or Peptide-Based siRNA Transfection Modules It has been shown that various peptide sequences, so called Cell Penetrating Peptides (CPPs) can be used to transfect siRNA molecules into human cancer cells. The TAT-peptide is one published example for transfection capability with peptides that possess CPP functionality. However, so far transfection of siRNA with CPP-derived modules could not easily be combined with targeting specificity. The digoxygenin binding bispecific antibodies with shown capabilities to target DIG-siRNA to various target cells (see Example 13) can be applied to target a complex of DIG-siRNA and siRNA binding CPPs to antigen expressing target cells. For achieve that, the CPP's need to be attached to the siRNA-Antibody targeting complex. CPPs can in some instances spontaneously form complexes with nucleic acids. Even more stable linkage between peptides with CPP-like functionalities and siRNAs can be achieved by connecting the peptides to entities that bind nucleic acids. Such entities can be oligo- or poly-arginine stretches that binds to double stranded siRNA molecules because of the ionic interactions between the negatively charged phosphate backbone and the positively charged amino groups of the arginines. More structured peptide or protein domains can also be applied for hooking up CPP to siRNA, for example domains that bind single-stranded or double-stranded nucleic acids and nucleic acid derivatives.

FIG. 56a shows the experimental setup that we applied to demonstrate that <Dig> bispecifics can be used to deliver siRNA-CPP complexes to target cells: The peptide-module with CPP-functionality that we applied for these analyses is a 30-mer peptide derived from the human NRTN gene. This peptide was recently identified by us to have CPP-like and siRNA-transfection functionality. To generate peptide derivatives for efficient attachment to siRNA, we fused this peptide to multiple arginines. The sequence of the resulting fusion of a siRNA-binding module and the CPP was (SEQ ID NO 63)
RRRRRRRRRR-------GAAEAAARVYDLGLRRLRQRRRLRRERVRA.

FIG. 56b demonstrates that the CPP like NRTN peptide that can be fused to the siRNA binding entity complexes with (digoxygenated) siRNA in a quite stable manner. This causes a strong protein-mediated retention of the complexed siRNA in gel electrophoresis experiments. The degree of gel-shift that we observed indicates that more than one siRNA-binding peptide fusion becomes complexed by each siRNA.

This indicates the formation of complexes that contain <Dig> siRNAs. These can be targeted by subsequent formation of 'supercomplexes' with bispecific <Dig> targeting vehicles (see FIG. 56a).

To analyze these complexes for their ability to specifically induce mRNA silencing in target cells, we compared targeted siRNA transfection of complexes that contained either a<LeY>-<DIG> and a <CD22>-<DIG> bispecific antibody, which were charged with a DIG labeled siRNA targeting either Aha1 or as a control luciferase. These complexes were formed by pre-incubation Dig-siRNA with <Dig> bispecific at room temperature for 30 minutes, followed by addition of the CPP-PolyArg (siRNA binding) entity to generate the full transfection competent complex. The entire complex was incubated for further 30 minutes at room temperature before adding to LeY positive MCF7 cells for a duration of three hours in Optimem medium. After subsequent incubation in growth medium for another 21 hours, the cells were lysed, and their mRNA content was analyzed using a bDNA assay. The results of these analyses are shown in FIG. 56c. They demonstrate that complexes of bispecific antibodies with siRNA and siRNA-complexed transfecting peptides or domains can be applied to achieve specifically targeted siRNA delivery and subsequent targeted RNAi. Reduction of Aha1 mRNA was observed with these complexes in LeY expressing MCF-7 cells that were targeted by the <Ley-Dig> bispecific antibody. Application of <CD22-Dig> as bispecific module under otherwise identical conditions showed reduced RNAi compared to the effects that could be reached with the <LeY-Dig> bispecific antibody. The significantly stronger RNAi effects with the <Ley>-<DIG> than with the <CD22>-<DIG> delivery towards MCF7 cells which are Ley positive and CD22 negative indicates antibody-mediated targeting the siRNA CPP complexes to the target cells.

Example 17

Digoxigenin (DIG)-Labeled siRNA-Lipid Nanoparticles in Combination with Bispecific Antibodies Directed Against a Specific Target and DIG (<Target-DIG>) Mediate Specific Cell Targeting, Uptake, and Specific RNAi In Vitro We investigated the question whether <Target-DIG> bispecific antibodies were capable of directing DIG-labeled siRNA-lipid nanoparticles to cells without interfering with the delivery mechanism of such nanoparticles. To address this question, we (i) synthesized DIG-coupled lipid components of siRNA-lipid nanoparticles, (ii) formulated with those DIG-labeled siRNA-lipid nanoparticles, (iii) generated complexes of DIG-labeled siRNA-lipid nanoparticles with <Target-DIG> bispecific antibodies, and, (iv) evaluated targeting- and mRNA silencing properties of DIG-labeled siRNA-lipid nanoparticles in combination with <Target-DIG> bispecific antibodies in vitro.

(i) Synthesis of DIG-Coupled 1,2-Distearoyl-Phosphatidylethanolamine [Methoxy (Polyethyleneglycol)-2000] (DSPE-PEG$_{2000}$-DIG).

DSPE-PEG$_{2000}$-DIG was synthesized by coupling NHS-activated DIG (Roche Diagnostics GmbH, Mannheim, Germany) to amine-functionalized DSPE-PEG2000 (Avanti Polar Lipids, Inc., Alabaster, AB).

(ii) Manufacturing of DIG-Labeled siRNA-Lipid Nanoparticles.

DIG-labeled siRNA-lipid nanoparticles consisted of 1,2-distearoyl-3-phosphatidylcholine (DPPC) (Avanti Polar Lipids, Inc., Alabaster, AB) 2,2-dilinoleyl-4-dimethylaminoethyl-[1,3]-dioxolane (synthesized in-house), cholesterol (Sigma-Aldrich Chemie GmbH, Munich, Germany), and polyethyleneglycol (PEG)$_{2000}$-lipid in a ratio of (7.1, 57.1, 34.4, and 1.4 mol %). The total PEG$_{2000}$-lipid content (1.4 mol %) was composed of Sunbright GM-020CE, α-[3'-(1,2-dimyristoyl-3-propanoxy)-carboxamide-propyl]-ω-methoxy-polyoxyethylene (NOF Europe, Grobbendonk, Belgium) at 1.4%, 1.36%, 1%, or 0.4%, respectively, and DSPE-PEG$_{2000}$-DIG (see above) at 0%, 0.04%, 0.4%, or 1%, respectively. Lipids and cholesterol were dissolved in ethanol. AHA1-, DIG-coupled AHA1-, or luciferase (LUC)-siRNAs were dissolved in citrate buffer, pH 4. siRNA-lipid nanoparticles were formed by rapid injection of appropriate volumes of ethanolic lipid mixture into buffered aqueous siRNA solution. siRNA-lipid nanoparticles were subsequently dialyzed against phosphate-buffered saline (PBS) using 10 kD MWCO Slide-A-Lyzer® cassettes (Thermo Scientific, Rockford. IL). The pH value of siRNA-lipid nanoparticle preparations was confirmed and the size-distribution and the zeta-potential of siRNA-lipid nanoparticles were determined by dynamic light scattering on a Zetasizer Nano-ZS (Malvern Instruments LTD, Malvern, UK). A modified RiboGreen assay (Invitrogen GmbH, Darmstadt, Germany) was conducted to quantify the degree of siRNA entrapment. The total siRNA content was determined spectrophotometrically after dissolving the siRNA-lipid complex in methanol:chloroform (10:1, vol:vol). Mean particles sizes of siRNA-lipid nanoparticles (RLX-107-RLX-115) ranged from 119 nm to 128 nm ($z_{average}$ values) with polydispersity indices ranging from 0.02 to 0.1. The zeta-potential in PBS ranged from −3 to −4 mV. The encapsulation efficiency was 95%-96% and the final siRNA concentration ranged from 0.4 mg/ml to 0.5 mg/ml.

(iii) Complexation of DIG-Labeled siRNA-Lipid Nanoparticles with <Target-DIG> Bispecific Antibodies.

DIG-labeled siRNA-lipid nanoparticles containing 1 pmol of AHA1-, DIG-coupled AHA1-, or luciferase (LUC)-siRNAs were incubated with 3.24 pmol of bispecific antibodies directed against either the tumor-associated LewisY oligosaccharide and DIG <LeY-DIG> or against the sialic acid-binding transmembrane protein, CD22, and DIG <CD22-DIG> or with Dulbecco's Phosphate Buffered Saline (D-PBS) (Invitrogen, Carlsbad, Calif.) in a final volume of 200 μl Opti-MEM® (Invitrogen GmbH, Darmstadt, Germany) at RT for 30 min.

(iv) Evaluation of Targeting- and mRNA Silencing Properties of DIG-Labeled siRNA-Lipid Nanoparticles in Combination with <Target-DIG> Bispecific Antibodies In Vitro;

MCF-7 cells were seeded on a 96-well plate with a density of 15,000 cells/well in 80 μl medium (RPMI 1640 Medium, 10% fetal calf serum, 100 U/ml penicillin/streptomycin; Biochrom AG, Berlin, Germany) and incubated overnight in a cell incubator (37° C., 95% H$_2$O, 5% CO2). Following preincubation of DIG-labeled siRNA-lipid nanoparticles with <Target-DIG> bispecific antibodies (see above), 20 μl of the mixtures were added to MCF-7 cells, leading to a final volume of 100 μl containing 1 nM siRNA and no antibodies (no AB) or 1 nM siRNA and 3.24 nM of either <LeY-DIG> (LeY) or <CD22-DIG> (CD22) antibodies. Cells were incubated for 12 hours in a cell incubator. As a control, cells were also incubated at the same antibody concentration but without siRNA or siRNA-lipid nanoparticles (AB only). As an additional control, cells were transfected with 50 nM of AHA1- or Luciferase-siRNA complexed with the commercially available transfection reagent Dharmafect 2 (Dh2) (Dharmacon Inc., Lafayette, Colo.) according to the manufacturer's instructions. After incubation, cells were lysed and AHA1- and GAPDH-mRNA concentrations were quantified using a commercially available bDNA-quantification system (Affymetrix Inc., Fremont, Calif.). AHA1-mRNA signals were normalized to GAPDH-mRNA signals and AHA1/GAPDH-mRNA ratios were reported relative to those following luciferase-siRNA transfection using Dh2 (set to 100%).

Without the use of the <LeY-DIG> bispecific antibodies, the potency of siRNA-lipid nanoparticles decreased with increasing DSPE-PEG$_{2000}$-DIG concentrations and siRNA-lipid nanoparticles containing 1% DSPE-PEG2000-DIG (RLX-107) did not mediate target AHA1-mRNA knockdown. In contrast, incubating MCF-7 cells for 12 hours with formulations not containing DSPE-PEG$_{2000}$-DIG (RLX-110 and RLX-115) lead to an AHA1-mRNA knockdown of 43% or 41%, respectively. More importantly, the AHA1-mRNA knockdown efficacy of liposomal formulations containing 1% (RLX-110), 0.4% (RLX-108), or 0.04% (RLX-109) DSPE-PEG$_{2000}$-DIG were significantly increased by 14%, 45%, or 31%, respectively, following addition of <LeY-DIG> bispecific antibodies to the incubation medium. Both, <LeY-DIG> and <CD22-DIG> bispecific antibodies had no effect on the efficacy of siRNA-lipid nanoparticles not containing DSPE-PEG$_{2000}$-DIG. Similarly, addition of non-targeting <CD22-DIG> bispecific antibodies to siRNA-lipid nanoparticles containing DSPE-PEG$_{2000}$-DIG had also no effect on AHA1-mRNA knockdown. Also, siRNA-lipid nanoparticles containing luciferase-siRNA (RLX-111-RLX-114) do not affect AHA1-mRNA levels irrespective of the bispecific antibodies used. When adding <LeY-DIG> bispecific antibodies to siRNA-lipid nanoparticles not containing DSPE-PEG$_{2000}$-DIG but instead DIG-modified AHA1-siRNA, the efficacy increased by only 5% as compared to adding <CD22-DIG> antibodies (RLX-115) (FIG. 57).

The results summarized in Table 12 and FIG. 57 imply that DIG-labeled siRNA-lipid nanoparticles can be efficiently and specifically delivered to cells that express the targeted antigen on their cell surface by using <Target-Dig> bispecific antibodies. The efficacy of DIG-labeled siRNA-lipid nanoparticles can thereby significantly be increased specifically in cells that express the target antigen. The specificity of this approach for, the antibody, the antigen, and the siRNA could convincingly been shown since <CD22-DIG> bispecific antibodies did not convey this effect in DIG-labeled siRNA-lipid nanoparticles and <LeY-DIG> bispecific antibodies did not convey this effect in siRNA-lipid nanoparticles that were identical in their compositions but did not contain the targeting moiety. Furthermore, AHA1 mRNA levels were unaffected after treatment of MCF-7 cells with siRNA-lipid nanoparticles containing Luc siRNA.

TABLE 12 siRNA mediated mRNA knockdown in MCF-7 cells following treatment with DIG-labeled siRNA-lipid nanoparticles complexed with <Target-Dig> bispecific antibodies. AHA1 mRNA levels (relative to GAPDH) were determined in MCF-7 breast cancer cells expressing the LeY antigen but not CD22 following 12 h incubation with DIG-labeled siRNA-lipid nanoparticles pre-incubated with <Target-DIG> bispecific antibodies.

| | | relative AHA1-mRNA concentration/[%] | | |
|---|---|---|---|---|
| siRNA (conc.) | formulation | no AB | CD22-DIG | LeY-DIG |
| AHA1 (50 nM) | Dharmafect 2 | 35.8 | — | — |
| no siRNA | only antibody | — | 96.3 | 94.6 |
| AHA1 (1 nM) | RLX-107 (1% DIG) | 95.9 | 94.2 | 81.7 |
| | RLX-108 (0.4% DIG) | 86.3 | 84.6 | 41.3 |
| | RLX-109 (0.04% DIG) | 67.2 | 70.7 | 36.1 |
| | RLX-110 (0% DIG) | 57.0 | 52.7 | 58.6 |
| DIG-AHA1 (1 nM) | RLX-115 (0% DIG) | 59.1 | 54.5 | 50.0 |
| LUC (1 nM) | RLX-111 (1% DIG) | 94.7 | 97.8 | 86.8 |
| | RLX-112 (0.4% DIG) | 95.0 | 95.8 | 98.0 |
| | RLX-109 (0.04% DIG) | 99.6 | 92.6 | 101.2 |
| | RLX-110 (0% DIG | 110.8 | 91.8 | 99.1 |

The invention claimed is:

1. A bi-specific antibody specific against a digoxigenin (DIG) and a target protein, comprising a first antigen-binding site that binds to said DIG and a second antigen-binding site that binds to a target protein, wherein the DIG is conjugated to a nucleic acid, wherein said first antigen-binding site comprises: (a) a heavy chain variable domain of SEQ ID NO: 2 or SEQ ID NO:3, wherein SEQ ID NO:3 comprises mutations of S49A, I57A and A60P; and (b) a light chain variable domain of SEQ ID NO: 5 or SEQ ID NO: 1.

2. The bispecific antibody of claim 1, comprising
   a) a monospecific bivalent antibody consisting of two full length antibody heavy chains and two full length antibody light chains whereby each chain comprises only one variable domain,
   b) two peptide-linkers,
   c) two monospecific monovalent single chain antibodies, each comprising said first antigen-binding site, wherein each single chain antibody consists of an antibody heavy chain variable domain, an antibody light chain variable domain, and a single-chain-linker between said antibody heavy chain variable domain and said antibody light chain variable domain; and optionally, said single chain antibodies are linked to the same terminus (C- or N-terminus) of the monospecific bivalent antibody heavy chains or, alternatively to the same terminus of the monospecific bivalent antibody light chains.

3. The bi-specific antibody of claim 1, wherein said antigen-binding site specifically binding to DIG comprises a heavy chain Fd-Fragment ($V_H$ and Ch1) of SEQ ID NO: 4 or SEQ ID NO: 36 and an L-chain of SEQ ID NO: 6 or SEQ ID NO: 37.

4. The bi-specific antibody of claim 1, wherein said first antigen-binding site specifically binds to DIG, and wherein said first antigen-binding site comprises a heavy chain Fd-Fragment ($V_H$ and CH1) of SEQ ID NO: 4 or SEQ ID NO: 36 and an L-chain of SEQ ID NO: 6 or SEQ ID NO: 37.

5. The bi-specific antibody of claim 1, wherein the antibody is humanized.

6. The bi-specific antibody of claim 1, wherein the target protein is a cell surface antigen.

7. The bi-specific antibody of claim 6, wherein the cell surface antigen is a tumor antigen.

8. The bi-specific antibody of claim 1, wherein the target protein is selected from the group consisting of Her2, IGFI R, CD22, CD33, LeY, VEGFRI.

9. The bi-specific antibody of claim 1, wherein the nucleic acid is a therapeutic or diagnostic agent.

10. The bi-specific antibody of claim 1, wherein the nucleic acid is a double-stranded RNA.

11. The bi-specific antibody of claim 1, wherein the nucleic acid is conjugated to a transfection reagent.

12. The bi-specific antibody of claim 11, wherein the transfection reagent is a liposomal transfection reagent or a transfecting peptide.

13. The bi-specific antibody of claim 1, wherein the nucleic acid is coupled to an endosome escape or a disruption module.

14. The bi-specific antibody of claim 13, wherein the nucleic acid is coupled to a peptide which mediates endosome escape or disruption.

15. The bi-specific antibody of claim 13, wherein the endosome escape or disruption modules comprises a dynamic polyconjugate (DPC).

16. The bi-specific antibody of claim 9, wherein the diagnostic agent is a digoxigenated Cy5-labeled nucleic acid.

17. A pharmaceutical composition comprising the bi-specific antibody of claim 1 coupled to a digoxigenated therapeutic or diagnostic nucleic acid.

* * * * *

SEQUENCE LISTING

<160> NUMBER OF SEQ ID NOS: 121

<210> SEQ ID NO 1
<211> LENGTH: 126
<212> TYPE: PRT
<213> ORGANISM: Mus musculus

<400> SEQUENCE: 1

Met Ser Ser Ala Gln Phe Leu Gly Leu Leu Leu Cys Phe Gln Gly
1               5                   10                  15

Thr Arg Cys Asp Val Gln Met Thr Gln Ser Thr Ser Ser Leu Ser Ala
                20                  25                  30

Ser Leu Gly Asp Arg Val Thr Ile Ser Cys Arg Ala Ser Gln Asp Ile
            35                  40                  45

Lys Asn Tyr Leu Asn Trp Tyr Gln Gln Lys Pro Gly Gly Thr Val Lys
        50                  55                  60

Leu Leu Ile Tyr Tyr Ser Ser Thr Leu Leu Ser Gly Val Pro Ser Arg
65                  70                  75                  80

Phe Ser Gly Arg Gly Ser Gly Thr Asp Phe Ser Leu Thr Ile Thr Asn
                85                  90                  95

Leu Glu Arg Glu Asp Ile Ala Thr Tyr Phe Cys Gln Gln Ser Ile Thr
            100                 105                 110

Leu Pro Pro Thr Phe Gly Gly Gly Thr Lys Leu Glu Ile Lys
        115                 120                 125

<210> SEQ ID NO 2
<211> LENGTH: 144
<212> TYPE: PRT
<213> ORGANISM: Mus musculus

<400> SEQUENCE: 2

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Val Ser Gly Phe Thr Phe
        35                  40                  45

Ser Asp Tyr Ala Met Ser Trp Ile Arg Gln Thr Pro Glu Asn Arg Leu
    50                  55                  60

Glu Trp Val Ala Ser Ile Asn Ile Gly Ala Thr Tyr Ala Tyr Tyr Pro
65                  70                  75                  80

Asp Ser Val Lys Gly Arg Phe Thr Ile Ser Arg Asp Asn Ala Lys Asn
                85                  90                  95

Thr Leu Phe Leu Gln Met Ser Ser Leu Gly Ser Glu Asp Thr Ala Met
            100                 105                 110

Tyr Tyr Cys Ala Arg Pro Gly Ser Pro Tyr Glu Tyr Asp Lys Ala Tyr
        115                 120                 125

Tyr Ser Met Ala Tyr Trp Gly Pro Gly Thr Ser Val Thr Val Ser Ser
    130                 135                 140

<210> SEQ ID NO 3
<211> LENGTH: 125
<212> TYPE: PRT
<213> ORGANISM: Artificial Sequence
<220> FEATURE:
<223> OTHER INFORMATION: Description of Artificial Sequence: Synthetic
      Humanized <dig> VH construct

<400> SEQUENCE: 3

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125

<210> SEQ ID NO 4
<211> LENGTH: 455

```
<212> TYPE: PRT
<213> ORGANISM: Artificial Sequence
<220> FEATURE:
<223> OTHER INFORMATION: Description of Artificial Sequence: Synthetic
      Humanized <dig> H-chain construct

<400> SEQUENCE: 4
```

| | | | | | | | | | | | | | | | |
|---|---|---|---|---|---|---|---|---|---|---|---|---|---|---|---|
|Gln|Val|Gln|Leu|Val|Glu|Ser|Gly|Gly|Gly|Leu|Val|Lys|Pro|Gly|Gly|
|1| | | |5| | | | |10| | | | |15| |
|Ser|Leu|Arg|Leu|Ser|Cys|Ala|Ala|Ser|Gly|Phe|Thr|Phe|Ser|Asp|Tyr|
| | | |20| | | | |25| | | | |30| | |
|Ala|Met|Ser|Trp|Ile|Arg|Gln|Ala|Pro|Gly|Lys|Gly|Leu|Glu|Trp|Val|
| | |35| | | | |40| | | | |45| | | |
|Ser|Ser|Ile|Asn|Ile|Gly|Ala|Thr|Tyr|Ile|Tyr|Tyr|Ala|Asp|Ser|Val|
|50| | | | |55| | | | |60| | | | | |
|Lys|Gly|Arg|Phe|Thr|Ile|Ser|Arg|Asp|Asn|Ala|Lys|Asn|Ser|Leu|Tyr|
|65| | | | |70| | | | |75| | | | |80|
|Leu|Gln|Met|Asn|Ser|Leu|Arg|Ala|Glu|Asp|Thr|Ala|Val|Tyr|Tyr|Cys|
| | | | |85| | | | |90| | | | |95| |
|Ala|Arg|Pro|Gly|Ser|Pro|Tyr|Glu|Tyr|Asp|Lys|Ala|Tyr|Tyr|Ser|Met|
| | | |100| | | | |105| | | | |110| | |
|Ala|Tyr|Trp|Gly|Gln|Gly|Thr|Thr|Val|Thr|Val|Ser|Ser|Ala|Ser|Thr|
| | |115| | | | |120| | | | |125| | | |
|Lys|Gly|Pro|Ser|Val|Phe|Pro|Leu|Ala|Pro|Ser|Ser|Lys|Ser|Thr|Ser|
|130| | | | |135| | | | |140| | | | | |
|Gly|Gly|Thr|Ala|Ala|Leu|Gly|Cys|Leu|Val|Lys|Asp|Tyr|Phe|Pro|Glu|
|145| | | | |150| | | | |155| | | | |160|
|Pro|Val|Thr|Val|Ser|Trp|Asn|Ser|Gly|Ala|Leu|Thr|Ser|Gly|Val|His|
| | | | |165| | | | |170| | | | |175| |
|Thr|Phe|Pro|Ala|Val|Leu|Gln|Ser|Ser|Gly|Leu|Tyr|Ser|Leu|Ser|Ser|
| | | |180| | | | |185| | | | |190| | |
|Val|Val|Thr|Val|Pro|Ser|Ser|Ser|Leu|Gly|Thr|Gln|Thr|Tyr|Ile|Cys|
| | |195| | | | |200| | | | |205| | | |
|Asn|Val|Asn|His|Lys|Pro|Ser|Asn|Thr|Lys|Val|Asp|Lys|Lys|Val|Glu|
|210| | | | |215| | | | |220| | | | | |
|Pro|Lys|Ser|Cys|Asp|Lys|Thr|His|Thr|Cys|Pro|Pro|Cys|Pro|Ala|Pro|
|225| | | | |230| | | | |235| | | | |240|
|Glu|Leu|Leu|Gly|Gly|Pro|Ser|Val|Phe|Leu|Phe|Pro|Pro|Lys|Pro|Lys|
| | | | |245| | | | |250| | | | |255| |
|Asp|Thr|Leu|Met|Ile|Ser|Arg|Thr|Pro|Glu|Val|Thr|Cys|Val|Val|Val|
| | | |260| | | | |265| | | | |270| | |
|Asp|Val|Ser|His|Glu|Asp|Pro|Glu|Val|Lys|Phe|Asn|Trp|Tyr|Val|Asp|
| | |275| | | | |280| | | | |285| | | |
|Gly|Val|Glu|Val|His|Asn|Ala|Lys|Thr|Lys|Pro|Arg|Glu|Glu|Gln|Tyr|
| |290| | | | |295| | | | |300| | | | |
|Asn|Ser|Thr|Tyr|Arg|Val|Val|Ser|Val|Leu|Thr|Val|Leu|His|Gln|Asp|
|305| | | | |310| | | | |315| | | | |320|
|Trp|Leu|Asn|Gly|Lys|Glu|Tyr|Lys|Cys|Lys|Val|Ser|Asn|Lys|Ala|Leu|
| | | | |325| | | | |330| | | | |335| |
|Pro|Ala|Pro|Ile|Glu|Lys|Thr|Ile|Ser|Lys|Ala|Lys|Gly|Gln|Pro|Arg|
| | | |340| | | | |345| | | | |350| | |
|Glu|Pro|Gln|Val|Tyr|Thr|Leu|Pro|Pro|Ser|Arg|Asp|Glu|Leu|Thr|Lys|
| | |355| | | | |360| | | | |365| | | |
|Asn|Gln|Val|Ser|Leu|Thr|Cys|Leu|Val|Lys|Gly|Phe|Tyr|Pro|Ser|Asp|
|370| | | | |375| | | | |380| | | | | |

```
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      humanized <dig> VL construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg
            100                 105

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      humanized <dig> L-chain construct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210
```

<210> SEQ ID NO 7
<211> LENGTH: 707
<212> TYPE: PRT
<213> ORGANISM: Artificial Sequence
<220> FEATURE:
<223> OTHER INFORMATION: Description of Artificial Sequence: Synthetic
      humanized <her2> <dig> H-chain construct

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Gly Ser Gln Val Gln Leu
                450                 455                 460

Val Glu Ser Gly Gly Gly Leu Val Lys Pro Gly Gly Ser Leu Arg Leu
465                 470                 475                 480

Ser Cys Ala Ala Ser Gly Phe Thr Phe Ser Asp Tyr Ala Met Ser Trp
                485                 490                 495

Ile Arg Gln Ala Pro Gly Lys Gly Leu Glu Trp Val Ser Ser Ile Asn
            500                 505                 510

Ile Gly Ala Thr Tyr Ile Tyr Tyr Ala Asp Ser Val Lys Gly Arg Phe
            515                 520                 525

Thr Ile Ser Arg Asp Asn Ala Lys Asn Ser Leu Tyr Leu Gln Met Asn
            530                 535                 540

Ser Leu Arg Ala Glu Asp Thr Ala Val Tyr Tyr Cys Ala Arg Pro Gly
545                 550                 555                 560

Ser Pro Tyr Glu Tyr Asp Lys Ala Tyr Tyr Ser Met Ala Tyr Trp Gly
                565                 570                 575

Gln Gly Thr Thr Val Thr Val Ser Ser Gly Gly Gly Gly Ser Gly Gly
                580                 585                 590

Gly Gly Ser Gly Gly Gly Gly Ser Asp Ile Gln Met Thr Gln Ser Pro
                595                 600                 605

Ser Ser Leu Ser Ala Ser Val Gly Asp Arg Val Thr Ile Thr Cys Arg
            610                 615                 620

Ala Ser Gln Asp Ile Lys Asn Tyr Leu Asn Trp Tyr Gln Gln Lys Pro
625                 630                 635                 640

Gly Lys Ala Pro Lys Leu Leu Ile Tyr Tyr Ser Ser Thr Leu Leu Ser
                645                 650                 655

Gly Val Pro Ser Arg Phe Ser Gly Ser Gly Ser Gly Thr Asp Phe Thr
                660                 665                 670
```

```
Leu Thr Ile Ser Ser Leu Gln Pro Glu Asp Phe Ala Thr Tyr Tyr Cys
        675                 680                 685

Gln Gln Ser Ile Thr Leu Pro Pro Thr Phe Gly Gly Gly Thr Lys Val
690                 695                 700

Glu Ile Lys
705

<210> SEQ ID NO 8
<211> LENGTH: 712
<212> TYPE: PRT
<213> ORGANISM: Artificial Sequence
<220> FEATURE:
<223> OTHER INFORMATION: Description of Artificial Sequence: Synthetic
      humanized <her2> <dig> H-chain, disulfide-stabilized construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
              305                 310                 315                 320
        Glu Tyr Lys Cys Lys Val Ser Asn Lys Ala Leu Pro Ala Pro Ile Glu
                            325                 330                 335

Lys Thr Ile Ser Lys Ala Lys Gly Gln Pro Arg Glu Pro Gln Val Tyr
                            340                 345                 350

Thr Leu Pro Pro Ser Arg Glu Glu Met Thr Lys Asn Gln Val Ser Leu
                            355                 360                 365

Thr Cys Leu Val Lys Gly Phe Tyr Pro Ser Asp Ile Ala Val Glu Trp
                            370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                            405                 410                 415

Lys Ser Arg Trp Gln Gln Gly Asn Val Phe Ser Cys Ser Val Met His
                            420                 425                 430

Glu Ala Leu His Asn His Tyr Thr Gln Lys Ser Leu Ser Leu Ser Pro
                            435                 440                 445

Gly Lys Gly Gly Gly Gly Ser Gly Gly Gly Gly Ser Gln Val Gln Leu
                    450                 455                 460

Val Glu Ser Gly Gly Gly Leu Val Lys Pro Gly Gly Ser Leu Arg Leu
        465                 470                 475                 480

Ser Cys Ala Ala Ser Gly Phe Thr Phe Ser Asp Tyr Ala Met Ser Trp
                            485                 490                 495

Ile Arg Gln Ala Pro Gly Lys Cys Leu Glu Trp Val Ser Ser Ile Asn
                            500                 505                 510

Ile Gly Ala Thr Tyr Ile Tyr Tyr Ala Asp Ser Val Lys Gly Arg Phe
                            515                 520                 525

Thr Ile Ser Arg Asp Asn Ala Lys Asn Ser Leu Tyr Leu Gln Met Asn
                            530                 535                 540

Ser Leu Arg Ala Glu Asp Thr Ala Val Tyr Tyr Cys Ala Arg Pro Gly
        545                 550                 555                 560

Ser Pro Tyr Glu Tyr Asp Lys Ala Tyr Tyr Ser Met Ala Tyr Trp Gly
                            565                 570                 575

Gln Gly Thr Thr Val Thr Val Ser Ser Gly Gly Gly Gly Ser Gly Gly
                            580                 585                 590

Gly Gly Ser Gly Gly Gly Gly Ser Gly Gly Gly Gly Ser Asp Ile Gln
                            595                 600                 605

Met Thr Gln Ser Pro Ser Ser Leu Ser Ala Ser Val Gly Asp Arg Val
                            610                 615                 620

Thr Ile Thr Cys Arg Ala Ser Gln Asp Ile Lys Asn Tyr Leu Asn Trp
        625                 630                 635                 640

Tyr Gln Gln Lys Pro Gly Lys Ala Pro Lys Leu Leu Ile Tyr Tyr Ser
                            645                 650                 655

Ser Thr Leu Leu Ser Gly Val Pro Ser Arg Phe Ser Gly Ser Gly Ser
                            660                 665                 670

Gly Thr Asp Phe Thr Leu Thr Ile Ser Ser Leu Gln Pro Glu Asp Phe
                            675                 680                 685

Ala Thr Tyr Tyr Cys Gln Gln Ser Ile Thr Leu Pro Pro Thr Phe Gly
                            690                 695                 700

Cys Gly Thr Lys Val Glu Ile Lys
        705                 710

<210> SEQ ID NO 9
```

<211> LENGTH: 214
<212> TYPE: PRT
<213> ORGANISM: Artificial Sequence
<220> FEATURE:
<223> OTHER INFORMATION: Description of Artificial Sequence:
      Synthetic humanized <her2> <dig> L-chain construct

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 10
<211> LENGTH: 705
<212> TYPE: PRT
<213> ORGANISM: Artificial Sequence
<220> FEATURE:
<223> OTHER INFORMATION: Description of Artificial Sequence: Synthetic
      humanized <IGFR1> <dig> H-chain construct

<400> SEQUENCE: 10

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95
```

```
Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Ser Gln Val Gln Leu Val Glu
    450                 455                 460

Ser Gly Gly Gly Leu Val Lys Pro Gly Gly Ser Leu Arg Leu Ser Cys
465                 470                 475                 480

Ala Ala Ser Gly Phe Thr Phe Ser Asp Tyr Ala Met Ser Trp Ile Arg
                485                 490                 495

Gln Ala Pro Gly Lys Gly Leu Glu Trp Val Ser Ser Ile Asn Ile Gly
            500                 505                 510
```

```
Ala Thr Tyr Ile Tyr Tyr Ala Asp Ser Val Lys Gly Arg Phe Thr Ile
            515                 520                 525

Ser Arg Asp Asn Ala Lys Asn Ser Leu Tyr Leu Gln Met Asn Ser Leu
    530                 535                 540

Arg Ala Glu Asp Thr Ala Val Tyr Tyr Cys Ala Arg Pro Gly Ser Pro
545                 550                 555                 560

Tyr Glu Tyr Asp Lys Ala Tyr Tyr Ser Met Ala Tyr Trp Gly Gln Gly
                565                 570                 575

Thr Thr Val Thr Val Ser Ser Gly Gly Gly Ser Gly Gly Gly
            580                 585                 590

Ser Gly Gly Gly Ser Asp Ile Gln Met Thr Gln Ser Pro Ser Ser
    595                 600                 605

Leu Ser Ala Ser Val Gly Asp Arg Val Thr Ile Thr Cys Arg Ala Ser
    610                 615                 620

Gln Asp Ile Lys Asn Tyr Leu Asn Trp Tyr Gln Gln Lys Pro Gly Lys
625                 630                 635                 640

Ala Pro Lys Leu Leu Ile Tyr Tyr Ser Thr Leu Leu Ser Gly Val
                645                 650                 655

Pro Ser Arg Phe Ser Gly Ser Gly Ser Gly Thr Asp Phe Thr Leu Thr
                660                 665                 670

Ile Ser Ser Leu Gln Pro Glu Asp Phe Ala Thr Tyr Tyr Cys Gln Gln
        675                 680                 685

Ser Ile Thr Leu Pro Pro Thr Phe Gly Gly Gly Thr Lys Val Glu Ile
    690                 695                 700

Lys
705

<210> SEQ ID NO 11
<211> LENGTH: 705
<212> TYPE: PRT
<213> ORGANISM: Artificial Sequence
<220> FEATURE:
<223> OTHER INFORMATION: Description of Artificial Sequence: Synthetic
      humanized <IGFR1> <dig> H-chain, disulfide-stabilized construct

<400> SEQUENCE: 11

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

-continued

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gln Val Gln Leu Val Glu
            450                 455                 460

Ser Gly Gly Gly Leu Val Lys Pro Gly Gly Ser Leu Arg Leu Ser Cys
465                 470                 475                 480

Ala Ala Ser Gly Phe Thr Phe Ser Asp Tyr Ala Met Ser Trp Ile Arg
            485                 490                 495

Gln Ala Pro Gly Lys Cys Leu Glu Trp Val Ser Ser Ile Asn Ile Gly
            500                 505                 510

Ala Thr Tyr Ile Tyr Tyr Ala Asp Ser Val Lys Gly Arg Phe Thr Ile
            515                 520                 525

Ser Arg Asp Asn Ala Lys Asn Ser Leu Tyr Leu Gln Met Asn Ser Leu
            530                 535                 540

Arg Ala Glu Asp Thr Ala Val Tyr Tyr Cys Ala Arg Pro Gly Ser Pro
545                 550                 555                 560

Tyr Glu Tyr Asp Lys Ala Tyr Tyr Ser Met Ala Tyr Trp Gly Gln Gly
            565                 570                 575

```
Thr Thr Val Thr Val Ser Ser Gly Gly Ser Gly Gly Gly
            580                 585                 590

Ser Gly Gly Gly Gly Ser Asp Ile Gln Met Thr Gln Ser Pro Ser Ser
        595                 600                 605

Leu Ser Ala Ser Val Gly Asp Arg Val Thr Ile Thr Cys Arg Ala Ser
610                 615                 620

Gln Asp Ile Lys Asn Tyr Leu Asn Trp Tyr Gln Gln Lys Pro Gly Lys
625                 630                 635                 640

Ala Pro Lys Leu Leu Ile Tyr Tyr Ser Thr Leu Leu Ser Gly Val
                645                 650                 655

Pro Ser Arg Phe Ser Gly Ser Gly Ser Gly Thr Asp Phe Thr Leu Thr
            660                 665                 670

Ile Ser Ser Leu Gln Pro Glu Asp Phe Ala Thr Tyr Tyr Cys Gln Gln
        675                 680                 685

Ser Ile Thr Leu Pro Pro Thr Phe Gly Cys Gly Thr Lys Val Glu Ile
    690                 695                 700

Lys
705

<210> SEQ ID NO 12
<211> LENGTH: 215
<212> TYPE: PRT
<213> ORGANISM: Artificial Sequence
<220> FEATURE:
<223> OTHER INFORMATION: Description of Artificial Sequence: Synthetic
      humanized <IGFR1> <dig> L-chain construct

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
            85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215
```

<210> SEQ ID NO 13
<211> LENGTH: 715
<212> TYPE: PRT
<213> ORGANISM: Artificial Sequence
<220> FEATURE:
<223> OTHER INFORMATION: Description of Artificial Sequence: Synthetic humanized <CD22> <dig> H-chain, disulfide-stabilized construct

<400> SEQUENCE: 13

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ala Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
```

```
            355                 360                 365
Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Gly Ser Gly Gln
    450                 455                 460

Val Gln Leu Val Glu Ser Gly Gly Gly Leu Val Lys Pro Gly Gly Ser
465                 470                 475                 480

Leu Arg Leu Ser Cys Ala Ala Ser Gly Phe Thr Phe Ser Asp Tyr Ala
                485                 490                 495

Met Ser Trp Ile Arg Gln Ala Pro Gly Lys Cys Leu Glu Trp Val Ser
            500                 505                 510

Ser Ile Asn Ile Gly Ala Thr Tyr Ile Tyr Tyr Ala Asp Ser Val Lys
        515                 520                 525

Gly Arg Phe Thr Ile Ser Arg Asp Asn Ala Lys Asn Ser Leu Tyr Leu
    530                 535                 540

Gln Met Asn Ser Leu Arg Ala Glu Asp Thr Ala Val Tyr Tyr Cys Ala
545                 550                 555                 560

Arg Pro Gly Ser Pro Tyr Glu Tyr Asp Lys Ala Tyr Tyr Ser Met Ala
                565                 570                 575

Tyr Trp Gly Gln Gly Thr Thr Val Thr Val Ser Ser Gly Gly Gly Gly
            580                 585                 590

Ser Gly Gly Gly Gly Ser Gly Gly Gly Ser Gly Gly Gly Gly Ser
        595                 600                 605

Asp Ile Gln Met Thr Gln Ser Pro Ser Ser Leu Ser Ala Ser Val Gly
    610                 615                 620

Asp Arg Val Thr Ile Thr Cys Arg Ala Ser Gln Asp Ile Lys Asn Tyr
625                 630                 635                 640

Leu Asn Trp Tyr Gln Gln Lys Pro Gly Lys Ala Pro Lys Leu Leu Ile
                645                 650                 655

Tyr Tyr Ser Ser Thr Leu Leu Ser Gly Val Pro Ser Arg Phe Ser Gly
            660                 665                 670

Ser Gly Ser Gly Thr Asp Phe Thr Leu Thr Ile Ser Ser Leu Gln Pro
        675                 680                 685

Glu Asp Phe Ala Thr Tyr Tyr Cys Gln Gln Ser Ile Thr Leu Pro Pro
    690                 695                 700

Thr Phe Gly Cys Gly Thr Lys Val Glu Ile Lys
705                 710                 715

<210> SEQ ID NO 14
<211> LENGTH: 213
<212> TYPE: PRT
<213> ORGANISM: Artificial Sequence
<220> FEATURE:
<223> OTHER INFORMATION: Description of Artificial Sequence: Synthetic
      humanized <CD22> <dig> L-chain construct

<400> SEQUENCE: 14
```

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer sequence VL region

<400> SEQUENCE: 15 tttttgcgg ccgccctaac actcattcct gttgaagctc                          40

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer sequence VH region

<400> SEQUENCE: 16 tttttgcgg ccgcgtacat atgcaaggct tacaaccaca atcc                     44

<210> SEQ ID NO 17
<211> LENGTH: 26
<212> TYPE: PRT
<213> ORGANISM: Homo sapiens

<400> SEQUENCE: 17

Gly Ile Gly Ala Val Leu Lys Val Leu Thr Thr Gly Leu Pro Ala Leu
1               5                   10                  15
```

```
Ile Ser Trp Ile Lys Arg Lys Arg Gln Gln
            20                  25
```

<210> SEQ ID NO 18
<211> LENGTH: 39
<212> TYPE: PRT
<213> ORGANISM: Homo sapiens

<400> SEQUENCE: 18

```
Phe Ala Leu Leu Gly Asp Phe Phe Arg Lys Ser Lys Glu Lys Ile Gly
1               5                   10                  15

Lys Glu Phe Lys Arg Ile Val Gln Arg Ile Lys Asp Phe Leu Arg Asn
            20                  25                  30

Leu Val Pro Arg Thr Glu Ser
            35
```

<210> SEQ ID NO 19
<211> LENGTH: 39
<212> TYPE: PRT
<213> ORGANISM: Homo sapiens

<400> SEQUENCE: 19

```
Asn Lys Arg Phe Ala Leu Leu Gly Asp Phe Phe Arg Lys Ser Lys Glu
1               5                   10                  15

Lys Ile Gly Lys Glu Phe Lys Arg Ile Val Gln Arg Ile Lys Asp Phe
            20                  25                  30

Leu Arg Asn Leu Val Pro Arg
            35
```

<210> SEQ ID NO 20
<211> LENGTH: 30
<212> TYPE: PRT
<213> ORGANISM: Homo sapiens

<400> SEQUENCE: 20

```
Gln His Arg Tyr Gln Gln Leu Gly Ala Gly Leu Lys Val Leu Phe Lys
1               5                   10                  15

Lys Thr His Arg Ile Leu Arg Arg Leu Phe Asn Leu Ala Lys
            20                  25                  30
```

<210> SEQ ID NO 21
<211> LENGTH: 23
<212> TYPE: PRT
<213> ORGANISM: Homo sapiens

<400> SEQUENCE: 21

```
Gly Leu Phe Glu Ala Ile Glu Gly Phe Ile Glu Asn Gly Trp Glu Gly
1               5                   10                  15

Met Ile Asp Gly Trp Tyr Gly
            20
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      dsRNA sense strand
<220> FEATURE:
<223> OTHER INFORMATION: Description of Combined DNA/RNA Molecule:
      Synthetic dsRNA sense strand

<400> SEQUENCE: 22

```
cuuacgcuga guacuucgat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      dsRNA sense strand
<220> FEATURE:
<223> OTHER INFORMATION: Description of Combined DNA/RNA Molecule:
      Synthetic dsRNA sense strand
<220> FEATURE:
<221> NAME/KEY: misc_feature
<222> LOCATION: (21)..(21)
<223> OTHER INFORMATION: nucleoside is conjugated to digoxigenin

<400> SEQUENCE: 23
cuuacgcuga guacuucgat t                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA sense strand

<400> SEQUENCE: 24
cugaagaccu gaagacaauu u                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA sense strand
<220> FEATURE:
<221> NAME/KEY: misc_feature
<222> LOCATION: (21)..(21)
<223> OTHER INFORMATION: nucleoside conjugated to digoxigenin

<400> SEQUENCE: 25
cugaagaccu gaagacaauu u                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA sense strand
<220> FEATURE:
<221> NAME/KEY: misc_feature
<222> LOCATION: (21)..(21)
<223> OTHER INFORMATION: nucleoside conjugated to digoxigenin

<400> SEQUENCE: 26
cugaagaccu gaagacaauu u                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA sense strand
<220> FEATURE:
<221> NAME/KEY: misc_feature
```

```
<222> LOCATION: (1)..(1)
<223> OTHER INFORMATION: nucleoside conjugated to cy5
<220> FEATURE:
<221> NAME/KEY: misc_feature
<222> LOCATION: (21)..(21)
<223> OTHER INFORMATION: nucleoside conjugated to digoxigenin

<400> SEQUENCE: 27
cugaagaccu gaagacaauu u                                              21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA sense strand
<220> FEATURE:
<221> NAME/KEY: misc_feature
<222> LOCATION: (1)..(1)
<223> OTHER INFORMATION: nucleoside conjugated to cy5
<220> FEATURE:
<221> NAME/KEY: misc_feature
<222> LOCATION: (21)..(21)
<223> OTHER INFORMATION: nucleoside conjugated to digoxigenin

<400> SEQUENCE: 28
cugaagaccu gaagacaauu u                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      dsRNA antisense strand
<220> FEATURE:
<223> OTHER INFORMATION: Description of Combined DNA/RNA Molecule:
      Synthetic dsRNA antisense strand

<400> SEQUENCE: 29
ucgaaguacu cagcguaagt t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      dsRNA antisense strand
<220> FEATURE:
<223> OTHER INFORMATION: Description of Combined DNA/RNA Molecule:
      Synthetic dsRNA antisense strand

<400> SEQUENCE: 30
ucgaaguacu cagcguaagt t                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA antisense strand

<400> SEQUENCE: 31
auugucuuca ggucuucagu u                                              21

<210> SEQ ID NO 32
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA antisense strand

<400> SEQUENCE: 32
auugucuuca ggucuucagu u                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA antisense strand
<220> FEATURE:
<221> NAME/KEY: misc_feature
<222> LOCATION: (21)..(21)
<223> OTHER INFORMATION: nucleoside conjugated to digoxigenin

<400> SEQUENCE: 33
auugucuuca ggucuucagu u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA antisense strand

<400> SEQUENCE: 34
auugucuuca ggucuucagu u                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      dsRNA antisense strand
<220> FEATURE:
<221> NAME/KEY: misc_feature
<222> LOCATION: (21)..(21)
<223> OTHER INFORMATION: nucleoside conjugated to digoxigenin

<400> SEQUENCE: 35
auugucuuca ggucuucagu u                                              21

<210> SEQ ID NO 36
<211> LENGTH: 455
<212> TYPE: PRT
<213> ORGANISM: Artificial Sequence
<220> FEATURE:
<223> OTHER INFORMATION: Description of Artificial Sequence: Synthetic
      Humanized <dig> H-chain-optimized sequence

<400> SEQUENCE: 36

Gln Val Gln Leu Val Glu Ser Gly Gly Gly Leu Val Lys Pro Gly Gly
1               5                   10                  15

Ser Leu Arg Leu Ser Gly Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ala Ser Ile Asn Ile Gly Ala Thr Tyr Ala Tyr Tyr Pro Asp Ser Val
```

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 37

<211> LENGTH: 214
<212> TYPE: PRT
<213> ORGANISM: Artificial Sequence
<220> FEATURE:
<223> OTHER INFORMATION: Description of Artificial Sequence: Synthetic humanized <dig> L-chain optimized construct

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 38
<211> LENGTH: 448
<212> TYPE: PRT
<213> ORGANISM: Artificial Sequence
<220> FEATURE:
<223> OTHER INFORMATION: Description of Artificial Sequence: Synthetic humanized <IGF1R> heavy chain construct

<400> SEQUENCE: 38

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95
```

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 39
<211> LENGTH: 477
<212> TYPE: PRT
<213> ORGANISM: Artificial Sequence
<220> FEATURE:
<223> OTHER INFORMATION: Description of Artificial Sequence: Synthetic
      humanized <IGF1R> <DIG(kappa)> light chain construct

<400> SEQUENCE: 39

Glu Ile Val Leu Thr Gln Ser Pro Ala Thr Leu Ser Leu Ser Pro Gly

```
  1               5                  10                 15
Glu Arg Ala Thr Leu Ser Cys Arg Ala Ser Gln Ser Val Ser Ser Tyr
                20                 25                 30

Leu Ala Trp Tyr Gln Gln Lys Pro Gly Gln Ala Pro Arg Leu Leu Ile
                35                 40                 45

Tyr Asp Ala Ser Lys Arg Ala Thr Gly Ile Pro Ala Arg Phe Ser Gly
                50                 55                 60

Ser Gly Ser Gly Thr Asp Phe Thr Leu Thr Ile Ser Ser Leu Glu Pro
 65                 70                 75                 80

Glu Asp Phe Ala Val Tyr Tyr Cys Gln Gln Arg Ser Lys Trp Pro Pro
                85                 90                 95

Trp Thr Phe Gly Gln Gly Thr Lys Val Glu Ser Lys Arg Thr Val Ala
               100                105                110

Ala Pro Ser Val Phe Ile Phe Pro Pro Ser Asp Glu Gln Leu Lys Ser
               115                120                125

Gly Thr Ala Ser Val Val Cys Leu Leu Asn Asn Phe Tyr Pro Arg Glu
               130                135                140

Ala Lys Val Gln Trp Lys Val Asp Asn Ala Leu Gln Ser Gly Asn Ser
145                150                155                160

Gln Glu Ser Val Thr Glu Gln Asp Ser Lys Asp Ser Thr Tyr Ser Leu
               165                170                175

Ser Ser Thr Leu Thr Leu Ser Lys Ala Asp Tyr Glu Lys His Lys Val
               180                185                190

Tyr Ala Cys Glu Val Thr His Gln Gly Leu Ser Ser Pro Val Thr Lys
               195                200                205

Ser Phe Asn Arg Gly Glu Cys Gly Gly Gly Ser Gly Gly Gly
               210                215                220

Ser Gln Val Gln Leu Val Glu Ser Gly Gly Gly Leu Val Lys Pro Gly
225                230                235                240

Gly Ser Leu Arg Leu Ser Cys Ala Ala Ser Gly Phe Thr Phe Ser Asp
               245                250                255

Tyr Ala Met Ser Trp Ile Arg Gln Ala Pro Gly Lys Cys Leu Glu Trp
               260                265                270

Val Ser Ser Ile Asn Ile Gly Ala Thr Tyr Ile Tyr Tyr Ala Asp Ser
               275                280                285

Val Lys Gly Arg Phe Thr Ile Ser Arg Asp Asn Ala Lys Asn Ser Leu
               290                295                300

Tyr Leu Gln Met Asn Ser Leu Arg Ala Glu Asp Thr Ala Val Tyr Tyr
305                310                315                320

Cys Ala Arg Pro Gly Ser Pro Tyr Glu Tyr Asp Lys Ala Tyr Tyr Ser
               325                330                335

Met Ala Tyr Trp Gly Gln Gly Thr Thr Val Thr Val Ser Ser Gly Gly
               340                345                350

Gly Gly Ser Gly Gly Gly Gly Ser Gly Gly Gly Gly Ser Gly Gly Gly
               355                360                365

Gly Ser Asp Ile Gln Met Thr Gln Ser Pro Ser Ser Leu Ser Ala Ser
               370                375                380

Val Gly Asp Arg Val Thr Ile Thr Cys Arg Ala Ser Gln Asp Ile Lys
385                390                395                400

Asn Tyr Leu Asn Trp Tyr Gln Gln Lys Pro Gly Lys Ala Pro Lys Leu
               405                410                415

Leu Ile Tyr Tyr Ser Ser Thr Leu Leu Ser Gly Val Pro Ser Arg Phe
               420                425                430
```

```
Ser Gly Ser Gly Ser Gly Thr Asp Phe Thr Leu Thr Ile Ser Ser Leu
        435                 440                 445

Gln Pro Glu Asp Phe Ala Thr Tyr Tyr Cys Gln Gln Ser Ile Thr Leu
    450                 455                 460

Pro Pro Thr Phe Gly Cys Gly Thr Lys Val Glu Ile Lys
465                 470                 475

<210> SEQ ID NO 40
<211> LENGTH: 705
<212> TYPE: PRT
<213> ORGANISM: Artificial Sequence
<220> FEATURE:
<223> OTHER INFORMATION: Description of Artificial Sequence: Synthetic
      humanized <IGF1R>-<DIG> heavy chain construct

<400> SEQUENCE: 40

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
            85                  90                  95

Ala Arg Glu Leu Gly Arg Arg Tyr Phe Asp Leu Trp Gly Arg Gly Thr
        100                 105                 110

Leu Val Ser Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
             305                 310                 315                 320
        Lys Cys Lys Val Ser Asn Lys Ala Leu Pro Ala Pro Ile Glu Lys Thr
                        325                 330                 335

Ile Ser Lys Ala Lys Gly Gln Pro Arg Glu Pro Gln Val Tyr Thr Leu
                        340                 345                 350

Pro Pro Ser Arg Asp Glu Leu Thr Lys Asn Gln Val Ser Leu Thr Cys
                        355                 360                 365

Leu Val Lys Gly Phe Tyr Pro Ser Asp Ile Ala Val Glu Trp Glu Ser
                        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Lys Leu Thr Val Asp Lys Ser
                        405                 410                 415

Arg Trp Gln Gln Gly Asn Val Phe Ser Cys Ser Val Met His Glu Ala
                        420                 425                 430

Leu His Asn His Tyr Thr Gln Lys Ser Leu Ser Leu Ser Pro Gly Lys
                        435                 440                 445

Gly Gly Gly Gly Ser Gly Gly Gly Gly Ser Gln Val Gln Leu Val Glu
                        450                 455                 460

Ser Gly Gly Gly Leu Val Lys Pro Gly Gly Ser Leu Arg Leu Ser Cys
        465                 470                 475                 480

Ala Ala Ser Gly Phe Thr Phe Ser Asp Tyr Ala Met Ser Trp Ile Arg
                        485                 490                 495

Gln Ala Pro Gly Lys Cys Leu Glu Trp Val Ser Ser Ile Asn Ile Gly
                        500                 505                 510

Ala Thr Tyr Ile Tyr Tyr Ala Asp Ser Val Lys Gly Arg Phe Thr Ile
                        515                 520                 525

Ser Arg Asp Asn Ala Lys Asn Ser Leu Tyr Leu Gln Met Asn Ser Leu
                        530                 535                 540

Arg Ala Glu Asp Thr Ala Val Tyr Tyr Cys Ala Arg Pro Gly Ser Pro
        545                 550                 555                 560

Tyr Glu Tyr Asp Lys Ala Tyr Tyr Ser Met Ala Tyr Trp Gly Gln Gly
                        565                 570                 575

Thr Thr Val Thr Val Ser Ser Gly Gly Gly Ser Gly Gly Gly Gly
                        580                 585                 590

Ser Gly Gly Gly Gly Ser Asp Ile Gln Met Thr Gln Ser Pro Ser Ser
                        595                 600                 605

Leu Ser Ala Ser Val Gly Asp Arg Val Thr Ile Thr Cys Arg Ala Ser
                        610                 615                 620

Gln Asp Ile Lys Asn Tyr Leu Asn Trp Tyr Gln Gln Lys Pro Gly Lys
        625                 630                 635                 640

Ala Pro Lys Leu Leu Ile Tyr Tyr Ser Ser Thr Leu Leu Ser Gly Val
                        645                 650                 655

Pro Ser Arg Phe Ser Gly Ser Gly Ser Gly Thr Asp Phe Thr Leu Thr
                        660                 665                 670

Ile Ser Ser Leu Gln Pro Glu Asp Phe Ala Thr Tyr Tyr Cys Gln Gln
                        675                 680                 685

Ser Ile Thr Leu Pro Pro Thr Phe Gly Cys Gly Thr Lys Val Glu Ile
                        690                 695                 700

Lys
        705

<210> SEQ ID NO 41
```

<211> LENGTH: 464
<212> TYPE: PRT
<213> ORGANISM: Artificial Sequence
<220> FEATURE:
<223> OTHER INFORMATION: Description of Artificial Sequence: Synthetic humanized <IGF1R> (C-terminal Citrine) light chain construct

<400> SEQUENCE: 41

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
    210                 215                 220

Ser Met Val Ser Lys Gly Glu Glu Leu Phe Thr Gly Val Val Pro Ile
225                 230                 235                 240

Leu Val Glu Leu Asp Gly Asp Val Asn Gly His Lys Phe Ser Val Ser
                245                 250                 255

Gly Glu Gly Glu Gly Asp Ala Thr Tyr Gly Lys Leu Thr Leu Lys Phe
            260                 265                 270

Ile Cys Thr Thr Gly Lys Leu Pro Val Pro Trp Pro Thr Leu Val Thr
        275                 280                 285

Thr Phe Gly Tyr Gly Leu Met Cys Phe Ala Arg Tyr Pro Asp His Met
    290                 295                 300

Lys Gln His Asp Phe Phe Lys Ser Ala Met Pro Glu Gly Tyr Val Gln
305                 310                 315                 320

Glu Arg Thr Ile Phe Phe Lys Asp Asp Gly Asn Tyr Lys Thr Arg Ala
                325                 330                 335

Glu Val Lys Phe Glu Gly Asp Thr Leu Val Asn Arg Ile Glu Leu Lys
            340                 345                 350

Gly Ile Asp Phe Lys Glu Asp Gly Asn Ile Leu Gly His Lys Leu Glu
        355                 360                 365

Tyr Asn Tyr Asn Ser His Asn Val Tyr Ile Met Ala Asp Lys Gln Lys
```

```
                    370                 375                 380
Asn Gly Ile Lys Val Asn Phe Lys Ile Arg His Asn Ile Glu Asp Gly
385                 390                 395                 400

Ser Val Gln Leu Ala Asp His Tyr Gln Gln Asn Thr Pro Ile Gly Asp
                405                 410                 415

Gly Pro Val Leu Leu Pro Asp Asn His Tyr Leu Ser Tyr Gln Ser Ala
                420                 425                 430

Leu Ser Lys Asp Pro Asn Glu Lys Arg Asp His Met Val Leu Leu Glu
                435                 440                 445

Phe Val Thr Ala Ala Gly Ile Thr Leu Gly Met Asp Glu Leu Tyr Lys
450                 455                 460

<210> SEQ ID NO 42
<211> LENGTH: 589
<212> TYPE: PRT
<213> ORGANISM: Artificial Sequence
<220> FEATURE:
<223> OTHER INFORMATION: Description of Artificial Sequence: Synthetic
      humanized <LeY>-<DIG>-dsFv heavy chain 1 construct

<400> SEQUENCE: 42

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Ser Asn Asp Asp Ser Ser Ala Ala Tyr Ser Asp Thr Val
        50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gln Val Gln Leu Val Glu Ser Gly Gly Gly Leu Val Lys Pro Gly Gly
465                 470                 475                 480

Ser Leu Arg Leu Ser Cys Ala Ala Ser Gly Phe Thr Phe Ser Asp Tyr
                485                 490                 495

Ala Met Ser Trp Ile Arg Gln Ala Pro Gly Lys Cys Leu Glu Trp Val
            500                 505                 510

Ser Ser Ile Asn Ile Gly Ala Thr Tyr Ile Tyr Tyr Ala Asp Ser Val
        515                 520                 525

Lys Gly Arg Phe Thr Ile Ser Arg Asp Asn Ala Lys Asn Ser Leu Tyr
    530                 535                 540

Leu Gln Met Asn Ser Leu Arg Ala Glu Asp Thr Ala Val Tyr Tyr Cys
545                 550                 555                 560

Ala Arg Pro Gly Ser Pro Tyr Glu Tyr Asp Lys Ala Tyr Tyr Ser Met
                565                 570                 575

Ala Tyr Trp Gly Gln Gly Thr Thr Val Thr Val Ser Ser
            580                 585

<210> SEQ ID NO 43
<211> LENGTH: 571
<212> TYPE: PRT
<213> ORGANISM: Artificial Sequence
<220> FEATURE:
<223> OTHER INFORMATION: Description of Artificial Sequence: Synthetic
      humanized <LeY>-<DIG>-dsFv heavy chain 2 construct

<400> SEQUENCE: 43

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45
```

```
Ala Tyr Ile Ser Asn Asp Asp Ser Ser Ala Tyr Ser Asp Thr Val
         50                  55                  60

Lys Gly Arg Phe Thr Ile Ser Arg Asp Asn Ala Arg Asn Thr Leu Tyr
 65                  70                  75                  80

Leu Gln Met Ser Arg Leu Lys Ser Glu Asp Thr Ala Ile Tyr Tyr Cys
                 85                  90                  95

Ala Arg Gly Leu Ala Trp Gly Ala Trp Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Ser Gly Gly Gly Gly Ser
        450                 455                 460
```

-continued

```
Asp Ile Gln Met Thr Gln Ser Pro Ser Ser Leu Ser Ala Ser Val Gly
465                 470                 475                 480

Asp Arg Val Thr Ile Thr Cys Arg Ala Ser Gln Asp Ile Lys Asn Tyr
            485                 490                 495

Leu Asn Trp Tyr Gln Gln Lys Pro Gly Lys Ala Pro Lys Leu Leu Ile
        500                 505                 510

Tyr Tyr Ser Ser Thr Leu Leu Ser Gly Val Pro Ser Arg Phe Ser Gly
    515                 520                 525

Ser Gly Ser Gly Thr Asp Phe Thr Leu Thr Ile Ser Ser Leu Gln Pro
530                 535                 540

Glu Asp Phe Ala Thr Tyr Tyr Cys Gln Gln Ser Ile Thr Leu Pro Pro
545                 550                 555                 560

Thr Phe Gly Cys Gly Thr Lys Val Glu Ile Lys
                565                 570
```

<210> SEQ ID NO 44
<211> LENGTH: 943
<212> TYPE: PRT
<213> ORGANISM: Artificial Sequence
<220> FEATURE:
<223> OTHER INFORMATION: Description of Artificial Sequence: Synthetic
      humanized <VEGFR2>(D1F7)-scFab <DIG> heavy chain construct

<400> SEQUENCE: 44

```
Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Phe Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Asp Tyr Tyr Asp Ser Ser Gly Val Ala Ser Pro Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Gly Gly Gly Ser Gly Gly Gly Gly
450                 455                 460

Ser Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Ile Lys Asn
                485                 490                 495

Tyr Leu Asn Trp Tyr Gln Gln Lys Pro Gly Lys Ala Pro Lys Leu Leu
            500                 505                 510

Ile Tyr Tyr Ser Ser Thr Leu Leu Ser Gly Val Pro Ser Arg Phe Ser
        515                 520                 525

Gly Ser Gly Ser Gly Thr Asp Phe Thr Leu Thr Ile Ser Ser Leu Gln
530                 535                 540

Pro Glu Asp Phe Ala Thr Tyr Tyr Cys Gln Gln Ser Ile Thr Leu Pro
545                 550                 555                 560

Pro Thr Phe Gly Gly Gly Thr Lys Val Glu Ile Lys Arg Thr Val Ala
                565                 570                 575

Ala Pro Ser Val Phe Ile Phe Pro Pro Ser Asp Glu Gln Leu Lys Ser
            580                 585                 590

Gly Thr Ala Ser Val Val Cys Leu Leu Asn Asn Phe Tyr Pro Arg Glu
        595                 600                 605

Ala Lys Val Gln Trp Lys Val Asp Asn Ala Leu Gln Ser Gly Asn Ser
610                 615                 620

Gln Glu Ser Val Thr Glu Gln Asp Ser Lys Asp Ser Thr Tyr Ser Leu
625                 630                 635                 640

Ser Ser Thr Leu Thr Leu Ser Lys Ala Asp Tyr Glu Lys His Lys Val
                645                 650                 655

Tyr Ala Cys Glu Val Thr His Gln Gly Leu Ser Ser Pro Val Thr Lys
            660                 665                 670
```

```
Ser Phe Asn Arg Gly Glu Cys Gly Gly Gly Ser Gly Gly Gly
        675                 680                 685

Ser Gly Gly Gly Ser Gly Gly Gly Ser Gly Gly Gly Ser
    690                 695                 700

Gly Gly Gly Ser Gly Gly Gln Val Gln Leu Val Glu Ser Gly Gly
705                 710                 715                 720

Gly Leu Val Lys Pro Gly Gly Ser Leu Arg Leu Ser Cys Ala Ala Ser
            725                 730                 735

Gly Phe Thr Phe Ser Asp Tyr Ala Met Ser Trp Ile Arg Gln Ala Pro
            740                 745                 750

Gly Lys Gly Leu Glu Trp Val Ser Ser Ile Asn Ile Gly Ala Thr Tyr
            755                 760                 765

Ile Tyr Tyr Ala Asp Ser Val Lys Gly Arg Phe Thr Ile Ser Arg Asp
            770                 775                 780

Asn Ala Lys Asn Ser Leu Tyr Leu Gln Met Asn Ser Leu Arg Ala Glu
785                 790                 795                 800

Asp Thr Ala Val Tyr Tyr Cys Ala Arg Pro Gly Ser Pro Tyr Glu Tyr
            805                 810                 815

Asp Lys Ala Tyr Tyr Ser Met Ala Tyr Trp Gly Gln Gly Thr Thr Val
            820                 825                 830

Thr Val Ser Ser Ala Ser Thr Lys Gly Pro Ser Val Phe Pro Leu Ala
            835                 840                 845

Pro Ser Ser Lys Ser Thr Ser Gly Gly Thr Ala Ala Leu Gly Cys Leu
            850                 855                 860

Val Lys Asp Tyr Phe Pro Glu Pro Val Thr Val Ser Trp Asn Ser Gly
865                 870                 875                 880

Ala Leu Thr Ser Gly Val His Thr Phe Pro Ala Val Leu Gln Ser Ser
            885                 890                 895

Gly Leu Tyr Ser Leu Ser Ser Val Val Thr Val Pro Ser Ser Ser Leu
            900                 905                 910

Gly Thr Gln Thr Tyr Ile Cys Asn Val Asn His Lys Pro Ser Asn Thr
            915                 920                 925

Lys Val Asp Lys Lys Val Glu Pro Lys Ser Cys Asp Lys Thr His
930                 935                 940

<210> SEQ ID NO 45
<211> LENGTH: 943
<212> TYPE: PRT
<213> ORGANISM: Artificial Sequence
<220> FEATURE:
<223> OTHER INFORMATION: Description of Artificial Sequence: Synthetic
      <VEGFR2>(D1F7)-scFab <DIG> heavy chain construct

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Phe Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Gly Tyr Asp Tyr Tyr Asp Ser Ser Gly Val Ala Ser Pro Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Gly Gly Gly Gly Ser Gly Gly Gly Gly
            450                 455                 460

Ser Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Ile Lys Asn
                    485                 490                 495

Tyr Leu Asn Trp Tyr Gln Gln Lys Pro Gly Lys Ala Pro Lys Leu Leu
            500                 505                 510
```

```
Ile Tyr Tyr Ser Ser Thr Leu Leu Ser Gly Val Pro Ser Arg Phe Ser
            515                 520                 525

Gly Ser Gly Ser Gly Thr Asp Phe Thr Leu Thr Ile Ser Ser Leu Gln
    530                 535                 540

Pro Glu Asp Phe Ala Thr Tyr Tyr Cys Gln Gln Ser Ile Thr Leu Pro
545                 550                 555                 560

Pro Thr Phe Gly Cys Gly Thr Lys Val Glu Ile Lys Arg Thr Val Ala
            565                 570                 575

Ala Pro Ser Val Phe Ile Phe Pro Pro Ser Asp Glu Gln Leu Lys Ser
            580                 585                 590

Gly Thr Ala Ser Val Val Cys Leu Leu Asn Asn Phe Tyr Pro Arg Glu
            595                 600                 605

Ala Lys Val Gln Trp Lys Val Asp Asn Ala Leu Gln Ser Gly Asn Ser
            610                 615                 620

Gln Glu Ser Val Thr Glu Gln Asp Ser Lys Asp Ser Thr Tyr Ser Leu
625                 630                 635                 640

Ser Ser Thr Leu Thr Leu Ser Lys Ala Asp Tyr Glu Lys His Lys Val
            645                 650                 655

Tyr Ala Cys Glu Val Thr His Gln Gly Leu Ser Ser Pro Val Thr Lys
            660                 665                 670

Ser Phe Asn Arg Gly Glu Cys Gly Gly Gly Ser Gly Gly Gly Gly
            675                 680                 685

Ser Gly Gly Gly Gly Ser Gly Gly Gly Gly Ser Gly Gly Gly Gly Ser
    690                 695                 700

Gly Gly Gly Gly Ser Gly Gly Gln Val Gln Leu Val Glu Ser Gly Gly
705                 710                 715                 720

Gly Leu Val Lys Pro Gly Gly Ser Leu Arg Leu Ser Cys Ala Ala Ser
            725                 730                 735

Gly Phe Thr Phe Ser Asp Tyr Ala Met Ser Trp Ile Arg Gln Ala Pro
            740                 745                 750

Gly Lys Cys Leu Glu Trp Val Ser Ser Ile Asn Ile Gly Ala Thr Tyr
            755                 760                 765

Ile Tyr Tyr Ala Asp Ser Val Lys Gly Arg Phe Thr Ile Ser Arg Asp
            770                 775                 780

Asn Ala Lys Asn Ser Leu Tyr Leu Gln Met Asn Ser Leu Arg Ala Glu
785                 790                 795                 800

Asp Thr Ala Val Tyr Tyr Cys Ala Arg Pro Gly Ser Pro Tyr Glu Tyr
            805                 810                 815

Asp Lys Ala Tyr Tyr Ser Met Ala Tyr Trp Gly Gln Gly Thr Thr Val
            820                 825                 830

Thr Val Ser Ser Ala Ser Thr Lys Gly Pro Ser Val Phe Pro Leu Ala
            835                 840                 845

Pro Ser Ser Lys Ser Thr Ser Gly Gly Thr Ala Ala Leu Gly Cys Leu
850                 855                 860

Val Lys Asp Tyr Phe Pro Glu Pro Val Thr Val Ser Trp Asn Ser Gly
865                 870                 875                 880

Ala Leu Thr Ser Gly Val His Thr Phe Pro Ala Val Leu Gln Ser Ser
            885                 890                 895

Gly Leu Tyr Ser Leu Ser Ser Val Val Thr Val Pro Ser Ser Ser Leu
            900                 905                 910

Gly Thr Gln Thr Tyr Ile Cys Asn Val Asn His Lys Pro Ser Asn Thr
            915                 920                 925

Lys Val Asp Lys Lys Val Glu Pro Lys Ser Cys Asp Lys Thr His
```

<210> SEQ ID NO 46
<211> LENGTH: 524
<212> TYPE: PRT
<213> ORGANISM: Artificial Sequence
<220> FEATURE:
<223> OTHER INFORMATION: Description of Artificial Sequence: Synthetic dsFV <IGF1R> (G4S)3G4T-dsFv <DIG> construct

<400> SEQUENCE: 46

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Gly Gly Gly Gly Ser Gly Gly Gly Gly Ser
        115                 120                 125

Gly Gly Gly Gly Ser Gly Gly Gly Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Gln Ser Val Ser Ser Tyr Leu Ala Trp Tyr Gln Gln
                165                 170                 175

Lys Pro Gly Gln Ala Pro Arg Leu Leu Ile Tyr Asp Ala Ser Lys Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Lys Trp Pro Pro Trp Thr Phe Gly Cys Gly
225                 230                 235                 240

Thr Lys Val Glu Ser Lys Gly Gly Gly Ser Gly Gly Gly Gly Ser
                245                 250                 255

Gly Gly Gly Gly Ser Gly Gly Gly Gly Thr Gln Val Gln Leu Val Glu
            260                 265                 270

Ser Gly Gly Gly Leu Val Lys Pro Gly Gly Ser Leu Arg Leu Ser Cys
        275                 280                 285

Ala Ala Ser Gly Phe Thr Phe Ser Asp Tyr Ala Met Ser Trp Ile Arg
    290                 295                 300

Gln Ala Pro Gly Lys Cys Leu Glu Trp Val Ser Ser Ile Asn Ile Gly
305                 310                 315                 320

Ala Thr Tyr Ile Tyr Tyr Ala Asp Ser Val Lys Gly Arg Phe Thr Ile
                325                 330                 335

Ser Arg Asp Asn Ala Lys Asn Ser Leu Tyr Leu Gln Met Asn Ser Leu
            340                 345                 350
```

```
Arg Ala Glu Asp Thr Ala Val Tyr Tyr Cys Ala Arg Pro Gly Ser Pro
            355                 360                 365

Tyr Glu Tyr Asp Lys Ala Tyr Tyr Ser Met Ala Tyr Trp Gly Gln Gly
    370                 375                 380

Thr Thr Val Thr Val Ser Ser Gly Gly Gly Ser Gly Gly Gly Gly
385                 390                 395                 400

Ser Gly Gly Gly Ser Gly Gly Gly Gly Ser Asp Ile Gln Met Thr
                405                 410                 415

Gln Ser Pro Ser Ser Leu Ser Ala Ser Val Gly Asp Arg Val Thr Ile
                420                 425                 430

Thr Cys Arg Ala Ser Gln Asp Ile Lys Asn Tyr Leu Asn Trp Tyr Gln
            435                 440                 445

Gln Lys Pro Gly Lys Ala Pro Lys Leu Leu Ile Tyr Tyr Ser Ser Thr
    450                 455                 460

Leu Leu Ser Gly Val Pro Ser Arg Phe Ser Gly Ser Gly Ser Gly Thr
465                 470                 475                 480

Asp Phe Thr Leu Thr Ile Ser Ser Leu Gln Pro Glu Asp Phe Ala Thr
                485                 490                 495

Tyr Tyr Cys Gln Gln Ser Ile Thr Leu Pro Pro Thr Phe Gly Cys Gly
            500                 505                 510

Thr Lys Val Glu Ile Lys His His His His His His
            515                 520
```

<210> SEQ ID NO 47
<211> LENGTH: 292
<212> TYPE: PRT
<213> ORGANISM: Artificial Sequence
<220> FEATURE:
<223> OTHER INFORMATION: Description of Artificial Sequence: Synthetic 10xGPP-dsFv <IGF1R> construct

<400> SEQUENCE: 47

```
Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Gly
                20                  25                  30

Gly Gly Ser Gly Gly Gly Gly Ser Gln Val Glu Leu Val Glu Ser Gly
            35                  40                  45

Gly Gly Val Val Gln Pro Gly Arg Ser Gln Arg Leu Ser Cys Ala Ala
    50                  55                  60

Ser Gly Phe Thr Phe Ser Ser Tyr Gly Met His Trp Val Arg Gln Ala
65                  70                  75                  80

Pro Gly Lys Cys Leu Glu Trp Val Ala Ile Ile Trp Phe Asp Gly Ser
                85                  90                  95

Ser Thr Tyr Tyr Ala Asp Ser Val Arg Gly Arg Phe Thr Ile Ser Arg
            100                 105                 110

Asp Asn Ser Lys Asn Thr Leu Tyr Leu Gln Met Asn Ser Leu Arg Ala
        115                 120                 125

Glu Asp Thr Ala Val Tyr Phe Cys Ala Arg Glu Leu Gly Arg Arg Tyr
    130                 135                 140

Phe Asp Leu Trp Gly Arg Gly Thr Leu Val Ser Val Ser Ser Gly Gly
145                 150                 155                 160

Gly Gly Ser Gly Gly Gly Gly Ser Gly Gly Gly Ser Gly Gly Gly
                165                 170                 175

Gly Ser Glu Ile Val Leu Thr Gln Ser Pro Ala Thr Leu Ser Leu Ser
            180                 185                 190
```

-continued

```
Pro Gly Glu Arg Ala Thr Leu Ser Cys Arg Ala Ser Gln Ser Val Ser
        195                 200                 205

Ser Tyr Leu Ala Trp Tyr Gln Gln Lys Pro Gly Gln Ala Pro Arg Leu
    210                 215                 220

Leu Ile Tyr Asp Ala Ser Lys Arg Ala Thr Gly Ile Pro Ala Arg Phe
225                 230                 235                 240

Ser Gly Ser Gly Ser Gly Thr Asp Phe Thr Leu Thr Ile Ser Ser Leu
            245                 250                 255

Glu Pro Glu Asp Phe Ala Val Tyr Tyr Cys Gln Gln Arg Ser Lys Trp
        260                 265                 270

Pro Pro Trp Thr Phe Gly Cys Gly Thr Lys Val Glu Ser Lys His His
    275                 280                 285

His His His His
    290

<210> SEQ ID NO 48
<211> LENGTH: 526
<212> TYPE: PRT
<213> ORGANISM: Artificial Sequence
<220> FEATURE:
<223> OTHER INFORMATION: Description of Artificial Sequence: Synthetic
      10xGPP-dsscFab-<DIG> construct

<400> SEQUENCE: 48

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Gly
            20                  25                  30

Gly Gly Ser Gly Gly Gly Gly Ser Asp Ile Gln Met Thr Gln Ser Pro
        35                  40                  45

Ser Ser Leu Ser Ala Ser Val Gly Asp Arg Val Thr Ile Thr Cys Arg
    50                  55                  60

Ala Ser Gln Asp Ile Lys Asn Tyr Leu Asn Trp Tyr Gln Gln Lys Pro
65                  70                  75                  80

Gly Lys Ala Pro Lys Leu Leu Ile Tyr Tyr Ser Ser Thr Leu Leu Ser
            85                  90                  95

Gly Val Pro Ser Arg Phe Ser Gly Ser Gly Ser Gly Thr Asp Phe Thr
        100                 105                 110

Leu Thr Ile Ser Ser Leu Gln Pro Glu Asp Phe Ala Thr Tyr Tyr Cys
    115                 120                 125

Gln Gln Ser Ile Thr Leu Pro Pro Thr Phe Gly Cys Gly Thr Lys Val
130                 135                 140

Glu Ile Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
            165                 170                 175

Asn Asn Phe Tyr Pro Arg Glu Ala Lys Val Gln Trp Lys Val Asp Asn
        180                 185                 190

Ala Leu Gln Ser Gly Asn Ser Gln Glu Ser Val Thr Glu Gln Asp Ser
    195                 200                 205

Lys Asp Ser Thr Tyr Ser Leu Ser Ser Thr Leu Thr Leu Ser Lys Ala
210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys Gly Gly
```

```
                    245                 250                 255
Gly Gly Ser Gly Gly Gly Ser Gly Gly Gly Ser Gly Gly
            260                 265                 270
Gly Ser Gly Gly Gly Ser Gly Gly Gly Ser Gly Gly Gln Val
        275                 280                 285
Gln Leu Val Glu Ser Gly Gly Leu Val Lys Pro Gly Gly Ser Leu
    290                 295                 300
Arg Leu Ser Cys Ala Ala Ser Gly Phe Thr Phe Ser Asp Tyr Ala Met
305                 310                 315                 320
Ser Trp Ile Arg Gln Ala Pro Gly Lys Cys Leu Glu Trp Val Ser Ser
                325                 330                 335
Ile Asn Ile Gly Ala Thr Tyr Ile Tyr Tyr Ala Asp Ser Val Lys Gly
            340                 345                 350
Arg Phe Thr Ile Ser Arg Asp Asn Ala Lys Asn Ser Leu Tyr Leu Gln
        355                 360                 365
Met Asn Ser Leu Arg Ala Glu Asp Thr Ala Val Tyr Tyr Cys Ala Arg
    370                 375                 380
Pro Gly Ser Pro Tyr Glu Tyr Asp Lys Ala Tyr Tyr Ser Met Ala Tyr
385                 390                 395                 400
Trp Gly Gln Gly Thr Thr Val Thr Val Ser Ala Ser Thr Lys Gly
                405                 410                 415
Pro Ser Val Phe Pro Leu Ala Pro Ser Ser Lys Ser Thr Ser Gly Gly
            420                 425                 430
Thr Ala Ala Leu Gly Cys Leu Val Lys Asp Tyr Phe Pro Glu Pro Val
        435                 440                 445
Thr Val Ser Trp Asn Ser Gly Ala Leu Thr Ser Gly Val His Thr Phe
    450                 455                 460
Pro Ala Val Leu Gln Ser Ser Gly Leu Tyr Ser Leu Ser Ser Val Val
465                 470                 475                 480
Thr Val Pro Ser Ser Ser Leu Gly Thr Gln Thr Tyr Ile Cys Asn Val
                485                 490                 495
Asn His Lys Pro Ser Asn Thr Lys Val Asp Lys Lys Val Glu Pro Lys
            500                 505                 510
Ser Cys Asp Lys Thr Tyr Pro Tyr Asp Val Pro Asp Tyr Ala
        515                 520                 525

<210> SEQ ID NO 49
<211> LENGTH: 651
<212> TYPE: PRT
<213> ORGANISM: Artificial Sequence
<220> FEATURE:
<223> OTHER INFORMATION: Description of Artificial Sequence: Synthetic
      dsFv <IGF1R>-coreStreptavidin-dsFv <DIG> construct

<400> SEQUENCE: 49

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
                20                  25                  30
Ala Met Ser Trp Ile Arg Gln Ala Pro Gly Lys Cys Leu Glu Trp Val
            35                  40                  45
Ser Ser Ile Asn Ile Gly Ala Thr Tyr Ile Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95
Ala Arg Pro Gly Ser Pro Tyr Glu Tyr Asp Lys Ala Tyr Tyr Ser Met
            100                 105                 110
Ala Tyr Trp Gly Gln Gly Thr Thr Val Thr Val Ser Ser Gly Gly Gly
        115                 120                 125
Gly Ser Gly Gly Gly Gly Ser Gly Gly Gly Gly Ser Gly Gly Gly Gly
    130                 135                 140
Ser Asp Ile Gln Met Thr Gln Ser Pro Ser Ser Leu Ser Ala Ser Val
145                 150                 155                 160
Gly Asp Arg Val Thr Ile Thr Cys Arg Ala Ser Gln Asp Ile Lys Asn
                165                 170                 175
Tyr Leu Asn Trp Tyr Gln Gln Lys Pro Gly Lys Ala Pro Lys Leu Leu
            180                 185                 190
Ile Tyr Tyr Ser Ser Thr Leu Leu Ser Gly Val Pro Ser Arg Phe Ser
        195                 200                 205
Gly Ser Gly Ser Gly Thr Asp Phe Thr Leu Thr Ile Ser Ser Leu Gln
    210                 215                 220
Pro Glu Asp Phe Ala Thr Tyr Tyr Cys Gln Gln Ser Ile Thr Leu Pro
225                 230                 235                 240
Pro Thr Phe Gly Cys Gly Thr Lys Val Glu Ile Lys Gly Gly Gly Gly
                245                 250                 255
Ser Gly Gly Gly Gly Ser Ala Glu Ala Gly Ile Thr Gly Thr Trp Tyr
            260                 265                 270
Asn Gln Leu Gly Ser Thr Phe Ile Val Thr Ala Gly Ala Asp Gly Ala
        275                 280                 285
Leu Thr Gly Thr Tyr Glu Ser Ala Val Gly Asn Ala Glu Ser Arg Tyr
    290                 295                 300
Val Leu Thr Gly Arg Tyr Asp Ser Ala Pro Ala Thr Asp Gly Ser Gly
305                 310                 315                 320
Thr Ala Leu Gly Trp Thr Val Ala Trp Lys Asn Asn Tyr Arg Asn Ala
                325                 330                 335
His Ser Ala Thr Thr Trp Ser Gly Gln Tyr Val Gly Gly Ala Glu Ala
            340                 345                 350
Arg Ile Asn Thr Gln Trp Leu Leu Thr Ser Gly Thr Thr Glu Ala Asn
        355                 360                 365
Ala Trp Lys Ser Thr Leu Val Gly His Asp Thr Phe Thr Lys Val Lys
    370                 375                 380
Pro Ser Ala Ala Ser Gly Gly Gly Ser Gly Gly Gly Gly Ser Gln
385                 390                 395                 400
Val Glu Leu Val Glu Ser Gly Gly Val Val Gln Pro Gly Arg Ser
                405                 410                 415
Gln Arg Leu Ser Cys Ala Ala Ser Gly Phe Thr Phe Ser Ser Tyr Gly
            420                 425                 430
Met His Trp Val Arg Gln Ala Pro Gly Lys Cys Leu Glu Trp Val Ala
        435                 440                 445
Ile Ile Trp Phe Asp Gly Ser Ser Thr Tyr Tyr Ala Asp Ser Val Arg
    450                 455                 460
Gly Arg Phe Thr Ile Ser Arg Asp Asn Ser Lys Asn Thr Leu Tyr Leu
465                 470                 475                 480
Gln Met Asn Ser Leu Arg Ala Glu Asp Thr Ala Val Tyr Phe Cys Ala
                485                 490                 495
Arg Glu Leu Gly Arg Arg Tyr Phe Asp Leu Trp Gly Arg Gly Thr Leu
```

```
                500             505             510
Val Ser Val Ser Ser Gly Gly Gly Ser Gly Gly Gly Ser Gly
        515             520             525
Gly Gly Gly Ser Gly Gly Gly Ser Glu Ile Val Leu Thr Gln Ser
        530             535             540
Pro Ala Thr Leu Ser Leu Ser Pro Gly Glu Arg Ala Thr Leu Ser Cys
545             550             555             560
Arg Ala Ser Gln Ser Val Ser Ser Tyr Leu Ala Trp Tyr Gln Gln Lys
                565             570             575
Pro Gly Gln Ala Pro Arg Leu Leu Ile Tyr Asp Ala Ser Lys Arg Ala
                580             585             590
Thr Gly Ile Pro Ala Arg Phe Ser Gly Ser Gly Ser Gly Thr Asp Phe
        595             600             605
Thr Leu Thr Ile Ser Ser Leu Glu Pro Glu Asp Phe Ala Val Tyr Tyr
        610             615             620
Cys Gln Gln Arg Ser Lys Trp Pro Pro Trp Thr Phe Gly Cys Gly Thr
625             630             635             640
Lys Val Glu Ser Lys His His His His His His
                645             650

<210> SEQ ID NO 50
<211> LENGTH: 639
<212> TYPE: PRT
<213> ORGANISM: Artificial Sequence
<220> FEATURE:
<223> OTHER INFORMATION: Description of Artificial Sequence: Synthetic
      dsFv <Her2> (Lieberman)-Pseudomonas ExodomainII-dsFv <DIG>
      construct

<400> SEQUENCE: 50

Gln Val Gln Leu Leu Gln Ser Gly Ala Glu Leu Lys Lys Pro Gly Glu
1               5                   10                  15
Ser Leu Lys Ile Ser Cys Lys Gly Ser Gly Tyr Ser Phe Thr Ser Tyr
                20                  25                  30
Trp Ile Ala Trp Val Arg Gln Met Pro Gly Lys Gly Leu Glu Tyr Met
            35                  40                  45
Gly Leu Ile Tyr Pro Gly Asp Ser Asp Thr Lys Tyr Ser Pro Ser Phe
        50                  55                  60
Gln Gly Gln Val Thr Ile Ser Val Asp Lys Ser Val Ser Thr Ala Tyr
65                  70                  75                  80
Leu Gln Trp Ser Ser Leu Lys Pro Ser Asp Ser Ala Val Tyr Phe Cys
                85                  90                  95
Ala Arg His Asp Val Gly Tyr Cys Ser Ser Ser Asn Cys Ala Lys Trp
                100                 105                 110
Pro Glu Tyr Phe Gln His Trp Gly Gln Gly Thr Leu Val Thr Val Ser
            115                 120                 125
Ser Gly Gly Gly Gly Ser Gly Gly Gly Gly Ser Gly Gly Gly Gly Ser
        130                 135                 140
Gly Gly Gly Gly Ser Gln Ser Val Leu Thr Gln Pro Pro Ser Val Ser
145                 150                 155                 160
Ala Ala Pro Gly Gln Lys Val Thr Ile Ser Cys Ser Gly Ser Ser Ser
                165                 170                 175
Asn Ile Gly Asn Asn Tyr Val Ser Trp Tyr Gln Gln Leu Pro Gly Thr
                180                 185                 190
Ala Pro Lys Leu Leu Ile Tyr Gly His Thr Asn Arg Pro Ala Gly Val
            195                 200                 205
```

```
Pro Asp Arg Phe Ser Gly Ser Lys Ser Gly Thr Ser Ala Ser Leu Ala
    210                 215                 220
Ile Ser Gly Phe Arg Ser Glu Asp Glu Ala Asp Tyr Tyr Cys Ala Ser
225                 230                 235                 240
Trp Asp Tyr Thr Leu Ser Gly Trp Val Phe Gly Gly Gly Thr Lys Leu
                245                 250                 255
Thr Val Leu Gly Gly Gly Gly Ser Gly Gly Ser Leu Ala Ala Leu
            260                 265                 270
Thr Ala His Gln Ala Cys His Leu Pro Leu Glu Thr Phe Thr Arg His
        275                 280                 285
Arg Gln Pro Arg Gly Trp Glu Gln Leu Glu Gln Cys Gly Tyr Pro Val
    290                 295                 300
Gln Arg Leu Val Ala Leu Tyr Leu Ala Ala Arg Leu Ser Trp Asn Gln
305                 310                 315                 320
Val Asp Gln Val Ile Arg Asn Ala Leu Ala Ser Pro Gly Ser Gly Gly
                325                 330                 335
Asp Leu Gly Glu Ala Ile Arg Glu Gln Pro Glu Gln Ala Arg Leu Ala
            340                 345                 350
Leu Thr Leu Ala Ala Ala Glu Ser Glu Arg Phe Val Arg Gln Gly Thr
        355                 360                 365
Gly Asn Asp Gly Gly Gly Gly Ser Gly Gly Gly Ser Gln Val Gln
    370                 375                 380
Leu Val Glu Ser Gly Gly Gly Leu Val Lys Pro Gly Gly Ser Leu Arg
385                 390                 395                 400
Leu Ser Cys Ala Ala Ser Gly Phe Thr Phe Ser Asp Tyr Ala Met Ser
                405                 410                 415
Trp Ile Arg Gln Ala Pro Gly Lys Cys Leu Glu Trp Val Ser Ser Ile
            420                 425                 430
Asn Ile Gly Ala Thr Tyr Ile Tyr Tyr Ala Asp Ser Val Lys Gly Arg
        435                 440                 445
Phe Thr Ile Ser Arg Asp Asn Ala Lys Asn Ser Leu Tyr Leu Gln Met
    450                 455                 460
Asn Ser Leu Arg Ala Glu Asp Thr Ala Val Tyr Tyr Cys Ala Arg Pro
465                 470                 475                 480
Gly Ser Pro Tyr Glu Tyr Asp Lys Ala Tyr Tyr Ser Met Ala Tyr Trp
                485                 490                 495
Gly Gln Gly Thr Thr Val Thr Val Ser Ser Gly Gly Gly Gly Ser Gly
            500                 505                 510
Gly Gly Gly Ser Gly Gly Gly Gly Ser Gly Gly Gly Gly Ser Asp Ile
        515                 520                 525
Gln Met Thr Gln Ser Pro Ser Ser Leu Ser Ala Ser Val Gly Asp Arg
    530                 535                 540
Val Thr Ile Thr Cys Arg Ala Ser Gln Asp Ile Lys Asn Tyr Leu Asn
545                 550                 555                 560
Trp Tyr Gln Gln Lys Pro Gly Lys Ala Pro Lys Leu Leu Ile Tyr Tyr
                565                 570                 575
Ser Ser Thr Leu Leu Ser Gly Val Pro Ser Arg Phe Ser Gly Ser Gly
            580                 585                 590
Ser Gly Thr Asp Phe Thr Leu Thr Ile Ser Ser Leu Gln Pro Glu Asp
        595                 600                 605
Phe Ala Thr Tyr Tyr Cys Gln Gln Ser Ile Thr Leu Pro Pro Thr Phe
    610                 615                 620
```

Gly Cys Gly Thr Lys Val Glu Ile Lys His His His His His His
625                 630                 635

<210> SEQ ID NO 51
<211> LENGTH: 712
<212> TYPE: PRT
<213> ORGANISM: Artificial Sequence
<220> FEATURE:
<223> OTHER INFORMATION: Description of Artificial Sequence: Synthetic
      humanized <VEGFR2(D1F7)><DIG> heavy chain construct

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Phe Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Asp Tyr Tyr Asp Ser Ser Gly Val Ala Ser Pro Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Gly Gly Gly Gly Ser Gly Gly Gly Gly
        450                 455                 460

Ser Gln Val Gln Leu Val Glu Ser Gly Gly Gly Leu Val Lys Pro Gly
465                 470                 475                 480

Gly Ser Leu Arg Leu Ser Cys Ala Ala Ser Gly Phe Thr Phe Ser Asp
                485                 490                 495

Tyr Ala Met Ser Trp Ile Arg Gln Ala Pro Gly Lys Cys Leu Glu Trp
                500                 505                 510

Val Ser Ser Ile Asn Ile Gly Ala Thr Tyr Ile Tyr Tyr Ala Asp Ser
            515                 520                 525

Val Lys Gly Arg Phe Thr Ile Ser Arg Asp Asn Ala Lys Asn Ser Leu
    530                 535                 540

Tyr Leu Gln Met Asn Ser Leu Arg Ala Glu Asp Thr Ala Val Tyr Tyr
545                 550                 555                 560

Cys Ala Arg Pro Gly Ser Pro Tyr Glu Tyr Asp Lys Ala Tyr Tyr Ser
                565                 570                 575

Met Ala Tyr Trp Gly Gln Gly Thr Thr Val Thr Val Ser Ser Gly Gly
                580                 585                 590

Gly Gly Ser Gly Gly Gly Gly Ser Gly Gly Gly Gly Ser Asp Ile Gln
        595                 600                 605

Met Thr Gln Ser Pro Ser Ser Leu Ser Ala Ser Val Gly Asp Arg Val
    610                 615                 620

Thr Ile Thr Cys Arg Ala Ser Gln Asp Ile Lys Asn Tyr Leu Asn Trp
625                 630                 635                 640

Tyr Gln Gln Lys Pro Gly Lys Ala Pro Lys Leu Leu Ile Tyr Tyr Ser
                645                 650                 655

Ser Thr Leu Leu Ser Gly Val Pro Ser Arg Phe Ser Gly Ser Gly Ser
                660                 665                 670

Gly Thr Asp Phe Thr Leu Thr Ile Ser Ser Leu Gln Pro Glu Asp Phe
            675                 680                 685

Ala Thr Tyr Tyr Cys Gln Gln Ser Ile Thr Leu Pro Pro Thr Phe Gly
        690                 695                 700

Cys Gly Thr Lys Val Glu Ile Lys
705                 710

<210> SEQ ID NO 52
<211> LENGTH: 218
<212> TYPE: PRT
<213> ORGANISM: Artificial Sequence
<220> FEATURE:
<223> OTHER INFORMATION: Description of Artificial Sequence: Synthetic
      humanized <VEGFR2(D1F7)><DIG> light chain construct -continued

```
<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Asn
            20                  25                  30

Thr Ala Asn Trp Phe Gln Gln Leu Pro Gly Thr Ala Pro Lys Leu Leu
        35                  40                  45

Ile His Asn Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Trp Val Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 53
<211> LENGTH: 716
<212> TYPE: PRT
<213> ORGANISM: Artificial Sequence
<220> FEATURE:
<223> OTHER INFORMATION: Description of Artificial Sequence: Synthetic
      humanized <Her2(Lieberman)>-<DIG> heavy chain construct

<400> SEQUENCE: 53

Gln Val Gln Leu Leu Gln Ser Gly Ala Glu Leu Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
        115                 120                 125
```

```
Ser Ala Ser Thr Lys Gly Pro Ser Val Phe Pro Leu Ala Pro Ser Ser
    130                 135                 140
Lys Ser Thr Ser Gly Gly Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Gln
        195                 200                 205
Thr Tyr Ile Cys Asn Val Asn His Lys Pro Ser Asn Thr Lys Val Asp
    210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
    290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Asp
        355                 360                 365
Glu Leu Thr Lys Asn Gln Val Ser Leu Thr Cys Leu Val Lys Gly Phe
    370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
Asn Val Phe Ser Cys Ser Val Met His Glu Ala Leu His Asn His Tyr
        435                 440                 445
Thr Gln Lys Ser Leu Ser Leu Ser Pro Gly Lys Gly Gly Gly Gly Ser
    450                 455                 460
Gly Gly Gly Gly Ser Gln Val Gln Leu Val Glu Ser Gly Gly Gly Leu
465                 470                 475                 480
Val Lys Pro Gly Gly Ser Leu Arg Leu Ser Cys Ala Ala Ser Gly Phe
                485                 490                 495
Thr Phe Ser Asp Tyr Ala Met Ser Trp Ile Arg Gln Ala Pro Gly Lys
            500                 505                 510
Cys Leu Glu Trp Val Ser Ser Ile Asn Ile Gly Ala Thr Tyr Ile Tyr
        515                 520                 525
Tyr Ala Asp Ser Val Lys Gly Arg Phe Thr Ile Ser Arg Asp Asn Ala
    530                 535                 540
Lys Asn Ser Leu Tyr Leu Gln Met Asn Ser Leu Arg Ala Glu Asp Thr
```

```
            545                 550                 555                 560
Ala Val Tyr Tyr Cys Ala Arg Pro Gly Ser Pro Tyr Glu Tyr Asp Lys
                565                 570                 575

Ala Tyr Tyr Ser Met Ala Tyr Trp Gly Gln Gly Thr Val Thr Val
            580                 585                 590

Ser Ser Gly Gly Gly Ser Gly Gly Gly Ser Gly Gly Gly
            595                 600                 605

Ser Asp Ile Gln Met Thr Gln Ser Pro Ser Ser Leu Ser Ala Ser Val
610                 615                 620

Gly Asp Arg Val Thr Ile Thr Cys Arg Ala Ser Gln Asp Ile Lys Asn
625                 630                 635                 640

Tyr Leu Asn Trp Tyr Gln Gln Lys Pro Gly Lys Ala Pro Lys Leu Leu
                645                 650                 655

Ile Tyr Tyr Ser Ser Thr Leu Leu Ser Gly Val Pro Ser Arg Phe Ser
                660                 665                 670

Gly Ser Gly Ser Gly Thr Asp Phe Thr Leu Thr Ile Ser Ser Leu Gln
                675                 680                 685

Pro Glu Asp Phe Ala Thr Tyr Tyr Cys Gln Gln Ser Ile Thr Leu Pro
            690                 695                 700

Pro Thr Phe Gly Cys Gly Thr Lys Val Glu Ile Lys
705                 710                 715

<210> SEQ ID NO 54
<211> LENGTH: 217
<212> TYPE: PRT
<213> ORGANISM: Artificial Sequence
<220> FEATURE:
<223> OTHER INFORMATION: Description of Artificial Sequence: Synthetic
      humanized <Her2(Lieberman)>-<DIG> light chain construct

<400> SEQUENCE: 54

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
        50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190
```

```
Lys Val Tyr Ala Cys Glu Val Thr His Gln Gly Leu Ser Ser Pro Val
            195                 200                 205

Thr Lys Ser Phe Asn Arg Gly Glu Cys
        210                 215

<210> SEQ ID NO 55
<211> LENGTH: 710
<212> TYPE: PRT
<213> ORGANISM: Artificial Sequence
<220> FEATURE:
<223> OTHER INFORMATION: Description of Artificial Sequence: Synthetic
      humanized <CD22><DIG> heavy chain construct

<400> SEQUENCE: 55

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ala Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335
```

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gln
        450                 455                 460

Val Gln Leu Val Glu Ser Gly Gly Gly Leu Val Lys Pro Gly Gly Ser
465                 470                 475                 480

Leu Arg Leu Ser Cys Ala Ala Ser Gly Phe Thr Phe Ser Asp Tyr Ala
            485                 490                 495

Met Ser Trp Ile Arg Gln Ala Pro Gly Lys Cys Leu Glu Trp Val Ser
            500                 505                 510

Ser Ile Asn Ile Gly Ala Thr Tyr Ile Tyr Tyr Ala Asp Ser Val Lys
        515                 520                 525

Gly Arg Phe Thr Ile Ser Arg Asp Asn Ala Lys Asn Ser Leu Tyr Leu
            530                 535                 540

Gln Met Asn Ser Leu Arg Ala Glu Asp Thr Ala Val Tyr Tyr Cys Ala
545                 550                 555                 560

Arg Pro Gly Ser Pro Tyr Glu Tyr Asp Lys Ala Tyr Tyr Ser Met Ala
            565                 570                 575

Tyr Trp Gly Gln Gly Thr Thr Val Thr Val Ser Ser Gly Gly Gly Gly
            580                 585                 590

Ser Gly Gly Gly Gly Ser Gly Gly Gly Ser Asp Ile Gln Met Thr
        595                 600                 605

Gln Ser Pro Ser Ser Leu Ser Ala Ser Val Gly Asp Arg Val Thr Ile
        610                 615                 620

Thr Cys Arg Ala Ser Gln Asp Ile Lys Asn Tyr Leu Asn Trp Tyr Gln
625                 630                 635                 640

Gln Lys Pro Gly Lys Ala Pro Lys Leu Leu Ile Tyr Tyr Ser Ser Thr
            645                 650                 655

Leu Leu Ser Gly Val Pro Ser Arg Phe Ser Gly Ser Gly Ser Gly Thr
            660                 665                 670

Asp Phe Thr Leu Thr Ile Ser Ser Leu Gln Pro Glu Asp Phe Ala Thr
        675                 680                 685

Tyr Tyr Cys Gln Gln Ser Ile Thr Leu Pro Pro Thr Phe Gly Cys Gly
            690                 695                 700

Thr Lys Val Glu Ile Lys
705                 710

<210> SEQ ID NO 56
<211> LENGTH: 214
<212> TYPE: PRT
<213> ORGANISM: Artificial Sequence
<220> FEATURE:

<223> OTHER INFORMATION: Description of Artificial Sequence: Synthetic
      humanized <CD22><DIG> light chain construct

<400> SEQUENCE: 56

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 57
<211> LENGTH: 706
<212> TYPE: PRT
<213> ORGANISM: Artificial Sequence
<220> FEATURE:
<223> OTHER INFORMATION: Description of Artificial Sequence: Synthetic
      humanized <LeY><DIG> heavy chain construct

<400> SEQUENCE: 57

```
Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gln Val Gln Leu Val
450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Asp Tyr Ala Met Ser Trp Ile
                485                 490                 495

Arg Gln Ala Pro Gly Lys Cys Leu Glu Trp Val Ser Ser Ile Asn Ile
                500                 505                 510

Gly Ala Thr Tyr Ile Tyr Tyr Ala Asp Ser Val Lys Gly Arg Phe Thr
                515                 520                 525

Ile Ser Arg Asp Asn Ala Lys Asn Ser Leu Tyr Leu Gln Met Asn Ser
```

```
                530              535                540
Leu Arg Ala Glu Asp Thr Ala Val Tyr Tyr Cys Ala Arg Pro Gly Ser
545                 550                 555                 560

Pro Tyr Glu Tyr Asp Lys Ala Tyr Tyr Ser Met Ala Tyr Trp Gly Gln
                565                 570                 575

Gly Thr Thr Val Thr Val Ser Ser Gly Gly Gly Ser Gly Gly Gly
            580                 585                 590

Gly Ser Gly Gly Gly Ser Asp Ile Gln Met Thr Gln Ser Pro Ser
        595                 600                 605

Ser Leu Ser Ala Ser Val Gly Asp Arg Val Thr Ile Thr Cys Arg Ala
610                 615                 620

Ser Gln Asp Ile Lys Asn Tyr Leu Asn Trp Tyr Gln Gln Lys Pro Gly
625                 630                 635                 640

Lys Ala Pro Lys Leu Leu Ile Tyr Tyr Ser Ser Thr Leu Leu Ser Gly
                645                 650                 655

Val Pro Ser Arg Phe Ser Gly Ser Gly Ser Gly Thr Asp Phe Thr Leu
                660                 665                 670

Thr Ile Ser Ser Leu Gln Pro Glu Asp Phe Ala Thr Tyr Tyr Cys Gln
            675                 680                 685

Gln Ser Ile Thr Leu Pro Pro Thr Phe Gly Cys Gly Thr Lys Val Glu
690                 695                 700

Ile Lys
705

<210> SEQ ID NO 58
<211> LENGTH: 219
<212> TYPE: PRT
<213> ORGANISM: Artificial Sequence
<220> FEATURE:
<223> OTHER INFORMATION: Description of Artificial Sequence: Synthetic
      humanized <LeY> light chain construct

<400> SEQUENCE: 58

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

-continued

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 59
<211> LENGTH: 703
<212> TYPE: PRT
<213> ORGANISM: Artificial Sequence
<220> FEATURE:
<223> OTHER INFORMATION: Description of Artificial Sequence: Synthetic
      humanized <CD33><DIG> heavy chain construct

<400> SEQUENCE: 59

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys Gly Gly
    435                 440                 445

Gly Gly Ser Gly Gly Gly Ser Gln Val Gln Leu Val Glu Ser Gly
        450                 455                 460

Gly Gly Leu Val Lys Pro Gly Gly Ser Leu Arg Leu Ser Cys Ala Ala
465                 470                 475                 480

Ser Gly Phe Thr Phe Ser Asp Tyr Ala Met Ser Trp Ile Arg Gln Ala
            485                 490                 495

Pro Gly Lys Cys Leu Glu Trp Val Ser Ser Ile Asn Ile Gly Ala Thr
        500                 505                 510

Tyr Ile Tyr Tyr Ala Asp Ser Val Lys Gly Arg Phe Thr Ile Ser Arg
    515                 520                 525

Asp Asn Ala Lys Asn Ser Leu Tyr Leu Gln Met Asn Ser Leu Arg Ala
530                 535                 540

Glu Asp Thr Ala Val Tyr Tyr Cys Ala Arg Pro Gly Ser Pro Tyr Glu
545                 550                 555                 560

Tyr Asp Lys Ala Tyr Tyr Ser Met Ala Tyr Trp Gly Gln Gly Thr Thr
            565                 570                 575

Val Thr Val Ser Ser Gly Gly Gly Gly Ser Gly Gly Gly Gly Ser Gly
        580                 585                 590

Gly Gly Gly Ser Asp Ile Gln Met Thr Gln Ser Pro Ser Ser Leu Ser
    595                 600                 605

Ala Ser Val Gly Asp Arg Val Thr Ile Thr Cys Arg Ala Ser Gln Asp
610                 615                 620

Ile Lys Asn Tyr Leu Asn Trp Tyr Gln Gln Lys Pro Gly Lys Ala Pro
625                 630                 635                 640

Lys Leu Leu Ile Tyr Tyr Ser Ser Thr Leu Leu Ser Gly Val Pro Ser
            645                 650                 655

Arg Phe Ser Gly Ser Gly Ser Gly Thr Asp Phe Thr Leu Thr Ile Ser
        660                 665                 670

Ser Leu Gln Pro Glu Asp Phe Ala Thr Tyr Tyr Cys Gln Gln Ser Ile
    675                 680                 685

Thr Leu Pro Pro Thr Phe Gly Cys Gly Thr Lys Val Glu Ile Lys
690                 695                 700

<210> SEQ ID NO 60
<211> LENGTH: 222
<212> TYPE: PRT
<213> ORGANISM: Artificial Sequence
<220> FEATURE:
```

<223> OTHER INFORMATION: Description of Artificial Sequence: Synthetic
humanized <CD33> light chain construct

<400> SEQUENCE: 60

```
Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Lys
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220
```

<210> SEQ ID NO 61
<211> LENGTH: 705
<212> TYPE: PRT
<213> ORGANISM: Artificial Sequence
<220> FEATURE:
<223> OTHER INFORMATION: Description of Artificial Sequence: Synthetic
humanized <IGF1R>-<Biotin> heavy chain construct

<400> SEQUENCE: 61

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110
```

```
Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Gly Gly Gly Ser Gly Gly Gly Gly Ser Glu Val Gln Leu Gln Gln
            450                 455                 460

Ser Gly Ala Glu Leu Val Lys Pro Gly Ala Ser Val Lys Leu Ser Cys
465                 470                 475                 480

Thr Ser Ser Gly Phe Asn Asn Lys Asp Thr Phe Phe Gln Trp Val Lys
                485                 490                 495

Gln Arg Pro Glu Glu Cys Leu Glu Trp Ile Gly Arg Ile Asp Pro Ala
            500                 505                 510

Asn Gly Phe Thr Lys Tyr Asp Pro Lys Phe Gln Gly Lys Ala Thr Ile
            515                 520                 525

Thr Val Asp Thr Ser Ser Asn Thr Ala Tyr Leu Gln Leu Asn Ser Leu
```

```
                530             535             540
Thr Ser Glu Asp Thr Ala Leu Tyr Tyr Cys Thr Arg Trp Asp Thr Tyr
545                 550             555             560

Gly Ala Ala Trp Phe Ala Tyr Trp Gly Gln Gly Thr Leu Val Thr Val
                565             570             575

Ser Ala Gly Gly Gly Ser Gly Gly Gly Ser Gly Gly Gly Gly
                580             585             590

Ser Gly Gly Gly Ser Asp Ile Gln Met Thr Gln Ser Pro Ala Ser
        595             600             605

Leu Ser Ala Ser Val Gly Glu Thr Val Thr Ile Thr Cys Arg Ala Ser
            610             615             620

Gly Asn Ile His Asn Tyr Leu Ser Trp Phe Gln Gln Lys Gln Gly Lys
625             630             635             640

Ser Pro Gln Leu Leu Val Tyr Ser Ala Lys Thr Leu Ala Asp Gly Val
                645             650             655

Pro Ser Arg Phe Ser Gly Ser Gly Ser Gly Thr Gln Tyr Ser Leu Lys
            660             665             670

Ile Asn Ser Leu Gln Pro Glu Asp Phe Gly Thr Tyr Tyr Cys Gln His
            675             680             685

Phe Trp Ser Ser Ile Tyr Thr Phe Gly Cys Gly Thr Lys Leu Glu Ile
        690             695             700

Lys
705

<210> SEQ ID NO 62
<211> LENGTH: 215
<212> TYPE: PRT
<213> ORGANISM: Artificial Sequence
<220> FEATURE:
<223> OTHER INFORMATION: Description of Artificial Sequence: Synthetic
      humanized <IGF1R> light chain construct

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
        210             215

<210> SEQ ID NO 63
<211> LENGTH: 40
<212> TYPE: PRT
<213> ORGANISM: Artificial Sequence
<220> FEATURE:
<223> OTHER INFORMATION: Description of Artificial Sequence: Synthetic
      fusion of a siRNA-binding module and CPP

<400> SEQUENCE: 63

Arg Arg Arg Arg Arg Arg Arg Arg Arg Gly Ala Ala Glu Ala Ala
1               5                   10                  15

Ala Arg Val Tyr Asp Leu Gly Leu Arg Arg Leu Arg Gln Arg Arg
            20                  25                  30

Leu Arg Arg Glu Arg Val Arg Ala
        35                  40

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      Synthetic peptide
<220> FEATURE:
<221> NAME/KEY: MOD_RES
<222> LOCATION: (7)..(7)
<223> OTHER INFORMATION: Any amino acid

<400> SEQUENCE: 64

Ala Ala Ala Gly Ser Gly Xaa Ser Gly Ala Ser Ala Ser
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 65

Gly Ser Ser Ser Ser Ser Ser Ser Ser Ser Ser Ser Ser Ser Ser Ser
1               5                   10                  15

Gly

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 66

Gly Ser Ser Ser Ser Ser Ser Ser Ser Ser Ser Ser Ser Ser Ser Ser
1               5                   10                  15

Gly Ala Ser
```

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 67

Gly Ser Gly Gly Gly Gly Ser Gly Gly Gly Gly Ser Gly Gly Gly Gly
1               5                   10                  15

Thr

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 68

Gly Ser Gly Ser Gly Ser Gly Ser Gly Ser
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 69

Gly Gly Gly Ser Gly Gly Gly Ser Gly Gly Gly Gly Ser Gly
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 70

Gly Gly Gly Ser Gly Gly Gly Ser Gly Gly Gly Gly Ser Gly Gly
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 71

Gly Gly Gly Ser Gly Gly Gly Ser Gly Gly Gly Gly Ser Gly Asn
1               5                   10                  15

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic Synthetic peptide

<400> SEQUENCE: 72

Gly Gly Gly Ser Gly Gly Gly Ser Gly Gly Gly Ser Gly Gly Gly Ser
1               5                   10                  15

Gly Gly Gly Ser
            20

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 73

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 74

Gly Gly Gly Gly Ser Gly Gly Gly Gly Ser
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 75

Gly Gly Gly Gly Ser Gly Gly Gly Gly Ser Gly Gly Gly Gly Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 76

Gly Gly Gly Gly Ser Gly Gly Gly Gly Ser Gly Gly Gly Gly Ser Gly
1               5                   10                  15

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 77

Gly Gly Gly Gly Ser Gly Gly Gly Ser Gly Gly Gly Gly Ser Gly
1               5                   10                  15

Gly

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 78

Gly Gly Gly Gly Ser Gly Gly Gly Ser Gly Gly Gly Gly Ser Gly
1               5                   10                  15

Gly Asn

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 79

Gly Gly Gly Gly Ser Gly Gly Gly Ser Gly Gly Gly Gly Ser Gly
1               5                   10                  15

Ala Ser

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 80

Gly Gly Gly Gly Ser Gly Gly Gly Ser Gly Gly Gly Gly Ser Gly
1               5                   10                  15

Gly Gly Gly Ser
            20

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 81

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 82
<211> LENGTH: 26
<212> TYPE: PRT
<213> ORGANISM: Artificial Sequence
<220> FEATURE:
<223> OTHER INFORMATION: Description of Artificial Sequence: Synthetic Synthetic peptide

<400> SEQUENCE: 82

Gly Gly Gly Gly Ser Gly Gly Gly Ser Gly Gly Gly Ser Gly
1               5                   10                  15

Gly Gly Ser Gly Gly Gly Ser Gly
            20                  25

<210> SEQ ID NO 83
<211> LENGTH: 27
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 83

Gly Gly Gly Gly Ser Gly Gly Gly Ser Gly Gly Gly Ser Gly
1               5                   10                  15

Gly Gly Ser Gly Gly Gly Ser Gly Gly
            20                  25

<210> SEQ ID NO 84
<211> LENGTH: 30
<212> TYPE: PRT
<213> ORGANISM: Artificial Sequence
<220> FEATURE:
<223> OTHER INFORMATION: Description of Artificial Sequence: Synthetic
      Synthetic polypeptide

<400> SEQUENCE: 84

Gly Gly Gly Gly Ser Gly Gly Gly Ser Gly Gly Gly Ser Gly
1               5                   10                  15

Gly Gly Ser Gly Gly Gly Ser Gly Gly Gly Gly Ser
            20                  25                  30

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 85

Gly Gln Gln Gln Gln Gly Gln Gln Gln Gln Gly Gln Gln Gln Gln
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 86

Gly Gln Gln Gln Gln Gly Gln Gln Gln Gln Gly Gln Gln Gln Gln Gly
1               5                   10                  15

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic Synthetic peptide

<400> SEQUENCE: 87

Gly Gln Gln Gln Gln Gly Gln Gln Gln Gln Gly Gln Gln Gln Gln Gly
1               5                   10                  15
Asn Asn

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 88

Lys Gly Gly Gly Gly Ser Gly Gly Gly Gly Ser Gly Gly Gly Gly Ser
1               5                   10                  15
Gly Gly Asn

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 89

Leu Ser Leu Ser Gly Gly
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 90

Leu Ser Leu Ser Pro Gly Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 91

Leu Ser Leu Ser Pro Gly Gly
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 92

Leu Ser Pro Asn Arg Gly Glu Cys

-continued

```
<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 93

Arg Thr Gly Gly Gly Ser Gly Gly Ser Gly Gly Gly Ser Gly Gly
1               5                   10                  15

Thr

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 94

Ser Gly Gly Gly Gly Ser Gly Gly Gly Ser Gly Gly Gly Gly
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 95

Ser Gly Gly Gly Gly Ser Gly Gly Gly Gly Ser Gly Gly Gly Gly
1               5                   10                  15

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 96

Ser Gly Gly Gly Gly Ser Gly Gly Gly Ser Gly Gly Gly Gly
1               5                   10                  15

Gly

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 97

Ser Gly Gly Gly Gly Ser Gly Gly Gly Ser Gly Gly Gly Gly
1               5                   10                  15

Gly Asn
```

```
<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 98

Ser Gly Gly Gly Gly Ser Gly Gly Gly Ser Gly Gly Gly Gly Gly
1               5                   10                  15

Gly Thr

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 99

Ser Gly Gly Gly Gly Ser Gly Gly Gly Ser Gly Gly Gly Gly Gly
1               5                   10                  15

Ala Ser

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 100

Ser Gly Gly Gly Gly Ser Gly Gly Gly Ser Gly Gly Gly Gly Ser
1               5                   10                  15

Gly Gly Gly Gly Ser Gly Gly Gly
            20                  25

<210> SEQ ID NO 101
<211> LENGTH: 26
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 101

Ser Gly Gly Gly Gly Ser Gly Gly Gly Ser Gly Gly Gly Gly Ser
1               5                   10                  15

Gly Gly Gly Gly Ser Gly Gly Gly Gly
            20                  25

<210> SEQ ID NO 102
<211> LENGTH: 27
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 102

Ser Gly Gly Gly Gly Ser Gly Gly Gly Gly Ser Gly Gly Gly Ser
1               5                   10                  15
```

```
Gly Gly Gly Gly Ser Gly Gly Gly Gly Gly
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 103

Ser Gly Gly Gly Gly Ser Gly Gly Gly Ser Gly Gly Gly Gly Ser
1               5                   10                  15

Gly Gly Gly Gly Ser Gly Gly Gly Gly Gly Ala Ser
            20                  25

<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 104

Gly Gly Ser Gly Gly Ser Gly Arg Thr Gly Gly Gly Ser Gly Gly Gly
1               5                   10                  15

Ser Gly Gly Gly Ser Gly Gly Thr
            20

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 105

Gly Gly Gly Ser Gly Gly Gly Ser Gly Gly Gly Ser
1               5                   10

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 106

Gly Gly Gly Ser Gly Gly Gly Ser Gly Gly Gly Ser Gly Gly Gly Ser
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 107

Ala Ala Ala Gly Ser Gly Gly Ala Ser Ala Ser
1               5                   10
```

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 108

Ala Gly Gln Gly Gly Val
1               5

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 109

Glu Gly Lys Ser Ser Gly Ser Gly Ser Glu Ser Lys Glu Phe
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 110

Glu Gly Lys Ser Ser Gly Ser Gly Ser Glu Ser Lys Ser Thr
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 111

Glu Gly Lys Ser Ser Gly Ser Gly Ser Glu Ser Lys Ser Thr Gln
1               5                   10                  15

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 112

Glu Gly Lys Ser Ser Gly Ser Gly Ser Glu Ser Lys Val Asp
1               5                   10

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      Synthetic peptide

```
<400> SEQUENCE: 113

Glu Ser Gly Ser Val Ser Ser Glu Glu Leu Ala Phe Arg Ser Leu Asp
1               5                   10                  15

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 114

Gly Gly Gly Ser Ala Ala Ala
1               5

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 115

Gly Ser Thr Ser Gly Ser Gly Lys Ser Ser Glu Gly Lys Gly
1               5                   10

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 116

Lys Glu Ser Gly Ser Val Ser Ser Glu Gln Leu Ala Gln Phe Arg Ser
1               5                   10                  15

Leu Asp

<210> SEQ ID NO 117
<211> LENGTH: 25
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 117

Ser Ser Ala Asp Asp Ala Lys Lys Asp Ala Lys Lys Asp Ala
1               5                   10                  15

Lys Lys Asp Asp Ala Lys Lys Asp Gly
                20                  25

<210> SEQ ID NO 118
<211> LENGTH: 26
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 118

Ser Ser Ala Asp Asp Ala Lys Lys Asp Ala Ala Lys Lys Asp Asp Ala
1               5                   10                  15
```

```
Lys Lys Asp Asp Ala Lys Lys Asp Ala Ser
        20                  25

<210> SEQ ID NO 119
<211> LENGTH: 25
<212> TYPE: PRT
<213> ORGANISM: Artificial Sequence
<220> FEATURE:
<223> OTHER INFORMATION: Description of Artificial Sequence: Synthetic
      Synthetic peptide

<400> SEQUENCE: 119

Ser Ser Ala Asp Asp Ala Lys Lys Asp Ala Lys Lys Asp Asp Ala
1               5                   10                  15

Lys Lys Asp Asp Ala Lys Lys Asp Gly
        20                  25

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      Synthetic polypeptide
<220> FEATURE:
<221> NAME/KEY: MISC_FEATURE
<222> LOCATION: (1)..(4)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (6)..(9)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (11)..(14)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (16)..(19)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (21)..(24)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (26)..(29)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (1)..(30)
<223> OTHER INFORMATION: This sequence may encompass 2-6 repeating
      "Gly Gly Gly Gly Ser" or "Gly Gly Gly Ser" units; See
      specification as filed for detailed description of substitutions
      and preferred embodiments

<400> SEQUENCE: 120

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 121
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      Synthetic polypeptide
<220> FEATURE:
<221> NAME/KEY: MISC_FEATURE
<222> LOCATION: (1)..(4)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (6)..(9)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (11)..(14)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (16)..(19)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (21)..(24)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (26)..(29)
<223> OTHER INFORMATION: This region may encompass 3-4 repeating "Gly"
      residues wherein one position may be absent
<220> FEATURE:
<221> NAME/KEY: MISC_FEATURE
<222> LOCATION: (1)..(30)
<223> OTHER INFORMATION: This sequence may encompass 2-6 repeating
      "Gly Gly Gly Gly Ser" or "Gly Gly Gly Ser" units; See
      specification as filed for detailed description of substitutions
      and preferred embodiments

<400> SEQUENCE: 121

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```